(12) United States Patent
Konradi et al.

(10) Patent No.: US 11,524,943 B1
(45) Date of Patent: Dec. 13, 2022

(54) BENZOCARBONYL COMPOUNDS

(71) Applicant: Vivace Therapeutics, Inc., San Mateo, CA (US)

(72) Inventors: Andrei W. Konradi, Burlingame, CA (US); Tracy Tzu-Ling Tang Lin, Redwood City, CA (US)

(73) Assignee: VIVACE THERAPEUTICS, INC., San Mateo, CA (US)

( * ) Notice: Subject to any disclaimer, the term of this patent is extended or adjusted under 35 U.S.C. 154(b) by 37 days.

(21) Appl. No.: 16/769,997

(22) PCT Filed: Dec. 5, 2018

(86) PCT No.: PCT/US2018/064104
§ 371 (c)(1),
(2) Date: Jun. 4, 2020

(87) PCT Pub. No.: WO2019/113236
PCT Pub. Date: Jun. 13, 2019

Related U.S. Application Data

(60) Provisional application No. 62/595,197, filed on Dec. 6, 2017.

(51) Int. Cl.

| | | |
|---|---|---|
| *C07D 257/04* | (2006.01) |
| *C07D 233/64* | (2006.01) |
| *C07D 213/24* | (2006.01) |
| *C07D 213/26* | (2006.01) |
| *C07D 213/28* | (2006.01) |
| *C07D 271/10* | (2006.01) |
| *C07D 277/24* | (2006.01) |
| *C07D 239/26* | (2006.01) |
| *C07D 241/12* | (2006.01) |
| *C07D 237/08* | (2006.01) |
| *C07D 269/02* | (2006.01) |
| *C07D 285/12* | (2006.01) |
| *C07D 283/02* | (2006.01) |
| *A61K 31/196* | (2006.01) |
| *A61K 31/235* | (2006.01) |
| *A61K 31/165* | (2006.01) |
| *A61P 35/00* | (2006.01) |
| *C07D 233/61* | (2006.01) |
| *C07D 213/55* | (2006.01) |
| *C07D 277/30* | (2006.01) |
| *C07D 271/06* | (2006.01) |
| *C07D 263/32* | (2006.01) |
| *C07D 213/73* | (2006.01) |

(52) U.S. Cl.
CPC ............ *C07D 239/26* (2013.01); *A61P 35/00* (2018.01); *C07D 213/55* (2013.01); *C07D 213/73* (2013.01); *C07D 233/61* (2013.01); *C07D 237/08* (2013.01); *C07D 257/04* (2013.01); *C07D 263/32* (2013.01); *C07D 271/06* (2013.01); *C07D 277/30* (2013.01)

(58) Field of Classification Search
CPC .. C07D 257/04; C07D 233/64; C07D 213/24; C07D 213/26; C07D 213/28; C07D 271/10; C07D 277/24; C07D 239/26; C07D 241/12; C07D 237/08; C07D 269/02; C07D 285/12; C07D 283/02; A61K 31/196; A61K 31/235; A61K 31/165; A61P 35/00
See application file for complete search history.

(56) References Cited

U.S. PATENT DOCUMENTS

| | | |
|---|---|---|
| 3,895,027 A | 7/1975 | Katner |
| 3,903,106 A | 9/1975 | Katner et al. |
| 4,010,273 A | 3/1977 | Bormann et al. |
| 4,492,710 A | 1/1985 | Merkel et al. |
| 4,962,119 A | 10/1990 | Boschelli et al. |
| 5,017,467 A | 5/1991 | Masukawa et al. |
| 5,066,668 A | 11/1991 | Boschelli et al. |
| 5,114,958 A | 5/1992 | Boschelli et al. |
| 5,462,952 A | 10/1995 | Boschelli et al. |
| 5,670,526 A | 9/1997 | Dodd et al. |
| 6,211,209 B1 | 4/2001 | Baragi et al. |
| 6,545,030 B1 | 4/2003 | Barrett et al. |
| 6,972,287 B1 | 12/2005 | Augelli-Szafran et al. |
| 7,019,033 B2 | 3/2006 | Barrett et al. |
| 7,956,191 B2 | 6/2011 | Abel et al. |
| 8,076,486 B2 | 12/2011 | Goutopoulos et al. |
| 8,198,457 B2 | 6/2012 | Abel et al. |
| 8,524,911 B2 | 9/2013 | Abel et al. |
| 8,841,459 B2 | 9/2014 | Deppe et al. |
| 9,790,229 B2 | 10/2017 | Bui et al. |
| 2003/0004193 A1 | 1/2003 | Barrett et al. |

(Continued)

FOREIGN PATENT DOCUMENTS

| | | |
|---|---|---|
| WO | WO-0042029 A1 | 7/2000 |
| WO | WO-0105391 A2 | 1/2001 |

(Continued)

OTHER PUBLICATIONS

Holmes et al., Discovery and structure-activity relationships of novel sulfonamides as potent PTP1B inhibitors. Bioorganic and Medicinal Chemistry Letters 15:4336-4341 (2005).
Pubchem Compound Summary CID 68170056 deposited Nov. 30, 2012.
Pubchem Substance record for SID 274578875, available date: Dec. 18, 2015 (retrieved on Jun. 22, 2018). Retrieved from https://pubchem.ncbi.nlm.nih.gov/substance/274578875.
Science IP Report 2017 (1079 pgs).

(Continued)

*Primary Examiner* — Bruck Kifle
(74) *Attorney, Agent, or Firm* — Wilson Sonsini Goodrich & Rosati

(57) ABSTRACT

Provided herein are compounds and pharmaceutical compositions comprising said compounds that are useful for treating cancers. Specific cancers include those that are mediated by YAP/TAZ or those that are modulated by the interaction between YAP/TAZ and TEAD.

20 Claims, 2 Drawing Sheets

(56) References Cited

U.S. PATENT DOCUMENTS

| | | |
|---|---|---|
| 2005/0004186 A1 | 1/2005 | Barrett et al. |
| 2007/0259051 A1 | 11/2007 | Feinmark et al. |
| 2009/0048301 A1 | 2/2009 | Chen et al. |
| 2009/0318438 A1 | 12/2009 | Chen et al. |
| 2015/0111885 A1 | 4/2015 | Bennett et al. |
| 2016/0289171 A1 | 10/2016 | Balog et al. |
| 2017/0137428 A1 | 5/2017 | Spangenberg |
| 2020/0062721 A1 | 2/2020 | Konradi et al. |
| 2020/0354325 A1 | 11/2020 | Konradi et al. |
| 2021/0238154 A1 | 8/2021 | Konradi et al. |

FOREIGN PATENT DOCUMENTS

| | | |
|---|---|---|
| WO | WO-03045912 A1 | 6/2003 |
| WO | WO-2004056789 A1 | 7/2004 |
| WO | WO-2005004818 A2 | 1/2005 |
| WO | WO-2007123936 A1 | 11/2007 |
| WO | WO-2009086163 A2 | 7/2009 |
| WO | WO-2013188138 A1 | 12/2013 |
| WO | WO-2016161269 A1 | 10/2016 |
| WO | WO-2016161279 A1 | 10/2016 |
| WO | WO-2016161286 A1 | 10/2016 |
| WO | WO-2017053706 A1 | 3/2017 |
| WO | WO-2017058716 A1 | 4/2017 |
| WO | WO-2017064277 A1 | 4/2017 |
| WO | WO-2018204532 A1 | 11/2018 |
| WO | WO-2019040380 A1 | 2/2019 |
| WO | WO-2019113236 A1 | 6/2019 |
| WO | WO-2019222431 A1 | 11/2019 |

OTHER PUBLICATIONS

Yokokawa et al., Discovery of potent non-nucleoside inhibitors of dengue viral RNA-dependent RNA polymerase from a fragment hit using structure-based drug design. Journal of Medicinal Chemistry59(8):3935-3952 (2016).

Sebio et al. Molecular Pathways: Hippo Signaling, a Critical Tumor Suppressor. Clin Cancer Res 21(22):5002-7 (2015).

Berge et al. Pharmaceutical Salts. Journal of Pharmaceutical Sciences 66(1):1-19 (Jan. 1977).

Bundgaard et al. Design of Prodrugs pp. 7-9, 21-24 (1985).

Fleisher et al. Improved oral drug delivery: solubility limitations overcome by the use of prodrugs. Advanced Drug Delivery Reviews 19:115-130 (1996).

PCT/US2018/064104 International Invitation to Pay Additional Fees dated Jan. 23, 2019.

PCT/US2018/064104 International Search Report and Written Opinion dated Mar. 27, 2019.

Pobbati et al. 'Targeting the Central Pocket in Human Transcription Factor TEAD as a Potential Cancer Therapeutic Strategy', Structure, 2015, vol. 23, pp. 2076-2086.

Manbeck et al. Photoluminescent Copper(I) Complexes with Amido-Triazolato Ligands. Inorganic Chemistry 50(8):3431-3441 (2011).

Ouyang et al. Synthesis and structure-activity relationships of 1,2,4-triazoles as a novel class of potent tubulin polymerization inhibitors. Bioorg Med Chem Lett 15(23):5154-5159 (2005).

BENZOCARBONYL COMPOUNDS

CROSS-REFERENCE

This application is a § 371 U.S. National Stage Entry of International Application No. PCT/US2018/064104, filed Dec. 5, 2018, which claims benefit of U.S. Provisional Patent Application No. 62/595,197 filed on Dec. 6, 2017, which are incorporated herein by reference in their entirely.

BACKGROUND OF THE DISCLOSUBE

YAP and TAZ are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with transcriptional enhancer associate domain (TEAD) transcription factors and coactivate the expression of target genes and promote cell proliferation. Hyperactivation of YAP and TAZ and/or mutations in one or more members of the Hippo pathway network have been implicated in numerous cancers. Described herein are inhibitors associated with one or more members of the Hippo pathway network, such as inhibitors of YAP/TAZ or inhibitors that modulate the interaction between YAP/TAZ and TEAD.

SUMMARY OF THE DISCLOSUBE

Provided herein are benzocarbonyl compounds and pharmaceutical compositions comprising said compounds. In some embodiments, the subject compounds are useful for the treatment of cancer.

Provided in one aspect is a compound of Formula (I), or a pharmaceutically acceptable salt thereof:

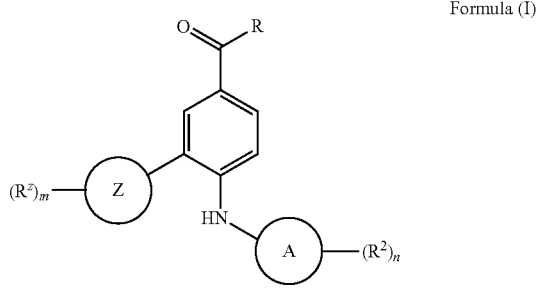

Formula (I)

wherein,

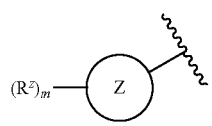

is a substituted or unsubstituted monocyclic 5-membered heterocyclic ring containing at least one N atom or a substituted or unsubstituted monocyclic 6-membered heteroaryl ring containing at least one N atom;

each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, -$L^1$-$Y^1$, or $L^2$-$L^3$-$Y^2$;

m is 0, 1, 2, 3, 4, or 5;

$L^1$ is substituted or unsubstituted $C_1$-$C_6$ alkylene, substituted or unsubstituted $C_2$-$C_{10}$ cycloalkylene, or substituted or unsubstituted $C_2$-$C_{20}$ heterocycloalkylene;

$Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

$L^2$ is absent, substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$ (C=O)—, —NR$^3$ (C=O)NR$^3$—, —O(C=O)NR$^3$—, —NR$^3$ (C=O)O—, —NR$^3$ (SO$_2$)NR$^3$—, —NR$^3$ (SO$_2$)—, —(SO$_2$)NR$^3$—, —(SO$_2$)NR$^3$—(C=O)—, —(C=O)—NR$^3$ (SO$_2$)—, —(SO$_2$)NR$^3$—(C=O)O—, —O(C=O)—NR$^3$ (SO$_2$)—, —NR$^3$ (SO$_2$)NR$^3$—(C=O)—, —(C=O)—NR$^3$ (SO$_2$)NR$^3$—, —O(C=O)—NR$^3$ (SO$_2$)—NR$^3$—, or —NR$^3$ (SO$_2$)NR$^3$—(C=O)O—;

each $R^3$ is independently H or substituted or unsubstituted $C_1$-$C_6$ alkyl;

$Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is —OR$^1$ or —N(R$^1$)$_2$;

each $R^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^1$ on the same N atom are taken together with the N atom to which they are attached to form a substituted or unsubstituted N-containing heterocycle;

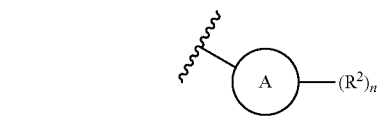

is substituted or unsubstituted phenyl or substituted or unsubstituted cyclohexyl;

each $R^2$ is independently H, —F, —I, —Cl, —N$_3$, —CN, —OR$^4$, —SR$^4$, —(SO$_2$)R$^4$, —N(R$^4$)$_2$, —CO$_2$R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or

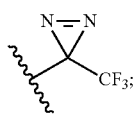

n is 0, 1, 2, 3, 4, or 5; and each $R^4$ is independently H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^4$ on the same N atom are taken together with the N atom to which they are attached to form a substituted or unsubstituted N-containing heterocycle.

In some embodiments,

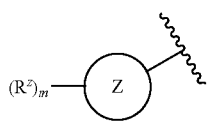

is a substituted or unsubstituted monocyclic 5-membered heterocyclic ring containing at least one N atom.

In some embodiments,

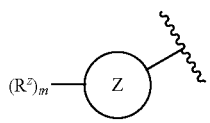

is a substituted or unsubstituted monocyclic 5-membered heterocyclic ring containing 1-4 N atoms, 0-2 O atoms, and 0-2 S atoms.

In some embodiments,

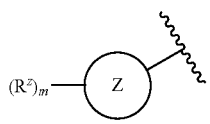

is

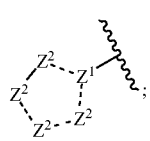

$Z^1$ is —N—, —CH—, or —C—;

each $Z^2$ is independently —$CR^z$—, —$CHR^z$—, —$C(R^z)_2$—, —$NR^z$—, —N—, —O—, or —S—;

each —— is independently a single or double bond; and with the provision that the 5-membered heterocyclic ring contains at least one N atom.

In some embodiments,

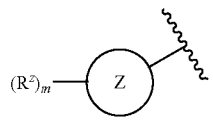

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

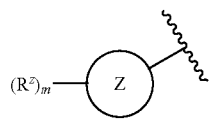

is

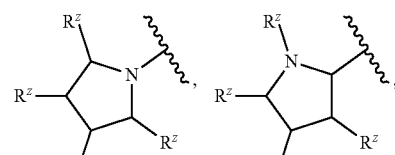
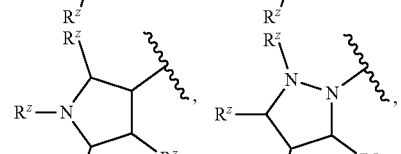
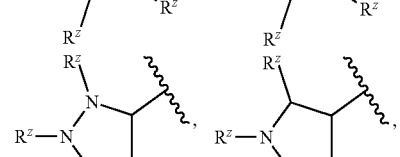
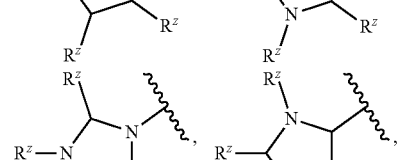
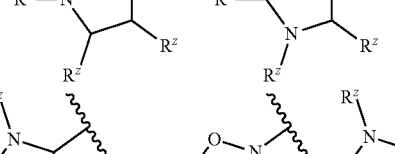
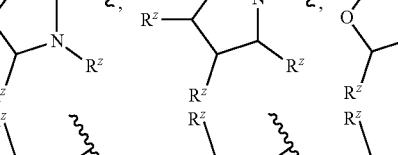
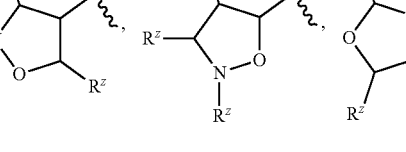

-continued

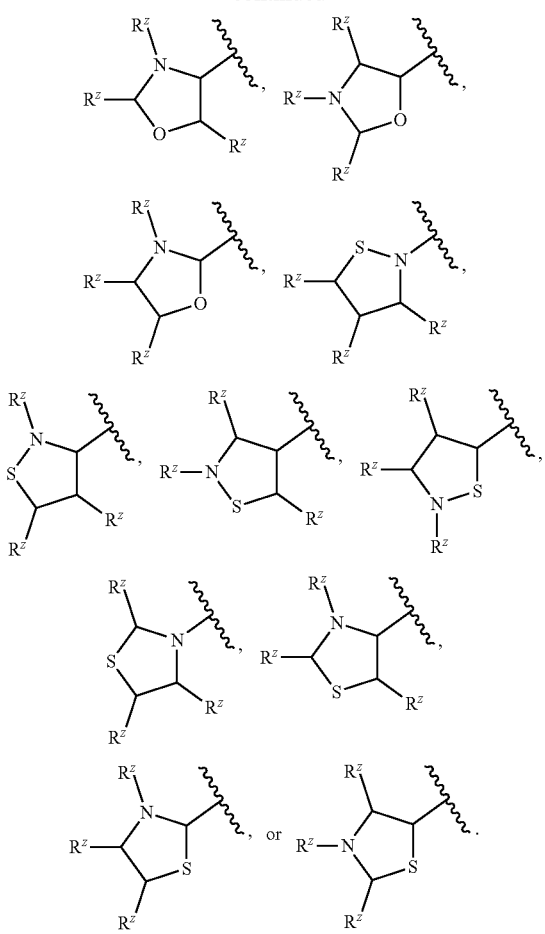

In some embodiments,

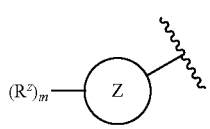

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

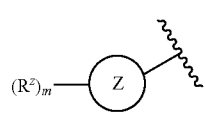

is

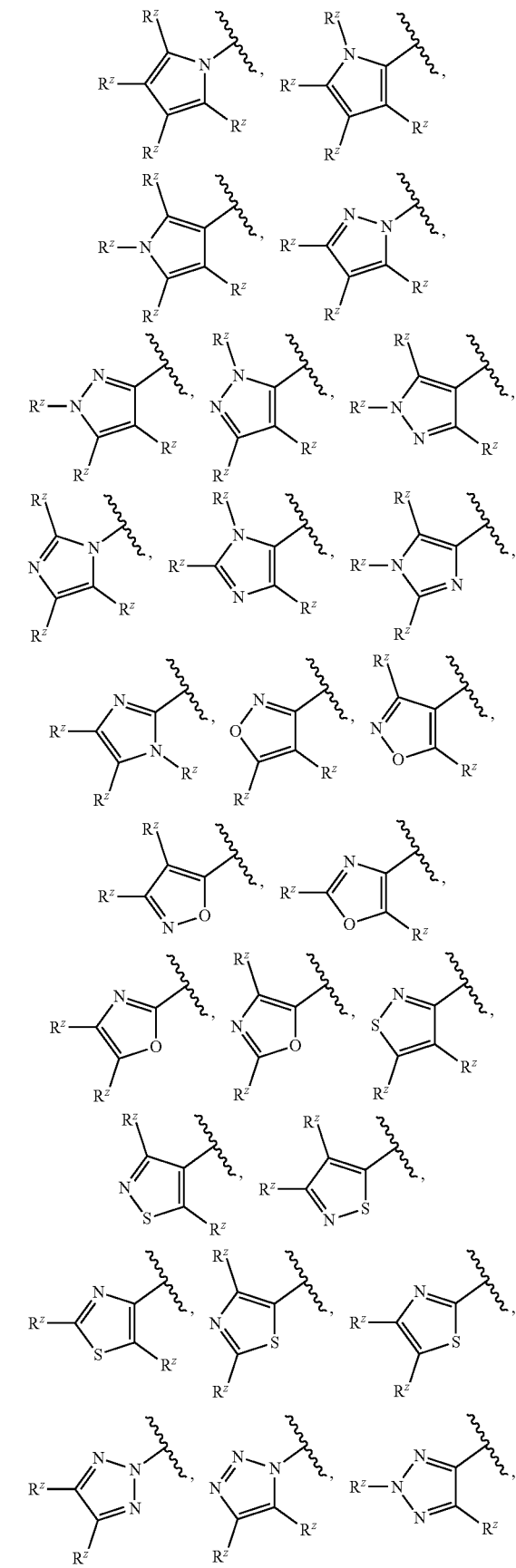

-continued

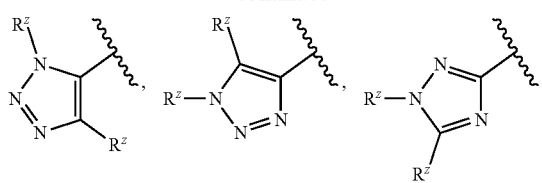

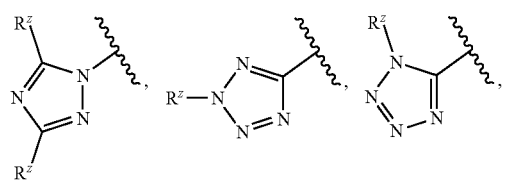

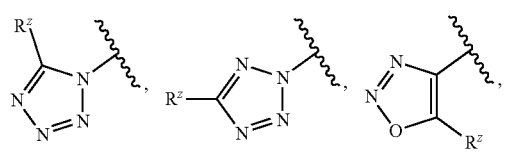

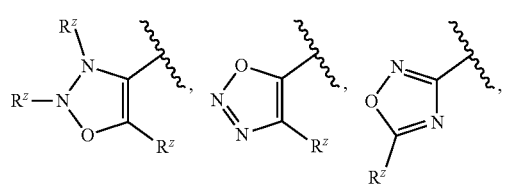

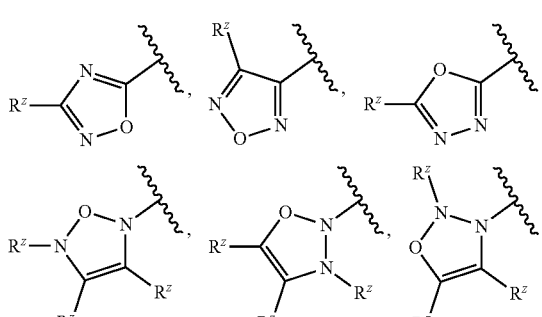

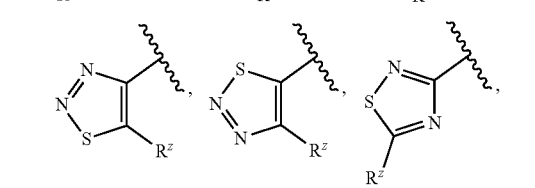

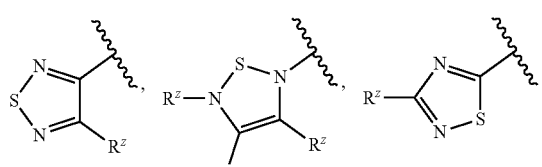

In some embodiments,

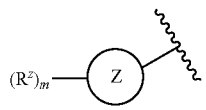

is a substituted or unsubstituted monocyclic 6-membered heteroaryl ring containing at least one N atom.

In some embodiments,

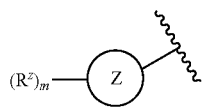

is a substituted or unsubstituted monocyclic 6-membered heteroaryl ring containing 1 or 2 N atoms.

In some embodiments,

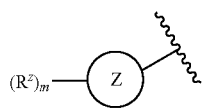

is

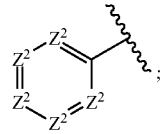

each $Z^2$ is independently $CR^z$ or N; and
at least one $Z^2$ is N.

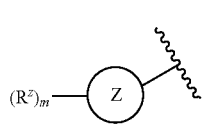

In some embodiments, is substituted or unsubstituted pyridinyl, substituted or unsubstituted pyrazinyl, substituted or unsubstituted pyrimidinyl, or substituted or unsubstituted pyridazinyl.

In some embodiments

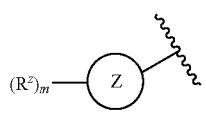

is

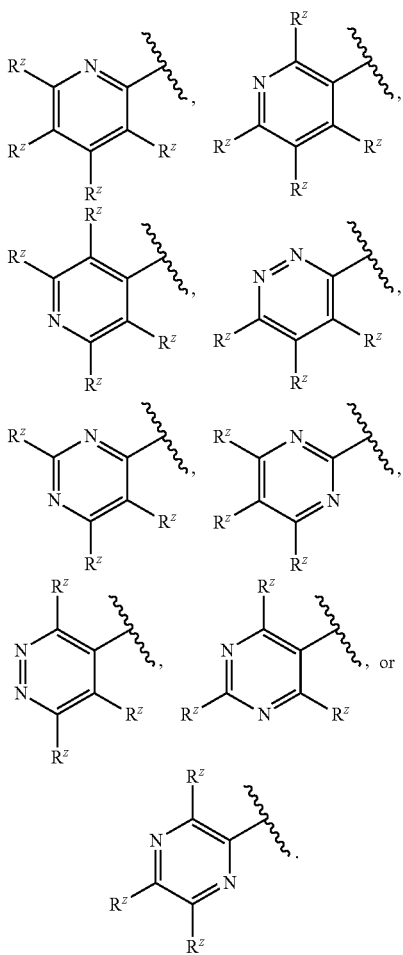

In some embodiments, the compound has the structure of Formula (Ia), or a pharmaceutically acceptable salt thereof:

Formula (Ia)

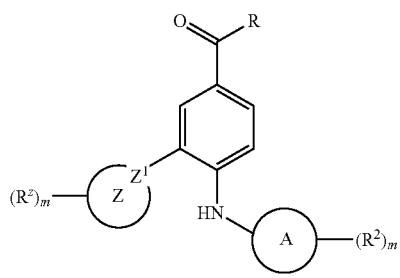

wherein:
$Z^1$ is —N—, —CH—, or —C—.
In some embodiments,

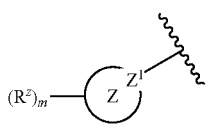

is a substituted or unsubstituted monocyclic 5-membered heterocyclic ring containing at least one N atom, and the at least one N atom is adjacent to $Z^1$.

In some embodiments,

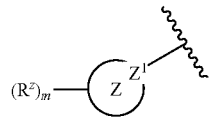

is

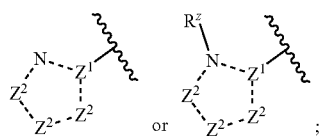

$Z^1$ is —N—, —CH—, or —C—;
each $Z^2$ is independently —CR$^z$, —CHR$^z$—, —C(R$^z$)$_2$—, —NR$^z$—, —N—, —O—, or —S—; and
each ——— is independently a single or double bond.

In some embodiments,

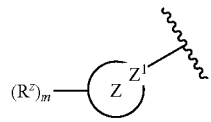

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

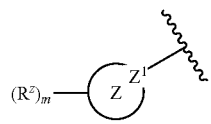

is

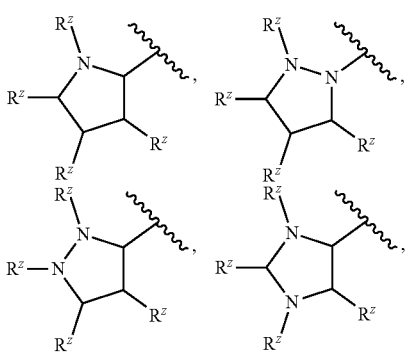

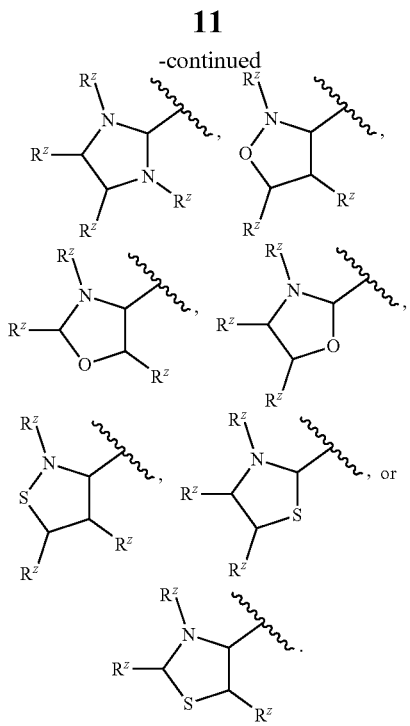

In some embodiments,

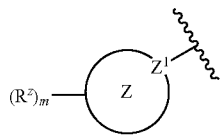

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

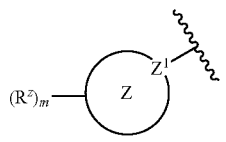

is

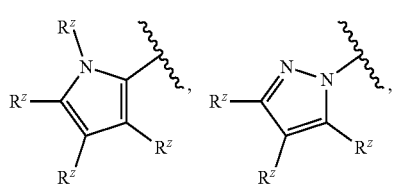

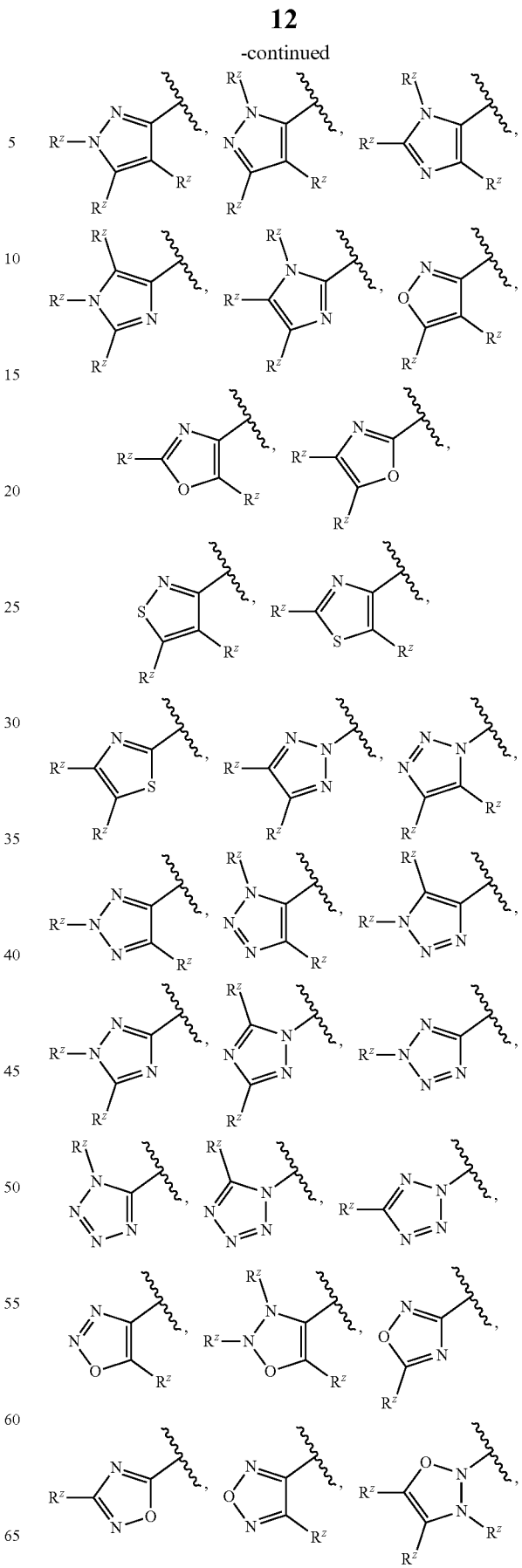

-continued

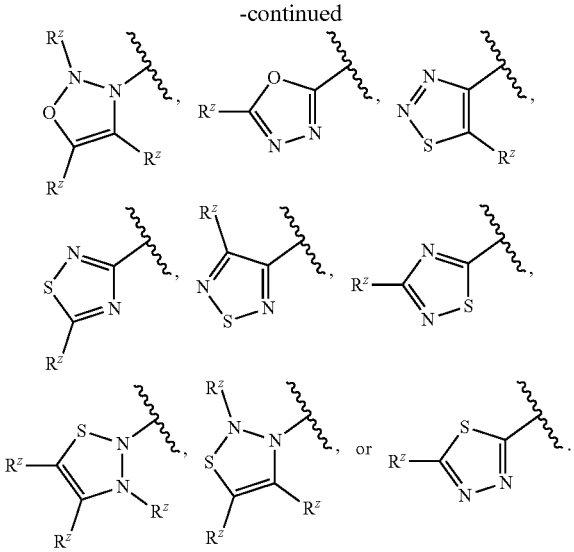

In some embodiments,

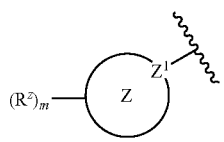

is a substituted or unsubstituted monocyclic 6-membered heteroaryl ring containing at least one N atom, and wherein the at least one N atom is adjacent to $Z^1$.

In some embodiments,

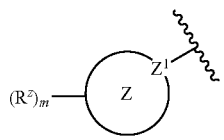

is

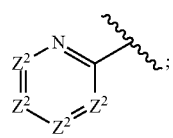

and each $Z^2$ is independently $CR^z$ or N.

In some embodiments,

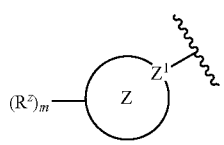

is substituted or unsubstituted pyridinyl, substituted or unsubstituted pyrazinyl, substituted or unsubstituted pyrimidinyl, or substituted or unsubstituted pyridazinyl.

In some embodiments,

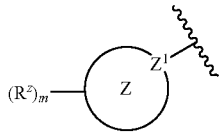

is

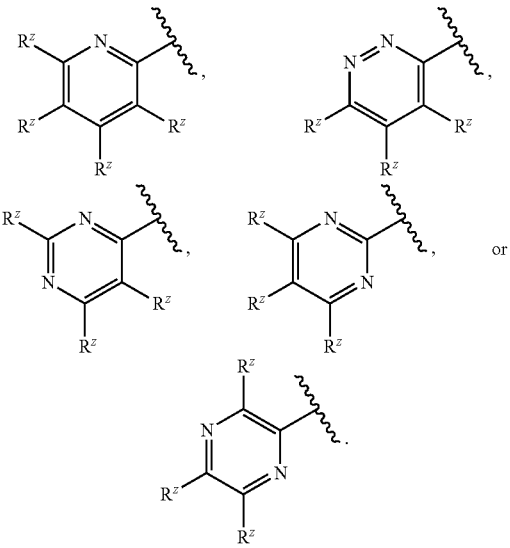

In some embodiments, each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, each $R^z$ is independently H, halogen, substituted or unsubstituted $C_1$-$C_6$ alkyl, substituted or unsubstituted $C_1$-$C_6$ haloalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, $L^1$ is substituted or unsubstituted $C_1$-$C_4$ alkylene; and $Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is -$L^2$-$L^3$-$Y^2$. In some embodiments, $L^2$ is substituted or unsubstituted $C_1$-$C_6$ alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$ (C=O)—, —NR$^3$ (C=O)NR$^3$—, —O(C=O)NR$^3$—, —NR$^3$ (C=O) O—, —NR$^3$ (SO$_2$)NR$^3$—, —NR$^3$ (SO$_2$)—, —(SO$_2$)NR$^3$—, —(SO$_2$)NR$^3$—(C=O)—, —(SO$_2$)NR$^3$—(C=O)O—, —NR³ (SO₂)NR³—(C=O)—, or —NR³ (SO₂)NR³—(C=O)O—; each R³ is independently H or substituted or unsubstituted C₁-C₆ alkyl; and Y² is H, substituted or unsubstituted C₁-C₆ alkyl, substituted or unsubstituted C₁-C₆ haloalkyl, substituted or unsubstituted C₁-C₆ heteroalkyl, substituted or unsubstituted C₃-C₁₀ cycloalkyl, substituted or unsubstituted C₂-C₁₀ heterocycloalkyl, substituted or unsubstituted aryl, or substituted or unsubstituted heteroaryl.

In some embodiments, L² is absent; L³ is —O—, —S—, —(S=O)—, —(SO₂)—, —NR³—, —(C=O)—, —(C=O)O—, —O(C=O)—, —(C=O)NR³—, —(C=O)NR³—O—, —NR³ (C=O)—, —NR³ (C=O)NR³—, —O(C=O)NR³—, —NR³ (C=O)O—, —NR³ (SO₂)NR³—, —NR³ (SO₂)—, —(SO₂)NR³—, —(SO₂)NR³—(C=O)—, —(SO₂)NR³—(C=O)O—, —NR³ (SO₂)NR³—(C=O)—, or —NR³ (SO₂)NR³—(C=O)O—; each R³ is independently H or substituted or unsubstituted C₁-C₆ alkyl; and Y² is H, substituted or unsubstituted C₁-C₆ alkyl, substituted or unsubstituted C₁-C₆ haloalkyl, substituted or unsubstituted C₁-C₆ heteroalkyl, substituted or unsubstituted C₃-C₁₀ cycloalkyl, substituted or unsubstituted C₂-C₁₀ heterocycloalkyl, substituted or unsubstituted aryl, or substituted or unsubstituted heteroaryl.

In some embodiments, R is —OR¹; and R¹ is H, substituted or unsubstituted C₁-C₆ alkyl, substituted or unsubstituted C₁-C₆ haloalkyl, substituted or unsubstituted C₁-C₆ heteroalkyl, substituted or unsubstituted C₃-C₁₀ cycloalkyl, substituted or unsubstituted C₂-C₁₀ heterocycloalkyl, substituted or unsubstituted aralkyl, substituted or unsubstituted aryl, or substituted or unsubstituted heteroaryl. In some embodiments, R¹ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is —N(R¹)₂; and each R¹ is independently H, —(SO₂)R⁴, substituted or unsubstituted C₁-C₆ alkyl, substituted or unsubstituted C₁-C₆ haloalkyl, substituted or unsubstituted C₁-C₆ heteroalkyl, substituted or unsubstituted C₃-C₁₀ cycloalkyl, substituted or unsubstituted C₂-C₁₀ heterocycloalkyl, substituted or unsubstituted aralkyl, substituted or unsubstituted aryl, or substituted or unsubstituted heteroaryl; or two R¹ on the same N atom are taken together with the N atom to which they are attached to form a substituted or unsubstituted N-containing heterocycle. In some embodiments, R¹ is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

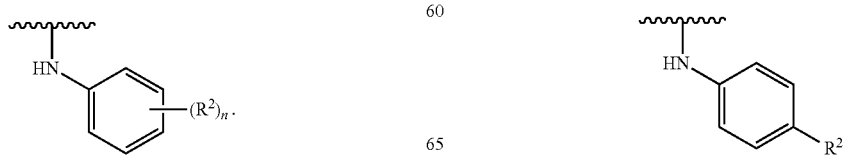

is

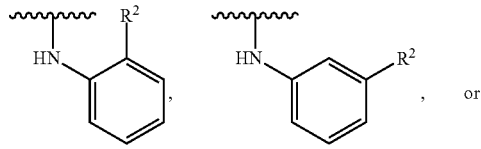

In some embodiments, the compound has the structure of Formula (Ib), or a pharmaceutically acceptable salt thereof:

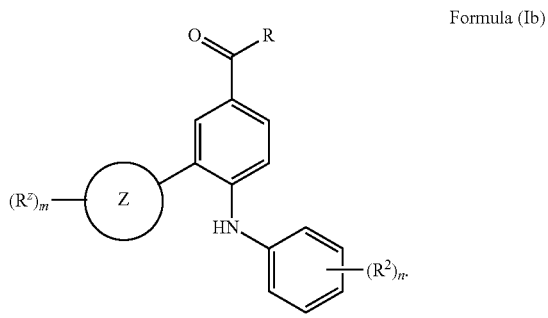

Formula (Ib)

In some embodiments

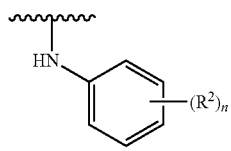

is

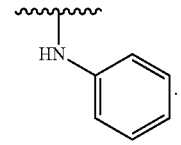

In some embodiments,

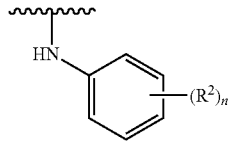

is

In some embodiments,
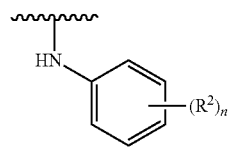
is
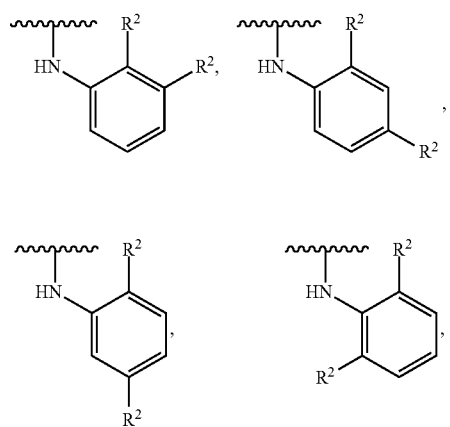
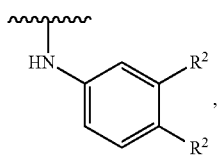 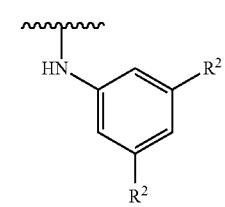, or 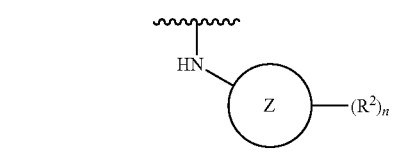.
In some embodiments,
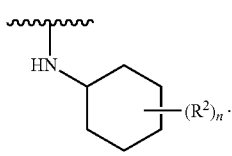
is
In some embodiments, the compound has the structure of Formula (Ic), or a pharmaceutically acceptable salt thereof:
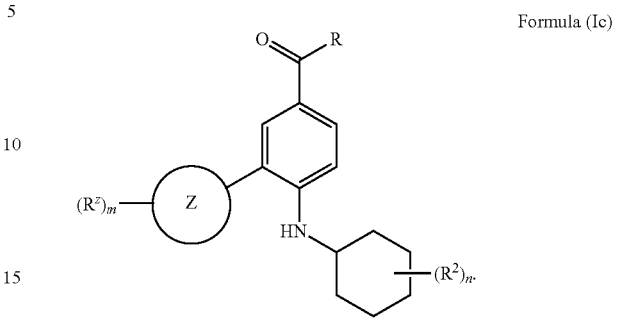
Formula (Ic)
In some embodiments,
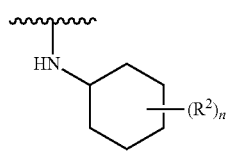
is
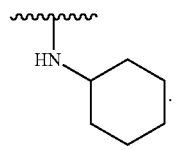 [SMILES: *NC1CCCCC1].
In some embodiments,
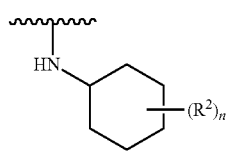
is
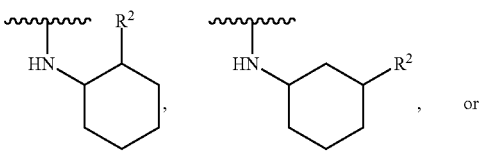, or
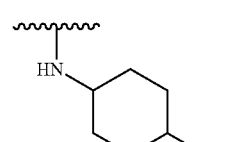.

In some embodiments,

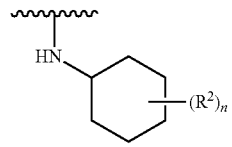

is

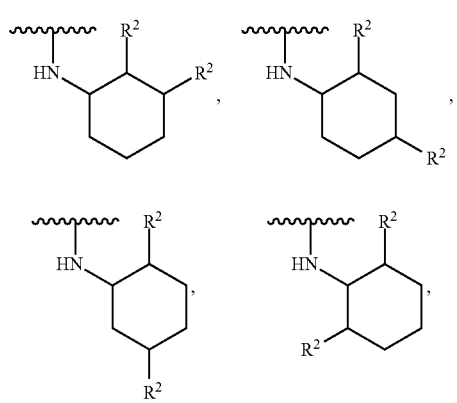

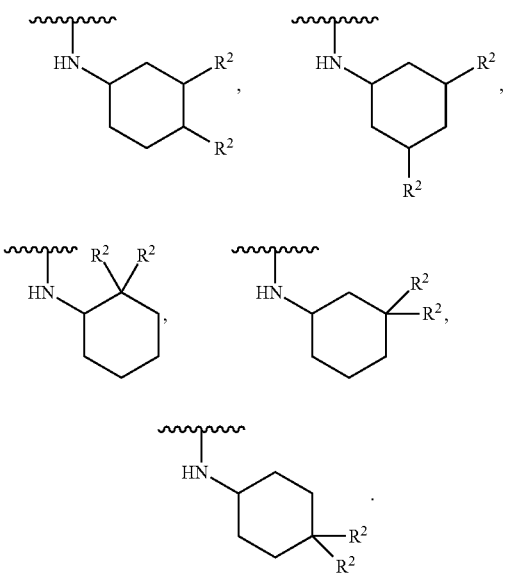

In some embodiments, each R² is independently H, —F, —I, —Cl, —N₃, —CN, —OR⁴, —SR⁴, —(SO₂)R⁴, —N(R⁴)₂, —CO₂R⁴, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, or substituted or unsubstituted aryl.

In some embodiments, the compound has the structure of Formula (Id), or a pharmaceutically acceptable salt thereof:

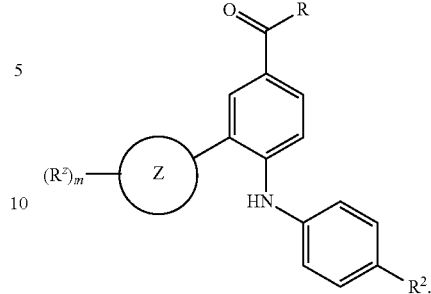

Formula (Id)

In some embodiments, the compound has the structure of Formula (Ie), or a pharmaceutically acceptable salt thereof:

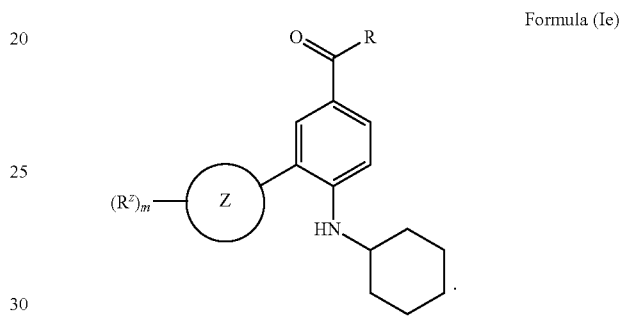

Formula (Ie)

Provided in another aspect is a compound of Formula (II), or a pharmaceutically acceptable salt thereof:

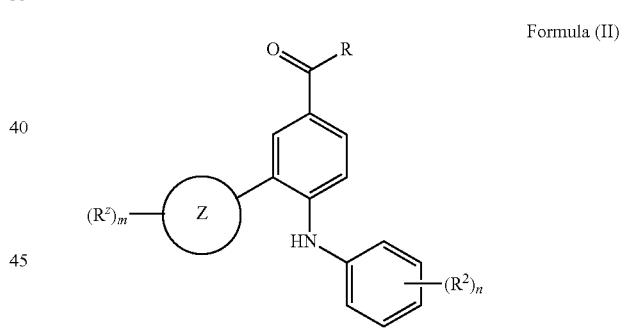

Formula (II)

wherein, is a substituted or unsubstituted monocyclic 5-membered heterocyclic ring containing at least one N atom or a substituted or unsubstituted monocyclic 6-membered heteroaryl ring containing at least one N atom;

each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, -L$^1$-Y$^1$, or -L$^2$-L$^3$-Y$^2$;

m is 0, 1, 2, 3, 4, or 5;

L$^1$ is substituted or unsubstituted C$_1$-C$_6$ alkylene, substituted or unsubstituted C$_2$-C$_{10}$ cycloalkylene, or substituted or unsubstituted C$_2$-C$_{10}$ heterocycloalkylene;

Y$^1$ is substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl;

L$^2$ is absent, substituted or unsubstituted C$_1$-C$_6$ alkylene, substituted or unsubstituted C$_2$-C$_{10}$ cycloalkylene, or substituted or unsubstituted C$_2$-C$_{10}$ heterocycloalkylene;

L$^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;

each R$^3$ is independently H or substituted or unsubstituted C$_1$-C$_6$ alkyl;

Y$^2$ is H, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl;

or R$^3$ and Y$^2$ on the same N atom are taken together with the N atom to which they are attached to form a substituted or unsubstituted N-containing heterocycle;

R is —OR$^1$ or —N(R$^1$)$_2$;

each R$^1$ is independently H, —(SO$_2$)R$^4$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_{10}$ cycloalkyl, substituted or unsubstituted C$_2$-C$_{10}$ heterocycloalkyl, substituted or unsubstituted aralkyl, substituted or unsubstituted aryl, or substituted or unsubstituted heteroaryl;

or two R$^1$ on the same N atom are taken together with the N atom to which they are attached to form a substituted or unsubstituted N-containing heterocycle;

each R$^2$ is independently H, —F, —I, —Cl, N$_3$, —CN, —OR$^4$, —SR$^4$, —(SO$_2$)R$^4$, —N(R$^4$)$_2$, —CO$_2$R$^4$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_{10}$ cycloalkyl, substituted or unsubstituted C$_2$-C$_{10}$ heterocycloalkyl, substituted or unsubstituted aralkyl, substituted or unsubstituted aryl, or

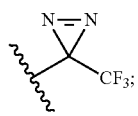

n is 0, 1, 2, 3, 4, or 5; and each R$^4$ is independently H, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_{10}$ cycloalkyl, substituted or unsubstituted C$_2$-C$_{10}$ heterocycloalkyl, substituted or unsubstituted aralkyl, substituted or unsubstituted aryl, or substituted or unsubstituted heteroaryl;

or two R$^4$ on the same N atom are taken together with the N atom to which they are attached to form a substituted or unsubstituted N-containing heterocycle.

In some embodiments,

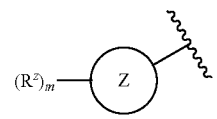

is a substituted or unsubstituted monocyclic 5-membered heterocyclic ring containing at least one N atom.

In some embodiments,

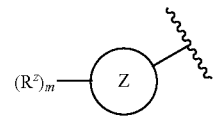

is a substituted or unsubstituted monocyclic 5-membered heterocyclic ring containing 1-4 N atoms, 0-2 O atoms, and 0-2 S atoms.

In some embodiments,

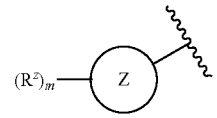

is

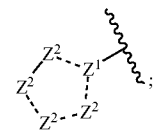

Z$^1$ is —N—, —CH—, or —C—;

each Z$^2$ is independently —CR$^z$—, —CHR$^z$—, —C(R$^z$)$_2$—, —NR$^z$—, —N—, —O—, or —S—;

each —— is independently a single or double bond; and with the provision that the 5-membered heterocyclic ring contains at least one N atom.

In some embodiments,

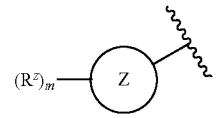

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazo lidinyl, substituted or unsubstituted thiazolidinyl, or substituted or unsubstituted isothiazolidinyl.

In some embodiments,

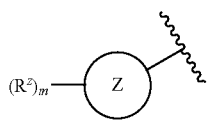

is

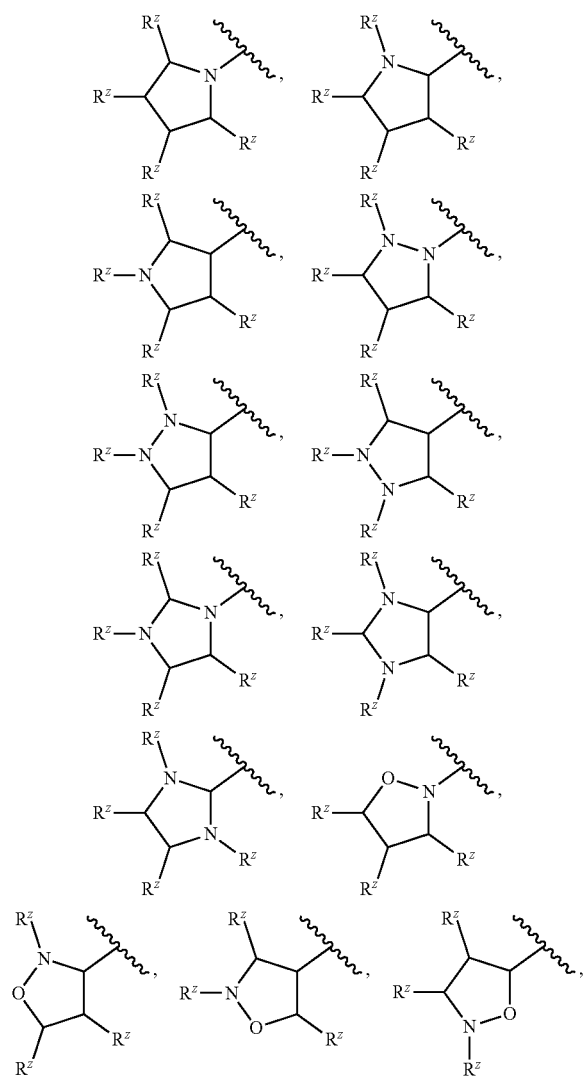

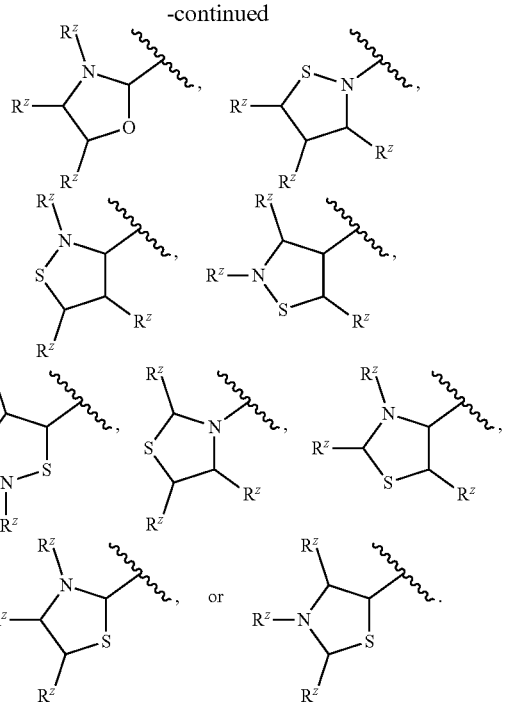

In some embodiments,

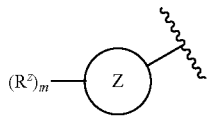

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

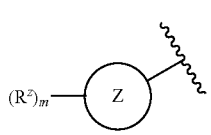

is

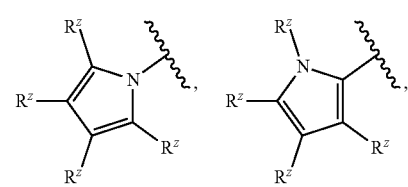

-continued
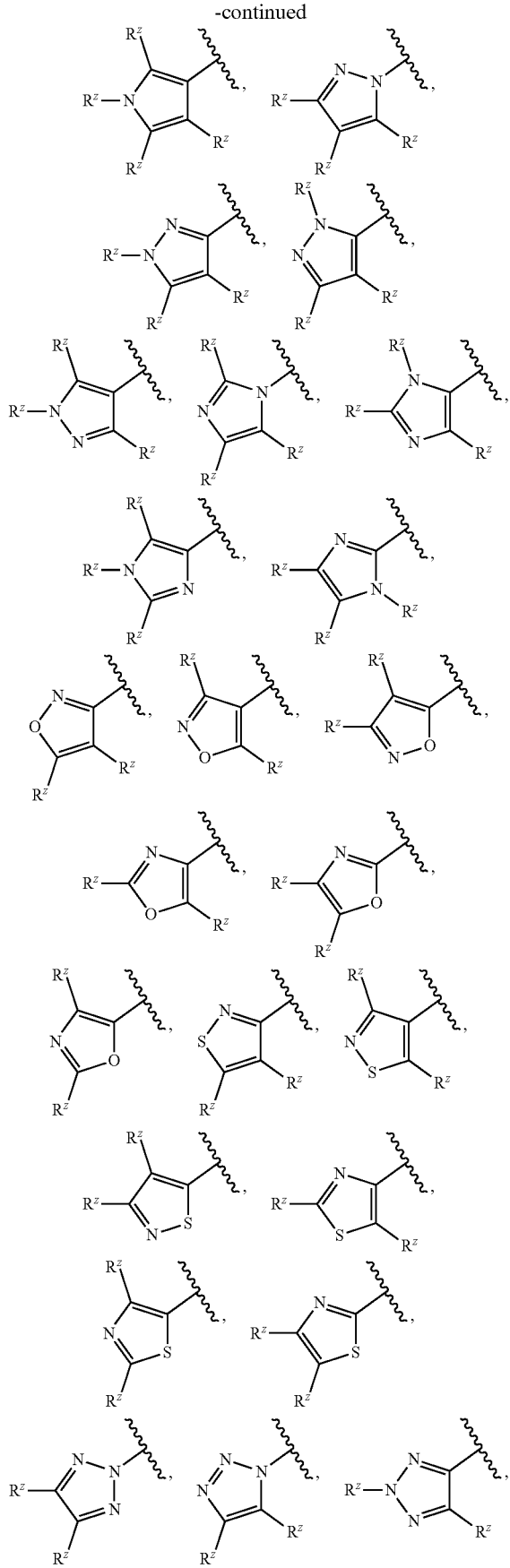
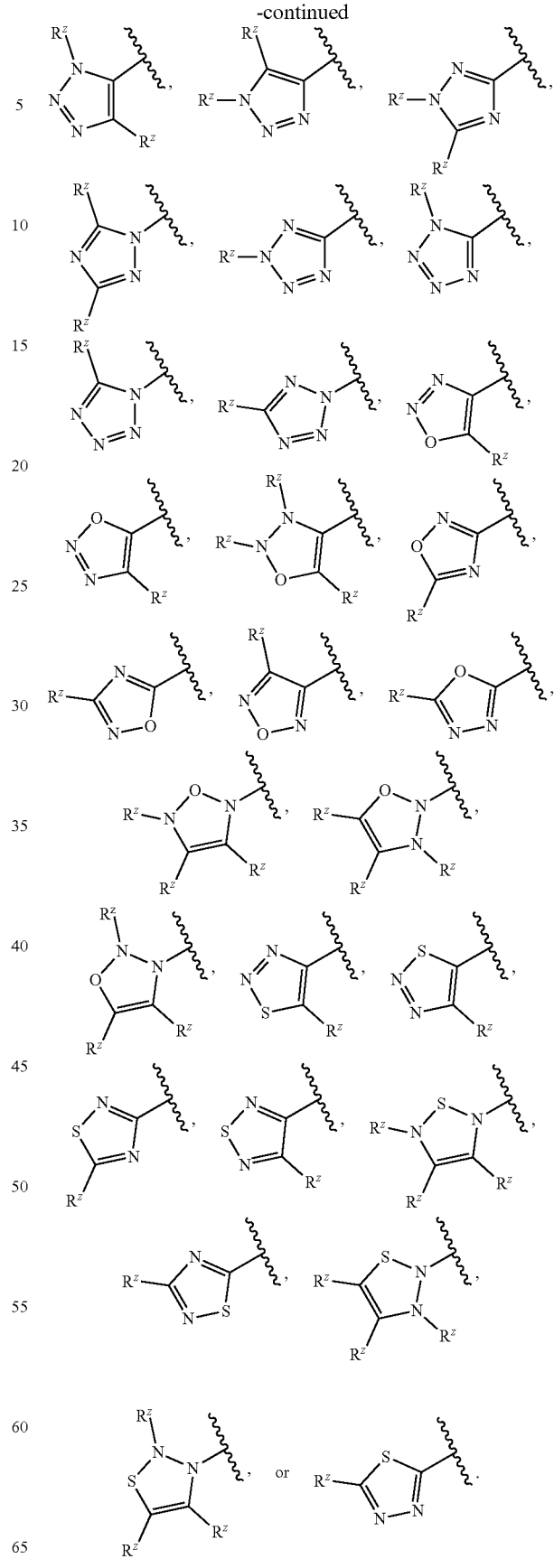

In some embodiments,

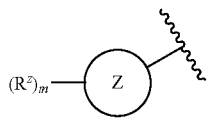

is a substituted or unsubstituted monocyclic 6-membered heteroaryl ring containing at least one N atom.

In some embodiments,

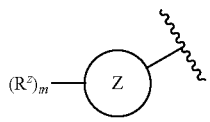

is a substituted or unsubstituted monocyclic 6-membered heteroaryl ring containing 1 or 2 N atoms.

In some embodiments,

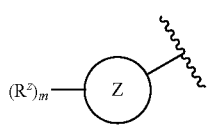

is

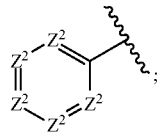

each $Z^2$ is independently CR or N; and
at least one $Z^2$ is N.

In some embodiments,

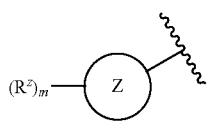

is substituted or unsubstituted pyridinyl, substituted or unsubstituted pyrazinyl, substituted or unsubstituted pyrimidinyl, or substituted or unsubstituted pyridazinyl.

In some embodiments,

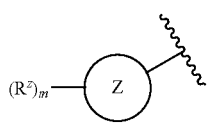

is

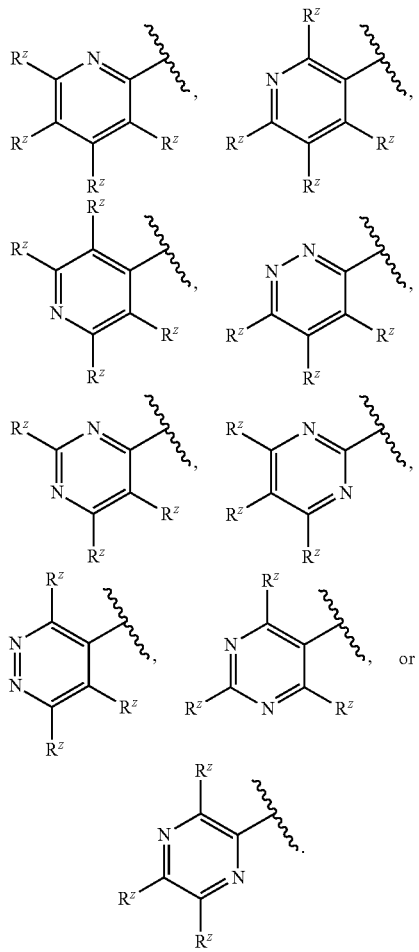

In some embodiments, the compound has the structure of Formula (IIa), or a pharmaceutically acceptable salt thereof:

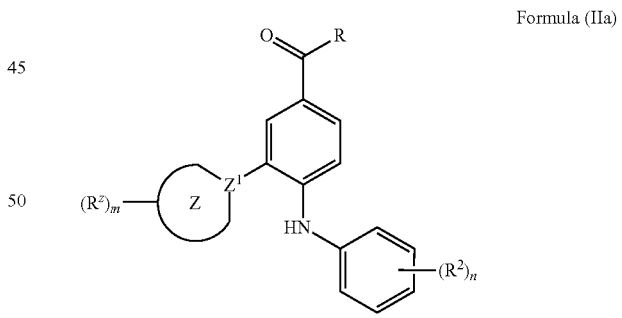

Formula (IIa)

wherein:
$Z^1$ is —N—, —CH—, or —C—.

In some embodiments,

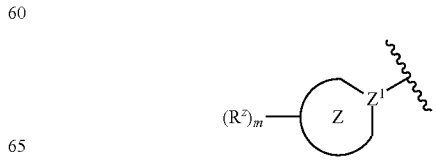

is a substituted or unsubstituted monocyclic 5-membered heterocyclic ring containing at least one N atom, and the at least one N atom is adjacent to Z.

In some embodiments,

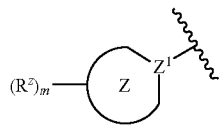

is

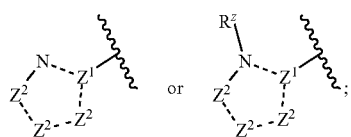

$Z^1$ is —N—, —CH—, or —C—;
each $Z^2$ is independently —CR$^z$—, —CHR$^z$—, —C(R$^z$)$_2$—, —NR$^z$—, —N—, —O—, or —S—; and
each —— is independently a single or double bond.

In some embodiments,

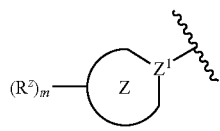

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

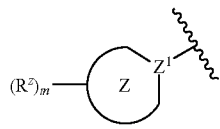

is

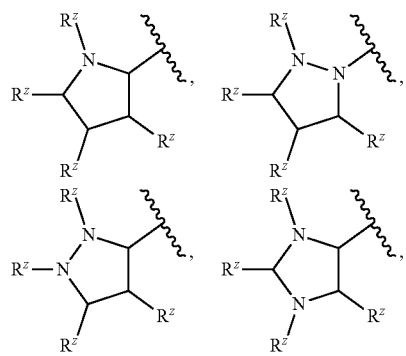

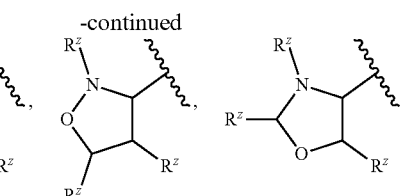

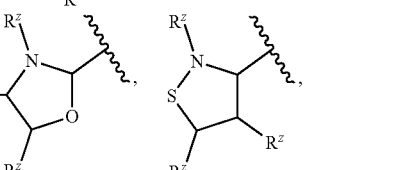

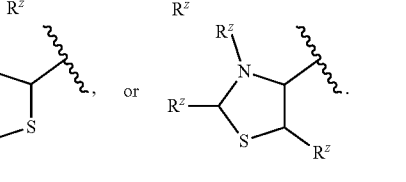

In some embodiments,

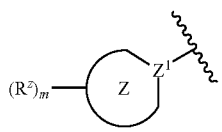

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

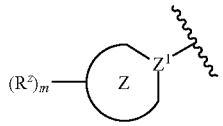

is

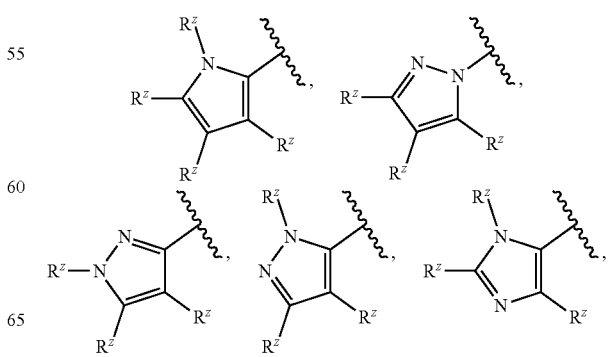

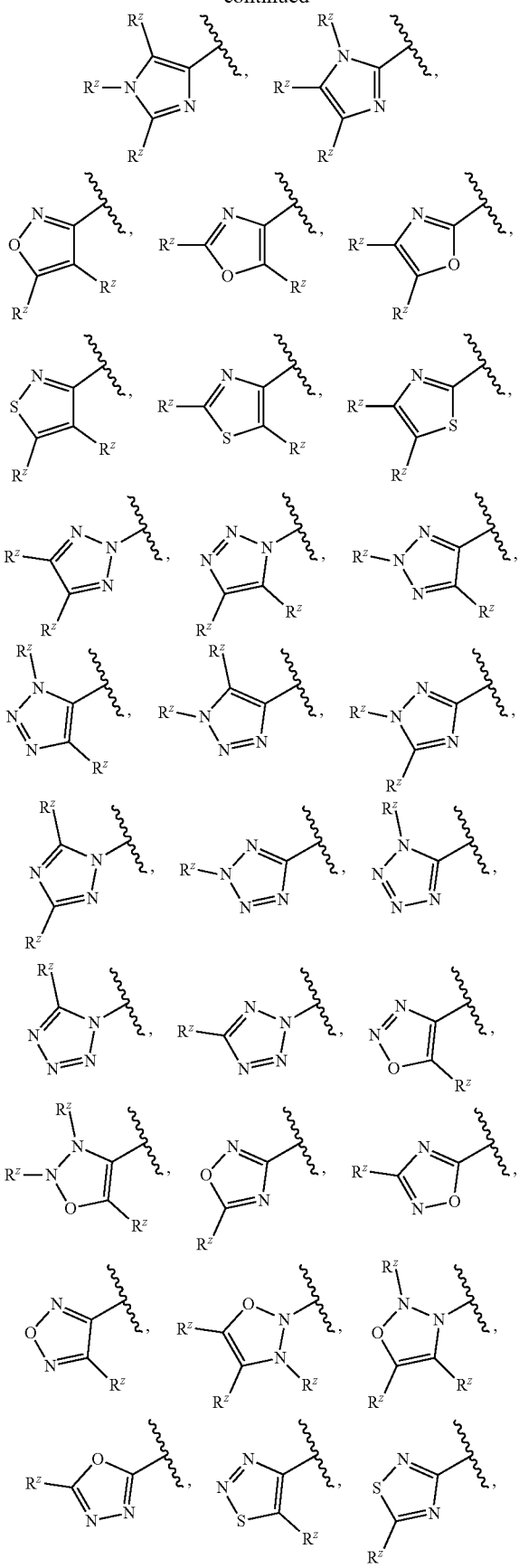

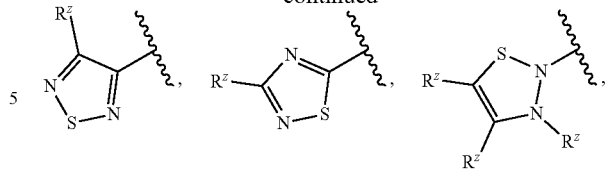

In some embodiments,

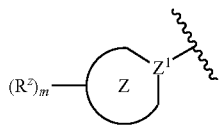

is a substituted or unsubstituted monocyclic 6-membered heteroaryl ring containing at least one N atom, and wherein the at least one N atom is adjacent to $Z^1$.

In some embodiments,

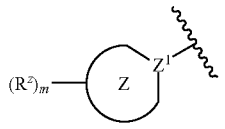

is

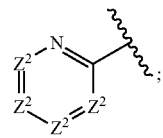

and each $Z^2$ is independently $CR^z$ or N.

In some embodiments,

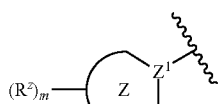

is substituted or unsubstituted pyridinyl, substituted or unsubstituted pyrazinyl, substituted or unsubstituted pyrimidinyl, or substituted or unsubstituted pyridazinyl.

In some embodiments,

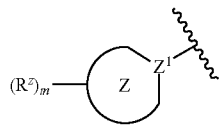

is

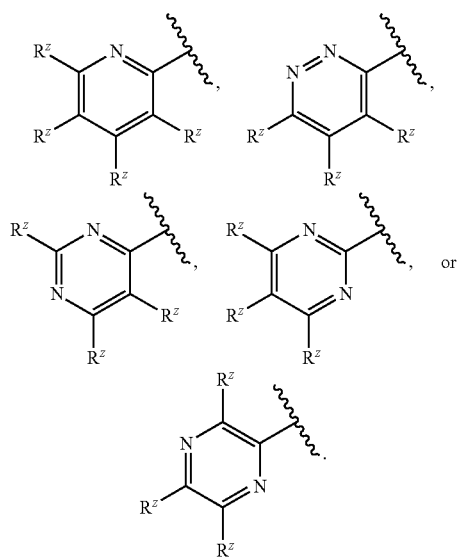

In some embodiments, each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, each $R^z$ is independently H, halogen, substituted or unsubstituted $C_1$-$C_6$ alkyl, substituted or unsubstituted $C_1$-$C_6$ haloalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, $L^1$ is substituted or unsubstituted $C_1$-$C_6$ alkylene; and $Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is -$L^2$-$L^3$-$Y^2$. In some embodiments, $L^2$ is substituted or unsubstituted $C_1$-$C_6$ alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$ (C=O)—, —NR$^3$ (C=O)NR$^3$—, —O(C=O)NR$^3$—, —NR$^3$ (C=O)O—, —NR$^3$ (SO$_2$)—, —NR$^3$ (SO$_2$)—, —(SO$_2$)NR$^3$—, —(SO$_2$)NR$^3$—(C=O)—, —(SO$_2$)NR$^3$—(C=O)O—, —NR$^3$ (SO$_2$)NR$^3$—(C=O)—, or —NR$^3$ (SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, $L^2$ is absent; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$ (C=O)—, —NR$^3$ (C=O)NR$^3$—, —O(C=O)NR$^3$—, —NR$^3$ (C=O)O—, —NR$^3$ (SO$_2$)NR$^3$—, —NR$^3$ (SO$_2$)—, —(SO$_2$)NR$^3$—, —(SO$_2$)NR$^3$—(C=O)—, —(SO$_2$)NR$^3$—(C=O)O—, —NR$^3$ (SO$_2$)NR$^3$—(C=O)—, or —NR$^3$ (SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, R is —OR$^1$; and R$^1$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl. In some embodiments, R$^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is —N(R$^1$)$_2$; and each R$^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl; or two R$^1$ on the same N atom are taken together with the N atom to which they are attached to form a substituted or unsubstituted N-containing heterocycle. In some embodiments, R$^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

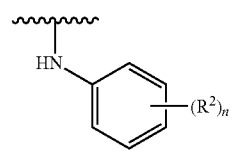

is

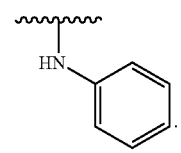 [SMILES: *Nc1ccccc1]

In some embodiments,

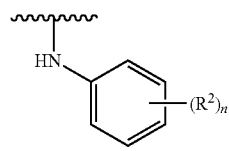

is

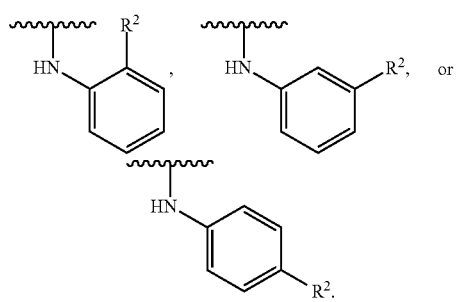

In some embodiments,

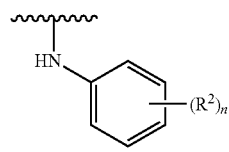

is

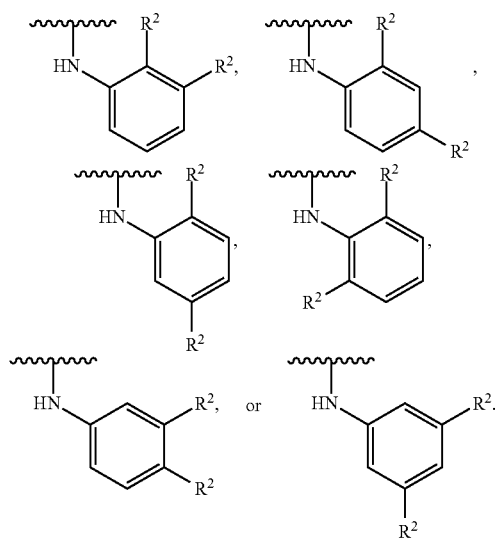

In some embodiments, each $R^2$ is independently H, —F, —I, —Cl, —N$_3$, —CN, —OR$^4$, —SR$^4$, —(SO$_2$)R$^4$, —N(R$^4$)$_2$, —CO$_2$R$^4$, substituted or unsubstituted C$_1$-C$_6$ alkyl, substituted or unsubstituted C$_1$-C$_6$ haloalkyl, substituted or un substituted C$_1$-C$_6$ heteroalkyl, substituted or unsubstituted C$_3$-C$_{10}$ cycloalkyl, substituted or unsubstituted C$_2$-C$_{10}$ heterocycloalkyl, substituted or unsubstituted aralkyl, or substituted or unsubstituted aryl.

In some embodiments, the compound has the structure of Formula (IIb), or a pharmaceutically acceptable salt thereof:

Formula (IIb)

Provided in another aspect is a compound of Formula (III), or a pharmaceutically acceptable salt thereof:

Formula (III)

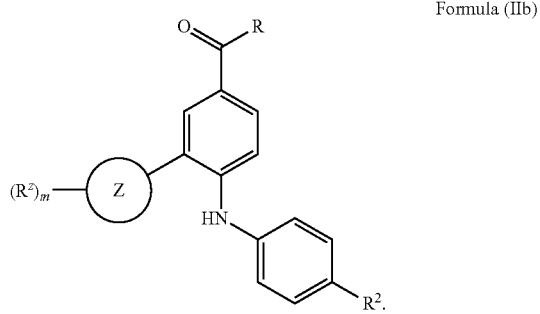

wherein, is a substituted or unsubstituted monocyclic 5-membered heterocyclic ring containing at least one N atom or a substituted or unsubstituted monocyclic 6-membered heteroaryl ring containing at least one N atom;
  each $R^z$ is independently H, halogen, —CN, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_{10}$ cycloalkyl, substituted or unsubstituted C$_2$-C$_{10}$ heterocycloalkyl, substituted or unsubstituted aralkyl, substituted or unsubstituted aryl, substituted or unsubstituted heteroaryl, -L$^1$-Y$^1$, or -L$^2$-L$^3$-Y$^2$;
  m is 0, 1, 2, 3, 4, or 5;
  L$^1$ is substituted or unsubstituted C$_1$-C$_6$ alkylene, substituted or unsubstituted C$_2$-C$_{10}$ cycloalkylene, or substituted or unsubstituted C$_2$-C$_{10}$ heterocycloalkylene;
  Y$^1$ is substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl;
  L$^2$ is absent, substituted or unsubstituted C$_1$-C$_6$ alkylene, substituted or unsubstituted C$_2$-C$_{10}$ cycloalkylene, or substituted or unsubstituted C$_2$-C$_{10}$ heterocycloalkylene;

$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$ (C=O)—, —NR$^3$ (C=O)—, —NR$^3$ (C=O)NR$^3$—, —O(C=O)NR$^3$—, —NR$^3$ (C=O)O—, —NR$^3$ (SO$_2$) NR$^3$—, —NR$^3$ (SO$_2$)—, —(SO$_2$)NR$^3$—, —(SO$_2$) NR$^3$—(C=O)—, —(C=O)—NR$^3$ (SO$_2$)—, —(SO$_2$) NR$^3$—(C=O)O—, —O(C=O)—NR$^3$ (SO$_2$)—, —NR$^3$ (SO$_2$)NR$^3$—(C=O)—, —(C=O)—NR$^3$ (SO$_2$) NR$^3$—, —O(C=O)—NR$^3$ (SO$_2$)—NR$^3$—, or —NR$^3$ (SO$_2$)NR$^3$—(C=O)O—;

each $R^3$ is independently H or substituted or unsubstituted $C_1$-$C_6$ alkyl;

$Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is —OR$^1$ or —N(R$^1$)$_2$;

each $R^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^1$ on the same N atom are taken together with the N atom to which they are attached to form a substituted or unsubstituted N-containing heterocycle;

each $R^2$ is independently H, halogen, —N$_3$, —CN, —OR$^4$, —SR$^4$, —(SO$_2$)R$^4$, —N(R$^4$)$_2$, —CO$_2$R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, or

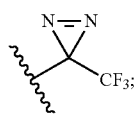

n is 0, 1, 2, 3, 4, or 5; and each $R^4$ is independently H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^4$ on the same N atom are taken together with the N atom to which they are attached to form a substituted or unsubstituted N-containing heterocycle.

In some embodiments,

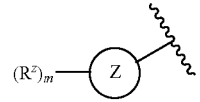

is a substituted or unsubstituted monocyclic 5-membered heterocyclic ring containing at least one N atom.

In some embodiments,

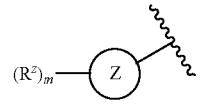

is a substituted or unsubstituted monocyclic 5-membered heterocyclic ring containing 1-4 N atoms, 0-2 O atoms, and 0-2 S atoms.

In some embodiments,

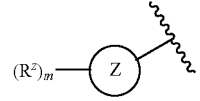

is

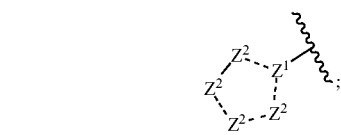

$Z^1$ is —N—, —CH—, or —C—;
each $Z^2$ is independently —CR$^z$—, —CHR$^z$—, —C(R$^z$)$_2$—, —NR$^z$—, —N—, —O—, or —S—;
each —— is independently a single or double bond; and
with the provision that the 5-membered heterocyclic ring contains at least one N.

In some embodiments,

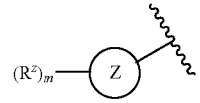

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

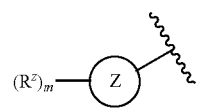

is

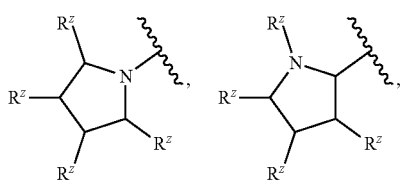
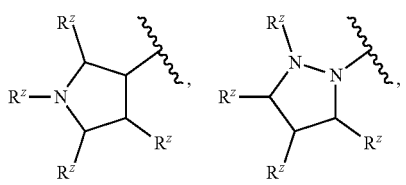
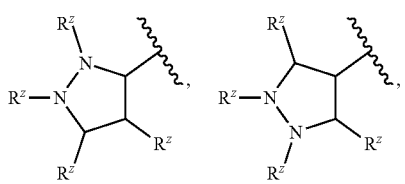
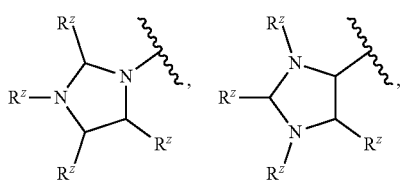
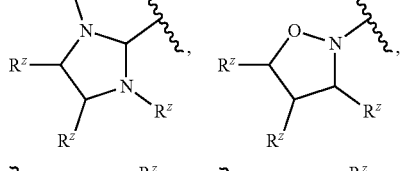
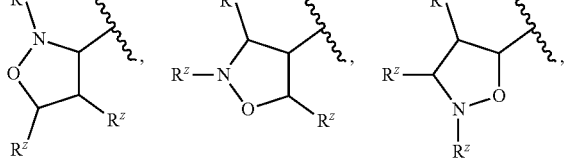
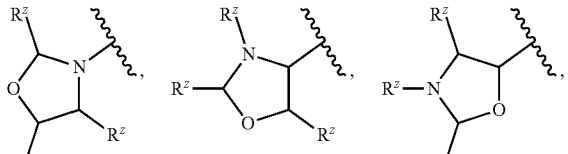
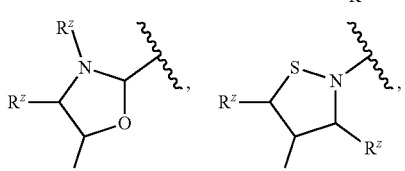
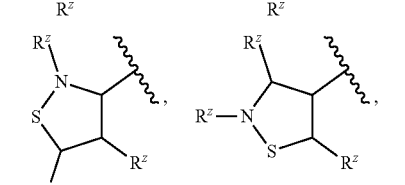

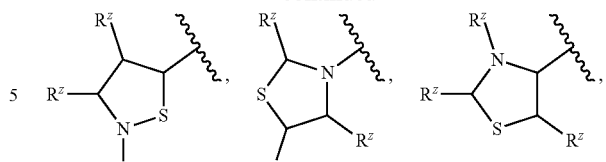

-continued

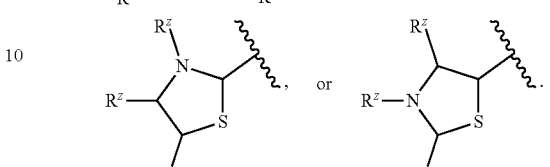

In some embodiments,

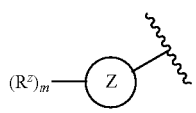

is substituted or unsubstituted pyrrolyl, substituted or unsubstituted imidazolyl, substituted or un substituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

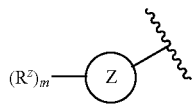

is

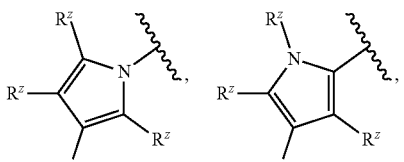
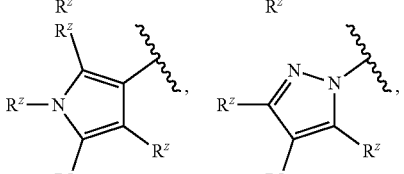
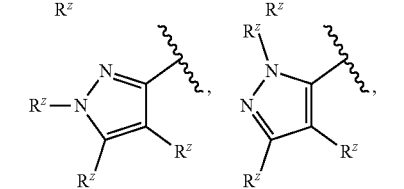

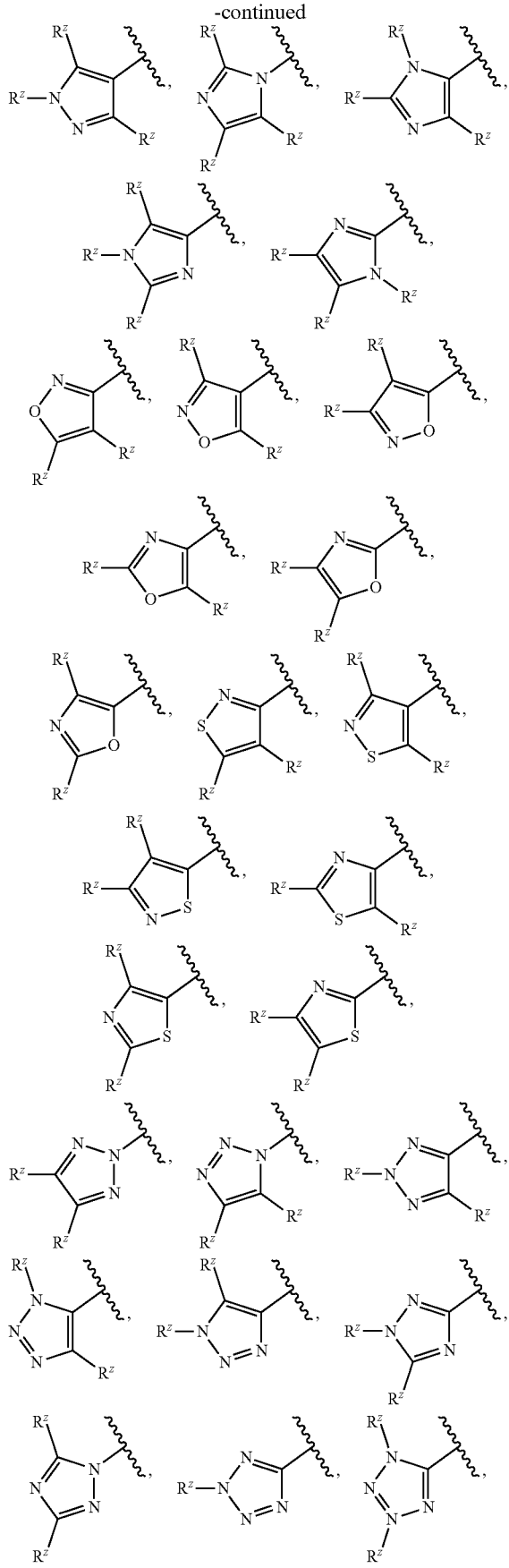
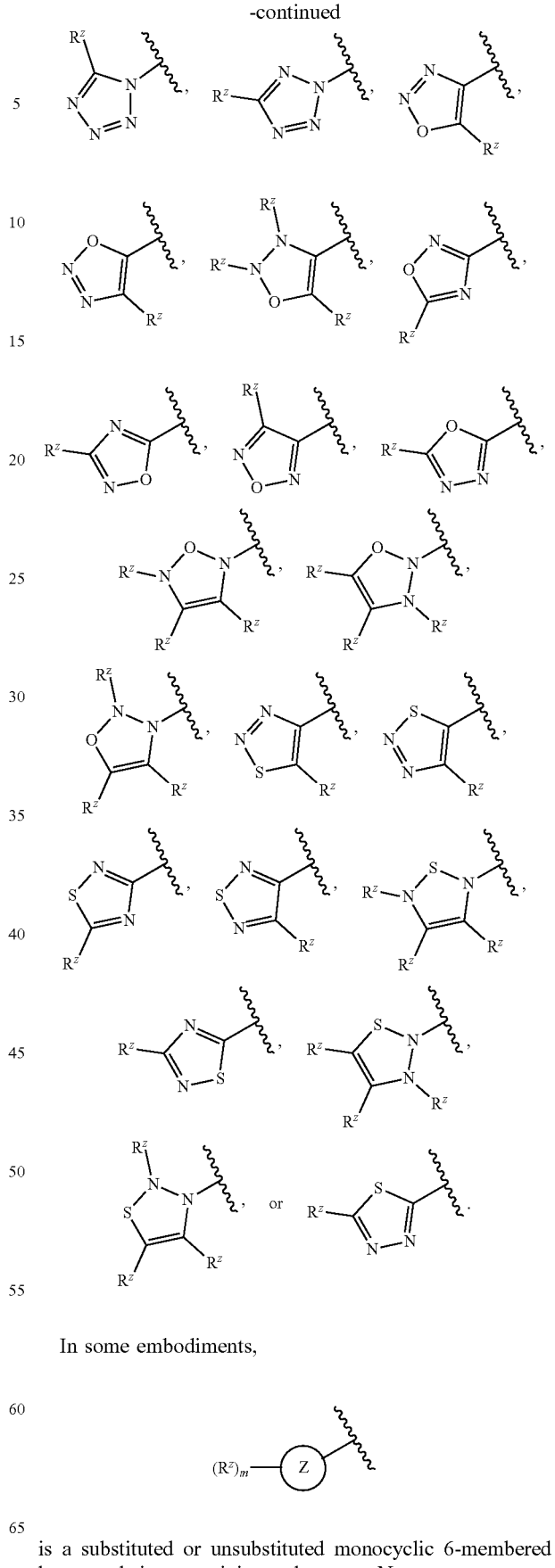
In some embodiments,
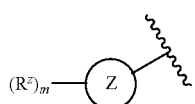
is a substituted or unsubstituted monocyclic 6-membered heteroaryl ring containing at least one N atom.

In some embodiments,

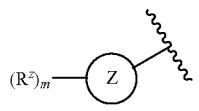

is a substituted or unsubstituted monocyclic 6-membered heteroaryl ring containing 1 or 2 N atoms.

In some embodiments,

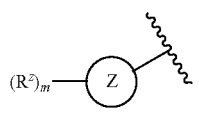

is

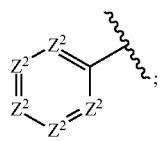

each $Z^2$ is independently $CR^z$ or N; and
at least one $Z^2$ is N.

In some embodiments,

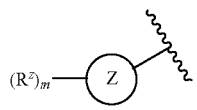

is substituted or unsubstituted pyridinyl, substituted or unsubstituted pyrazinyl, substituted or unsubstituted pyrimidinyl, or substituted or unsubstituted pyridazinyl.

In some embodiments,

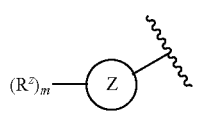

is

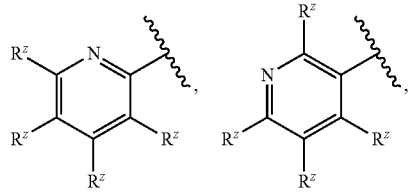

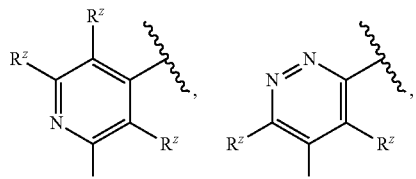

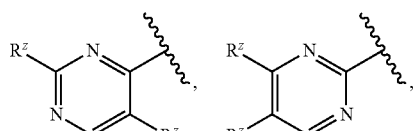

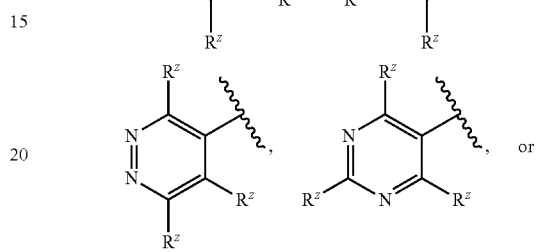

In some embodiments, the compound has the structure of Formula (IIIa), or a pharmaceutically acceptable salt thereof:

Formula (IIIa)

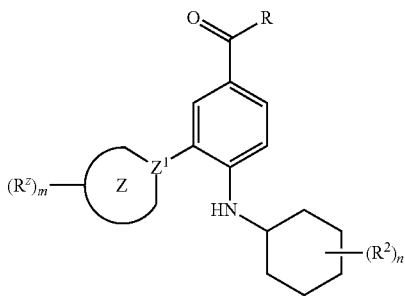

wherein:
$Z^1$ is —N—, —CH—, or —C—.

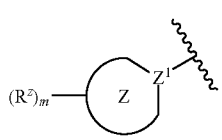

In some embodiments, is a substituted or unsubstituted monocyclic 5-membered heterocyclic ring containing at least one N atom, and the at least one N atom is adjacent to $Z^1$.

In some embodiments,

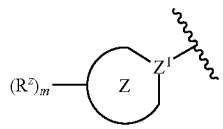

is

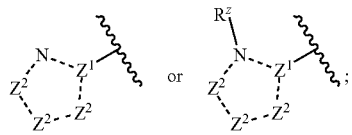

$Z^1$ is —N—, —CH—, or —C—;
each $Z^2$ is independently —$CR^z$—, —$CHR^z$—, —$C(R^z)_2$—, —$NR^z$—, —N—, —O—, or —S—; and
each —— is independently a single or double bond.

In some embodiments,

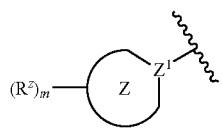

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

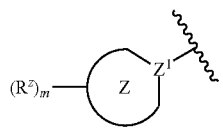

is

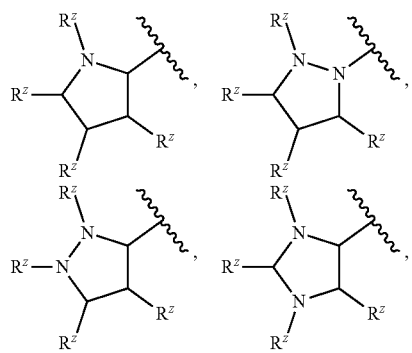

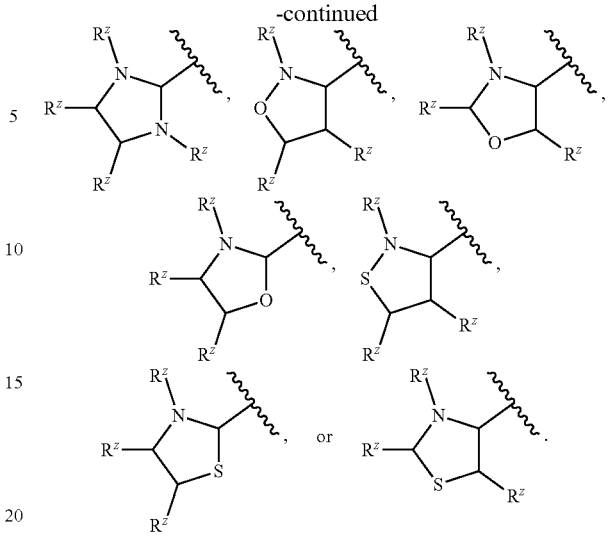

In some embodiments,

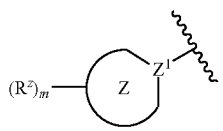

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

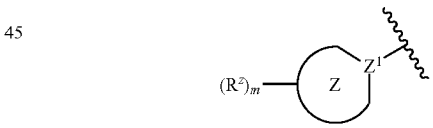

is

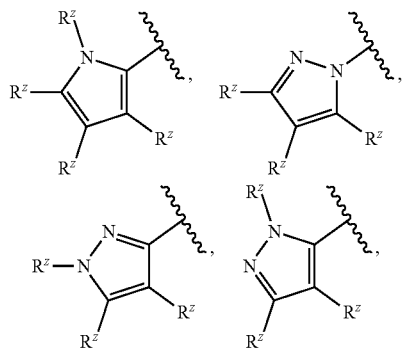

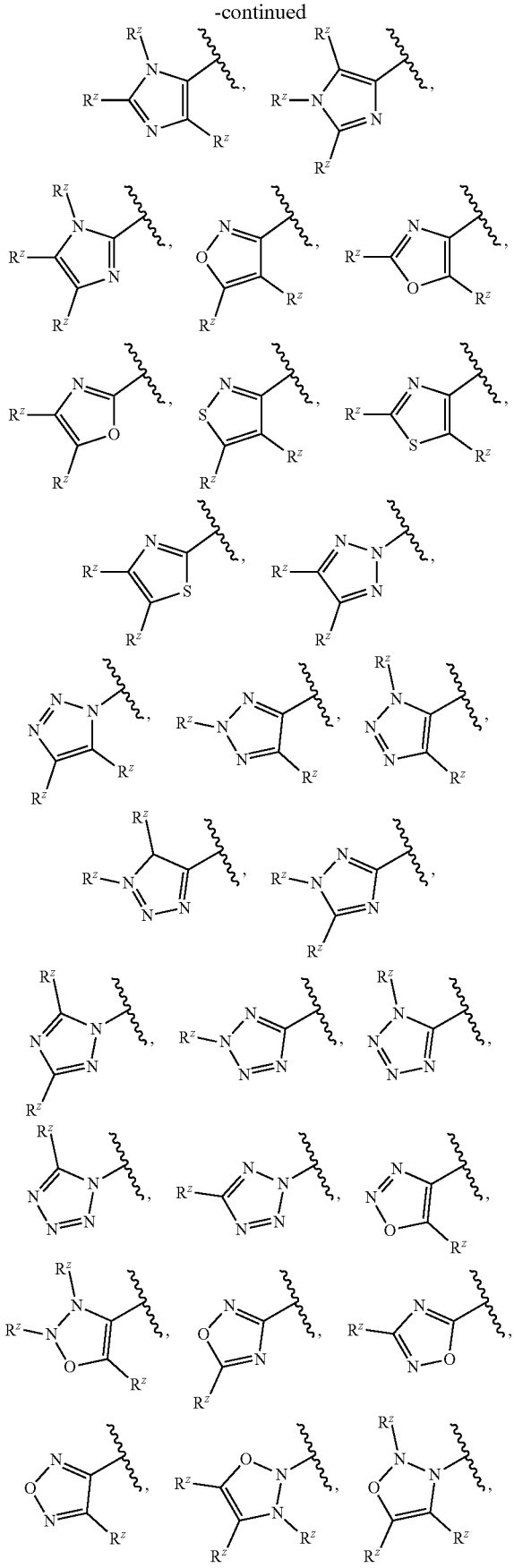

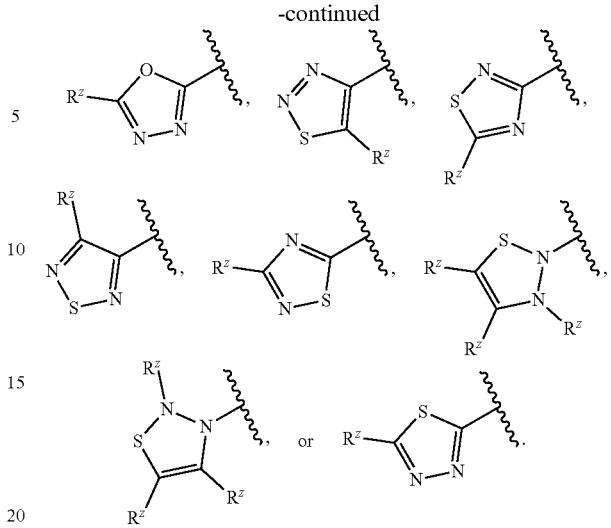

In some embodiments,

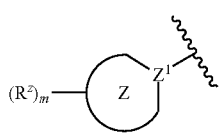

is a substituted or unsubstituted monocyclic 6-membered heteroaryl ring containing at least one N atom, and wherein the at least one N atom is adjacent to $Z^1$.

In some embodiments,

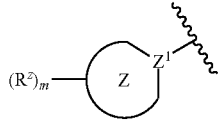

is

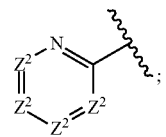

and each $Z^2$ is independently $CR^z$ or N.

In some embodiments,

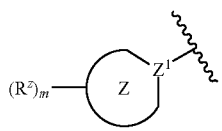

is substituted or unsubstituted pyridinyl, substituted or unsubstituted pyrazinyl, substituted or unsubstituted pyrimidinyl, or substituted or unsubstituted pyridazinyl.

In some embodiments,

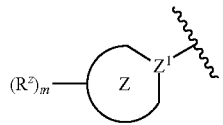

is

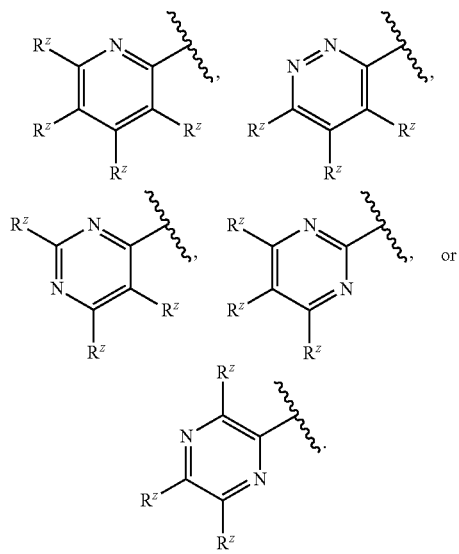

In some embodiments, each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, each $R^z$ is independently H, halogen, substituted or unsubstituted $C_1$-$C_6$ alkyl, substituted or unsubstituted $C_1$-$C_6$ haloalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, $L^1$ is substituted or unsubstituted $C_1$-$C_4$ alkylene; and $Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is -$L^2$-$L^3$-$Y^2$. In some embodiments, $L^2$ is substituted or unsubstituted $C_1$-$C_6$ alkylene; $L^3$ is —O—, —S—, —(S═O)—, —(SO$_2$)—, —NR$^3$—, —(C═O)—, —(C═O)O—, —O(C═O)—, —(C═O)NR$^3$—, —(C═O)NR$^3$—O—, —NR$^3$ (C═O)—, —NR$^3$ (C═O)NR$^3$—, —O(C═O)NR$^3$—, —NR$^3$ (C═O)O—, —NR$^3$ (SO$_2$)NR$^3$—, —NR$^3$ (SO$_2$)—, —(SO$_2$)NR$^3$—, —(SO$_2$)NR$^3$—(C═O)—, —(SO$_2$)NR$^3$—(C═O)O—, —NR$^3$ (SO$_2$)NR$^3$, —(C═O)—, or —NR$^3$ (SO$_2$)NR$^3$—(C═O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, $L^2$ is absent; $L^3$ is —O—, —S—, —(S═O)—, —(SO$_2$)—, —NR$^3$—, —(C═O)—, —(C═O)O—, —O(C═O)—, —(C═O)NR$^3$—, —(C═O)NR$^3$—O—, —NR$^3$ (C═O)—, —NR$^3$ (C═O)NR$^3$—, —O(C═O)NR$^3$—, —NR$^3$ (C═O)O—, —NR$^3$ (SO$_2$)NR$^3$—, —NR$^3$ (SO$_2$)—, —(SO$_2$)NR$^3$—, —(SO$_2$)NR$^3$—(C═O)—, —(SO$_2$)NR$^3$—(C═O)O—, —NR$^3$ (SO$_2$)NR$^3$—(C═O)—, or —NR$^3$ (SO$_2$)NR$^3$—(C═O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, R is —OR$^1$; and $R^1$ is H, substituted or unsubstituted $C_1$-$C_6$ alkyl, substituted or unsubstituted $C_3$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is —N($R^1$)$_2$; and each $R^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl; or two $R^1$ on the same N atom are taken together with the N atom to which they are attached to form a substituted or unsubstituted N-containing heterocycle. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

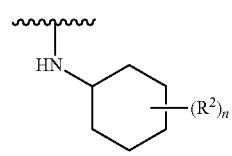

is

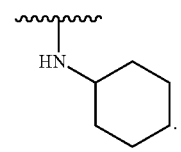 [SMILES: *NC1CCCCC1]

In some embodiments,

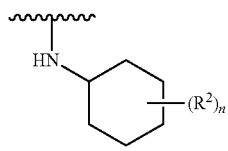

is

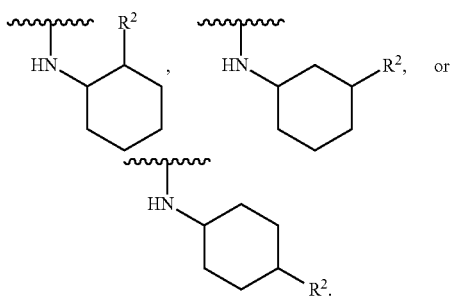

In some embodiments,

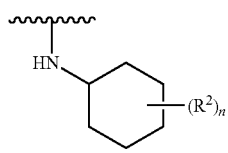

is

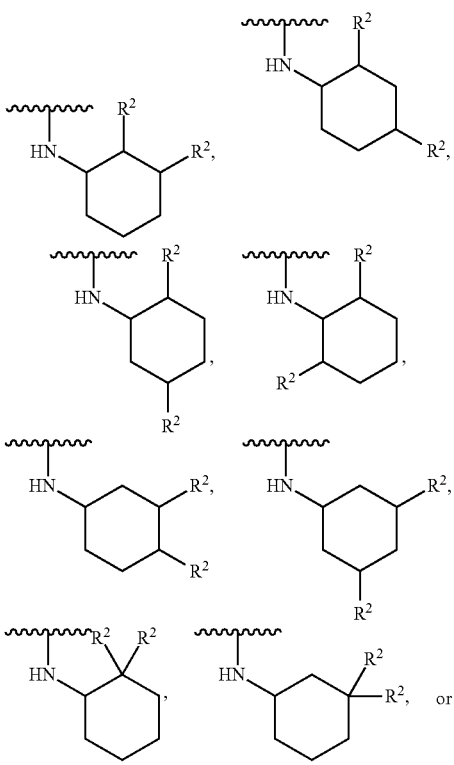

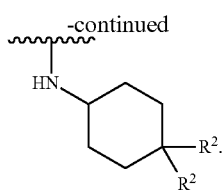

In some embodiments, each $R^2$ is independently H, halogen, —$N_3$, —CN, —$OR^4$, —$SR^4$, —$(SO_2)R^4$, —$N(R^4)_2$, —$CO_2R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, the compound has the structure of Formula (IIIb), or a pharmaceutically acceptable salt thereof:

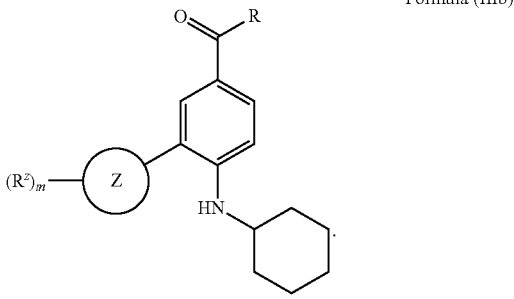

Formula (IIIb)

In some embodiments, the compound exhibits an $IC_{50}$ of no more than about 3.000 µM.

Provided in another aspect is a compound, or pharmaceutically acceptable salt thereof, wherein the compound is a compound from Table 1, or a pharmaceutically acceptable salt thereof.

Provided in another aspect is a pharmaceutical composition comprising a pharmaceutically acceptable excipient and any one of the compounds disclosed herein or a pharmaceutically acceptable salt thereof.

Provided herein is a method for treating a cancer in a subject in need thereof comprising administering a therapeutically effective amount of a compound of any one of the compounds disclosed herein, or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSUBE

Certain Terminology

Figure 1:
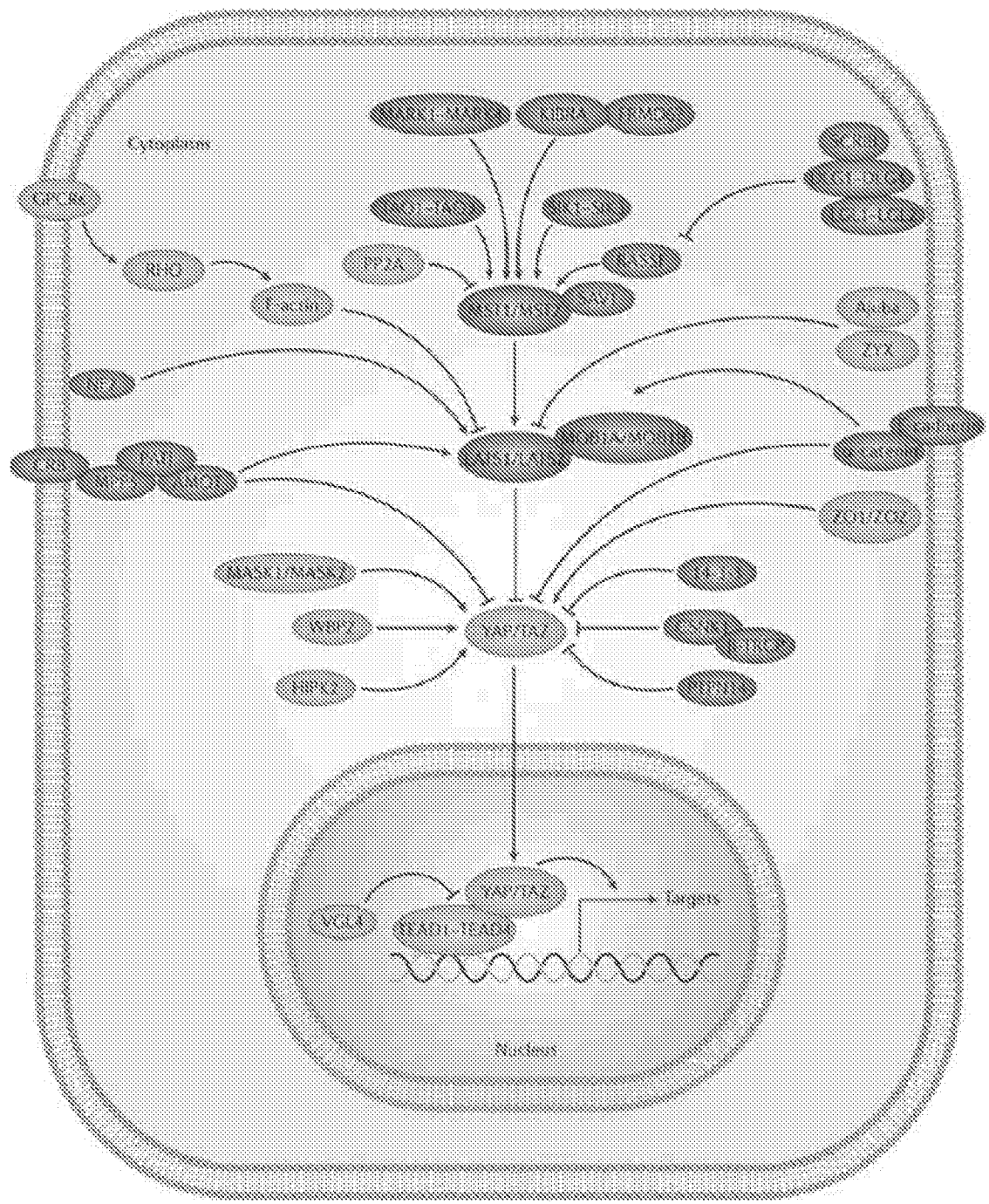
FIG. 1 illustrates a schematic representation of the Hippo signaling network. Hippo pathway components shaded in dark gray indicate components that inhibit YAP/TAZ activity. Hippo pathway components shaded in light gray indicate components that promote YAP/TAZ activity. Pointed and blunt arrowheads indicate activating and inhibitory interactions, respectively. Abbreviations: α-CAT (α-Catenin), AJUB (Ajuba), AMOT (Angiomotin), β-TRCP (β-transducing repeat containing protein), CK1 (Casein Kinase 1), CRB (Crumbs), E-CAD (E-cadherin), EX (Expanded), GPCR (G-protein coupled receptor), HIPK (Homeodomain interacting protein kinase), KIBRA (Kidney brain), LATS (Large tumor suppressor), LGL (Lethal giant larvae), MASK (Multiple ankyrin single KH), MER (Merlin), MOB (Mps one binder), MST (Mammalian sterile 20 like), PALS (Protein Associated with Lin-7), PATJ (Pals1-associated tight junction protein), PP2A (Protein phosphatase 2A), PTPN14 (Protein tyrosine phosphatase non-receptor type 14), RASSF (Ras associated factor), SAV (Salvador), SCRIB (Scribble), SIK (Salt inducible kinase), TAO (Thousand and one amino acid protein), TAZ (transcriptional coactivator with PDZ-binding motif), TEAD (TEA domain protein), VGL4 (Vestigial-like 4), WBP2 (WW domain binding protein 2), YAP (Yes associated protein), ZO (Zonula occludens), ZYX (Zyxin).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, in some embodiments, ranges and amounts are expressed as "about" a particular value or range. About also includes the exact amount. Hence "about 5 μL" means "about 5 μL" and also "5 μL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl(n-butyl), 1-methylpropyl(sec-butyl), 2-methylpropyl(iso-butyl), 1,1-dimethylethyl(tert-butyl), and 1-pentyl(n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkoxy" refers to a radical bonded through an oxygen atom of the formula —O— alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$), —N(R$^a$)C(O)OR$^f$, —OC(O)—NR$^a$R$^f$, —N(R$^a$)C(O)R$^f$; —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)(O)OR$^f$, —OC(O)— NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)R$^f$ (where t is 1 or 2), and —S(O)$_t$N(R$^8$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$) C(O)OR$^f$, —OC(O)— NR$^a$R, —N(R$^a$)C(O)R$^f$, —N(R$^a$)S (O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon fully five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—CN, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S (O)$_t$N(R$^a$)$_2$ (where t is 1 or 2), where each R$^a$ is independently hydrogen, alkyl, fluoroalkyl, cycloalkyl, cycloalkylalkyl, aryl(optionally substituted with one or more halo groups), aralkyl, heterocyclyl, heterocyclylalkyl, heteroaryl, or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, and in some embodiments, include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. In some embodiments, the carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)($R^a$ (where t is 1 or 2), —$R^b$—S(O)$_t$$OR^a$ (where t is 1 or 2), —$R^b$—S(O)$_t$RR (where t is 1 or 2), and —$R^b$—S(O)N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each Rh is independently a direct bond or a straight or branched alkylene or alkenylene chain, and $R^t$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro, or iodo substituents.

"Fluoroalkyl" refers to an alkyl radical, as defined above, that is substituted by one or more fluoro radicals, for example, trifluoromethyl, difluoromethyl, fluoromethyl, 2,2,2-trifluoroethyl, 1-fluoromethyl-2-fluoroethyl, and the like.

In some embodiments, the alkyl part of the fluoroalkyl radical is optionally substituted as defined above for an alkyl group.

"Heterocyclyl" or "heterocycle" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocyclyl radical is a monocyclic, bicyclic, tricyclic, or tetracyclic ring system, which include fused or bridged ring systems in some embodiments. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). In some embodiments, the heterocyclyl is saturated, (i.e., containing single bonds only) or unsaturated (i.e., containing one or more double bonds or triple bonds.) A fully saturated heterocyclyl radical is also referred to as "heterocycloalkyl." Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—CN, —$R^b$—$OR^a$, —$R^b$—OC(O)—$R^a$, —$R^b$—OC(O)—$OR^a$, —$R^b$—OC(O)—N($R^a$)$_2$, —$R^b$—N ($R^a$)$_2$, —$R^b$—C(O)$R^a$, —$R^b$—C(O)$OR^a$, —$R^b$—C(O)N($R^a$)$_2$, —$R^b$—O—$R^b$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$ heteroalkyl. In some embodiments, the alkyl part of the heteroalkyl radical is optionally substituted as defined for an alkyl group.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, in some embodiments, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems.

The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl(i.e., thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—C(O)$N(R^a)_2$, —$R^b$—O—$R^c$—C(O)$N(R^a)_7$, —$R^b$—$N(R^a)$C(O)$OR^a$, —$R^b$—$N(R^a)$C(O)$R^a$, —$R^bN(R^a)$S(O)$_tR^a$ (where t is 1 or 2), —$R^b$—S(O)$_tOR^a$ (where t is 1 or 2), —$R^b$—S(O)$_tR^a$ (where t is 1 or 2), and —$R^b$—S(O)$_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

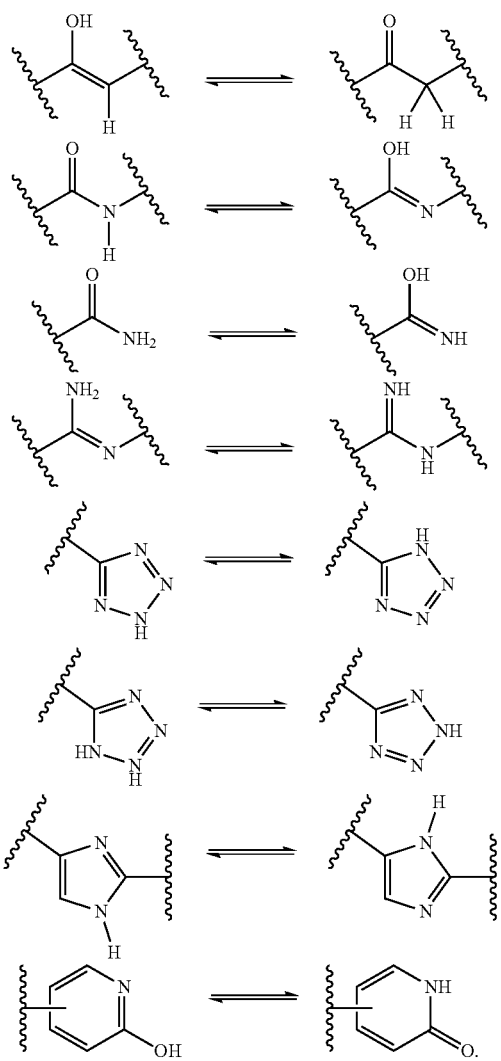

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Pharmaceutically acceptable salts of the compounds described herein are optionally pharmaceutically acceptable acid addition salts and pharmaceutically acceptable base addition salts.

"Pharmaceutically acceptable acid addition salt" refers to those salts which retain the biological effectiveness and properties of the free bases, which are not biologic ally or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlombenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines, and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino, or free mercapto group, respectively. Examples of prodrugs include, but are not limited to, acetate, formate, and benzoate derivatives of alcohol or amine functional groups in the active compounds and the like.

Compounds

In some embodiments, the compounds disclosed herein are benzocarbonyl compounds.

Provided in one aspect is a compound of Formula (I), or a pharmaceutically acceptable salt thereof:

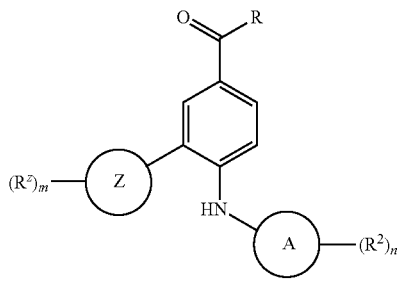

Formula (I)

wherein,

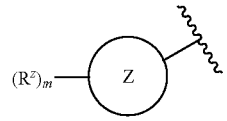

is a substituted or unsubstituted monocyclic 5-membered heterocyclic ring containing at least one N atom or a substituted or unsubstituted monocyclic 6-membered heteroaryl ring containing at least one N atom;

each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, -$L^1$-$Y^1$, or -$L^2$-$L^3$-$Y^2$;

m is 0, 1, 2, 3, 4, or 5;

$L^1$ is substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

$Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

$L^2$ is absent, substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;

each $R^3$ is independently H or substituted or unsubstituted $C_1$-$C_6$ alkyl;

$Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is —OR$^1$ or —N(R$^1$)$_2$;

each $R^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^1$ on the same N atom are taken together with the N atom to which they are attached to form a substituted or unsubstituted N-containing heterocycle;

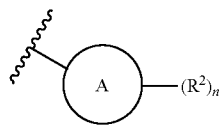

is substituted or unsubstituted phenyl or substituted or unsubstituted cyclohexyl;

each $R^2$ is independently H, —F, —I, —Cl, —$N_3$, —CN, —$OR^4$, —$SR^4$, —$(SO_2)R^4$, —$N(R^4)_2$, —$CO_2R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or

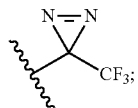

n is 0, 1, 2, 3, 4, or 5; and each $R^4$ is independently H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^4$ on the same N atom are taken together with the N atom to which they are attached to form a substituted or unsubstituted N-containing heterocycle.

In some embodiments,

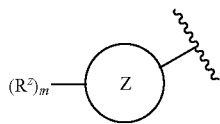

is a substituted or unsubstituted monocyclic 5-membered heterocyclic ring containing at least one N atom.

In some embodiments,

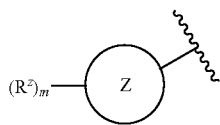

is a substituted or unsubstituted monocyclic 5-membered heterocyclic ring containing 1-4 N atoms, 0-2 O atoms, and 0-2 S atoms.

In some embodiments,

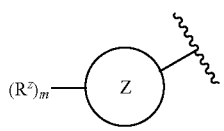

is

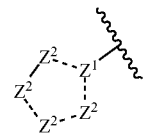

$Z^1$ is —N—, —CH—, or —C—;

each $Z^2$ is independently —$CR^z$—, —$CHR^z$—, —$C(R^z)_2$—, —$NR^z$—, —N—, —O—, or —S—;

each —— is independently a single or double bond; and with the provision that the 5-membered heterocyclic ring contains at least one N atom.

In some embodiments,

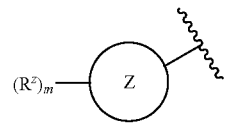

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

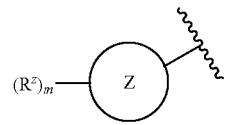

is

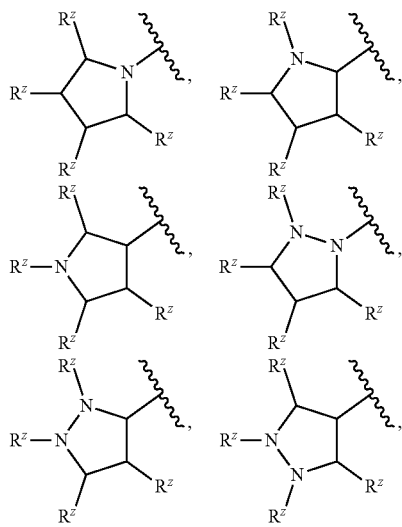

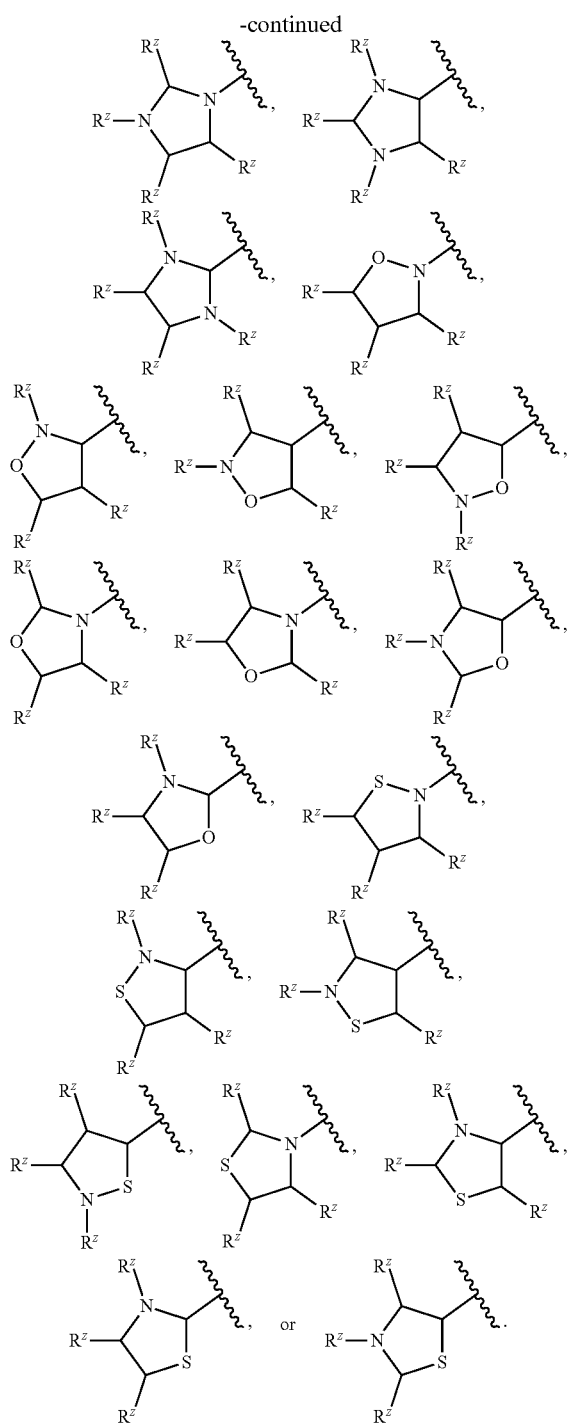

In some embodiments,

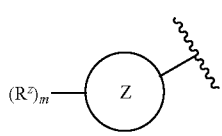

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

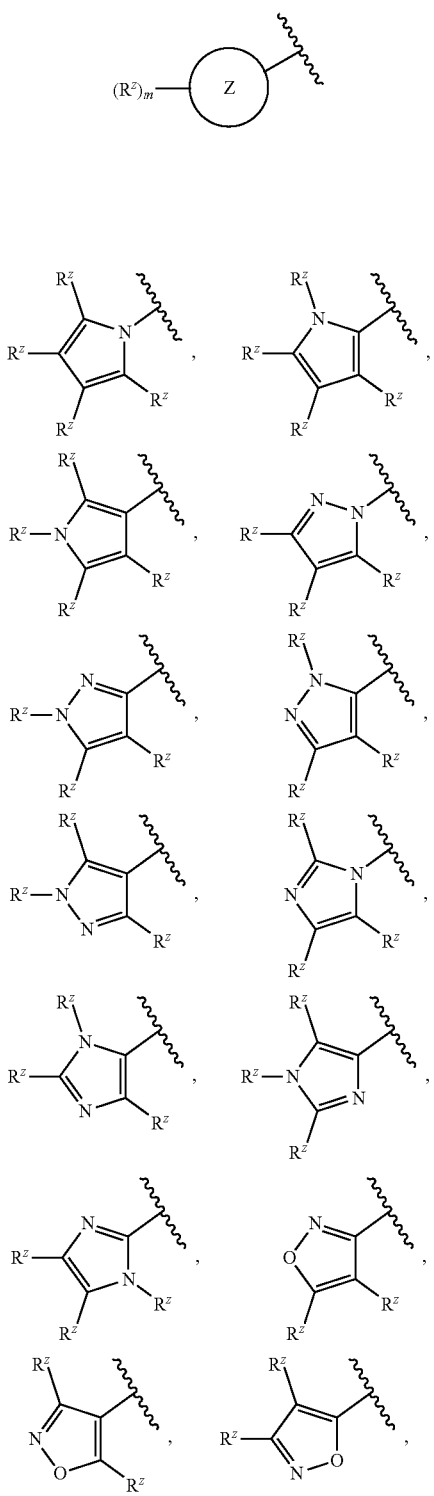

is

-continued

In some embodiments,

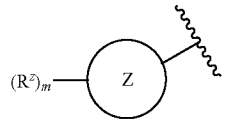

is a substituted or unsubstituted monocyclic 6-membered heteroaryl ring containing at least one N atom.

In some embodiments,

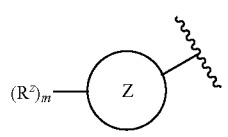

is a substituted or unsubstituted monocyclic 6-membered heteroaryl ring containing 1 or 2 N atoms.

In some embodiments,

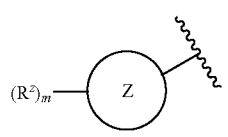

is

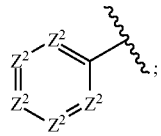

each $Z^2$ is independently $CR^z$ or N; and
at least one $Z^2$ is N.

In some embodiments,

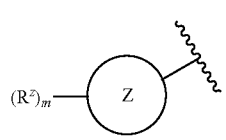

is substituted or unsubstituted pyridinyl, substituted or unsubstituted pyrazinyl, substituted or unsubstituted pyrimidinyl, or substituted or unsubstituted pyridazinyl.

In some embodiments,

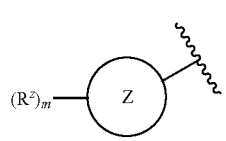

is

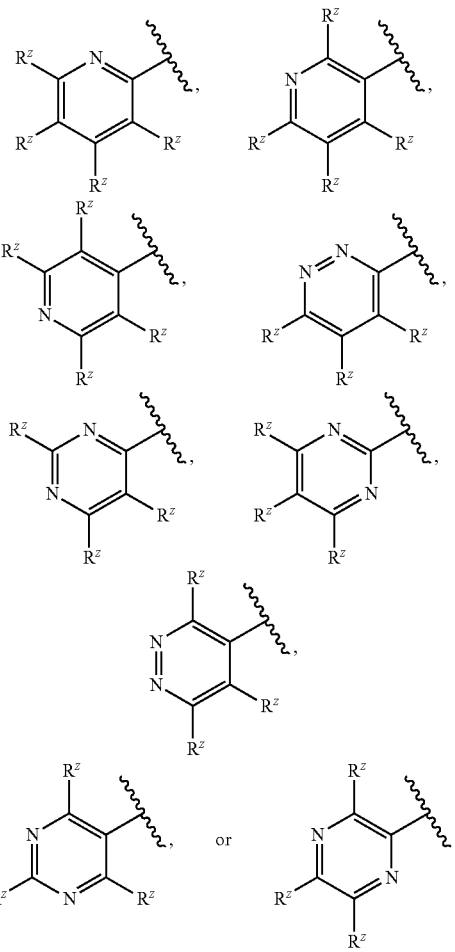

In some embodiments, the compound has the structure of Formula (Ia), or a pharmaceutically acceptable salt thereof:

Formula (Ia)

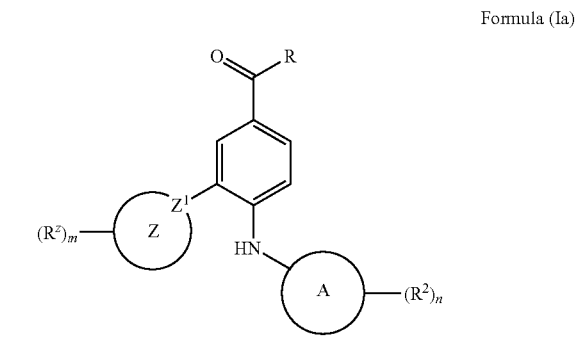

wherein:
$Z^1$ is —N—, —CH—, or —C—.

In some embodiments,

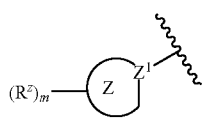

is a substituted or unsubstituted monocyclic 5-membered heterocyclic ring containing at least one N atom, and the at least one N atom is adjacent to Z.

In some embodiments,

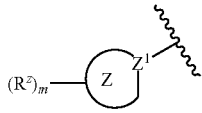

is

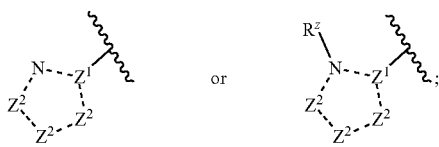

$Z^1$ is —N—, —CH—, or —C—;
each $Z^2$ is independently —CR$^z$—, —CHR$^z$—, —C(R$^z$)$_2$—, —NR$^z$—, —N—, —O—, or —S—; and
each —— is independently a single or double bond.

In some embodiments,

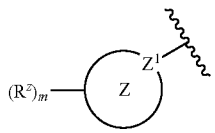

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

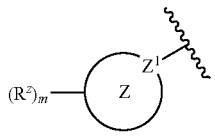

is

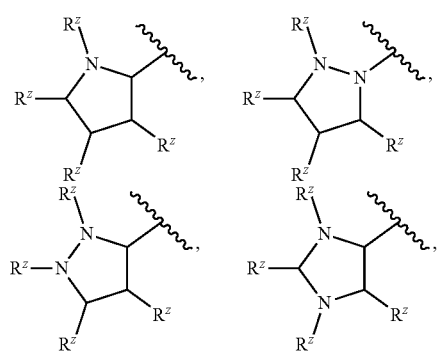

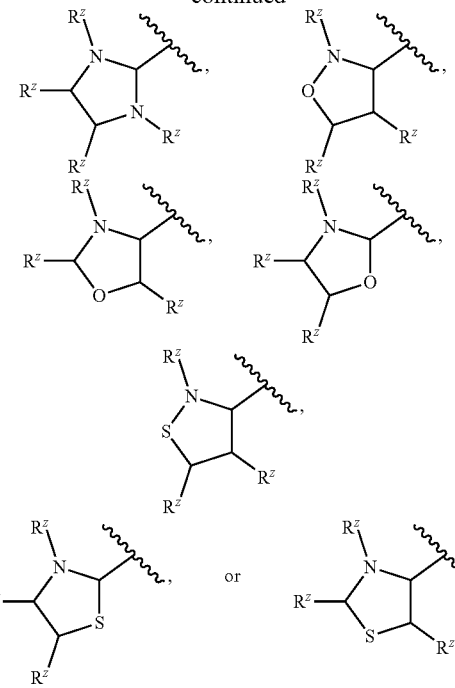

In some embodiments,

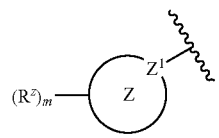

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

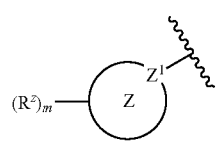

is

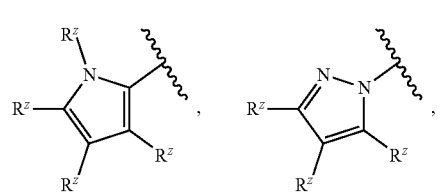

-continued
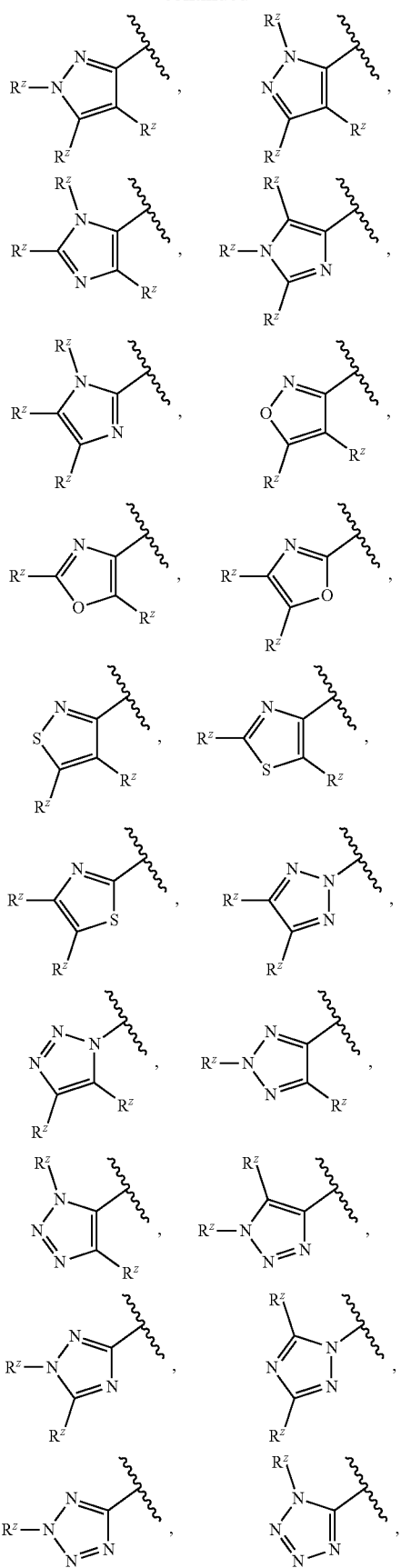
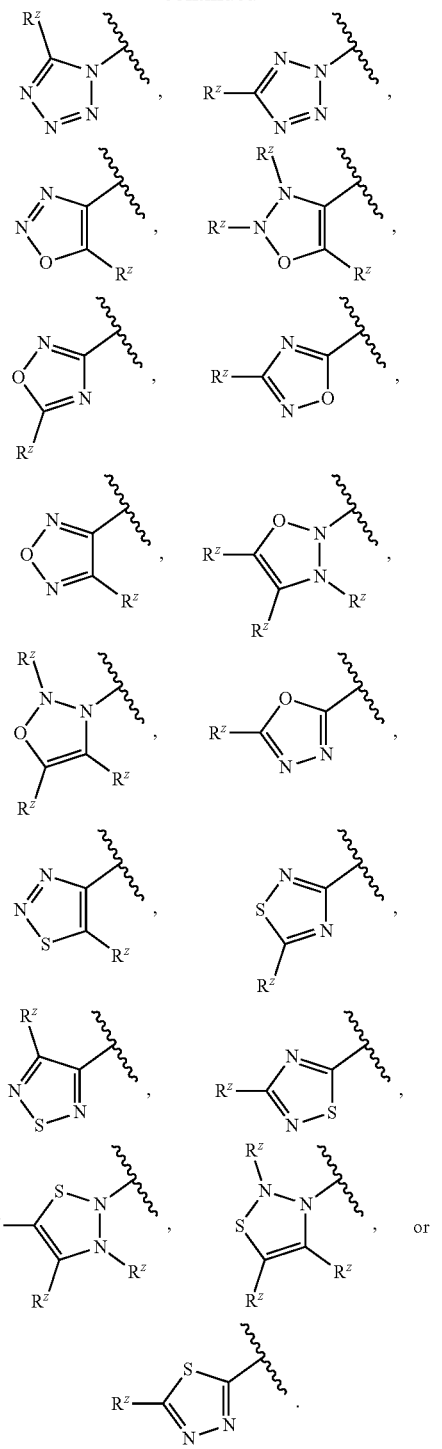
In some embodiments,
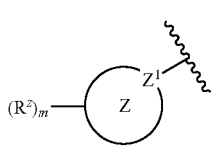

is a substituted or unsubstituted monocyclic 6-membered heteroaryl ring containing at least one N atom, and wherein the at least one N atom is adjacent to $Z^1$.

In some embodiments,

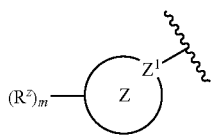

is

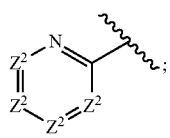

and each $Z^2$ is independently $CR^z$ or N.

In some embodiments,

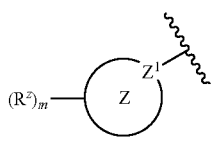

is substituted or unsubstituted pyridinyl, substituted or unsubstituted pyrazinyl, substituted or unsubstituted pyrimidinyl, or substituted or unsubstituted pyridazinyl.

In some embodiments,

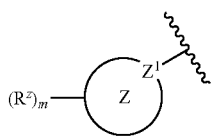

is

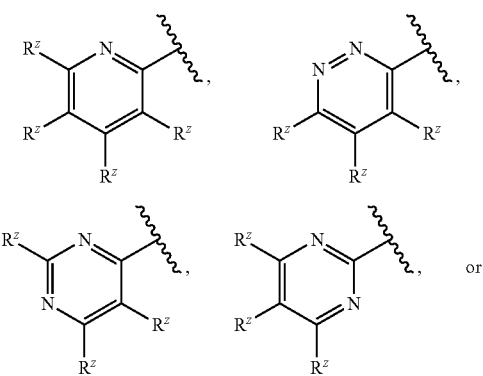

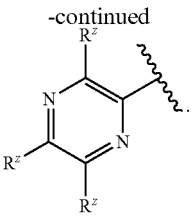

In some embodiments, each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, each $R^z$ is independently H, halogen, substituted or unsubstituted $C_1$-$C_6$ alkyl, substituted or unsubstituted $C_1$-$C_6$ haloalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, $L^1$ is substituted or unsubstituted $C_1$-$C_4$ alkylene; and $Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is -$L^2$-$L^3$-$Y^2$. In some embodiments, $L^2$ is substituted or unsubstituted $C_1$-$C_6$ alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, $L^2$ is absent; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, R is —OR$^1$; and $R^1$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is —N($R^1$)$_2$; and each $R^1$ is independently H, —(SO$_2$)$R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl; or two $R^1$ on the same N atom are taken together with the N atom to which they are attached to form a substituted or unsubstituted N-containing heterocycle. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

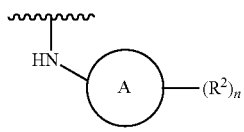

is

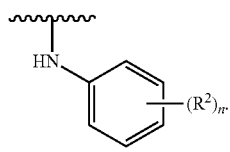

In some embodiments, the compound has the structure of Formula (Ib), or a pharmaceutically acceptable salt thereof:

Formula (Ib)

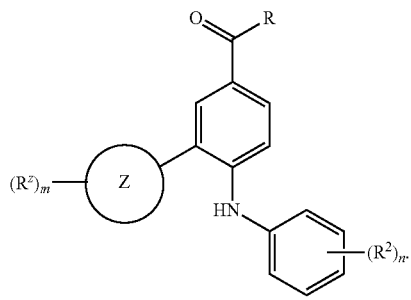

In some embodiments,

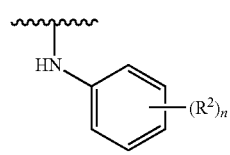

is

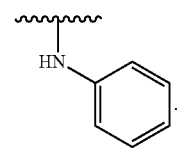

In some embodiments,

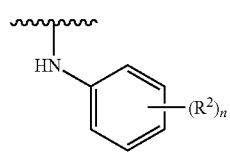

is

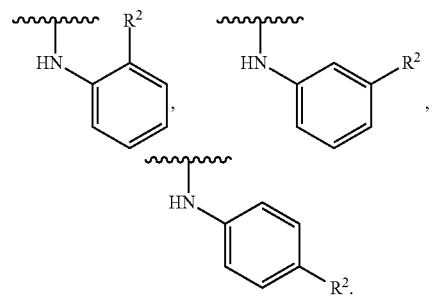

, or

In some embodiments,

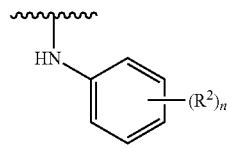

is

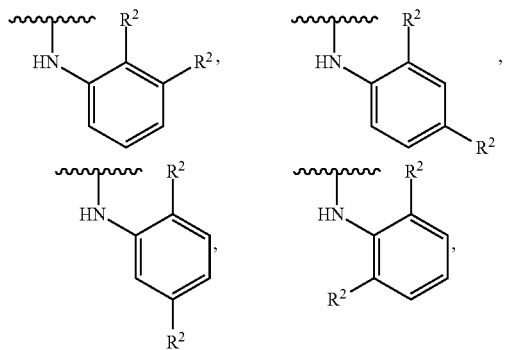

-continued
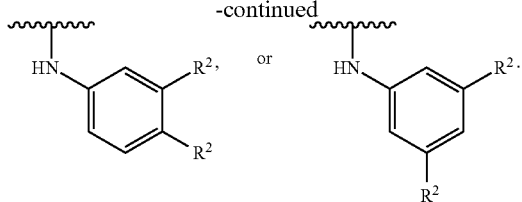
In some embodiments,
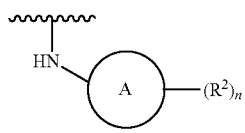
is
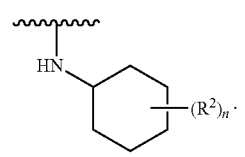
In some embodiments, the compound has the structure of Formula (Ic), or a pharmaceutically acceptable salt thereof:
Formula (Ic)
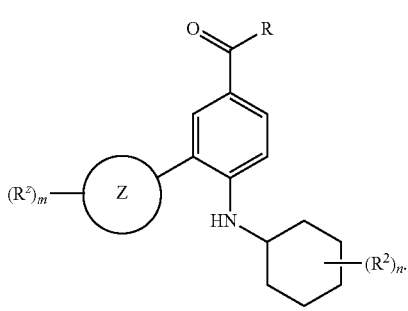
In some embodiments,
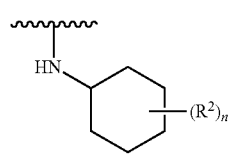
is
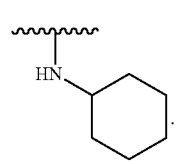
In some embodiments,
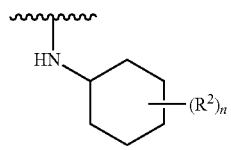
is
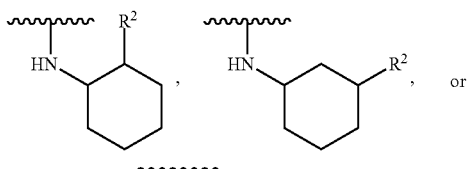
In some embodiments,
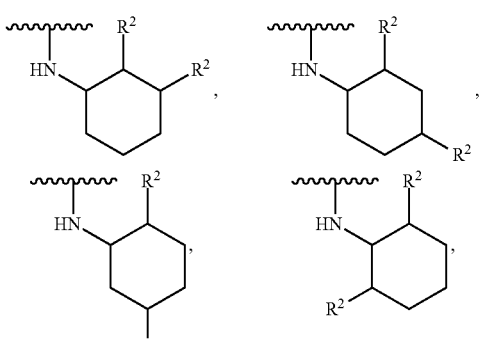
is
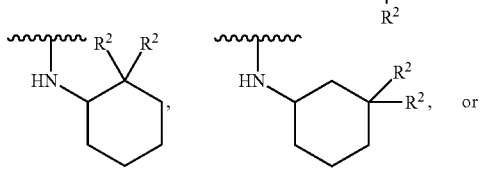

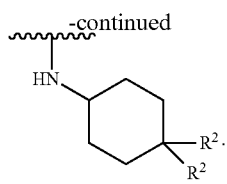

In some embodiments, each R² is independently H, —F, —I, —Cl, —N₃, —CN, —OR⁴, —SR⁴, —(SO₂)R⁴, —N(R⁴)₂, —CO₂R⁴, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, or substituted or unsubstituted aryl.

In some embodiments, the compound has the structure of Formula (Id), or a pharmaceutically acceptable salt thereof:

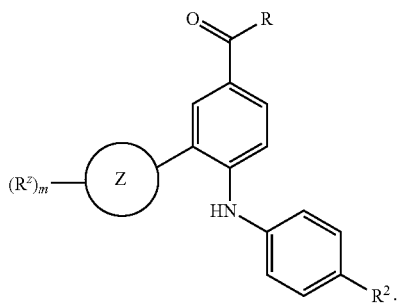

Formula (Id)

In some embodiments, the compound has the structure of Formula (Ie), or a pharmaceutically acceptable salt thereof:

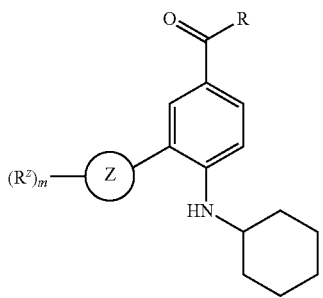

Formula (Ie)

Provided in another aspect is a compound of Formula (II), or a pharmaceutically acceptable salt thereof:

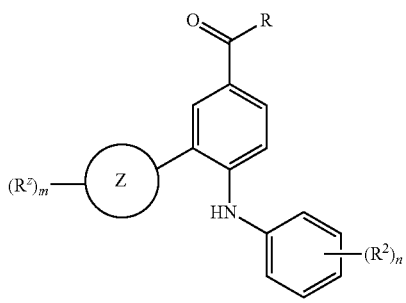

Formula (II)

wherein,

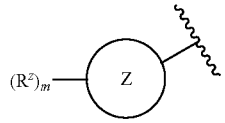

is a substituted or unsubstituted monocyclic 5-membered heterocyclic ring containing at least one N atom or a substituted or unsubstituted monocyclic 6-membered heteroaryl ring containing at least one N atom;

each R$^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, -L¹-Y¹, or -L²-L³-Y²;

m is 0, 1, 2, 3, 4, or 5;

L¹ is substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

Y¹ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

L² is absent, substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

L³ is —O—, —S—, —(S=O)—, —(SO₂)—, —NR³—, —(C=O)—, —(C=O)O—, —O(C=O)—, —(C=O)NR³—, —(C=O)NR³—O—, —O—NR³ (C=O)—, —NR³ (C=O)—, —NR³ (C=O)NR³—, —O(C=O)NR³—, —NR³ (C=O)O—, —NR³ (SO₂) NR³—, —NR³ (SO₂)—, —(SO₂)NR³—, —(SO₂) NR³—(C=O)—, —(C=O)—NR³ (SO₂)—, —(SO₂) NR³—(C=O)O—, —O(C=O)—NR³ (SO₂)—, —NR³ (SO₂)NR³—(C=O)—, —(C=O)—NR³ (SO₂) NR³—, —O(C=O)—NR³ (SO₂)—NR³—, or —NR³ (SO₂)NR³—(C=O)O—;

each R³ is independently H or substituted or unsubstituted $C_1$-$C_6$ alkyl;

Y² is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or R³ and Y² on the same N atom are taken together with the N atom to which they are attached to form a substituted or unsubstituted N-containing heterocycle;

R is —OR¹ or —N(R¹)₂;

each R¹ is independently H, —(SO₂)R⁴, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two R¹ on the same N atom are taken together with the N atom to which they are attached to form a substituted or unsubstituted N-containing heterocycle;

each $R^2$ is independently H, —F, —I, —Cl, $N_3$, —CN, —$OR^4$, —$SR^4$, —$(SO_2)R^4$, —$N(R^4)_2$, —$CO_2R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted Cr $C_1$-$C_{10}$ cycloalkyl, substituted or unsubstituted $C_2$-$C_{10}$ heterocycloalkyl, substituted or unsubstituted aralkyl, substituted or unsubstituted aryl, or

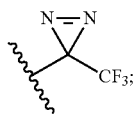 [SMILES: *C1(C(F)(F)F)N=N1]

n is 0, 1, 2, 3, 4, or 5; and each $R^4$ is independently H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^4$ on the same N atom are taken together with the N atom to which they are attached to form a substituted or unsubstituted N-containing heterocycle.

In some embodiments,

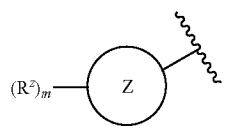

is a substituted or unsubstituted monocyclic 5-membered heterocyclic ring containing at least one N atom.

In some embodiments,

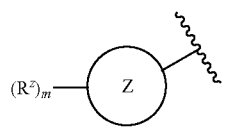

is a substituted or unsubstituted monocyclic 5-membered heterocyclic ring containing 1-4 N atoms, 0-2 O atoms, and 0-2 S atoms.

In some embodiments,

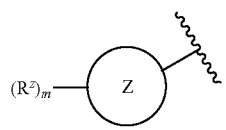

is

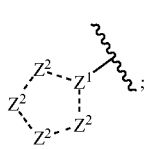

$Z^1$ is —N—, —CH—, or —C—;

each Z is independently —$CR^z$—, —$CHR^z$—, —$C(R^z)_2$—, —$NR^z$—, —N—, —O—, or —S—;

each —— is independently a single or double bond; and with the provision that the 5-membered heterocyclic ring contains at least one N atom.

In some embodiments,

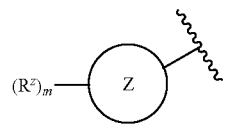

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

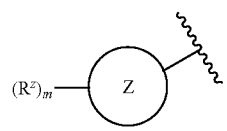

is

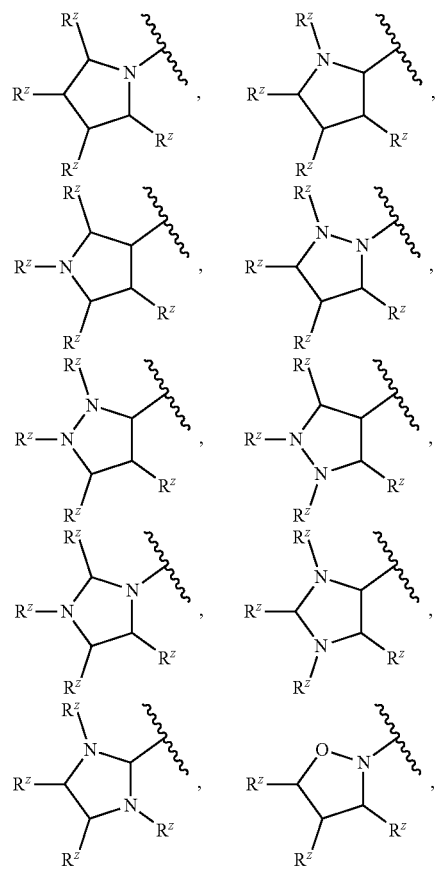

-continued

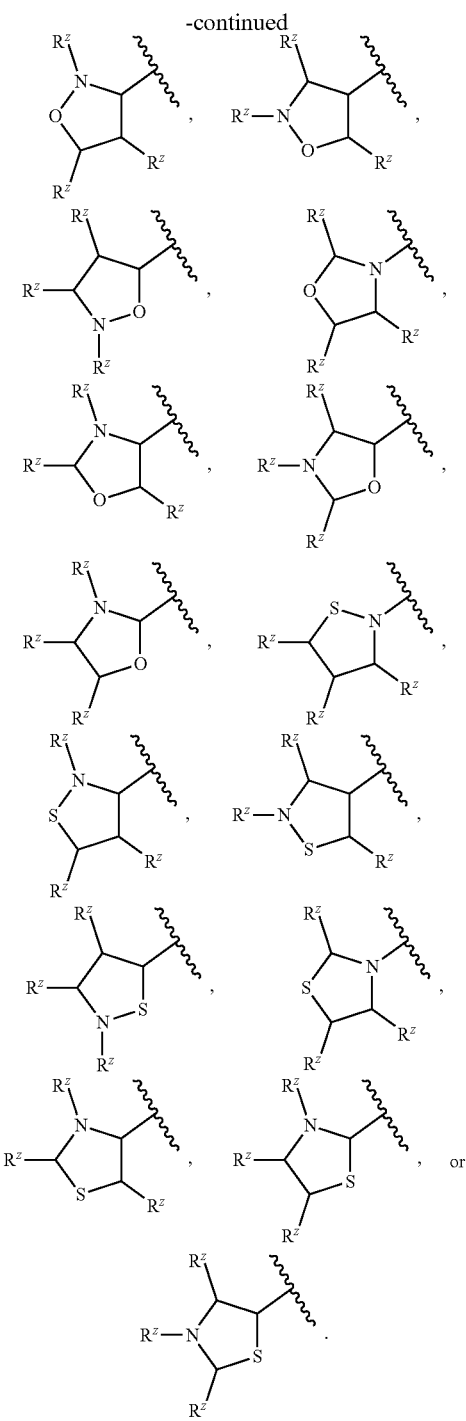

In some embodiments,

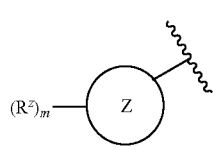

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

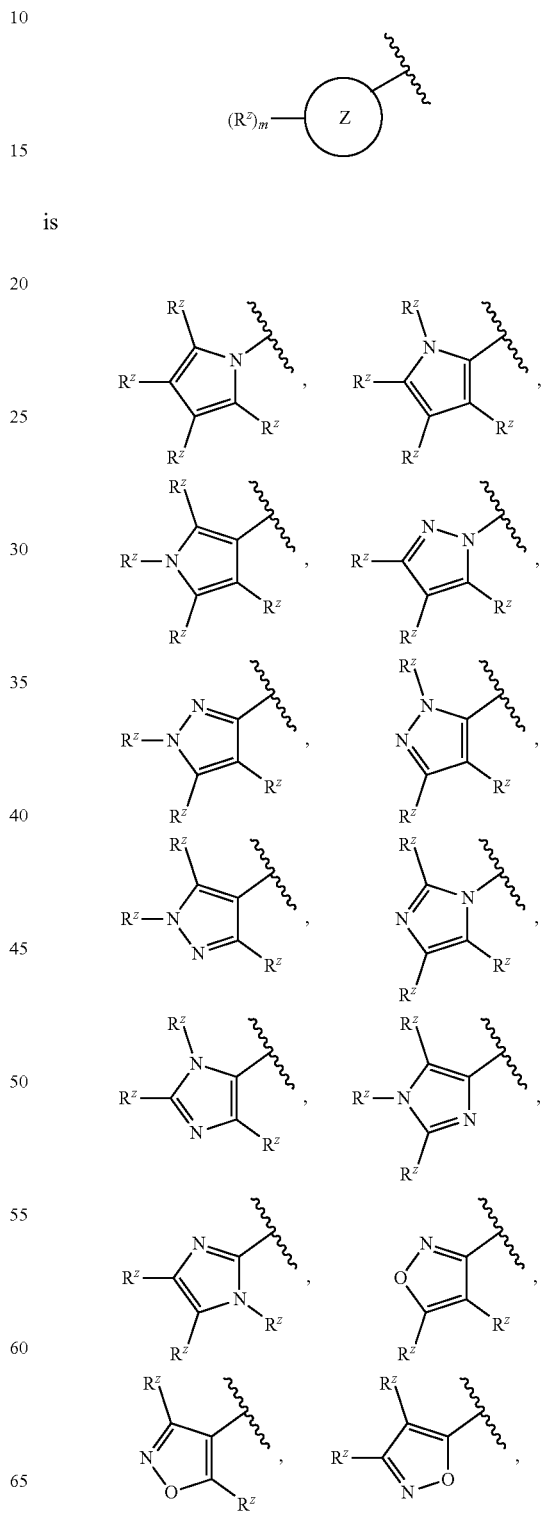

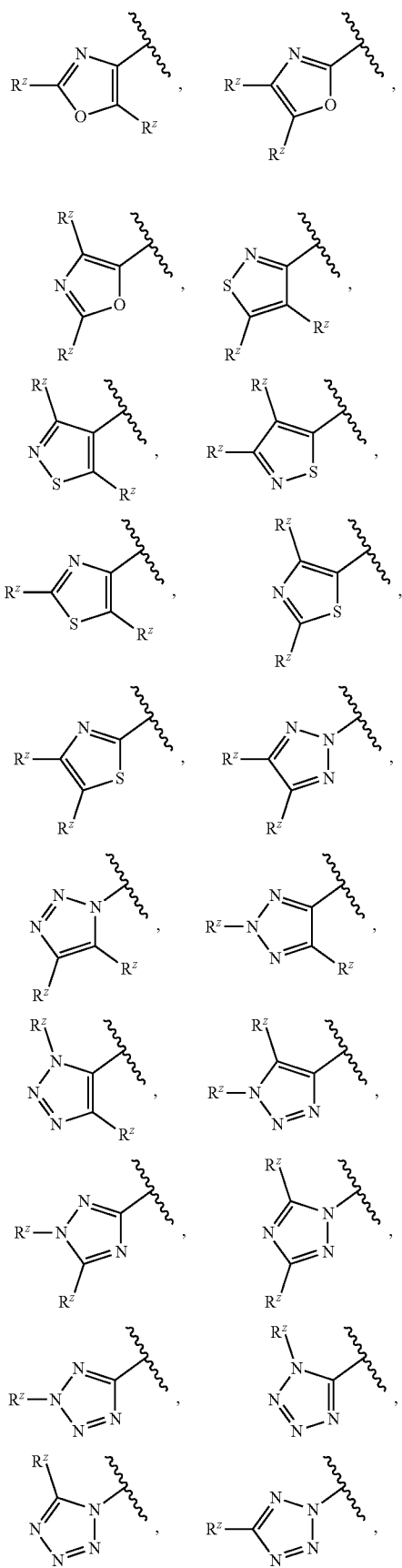
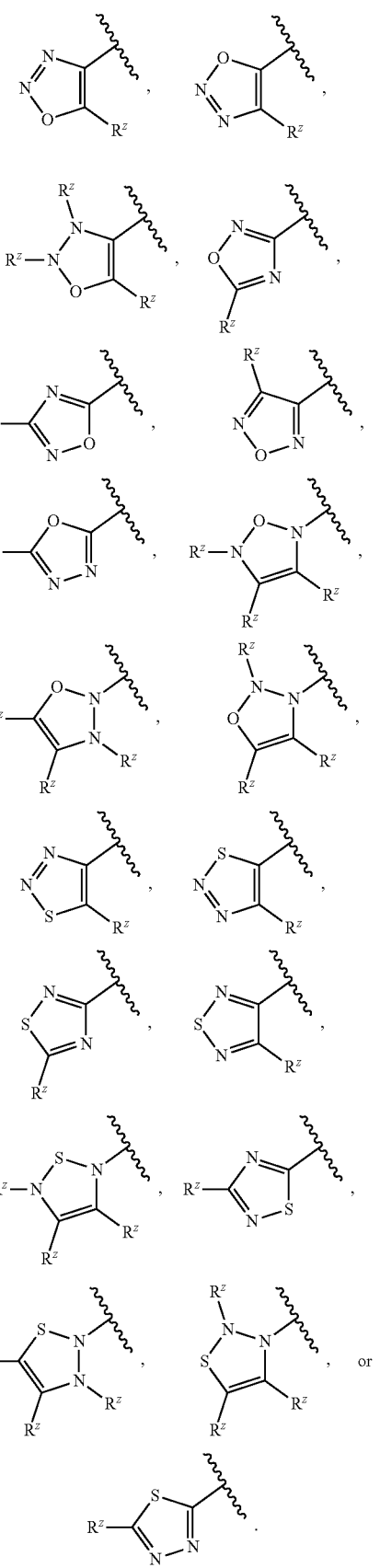

In some embodiments,

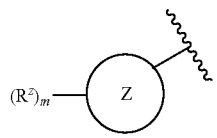

is a substituted or unsubstituted monocyclic 6-membered heteroaryl ring containing at least one N atom.

In some embodiments,

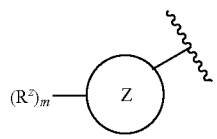

is a substituted or unsubstituted monocyclic 6-membered heteroaryl ring containing at least 1 or 2 N atoms.

In some embodiments,

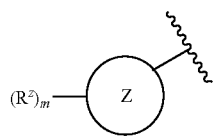

is

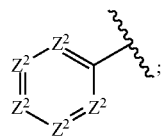

each $Z^2$ is independently $CR^z$ or N; and at least one $Z^2$ is N.

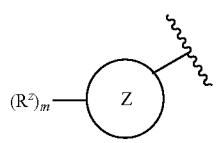

In some embodiments, is substituted or unsubstituted pyridinyl, substituted or unsubstituted pyrazinyl, substituted or unsubstituted pyrimidinyl, or substituted or unsubstituted pyridazinyl.

In some embodiments,

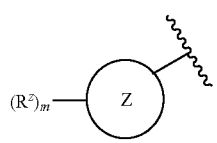

is

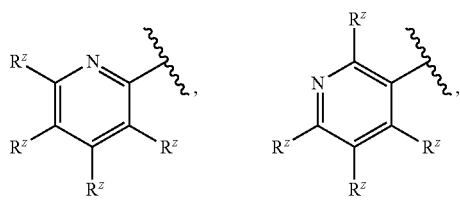

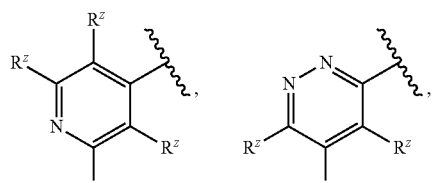

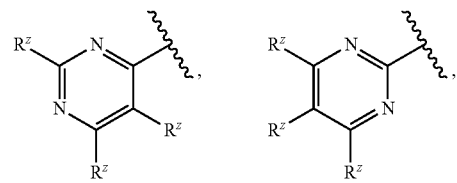

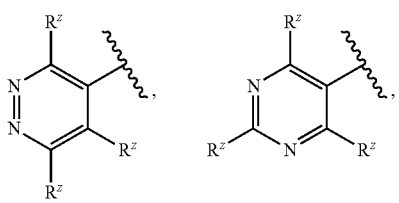 or

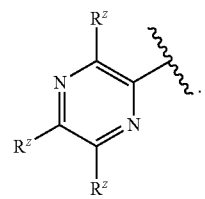

In some embodiments, the compound has the structure of Formula (IIa), or a pharmaceutically acceptable salt thereof:

Formula (IIa)

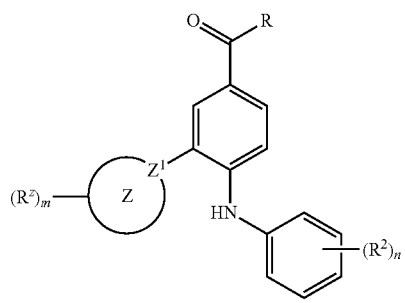

wherein:

$Z^1$ is —N—, —CH—, or —C—.

In some embodiments,

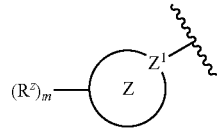

is a substituted or unsubstituted monocyclic 5-membered heterocyclic ring containing at least one N atom, and the at least one N atom is adjacent to $Z^1$.

In some embodiments,

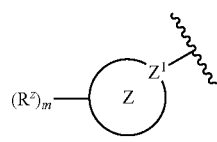

is

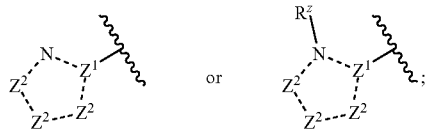

$Z^1$ is —N—, —CH—, or —C—;
each $Z^2$ is independently —CR$^z$—, —CHR$^z$, —C(R$^z$)$_2$—, —NR$^z$—, —N—, —O—, or —S—; and
each —— is independently a single or double bond.

In some embodiments,

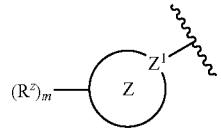

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

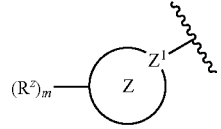

is

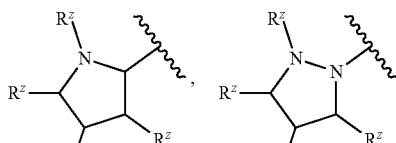

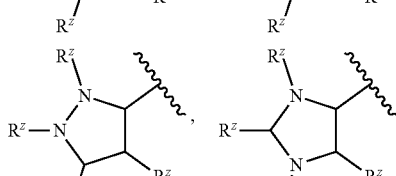

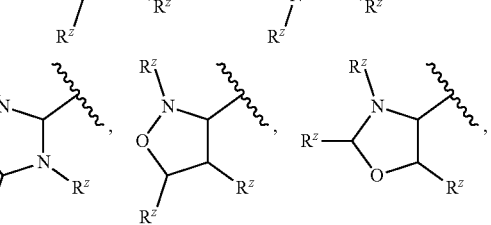

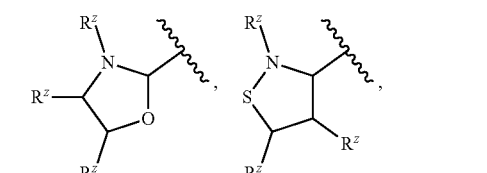

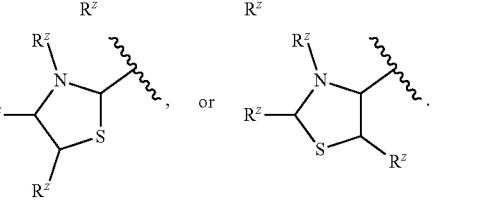

In some embodiments,

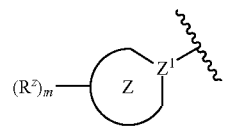

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

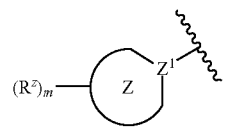

is

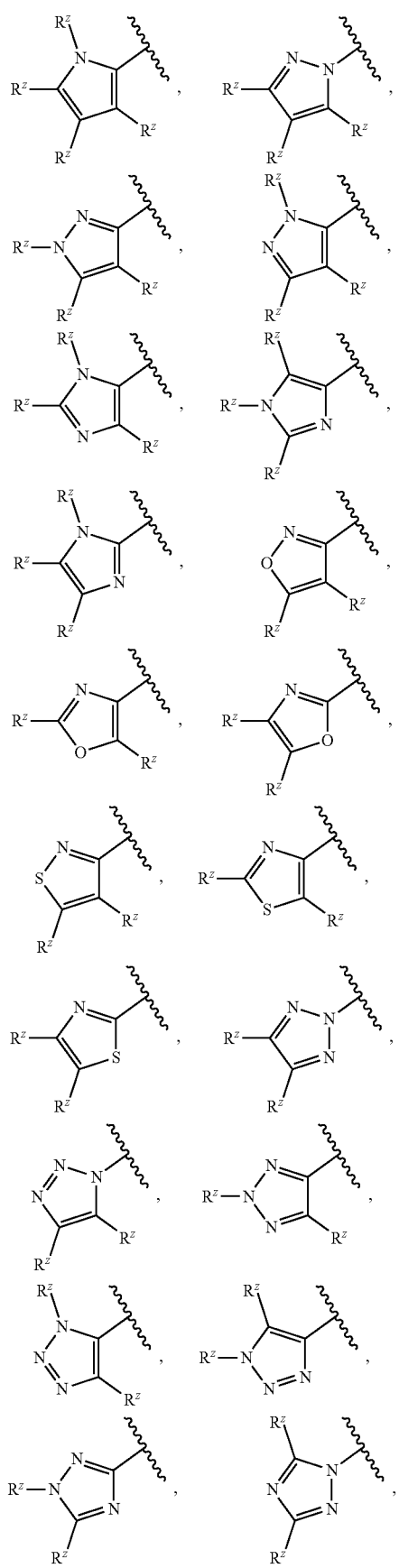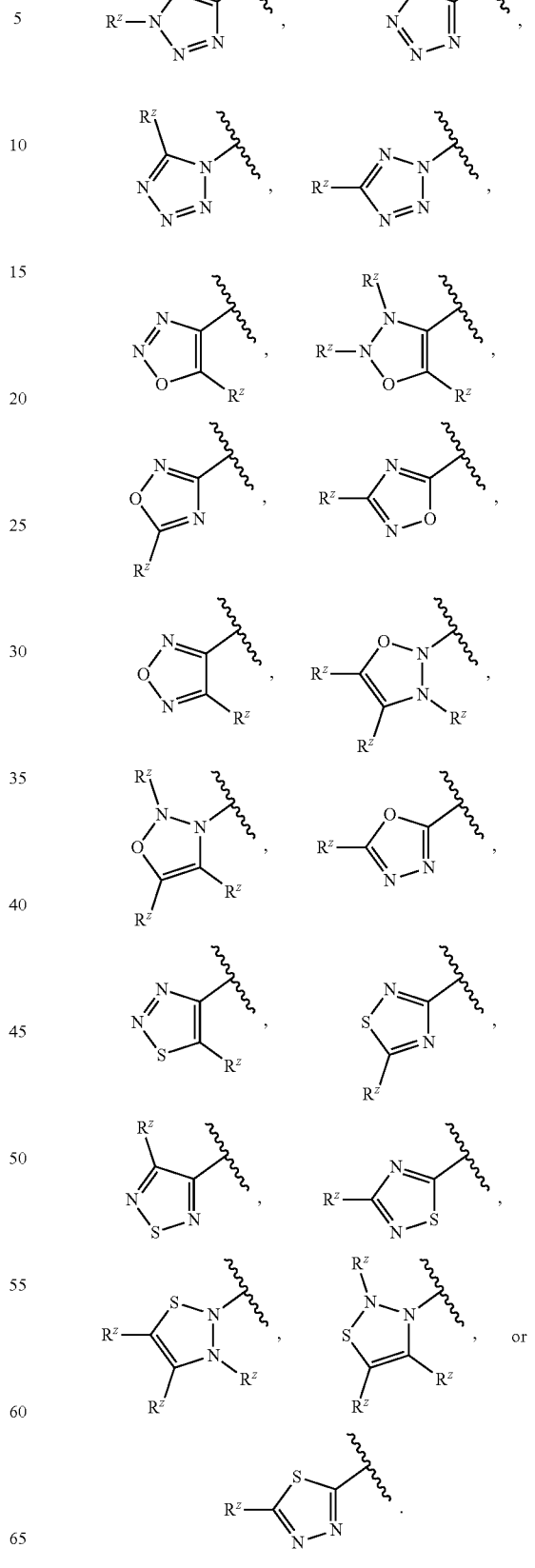

In some embodiments,

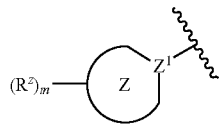

is a substituted or unsubstituted monocyclic 6-membered heteroaryl ring containing at least one N atom, and wherein the at least one N atom is adjacent to $Z^1$.

In some embodiments,

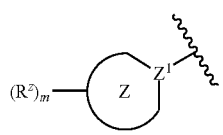

is

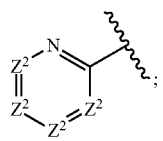

and each $Z^2$ is independently $CR^z$ or N.

In some embodiments,

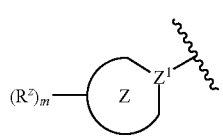

is substituted or unsubstituted pyridinyl, substituted or unsubstituted pyrazinyl substituted or unsubstituted pyrimidinyl, or substituted or unsubstituted pyridazinyl.

In some embodiments,

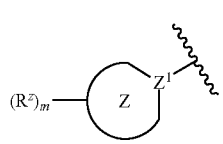

is

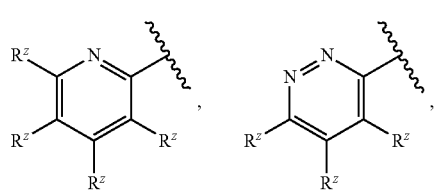

-continued

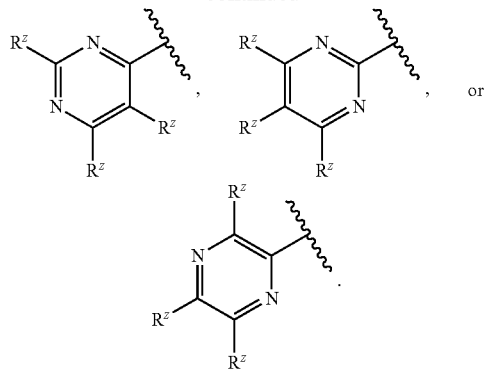

In some embodiments, each R is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, each $R^z$ is independently H, halogen, substituted or unsubstituted $C_1$-$C_6$ alkyl, substituted or unsubstituted $C_1$-$C_6$ haloalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, Lt is substituted or unsubstituted $C_1$-$C_4$ alkylene; and $Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is -$L^2$-$L^3$-$Y^2$. In some embodiments, $L^2$ is substituted or unsubstituted $C_1$-$C_6$ alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$ (C=O)—, —NR$^3$ (C=O)NR$^3$—, —O(C=O)NR$^3$—, —NR$^3$ (C=O)O—, —NR$^3$ (SO$_2$)NR$^3$—, —NR$^3$ (SO$_2$)—, —(SO$_2$)NR$^3$—, —(SO$_2$)NR$^3$—(C=O)—, —(SO$_2$)NR$^3$—(C=O)O—, —NR$^3$ (SO$_2$)NR$^3$—(C=O)—, or —NR$^3$ (SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, $L^2$ is absent; $L^3$ is —O—, —S—, —(S=O)—, —(SO$_2$)—, —NR$^3$—, —(C=O)—, —(C=O) O—, —O(C=O)—, —(C=O)NR$^3$—, —(C=O)NR$^3$— O—, —NR$^3$ (C=O)~, —NR$^3$ (C=O)NR$^3$—, —O(C=O) NR$^3$—, —NR$^3$ (C=O)O—, —NR$^3$ (SO$_2$)NR$^3$—, —NR$^3$ (SO$_2$)—, —(SO$_2$)NR$^3$—, —(SO$_2$)NR$^3$—(C=O)—, —(SO$_2$)NR$^3$—(C=O)O—, —NR$^3$ (SO$_2$)NR$^3$—(C=O)—, or —NR$^3$ (SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, R is —$OR^1$; and $R^1$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is —$N(R^1)_2$; and each $R^1$ is independently H, —$(SO_2)R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl; or two $R^1$ on the same N atom are taken together with the N atom to which they are attached to form a substituted or unsubstituted N-containing heterocycle. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

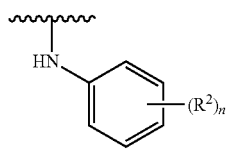

is

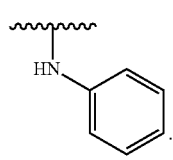

In some embodiments,

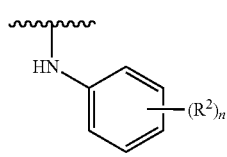

is

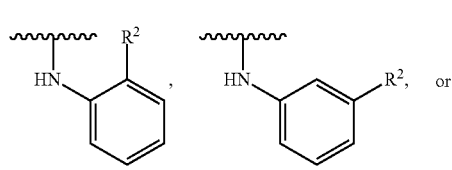

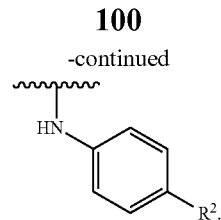

In some embodiments,

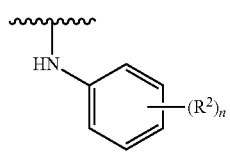

is

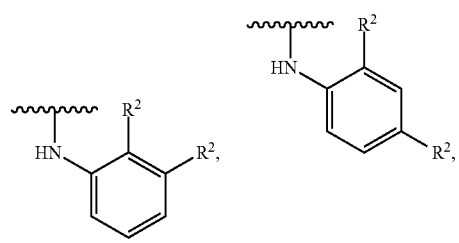

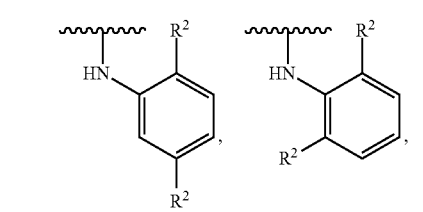

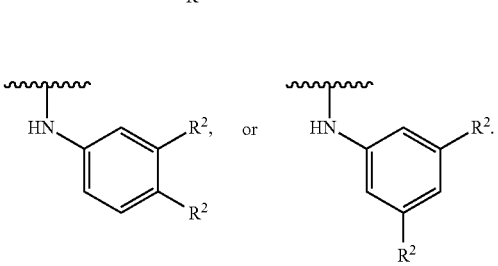

in some embodiments, each $R^2$ is independently H, —F, —I, —Cl, —$N_3$, —CN, —$OR^4$, —$SR^4$, —$(SO_2)R^4$, —$N(R^4)_2$, —$CO_2R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, or substituted or unsubstituted aryl.

In some embodiments, the compound has the structure of Formula (IIb), or a pharmaceutically acceptable salt thereof:

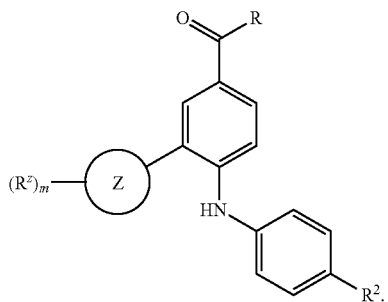

Formula (IIb)

Provided in another aspect is a compound of Formula (III), or a pharmaceutically acceptable salt thereof:

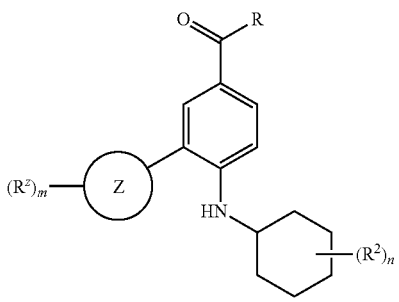

Formula (III)

wherein,

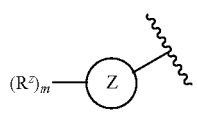

is a substituted or unsubstituted monocyclic 5-membered heterocyclic ring containing at least one N atom or a substituted or unsubstituted monocyclic 6-membered heteroaryl ring containing at least one N atom;

each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, -$L^1$-$Y^1$, or -$L^2$-$L^3$-$Y^2$;

m is 0, 1, 2, 3, 4, or 5;

$L^1$ is substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

$Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

$L^2$ is absent, substituted or unsubstituted $C_1$-$C_6$ alkylene, substituted or unsubstituted $C_2$-$C_{10}$ cycloalkylene, or substituted or unsubstituted $C_2$-$C_{10}$ heterocycloalkylene;

$L^3$ is —O—, —S—, —(S=O)—, —(SO$_2$)—, —NR$^3$—(C=O)—, —(C=O)O—, —O(C=O)—, —(C=O)NR$^3$—, —(C=O)NR$^3$—O—, —O—NR$^3$ (C=O)—, —NR$^3$ (C=O)—, —NR$^3$ (C=O)NR$^3$—, —O(C=O)NR$^3$—, —NR$^3$ (C=O)O—, —NR$^3$ (SO$_2$)NR$^3$—, —NR$^3$ (SO$_2$)—, —(SO$_2$)NR$^3$—, —(SO$_2$)NR$^3$—(C=O)—, —(C=O)—NR$^3$ (SO$_2$)—, —(SO$_2$)NR$^3$—(C=O)O—, —O(C=O)—NR$^3$ (SO$_2$)—, —NR$^3$ (SO$_2$)NR$^3$—(C=O)—, —(C=O)—NR$^3$ (SO$_2$)NR$^3$—, —O(C=O)—NR$^3$ (SO$_2$)—NR$^3$—, or —NR$^3$ (SO$_2$)NR$^3$—(C=O)O—;

each $R^3$ is independently H or substituted or unsubstituted $C_1$-$C_6$ alkyl;

$Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is —OR$^1$ or —N(R$^1$)$_2$;

each $R^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^1$ on the same N atom are taken together with the N atom to which they are attached to form a substituted or unsubstituted N-containing heterocycle;

each $R^2$ is independently H, halogen, —N$_3$, —CN, —OR$^4$, —SR$^4$, —(SO$_2$)R$^4$, —N(R$^4$)$_2$, —CO$_2$R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, substituted or unsubstituted heteroaryl, or

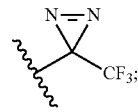

n is 0, 1, 2, 3, 4, or 5; and each $R^4$ is independently 1H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl;

or two $R^4$ on the same N atom are taken together with the N atom to which they are attached to form a substituted or unsubstituted N-containing heterocycle.

In some embodiments,

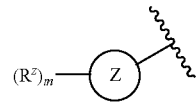

is a substituted or unsubstituted monocyclic 5-membered heterocyclic ring containing at least one N atom.

In some embodiments,

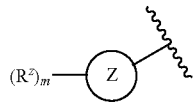

is a substituted or unsubstituted monocyclic 5-membered heterocyclic ring containing 1-4 N atoms, 0-2 O atoms, and 0-2 S atoms.

In some embodiments,

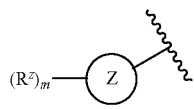

is

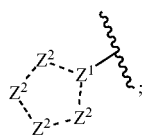

$Z^1$ is —N—, —CH—, or —C—;

each $Z^2$ is independently —$CR^z$—, —$CHR^z$—, —$C(R^z)_2$—, —$NR^z$—, —N—, —O—, or —S—;

each —— is independently a single or double bond; and with the provision that the 5-membered heterocyclic ring contains at least one N.

In some embodiments,

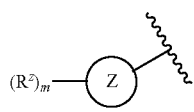

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

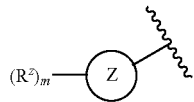

is

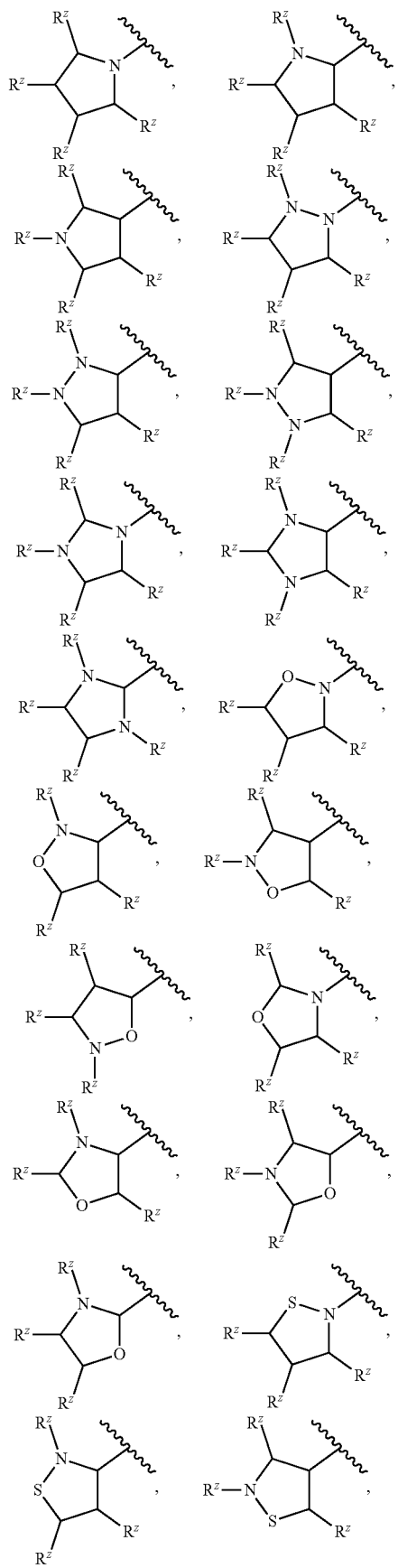

-continued

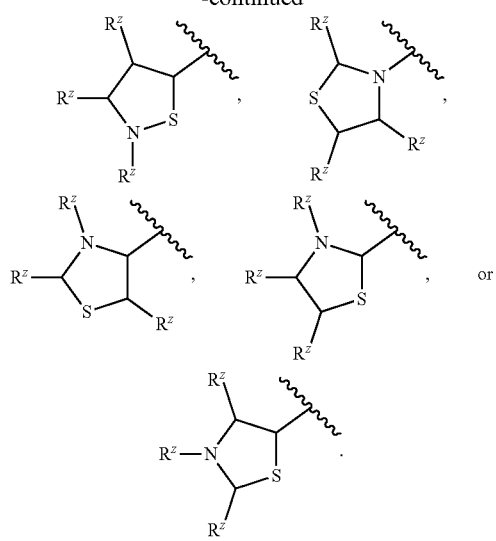

In some embodiments,

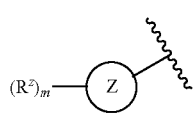

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

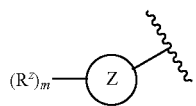

is

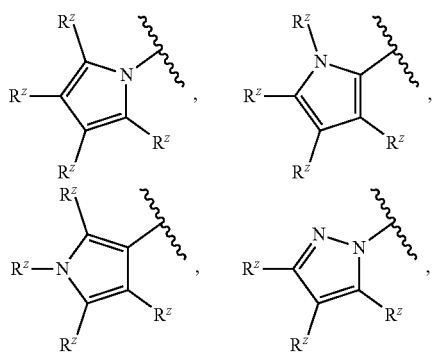

-continued

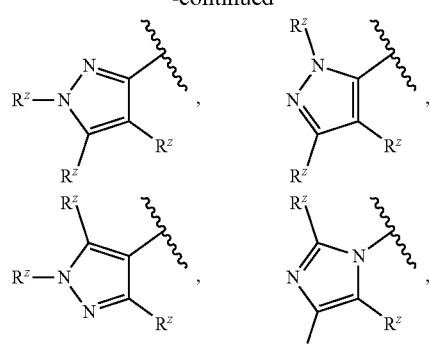
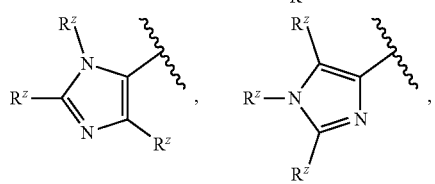
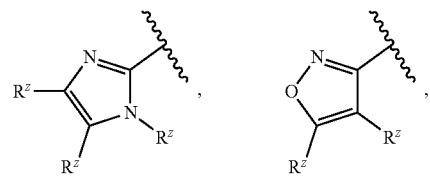
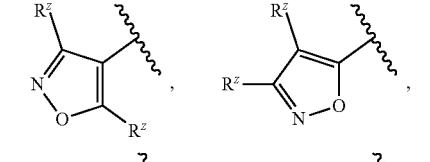
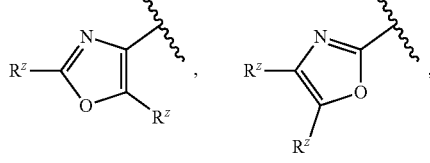
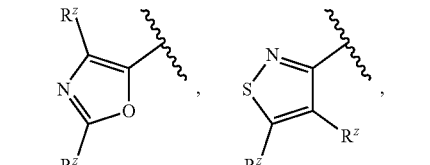
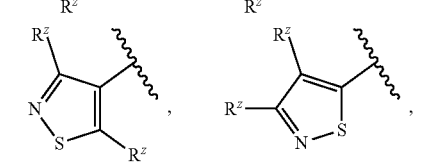
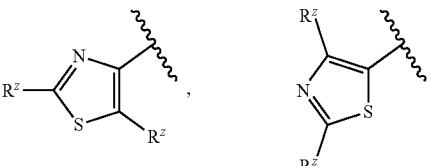
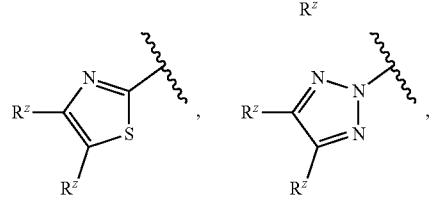

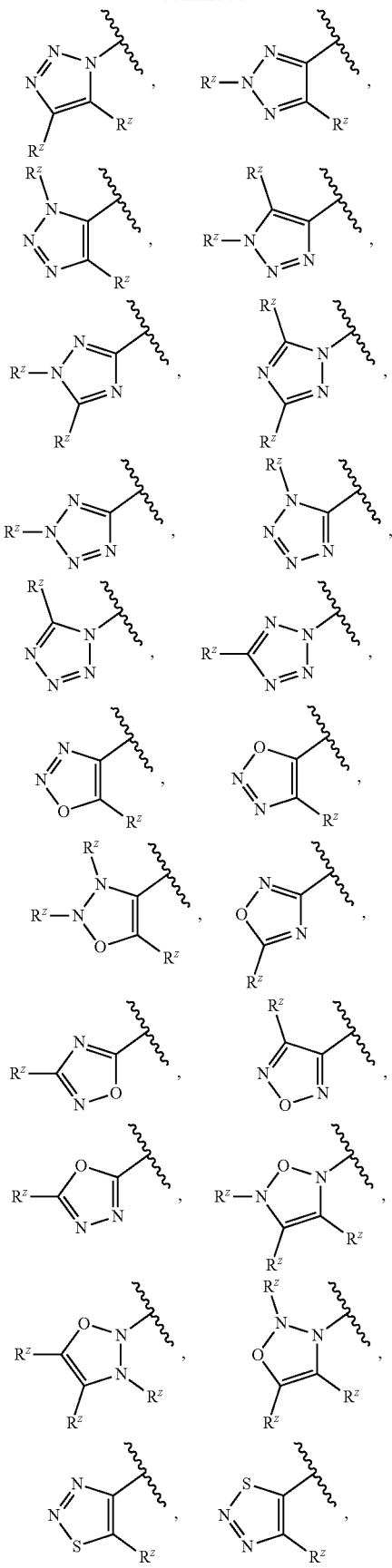
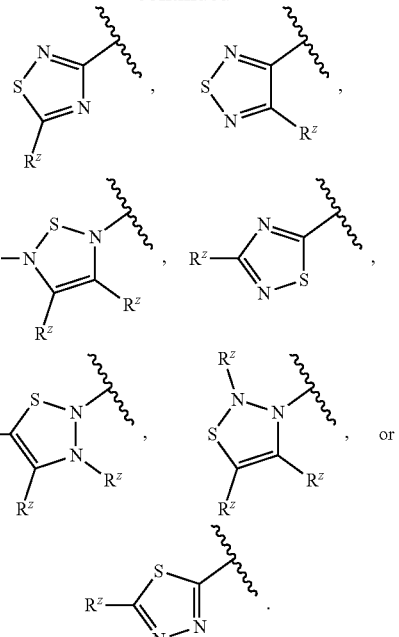
In some embodiments,
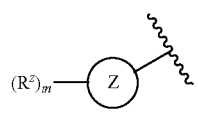
is a substituted or unsubstituted monocyclic 6-membered heteroaryl ring containing at least one N atom.
In some embodiments,
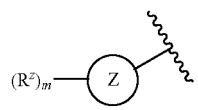
is a substituted or unsubstituted monocyclic 6-membered heteroaryl ring containing 1 or 2 N atoms.
In some embodiments,
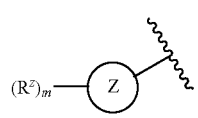
is
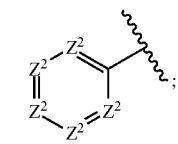
each $Z^2$ is independently $CR^z$ or N; and at least one $Z^2$ is N.

In some embodiments,

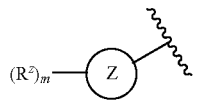

is substituted or unsubstituted pyridinyl, substituted or unsubstituted pyrazinyl, substituted or unsubstituted pyrimidinyl, or substituted or unsubstituted pyridazinyl.

In some embodiments,

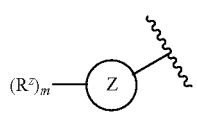

is

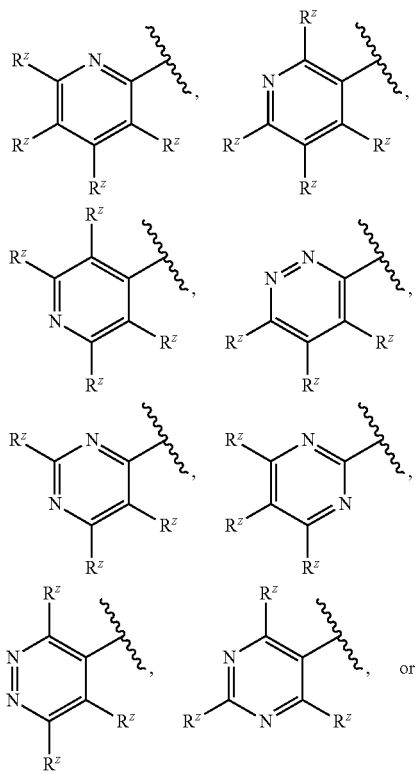

In some embodiments, the compound has the structure of Formula (IIIa), or a pharmaceutically acceptable salt thereof:

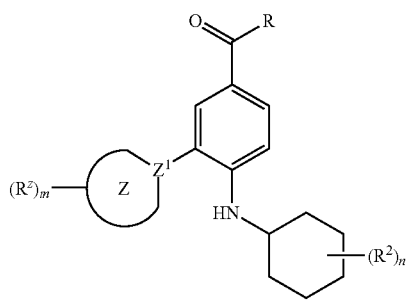

Formula (IIIa)

wherein:
$Z^1$ is —N—, —CH—, or —C—.

In some embodiments,

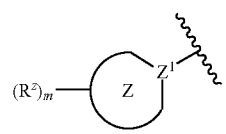

is a substituted or unsubstituted monocyclic 5-membered heterocyclic ring containing at least one N atom, and the at least one N atom is adjacent to $Z^1$.

In some embodiments,

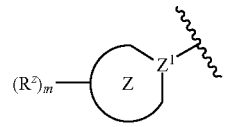

is

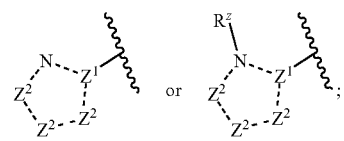

$Z^1$ is —N—, —CH—, or —C—;
each $Z^2$ is independently —$CR^z$—, —$CHR^z$—, —$C(R^z)_2$—, —$NR^z$—, —N—, —O—, or —S—; and
each ——— is independently a single or double bond.

In some embodiments,

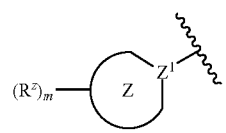

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

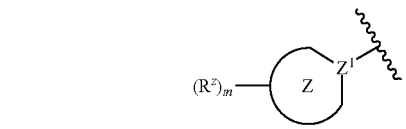

is

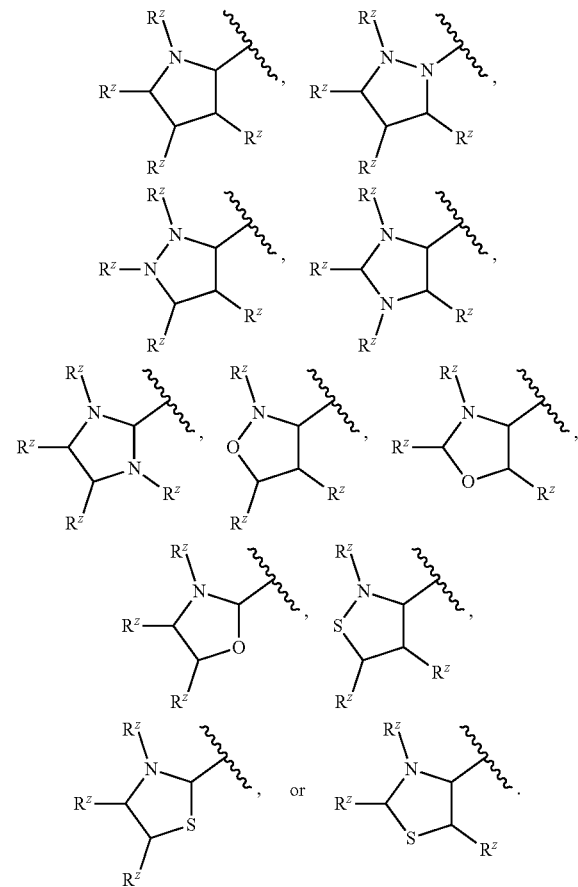

In some embodiments,

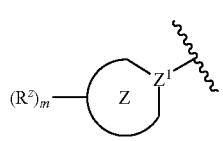

is substituted or un substituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments,

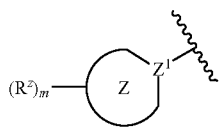

is

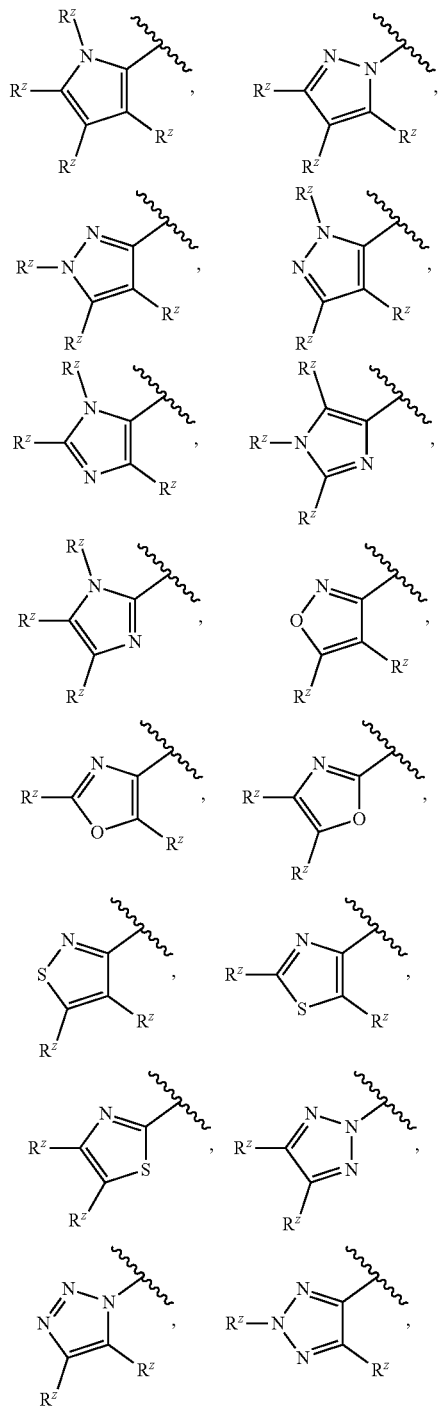

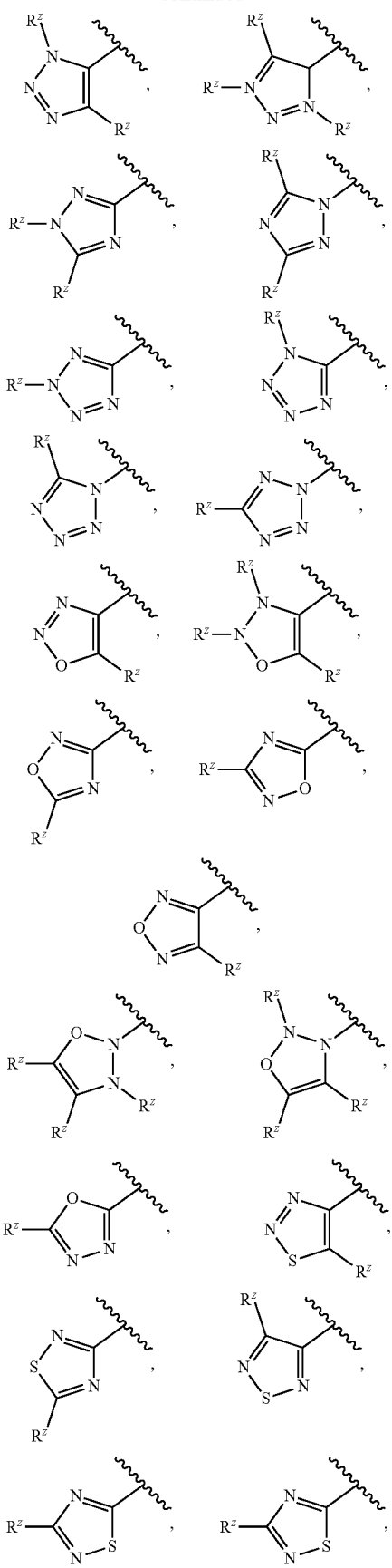

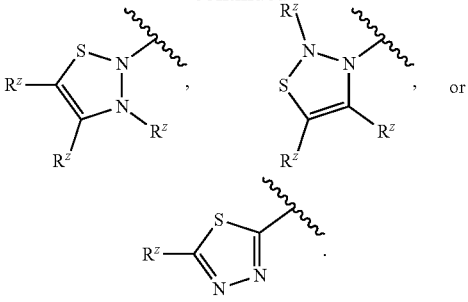

In some embodiments,

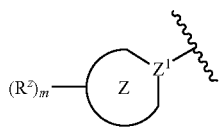

is a substituted or unsubstituted monocyclic 6-membered heteroaryl ring containing at least one N atom, and wherein the at least one N atom is adjacent to $Z^1$.

In some embodiments,

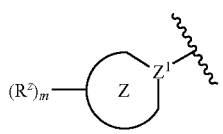

is

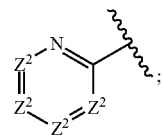

and each $Z^2$ is independently $CR^z$ or N.

In some embodiments,

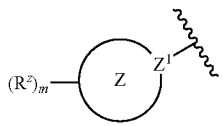

is substituted or unsubstituted pyridinyl, substituted or unsubstituted pyrazinyl, substituted or unsubstituted pyrimidinyl, or substituted or unsubstituted pyridazinyl.

In some embodiments,

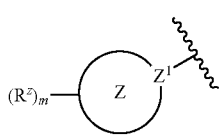

is

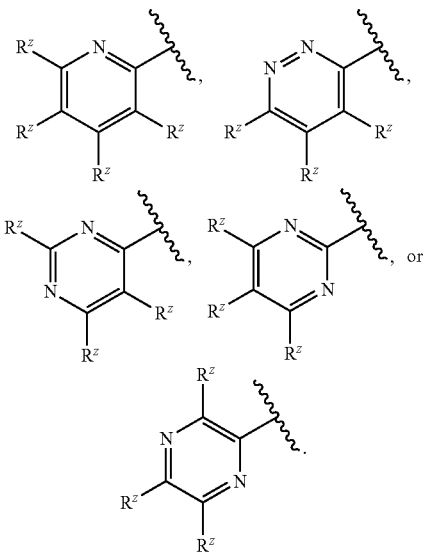

In some embodiments, each $R^z$ is independently H, halogen, —CN, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, each $R^z$ is independently H, halogen, substituted or unsubstituted $C_1$-$C_6$ alkyl, substituted or unsubstituted $C_1$-$C_6$ haloalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, L is substituted or unsubstituted $C_1$-$C_4$ alkylene; and $Y^1$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, each $R^z$ is -$L^2$-$L^3$-$Y^2$. In some embodiments, $L^2$ is substituted or unsubstituted $C_1$-$C_6$ alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$ (C=O)—, —NR$^3$ (C=O)NR$^3$. —O(C=O)NR$^3$—, —NR$^3$ (C=O) O—, —NR$^3$ (SO$_2$)NR$^3$—, —NR$^3$ (SO$_2$)—, —(SO$_2$)NR$^3$—, —(SO$_2$)NR$^3$—(C=O)—, —(SO$_2$)NR$^3$—(C=O)O—, —NR$^3$ (SO$_2$)NR$^3$—(C=O)—, or —NR$^3$ (SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, $L^2$ is absent; $L^3$ is —O—, —S—, —(S=O)—, —(SO$_2$)—, —NR$^3$—, —(C=O)—, —(C=O) O—, —O(C=O)—, —(C=O)NR$^3$—, —(C=O)NR$^3$— O—, —NR$^3$ (C=O)—, —NR$^3$ (C=O)NR$^3$—, —O(C=O) NR$^3$—, —NR$^3$ (C=O)O—, —NR$^3$ (SO$_2$)NR$^3$—, —NR$^3$ (SO$_2$)—, —(SO$_2$)NR$^3$—, —(SO$_2$)NR$^3$—(C=O)—, —(SO$_2$)NR$^3$—(C=O)O—, —NR$^3$ (SO$_2$)NR$^3$—(C=O)—, or —NR$^3$ (SO$_2$)NR$^3$—(C=O)O—; each $R^3$ is independently H or substituted or unsubstituted $C_1$-$C_6$ alkyl; and $Y^2$ is H, substituted or unsubstituted $C_1$-$C_6$ alkyl, substituted or un substituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl.

In some embodiments, R is —OR$^1$; and $R^1$ is H, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is —N(R$^1$)$_2$; and each $R^1$ is independently H, —(SO$_2$)R$^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl; or two $R^1$ on the same N atom are taken together with the N atom to which they are attached to form a substituted or unsubstituted N-containing heterocycle. In some embodiments, $R^1$ is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

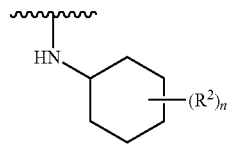

is

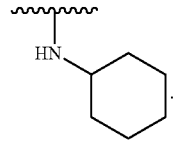

In some embodiments,

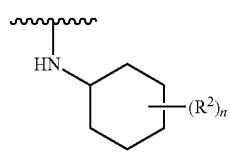

is

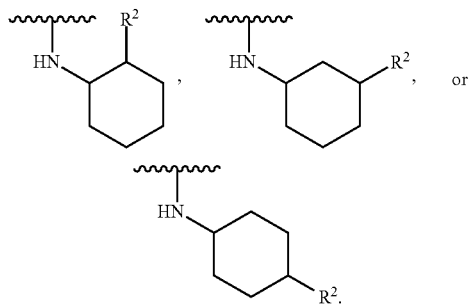

In some embodiments,

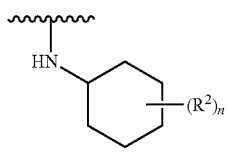

is

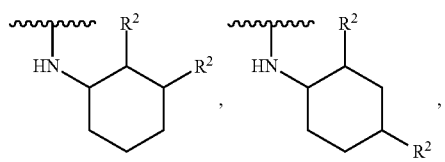

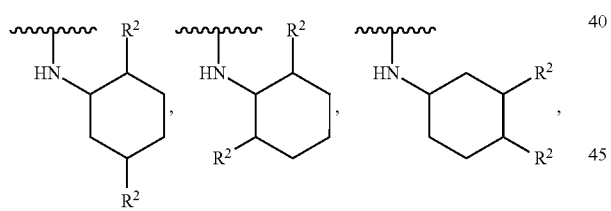

-continued

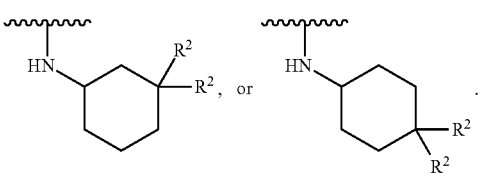

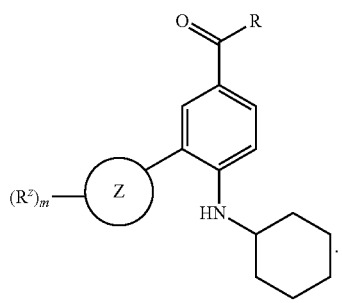

In some embodiments, each $R^2$ is independently H, halogen, $-N_3$, $-CN$, $-OR^4$, $-SR^4$, $-(SO_2)R^4$, $-N(R^4)_2$, $-CO_2R^4$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_{10}$ cycloalkyl, substituted or unsubstituted $C_2$-$C_{10}$ heterocycloalkyl, substituted or unsubstituted aralkyl, substituted or unsubstituted aryl, or substituted or unsubstituted heteroaryl.

In some embodiments, the compound has the structure of Formula (IIb), or a pharmaceutically acceptable salt thereof:

Formula (IIIb)

In some embodiments, the compound disclosed herein has the structure provided in Table 1.

TABLE 1

| Compound No. | Structure | Name |
|---|---|---|
| 1 | 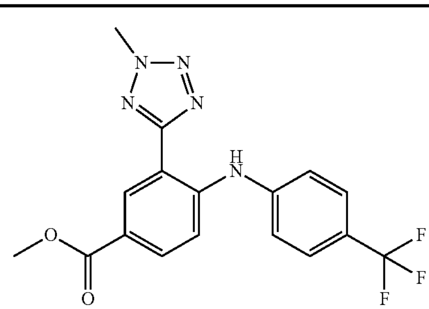 | methyl 3-(2-methyl-2H-tetrazol-5-yl)-4-((4-(trifluoromethyl)phenyl)amino)benzoate |

TABLE 1-continued

| Compound No. | Structure | Name |
|---|---|---|
| 2 | 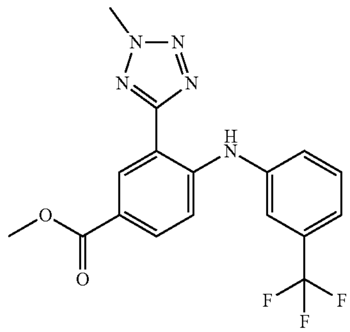 [SMILES: COC(=O)c1ccc(Nc2cccc(C(F)(F)F)c2)c(-c2nnn(C)n2)c1] | methyl 3-(2-methyl-2H-tetrazol-5-yl)-4-((3-(trifluoromethyl)phenyl)amino)benzoate |
| 3 | 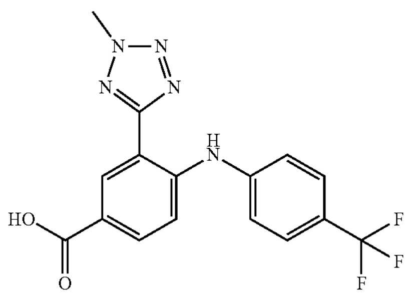 | 3-(2-methyl-2H-tetrazol-5-yl)-4-((4-(trifluoromethyl)phenyl)amino)benzoic acid |
| 4 | 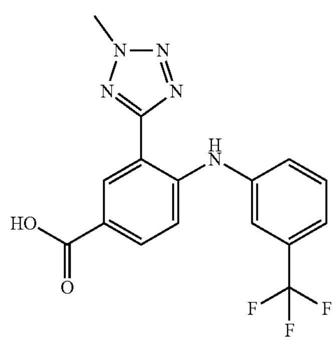 [SMILES: Cn1nnc(-c2cc(C(=O)O)ccc2Nc2cccc(C(F)(F)F)c2)n1] | 3-(2-methyl-2H-tetrazol-5-yl)-4-((3-(trifluoromethyl)phenyl)amino)benzoic acid |
| 5 | 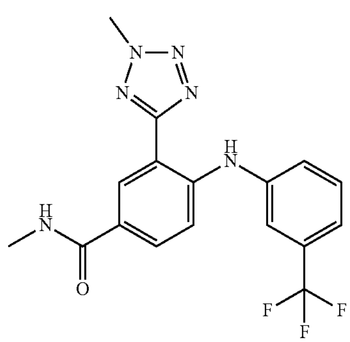 [SMILES: CNC(=O)c1ccc(Nc2cccc(C(F)(F)F)c2)c(-c2nnn(C)n2)c1] | N-methyl-3-(2-methyl-2H-tetrazol-5-yl)-4-((3-(trifluoromethyl)phenyl)amino)benzamide |

TABLE 1-continued

| Compound No. | Structure | Name |
|---|---|---|
| 6 | 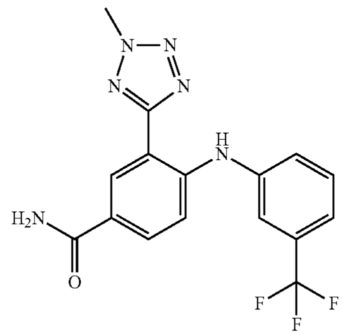 [SMILES: Cn1nnc(-c2cc(C(N)=O)ccc2Nc2cccc(C(F)(F)F)c2)n1] | 3-(2-methyl-2H-tetrazol-5-yl)-4-((3-(trifluoromethyl)phenyl)amino)benzamide |
| 7 | 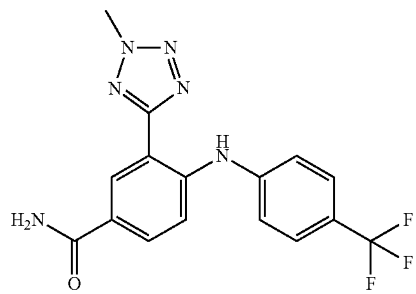 [SMILES: Cn1nnc(-c2cc(C(N)=O)ccc2Nc2ccc(C(F)(F)F)cc2)n1] | 3-(2-methyl-2H-tetrazol-5-yl)-4-((4-(trifluoromethyl)phenyl)amino)benzamide |
| 8 | 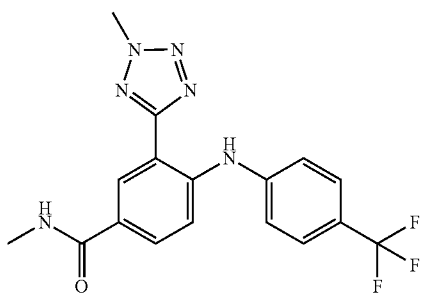 [SMILES: CNC(=O)c1ccc(Nc2ccc(C(F)(F)F)cc2)c(-c2nnn(C)n2)c1] | N-methyl-3-(2-methyl-2H-tetrazol-5-yl)-4-((4-(trifluoromethyl)phenyl)amino)benzamide |
| 9 | 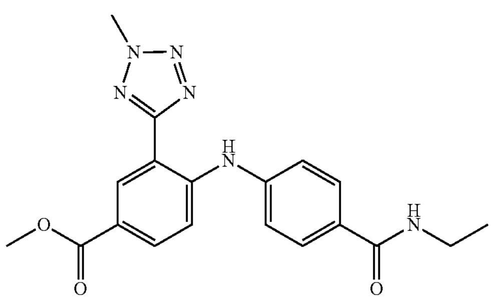 [SMILES: CCNC(=O)c1ccc(Nc2ccc(C(=O)OC)cc2-c2nnn(C)n2)cc1] | methyl 4-((4-(ethylcarbamoyl)phenyl)amino)-3-(2-methyl-2H-tetrazol-5-yl)benzoate |
| 10 | 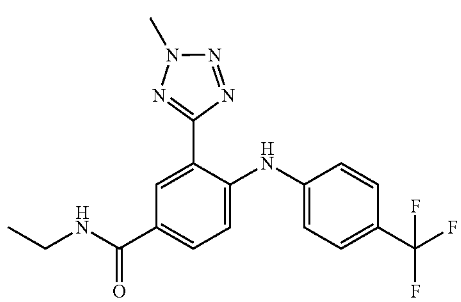 [SMILES: CCNC(=O)c1ccc(Nc2ccc(C(F)(F)F)cc2)c(-c2nnn(C)n2)c1] | N-ethyl-3-(2-methyl-2H-tetrazol-5-yl)-4-((4-(trifluoromethyl)phenyl)amino)benzamide |

TABLE 1-continued

| Compound No. | Structure | Name |
|---|---|---|
| 11 | 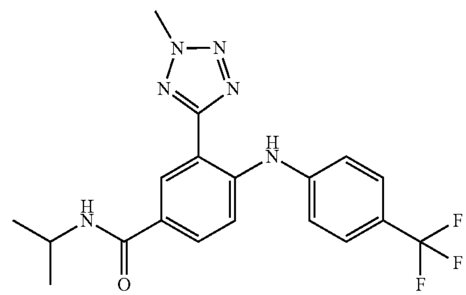 [SMILES: CC(C)NC(=O)c1ccc(Nc2ccc(C(F)(F)F)cc2)c(-c2nnn(C)n2)c1] | N-isopropyl-3-(2-methyl-2H-tetrazol-5-yl)-4-((4-(trifluoromethyl)phenyl)amino)benzamide |
| 12 | 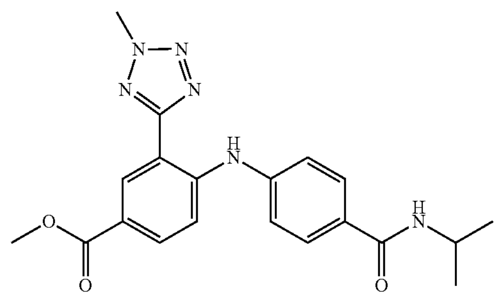 [SMILES: COC(=O)c1ccc(Nc2ccc(C(=O)NC(C)C)cc2)c(-c2nnn(C)n2)c1] | methyl 4-((4-(isopropylcarbamoyl)phenyl)amino)-3-(2-methyl-2H-tetrazol-5-yl)benzoate |
| 13 | 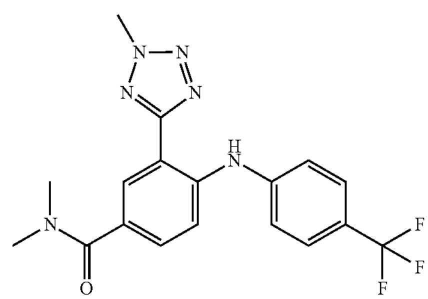 [SMILES: CN(C)C(=O)c1ccc(Nc2ccc(C(F)(F)F)cc2)c(-c2nnn(C)n2)c1] | N,N-dimethyl-3-(2-methyl-2H-tetrazol-5-yl)-4-((4-(trifluoromethyl)phenyl)amino)benzamide |
| 14 | 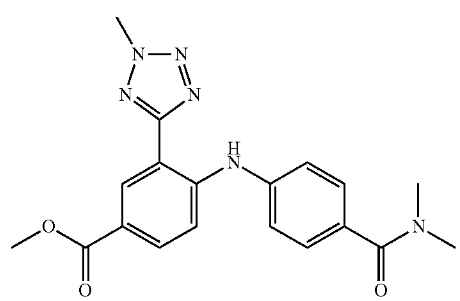 | methyl 4-((4-(dimethylcarbamoyl)phenyl)amino)-3-(2-methyl-2H-tetrazol-5-yl)benzoate |
| 15 | 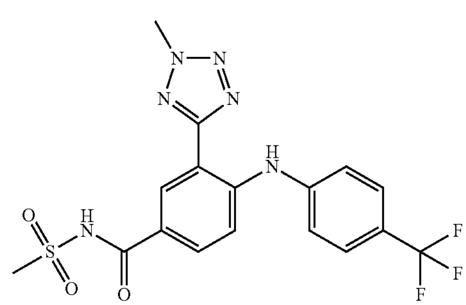 [SMILES: Cn1nnc(-c2cc(C(=O)NS(C)(=O)=O)ccc2Nc2ccc(C(F)(F)F)cc2)n1] | 3-(2-methyl-2H-tetrazol-5-yl)-N-(methylsulfonyl)-4-((4-(trifluoromethyl)phenyl)amino)benzamide |

TABLE 1-continued

| Compound No. | Structure | Name |
|---|---|---|
| 16 | 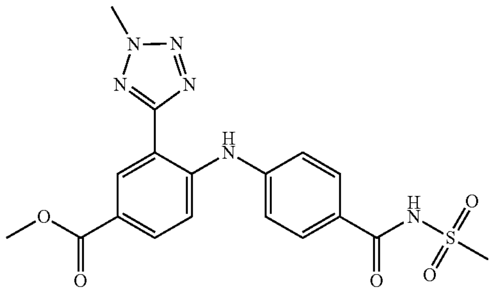 | methyl 3-(2-methyl-2H-tetrazol-5-yl)-4-((4-((methylsulfonyl)carbamoyl)phenyl)amino)benzoate |
| 17 | 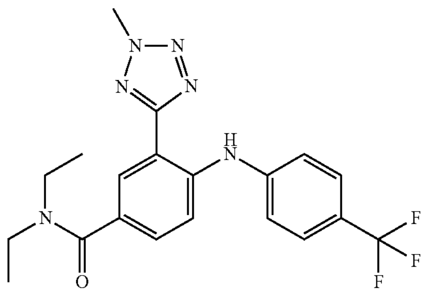 [SMILES: CCN(CC)C(=O)c1ccc(Nc2ccc(C(F)(F)F)cc2)c(-c2nnn(C)n2)c1] | N,N-diethyl-3-(2-methyl-2H-tetrazol-5-yl)-4-((4-(trifluoromethyl)phenyl)amino)benzamide |
| 18 | 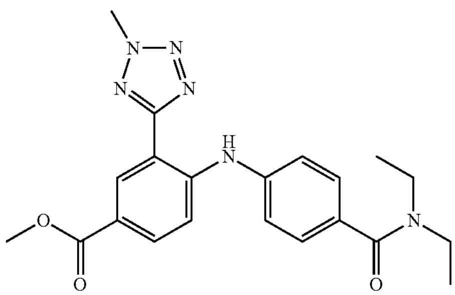 [SMILES: CCN(CC)C(=O)c1ccc(Nc2ccc(C(=O)OC)cc2-c2nnn(C)n2)cc1] | methyl 4-((4-(diethylcarbamoyl)phenyl)amino)-3-(2-methyl-2H-tetrazol-5-yl)benzoate |
| 19 | 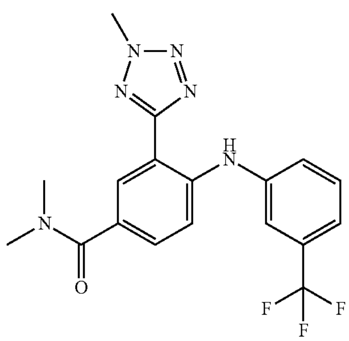 [SMILES: CN(C)C(=O)c1ccc(Nc2cccc(C(F)(F)F)c2)c(-c2nnn(C)n2)c1] | N,N-dimethyl-3-(2-methyl-2H-tetrazol-5-yl)-4-((3-(trifluoromethyl)phenyl)amino)benzamide |
| 20 | 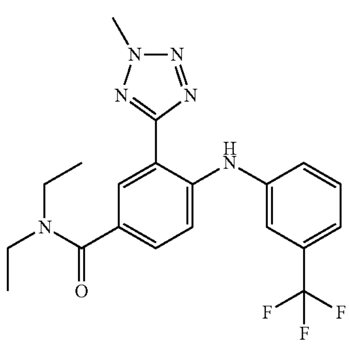 [SMILES: CCN(CC)C(=O)c1ccc(Nc2cccc(C(F)(F)F)c2)c(-c2nnn(C)n2)c1] | N,N-diethyl-3-(2-methyl-2H-tetrazol-5-yl)-4-((3-(trifluoromethyl)phenyl)amino)benzamide |

TABLE 1-continued

| Compound No. | Structure | Name |
|---|---|---|
| 21 | 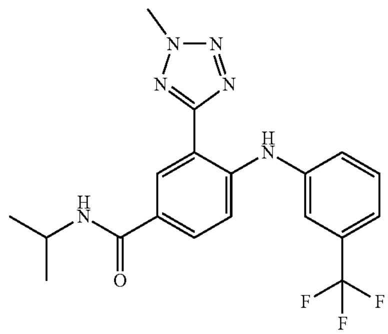 [SMILES: CC(C)NC(=O)c1ccc(Nc2cccc(C(F)(F)F)c2)c(-c2nnn(C)n2)c1] | N-isopropyl-3-(2-methyl-2H-tetrazol-5-yl)-4-((3-(trifluoromethyl)phenyl)amino)benzamide |
| 22 | 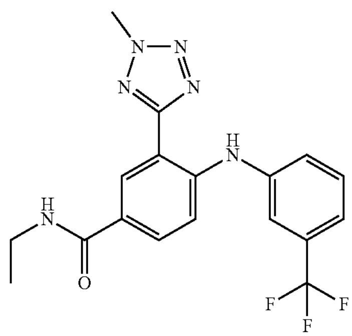 [SMILES: CCNC(=O)c1ccc(Nc2cccc(C(F)(F)F)c2)c(-c2nnn(C)n2)c1] | N-ethyl-3-(2-methyl-2H-tetrazol-5-yl)-4-((3-(trifluoromethyl)phenyl)amino)benzamide |
| 23 | 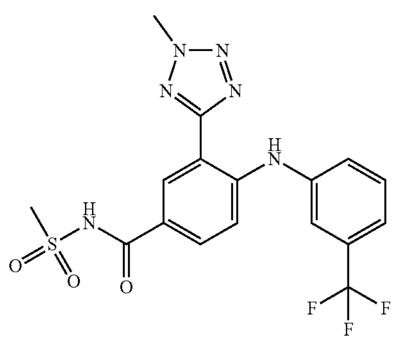 [SMILES: Cn1nnc(-c2cc(C(=O)NS(C)(=O)=O)ccc2Nc2cccc(C(F)(F)F)c2)n1] | 3-(2-methyl-2H-tetrazol-5-yl)-N-(methylsulfonyl)-4-((3-(trifluoromethyl)phenyl)amino)benzamide |
| 24 | 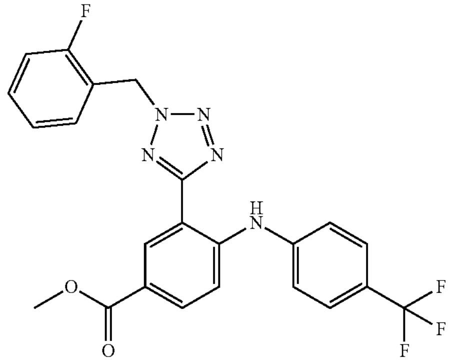 [SMILES: COC(=O)c1ccc(Nc2ccc(C(F)(F)F)cc2)c(-c2nnn(Cc3ccccc3F)n2)c1] | methyl 3-(2-(2-fluorobenzyl)-2H-tetrazol-5-yl)-4-((4-(trifluoromethyl)phenyl)amino)benzoate |

TABLE 1-continued

| Compound No. | Structure | Name |
|---|---|---|
| 25 | 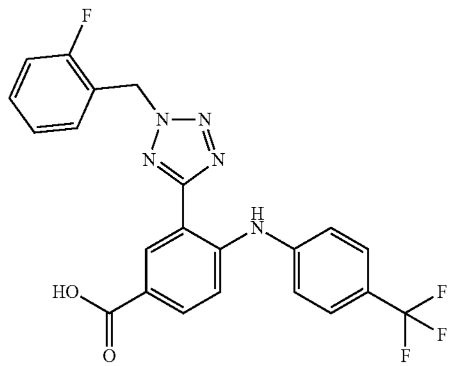 [SMILES: O=C(O)c1ccc(Nc2ccc(C(F)(F)F)cc2)c(-c2nnn(Cc3ccccc3F)n2)c1] | 3-(2-(2-fluorobenzyl)-2H-tetrazol-5-yl)-4-((4-(trifluoromethyl)phenyl)amino)benzoic acid |
| 26 | 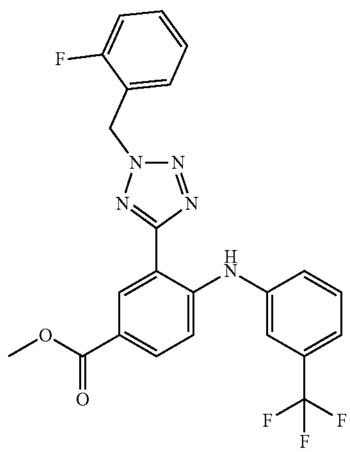 [SMILES: COC(=O)c1ccc(Nc2cccc(C(F)(F)F)c2)c(-c2nnn(Cc3ccccc3F)n2)c1] | methyl 3-(2-(2-fluorobenzyl)-2H-tetrazol-5-yl)-4-((3-(trifluoromethyl)phenyl)amino)benzoate |
| 27 | 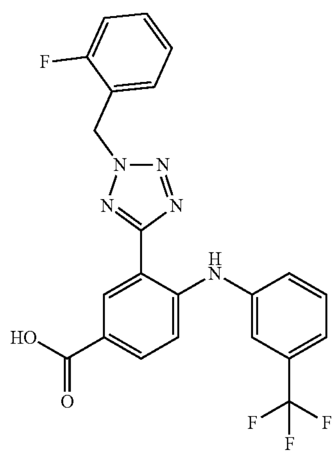 [SMILES: O=C(O)c1ccc(Nc2cccc(C(F)(F)F)c2)c(-c2nnn(Cc3ccccc3F)n2)c1] | 3-(2-(2-fluorobenzyl)-2H-tetrazol-5-yl)-4-((3-(trifluoromethyl)phenyl)amino)benzoic acid |
| 28 | 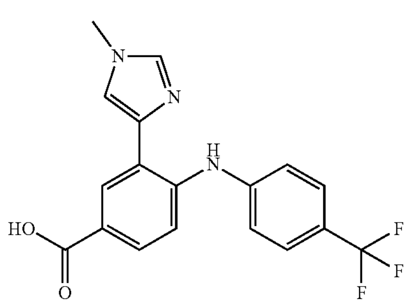 [SMILES: Cn1cnc(-c2cc(C(=O)O)ccc2Nc2ccc(C(F)(F)F)cc2)c1] | 3-(1-methyl-1H-imidazol-4-yl)-4-((4-(trifluoromethyl)phenyl)amino)benzoic acid |

TABLE 1-continued

| Compound No. | Structure | Name |
| --- | --- | --- |
| 29 | 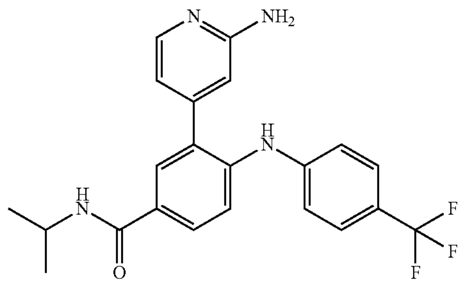 [SMILES: CC(C)NC(=O)c1ccc(Nc2ccc(C(F)(F)F)cc2)c(-c2ccnc(N)c2)c1] | 3-(2-aminopyridin-4-yl)-N-isopropyl-4-((4-(trifluoromethyl)phenyl)amino)benzamide |
| 30 | 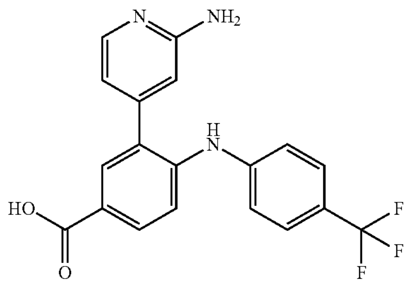 | 3-(2-aminopyridin-4-yl)-4-((4-(trifluoromethyl)phenyl)amino)benzoic acid |
| 31 | 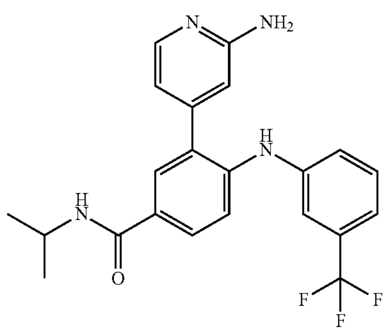 [SMILES: CC(C)NC(=O)c1ccc(Nc2cccc(C(F)(F)F)c2)c(-c2ccnc(N)c2)c1] | 3-(2-aminopyridin-4-yl)-N-isopropyl-4-((3-(trifluoromethyl)phenyl)amino)benzamide |
| 32 | 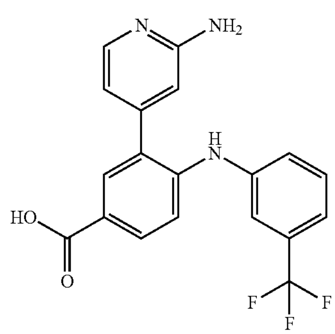 [SMILES: Nc1cc(-c2cc(C(=O)O)ccc2Nc2cccc(C(F)(F)F)c2)ccn1] | 3-(2-aminopyridin-4-yl)-4-((3-(trifluoromethyl)phenyl)amino)benzoic acid |
| 33 | 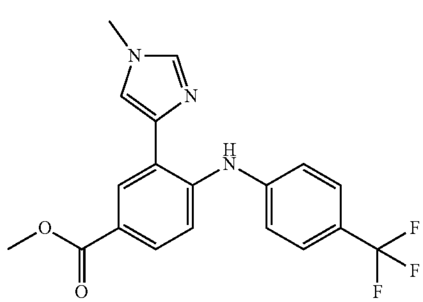 [SMILES: COC(=O)c1ccc(Nc2ccc(C(F)(F)F)cc2)c(-c2cn(C)cn2)c1] | methyl 3-(1-methyl-1H-imidazol-4-yl)-4-((4-(trifluoromethyl)phenyl)amino)benzoate |

TABLE 1-continued

| Compound No. | Structure | Name |
|---|---|---|
| 34 | 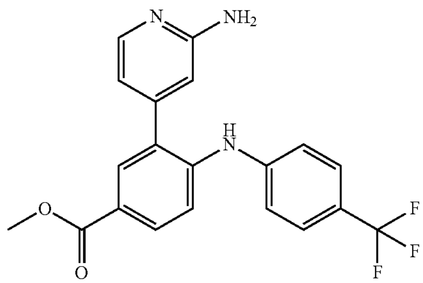 [SMILES: COC(=O)c1ccc(Nc2ccc(C(F)(F)F)cc2)c(-c2ccnc(N)c2)c1] | methyl 3-(2-amino-4-pyridyl)-4-[4-(trifluoromethyl)anilino]benzoate |
| 35 | 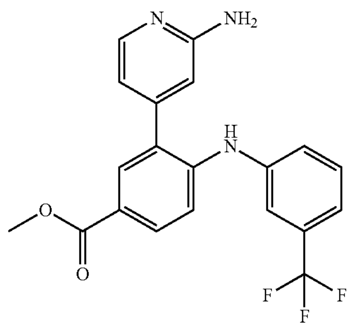 [SMILES: COC(=O)c1ccc(Nc2cccc(C(F)(F)F)c2)c(-c2ccnc(N)c2)c1] | methyl 3-(2-amino-4-pyridyl)-4-[3-(trifluoromethyl)anilino]benzoate |
| 36 | 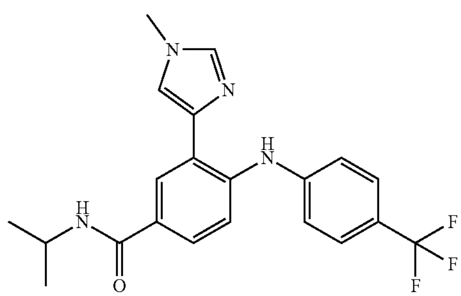 [SMILES: CC(C)NC(=O)c1ccc(Nc2ccc(C(F)(F)F)cc2)c(-c2cn(C)cn2)c1] | N-Isopropyl-3-(-methylimidazol-4-yl)-4-[4-(trifluoromethyl)anilino]benzamide |
| 37 | 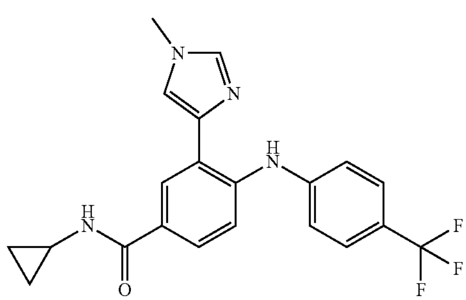 [SMILES: Cn1cnc(-c2cc(C(=O)NC3CC3)ccc2Nc2ccc(C(F)(F)F)cc2)c1] | N-cyclopropyl-3-(1-methylimidazol-4-yl)-4-[4(trifluoromethyl)anilino]benzamide |
| 38 | 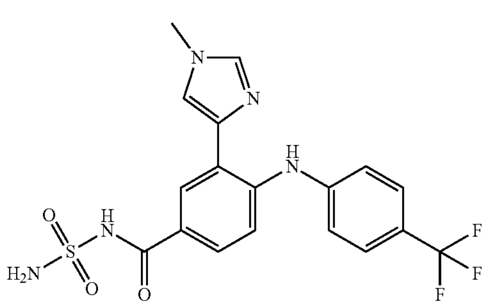 [SMILES: Cn1cnc(-c2cc(C(=O)NS(N)(=O)=O)ccc2Nc2ccc(C(F)(F)F)cc2)c1] | 3-(1-methylimidazol-4-yl)-N-sulfamoyl-4-[4-(trifluoromethyl)anilino]benzamide |

TABLE 1-continued

| Compound No. | Structure | Name |
|---|---|---|
| 39 | 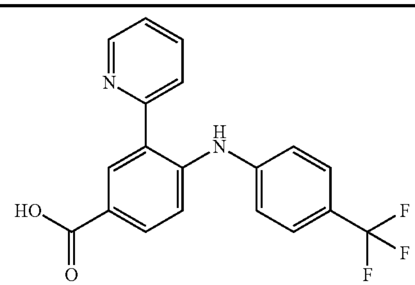 | 3-(pyridin-2-yl)-4-((4-(trifluoromethyl)phenyl)amino)benzoic acid |
| 40 | 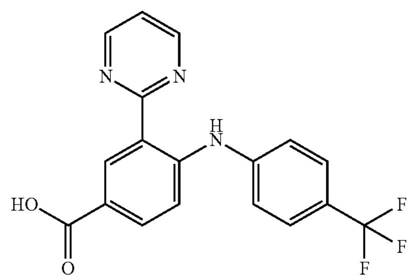 | 3-(pyrimidin-2-yl)-4-((4-(trifluoromethyl)phenyl)amino)benzoic acid |
| 41 | 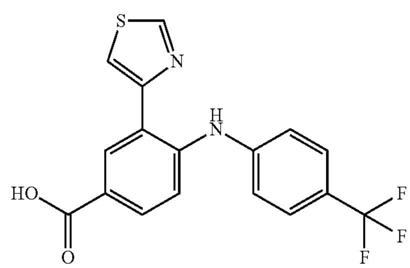 | 3-(thiazol-4-yl)-4-((4-(trifluoromethyl)phenyl)amino)benzoic acid |
| 42 | 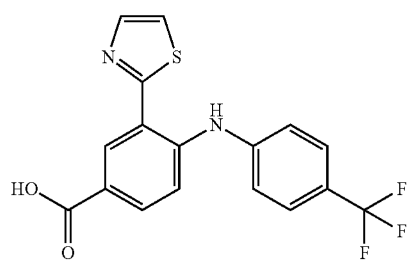 | 3-(thiazol-2-yl)-4-((4-(trifluoromethyl)phenyl)amino)benzoic acid |
| 43 | 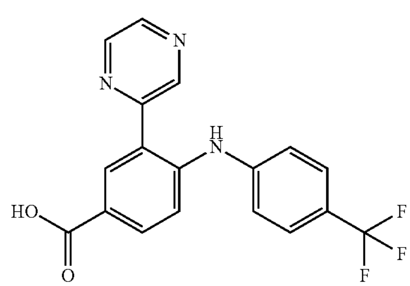 | 3-(pyrazin-2-yl)-4-((4-(trifluoromethyl)phenyl)amino)benzoic acid |
| 44 | 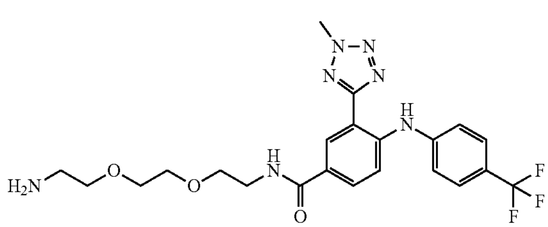 [SMILES: Cn1nnc(-c2cc(C(=O)NCCOCCOCCN)ccc2Nc2ccc(C(F)(F)F)cc2)n1] | N-(2-(2-(2-aminoethoxy)ethoxy)ethyl)-3-(2-methyl-2H-tetrazol-5-yl)-4-((4-(trifluoromethyl)phenyl)amino)benzamide |

TABLE 1-continued

| Compound No. | Structure | Name |
|---|---|---|
| 45 | 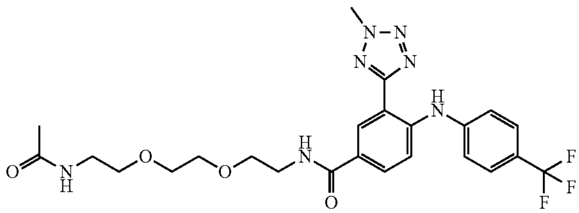 [SMILES: CC(=O)NCCOCCOCCNC(=O)c1ccc(Nc2ccc(C(F)(F)F)cc2)c(-c2nnn(C)n2)c1] | N-(2-(2-(2-acetamidoethoxy)ethoxy)ethyl)-3-(2-methyl-2H-tetrazol-5-yl)-4-((4-(trifluoromethyl)phenyl)amino)benzamide |
| 46 | 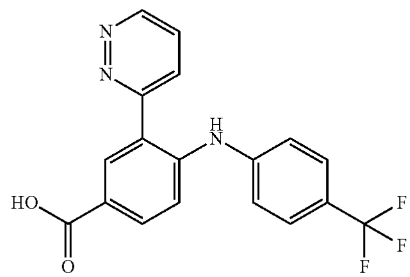 | 3-pyridazin-3-yl-4-[4-(trifluoromethyl)anilino]benzoic acid |
| 47 | 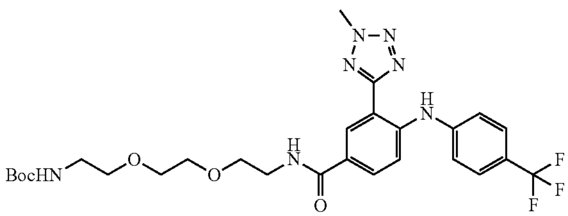 [SMILES: Cn1nnc(-c2cc(C(=O)NCCOCCOCCNC(=O)OC(C)(C)C)ccc2Nc2ccc(C(F)(F)F)cc2)n1] | tert-butyl (2-(2-(2-(3-(2-methyl-2H-tetrazol-5-yl)-4-((4-(trifluoromethyl)phenyl)amino)benzamido)ethoxy)ethoxy)ethyl)carbamate |
| 48 | 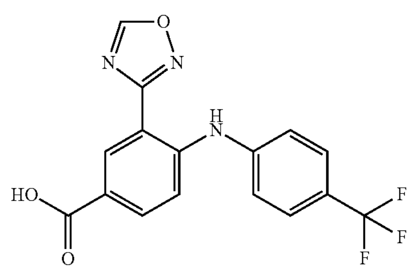 [SMILES: O=C(O)c1ccc(Nc2ccc(C(F)(F)F)cc2)c(-c2ncon2)c1] | 3-(1,2,4-oxadiazol-3-yl)-4-[4-(trifluoromethyl)anilino]benzoic acid |
| 49 | 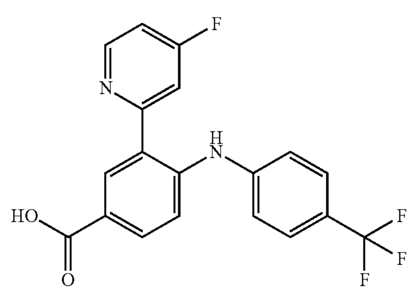 | 3-(4-fluoro-2-pyridyl)-4-[4-(trifluoromethyl)anilino]benzoic acid |
| 50 | 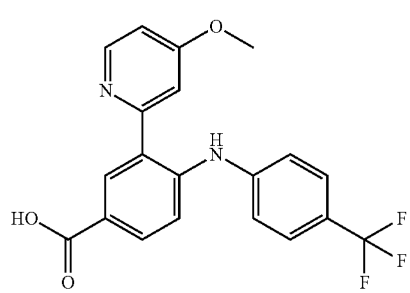 | 3-(pyrazin-2-yl)-4-((4-(trifluoromethyl)phenyl)amino)benzoic acid |

TABLE 1-continued

| Compound No. | Structure | Name |
|---|---|---|
| 51 | 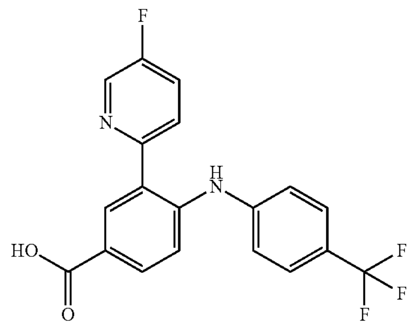 | 3-(5-fluoro-2-pyridyl)-4-[4-(trifluoromethyl)anilino] benzoic acid |
| 52 | 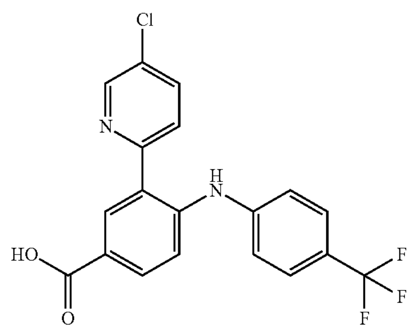 | 3-(5-chloro-2-pyridyl)-4-[4 (trifluoromethyl)anilino] benzoic acid |
| 53 | 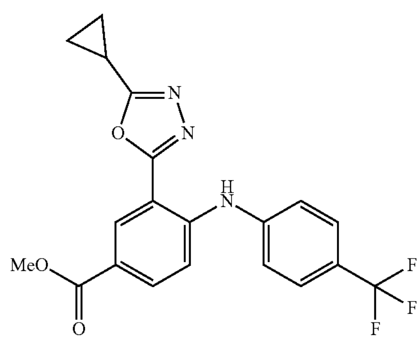 [SMILES: COC(=O)c1ccc(Nc2ccc(C(F)(F)F)cc2)c(-c2nnc(C3CC3)o2)c1] | methyl 3-(5-cyclopropyl-1,3,4-oxadiazol-2-yl)-4-((4-(trifluoromethyl)phenyl) amino)benzoate |
| 54 | 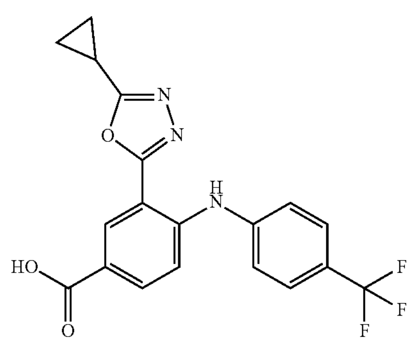 | 3-(5-cyclopropyl-1,3,4-oxadiazol-2-yl)-4-((4-(trifluoromethyl)phenyl)amino) benzoic acid |

TABLE 1-continued

| Compound No. | Structure | Name |
|---|---|---|
| 55 | 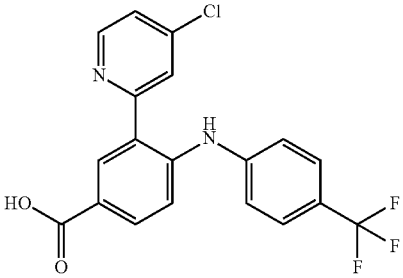 | 3-(4-chloro-2-pyridyl)-4-[4-(trifluoromethyl)anilino]benzoic acid |
| 56 | 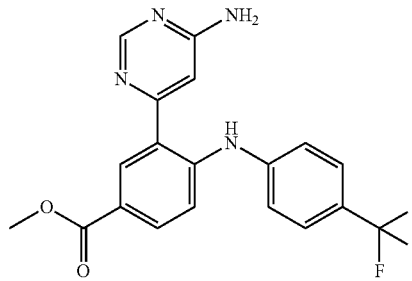 | methyl 3-(6-aminopyrimidin-4-yl)-4-[4-(trifluoromethyl)anilino]benzoate |
| 57 | 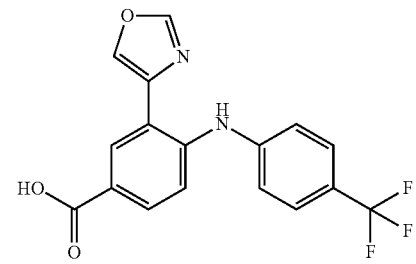 | 3-(oxazol-4-yl)-4-((4-(trifluoromethyl)phenyl)amino)benzoic acid |
| 58 | 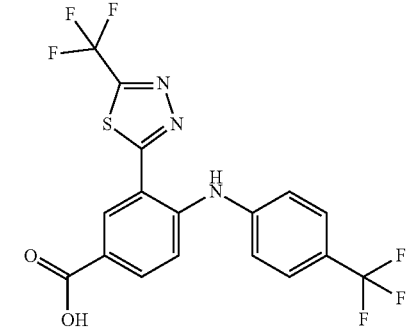 [SMILES: O=C(O)c1ccc(Nc2ccc(C(F)(F)F)cc2)c(-c2nnc(C(F)(F)F)s2)c1] | 4-[4-(trifluoromethyl)anilino]-3-[5-(trifluoromethyl)-1,3,4-thiadiazol-2-yl]benzoic acid |
| 59 | 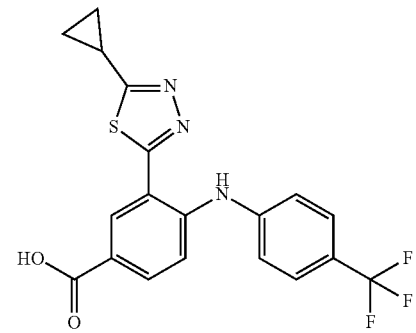 | 3-(5-cyclopropyl-1,3,4-thiadiazol-2-yl)-4-((4-(trifluoromethyl)phenyl)amino)benzoic acid |

TABLE 1-continued

| Compound No. | Structure | Name |
|---|---|---|
| 60 | 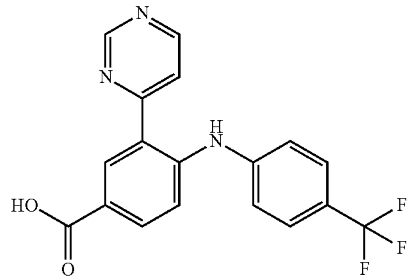 | 3-pyrimidin-4-yl-4-[4-(trifluoromethyl)anilino]benzoic acid |
| 61 | 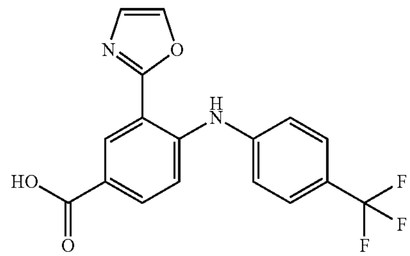 | 3-(oxazol-2-yl)-4-((4-(trifluoromethyl)phenyl)amino)benzoic acid |
| 62 | 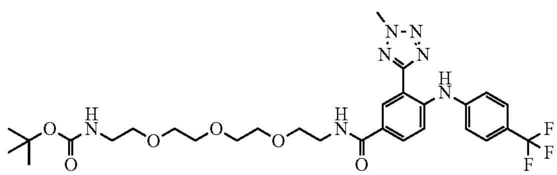 [SMILES: Cn1nnc(-c2cc(C(=O)NCCOCCOCCOCCNC(=O)OC(C)(C)C)ccc2Nc2ccc(C(F)(F)F)cc2)n1] | tert-butyl (1-(3-(2-methyl-2H-tetrazol-5-yl)-4-((4-(trifluoromethyl)phenyl)amino)phenyl)-1-oxo-5,8,11-trioxa-2-azatridecan-13-yl)carbamate |
| 63 | 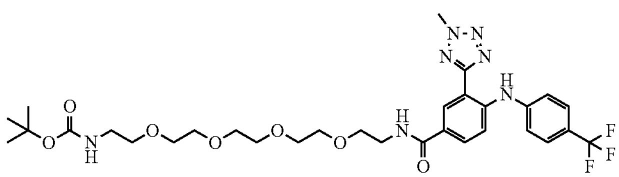 [SMILES: Cn1nnc(-c2cc(C(=O)NCCOCCOCCOCCOCCNC(=O)OC(C)(C)C)ccc2Nc2ccc(C(F)(F)F)cc2)n1] | tert-butyl (1-(3-(2-methyl-2H-tetrazol-5-yl)-4-((4-(trifluoromethyl)phenyl)amino)phenyl)-1-oxo-5,8,11,14-tetraoxa-2-azahexadecan-16-yl)carbamate |
| 64 | 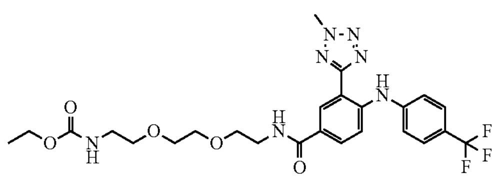 [SMILES: CCOC(=O)NCCOCCOCCNC(=O)c1ccc(Nc2ccc(C(F)(F)F)cc2)c(-c2nnn(C)n2)c1] | 3-(2-methyl-2H-tetrazol-5-yl)-N-(4-oxo-2,8,11-trioxa-5-azatridecan-13-yl)-4-((4-(trifluoromethyl)phenyl)amino)benzamide |
| 65 | 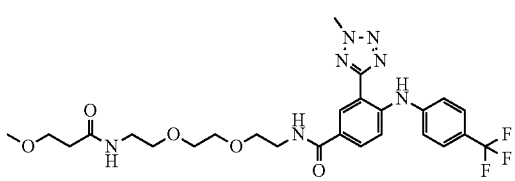 [SMILES: COCCC(=O)NCCOCCOCCNC(=O)c1ccc(Nc2ccc(C(F)(F)F)cc2)c(-c2nnn(C)n2)c1] | 3-(2-methyl-2H-tetrazol-5-yl)-N-(5-oxo-2,9,12-trioxa-6-azatetradecan-14-yl)-4-((4-(trifluoromethyl)phenyl)amino)benzamide |

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; 1. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some instances, specific and analogous reactants are identified through the indices of known chemicals prepared by the Chemical Abstract Service of the American Chemical Society, which are available in most public and university libraries, as well as through on-line databases (the American Chemical Society, Washington, D.C., is contacted for more details). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds disclosed herein are prepared as described in the Examples section.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. In some embodiments, examples of isotopes that are incorporated into compounds of the disclosure include isotopes of hydrogen, carbon, nitrogen, oxygen, phosphorous, sulfur, fluorine, and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvates, hydrates, or derivatives thereof which contain the aforementioned isotopes and/or other isotopes of other atoms are within the scope of this disclosure. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In some embodiments, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three, or four) amino acid residues is covalently joined through an amide or ester bond to a free amino, hydroxy, or carboxylic acid group of compounds of the present disclosure. The amino acid residues include, but are not limited to, the 20 naturally occurring amino acids and also include 4-hydroxyproline, hydroxylysine, demosine, isodemosine, 3-methylhistidine, norvaline, beta-alanine, gamma-aminobutyric acid, citrulline, homocysteine, homoserine, ornithine, and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including, but not limited to, ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, sulfonate esters, sulfate esters and disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine-derived prodrugs include, but are not limited to, the following groups and combinations of groups:

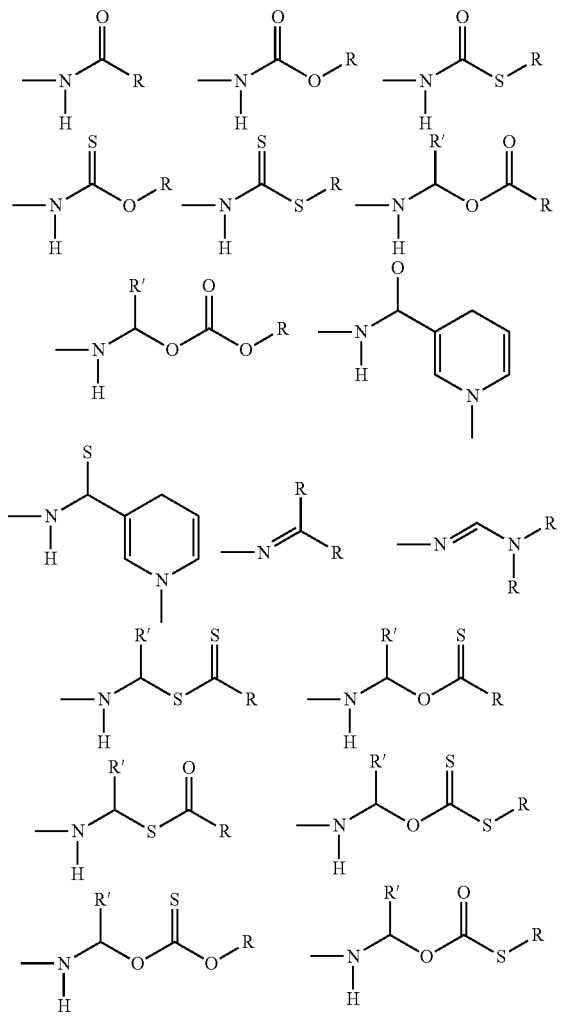

-continued

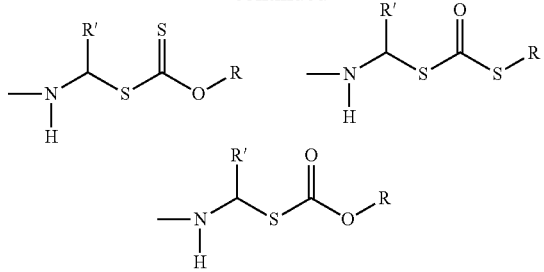

as well as sulfonamides and phosphonamides.

In certain instances, sites on any aromatic ring portions are susceptible to various metabolic reactions, therefore incorporation of appropriate substituents on the aromatic ring structures reduce, minimize, or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen or an alkyl group.

In additional or further embodiments, the compounds described herein are metabolized upon administration to an organism in need to produce a metabolite that is then used to produce a desired effect, including a desired therapeutic effect.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one compound described herein, or a stereoisomer, pharmaceutically acceptable salt, hydrate, solvate, or N-oxide thereof, together with one or more pharmaceutically acceptable carriers. The carrier(s)(or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and any one of the compounds disclosed herein or a pharmaceutically acceptable salt thereof.

Another embodiment provides a pharmaceutical composition consisting essentially of a pharmaceutically acceptable carrier and any one of the compounds disclosed herein, or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

In some instances, exemplary pharmaceutical compositions are used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets in some instances, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions also comprise buffering agents in some embodiments. Solid compositions of a similar type are also employed as fillers in soft and hard-filled gelatin capsules using such excipients as lactose or milk sugars, as well as high molecular weight polyethylene glycols and the like.

In some instances, a tablet is made by compression or molding, optionally with one or more accessory ingredients.

Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the subject composition moistened with an inert liquid diluent. Tablets, and other solid dosage forms, such as dragees, capsules, pills and granules, are optionally be scored or prepared with coatings and shells, such as enteric coatings and other coatings well known in the pharmaceutical-formulating art.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, the liquid dosage forms contain optionally inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, optionally contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches, and inhalants. The active component is optionally mixed under sterile conditions with a pharmaceutically acceptable carrier, and with any preservatives, buffers, or propellants which are required in some embodiments.

In some embodiments, the ointments, pastes, creams, and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. Sprays additionally contain customary propellants, such as chlorofluorohydrocarbons and volatile unsubstituted hydrocarbons, such as butane and propane.

Compositions and compounds disclosed herein are alternatively administered by aerosol. This is accomplished by preparing an aqueous aerosol, liposomal preparation, or solid particles containing the compound. A non-aqueous (e.g., fluorocarbon propellant) suspension could be used.

Sonic nebulizers are used because they minimize exposing the agent to shear, which result in degradation of the compounds contained in the subject compositions in some embodiments. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids, such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which optionally contain antioxidants, buffers, bacteriostats, solutes which render the formulation isotonic with the blood of the intended recipient or suspending or thickening agents.

Examples of suitable aqueous and non-aqueous carriers employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. In some embodiments, proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5, and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methylacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure will recognize that it is not comprehensive and that there are other enteric materials that meet the objectives of the present disclosure.

In some embodiments, the dose of the composition comprising at least one compound as described herein differ, depending upon the patient's (e.g., human) condition, that is, stage of the disease, general health status, age, and other factors that a person skilled in the medical art will use to determine dose.

In some instances, pharmaceutical compositions are administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

In some embodiments, oral doses typically range from about 1.0 mg to about 1000 mg, one to four times, or more, per day.

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1) (FIG. 1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in *Drosophila*), Lats1/2 (homologues of Warts/Wts), and their adaptor proteins Sav1 (homologue of Salvador/Sav) and Mob (MOBKL1A and MOBKL1B; homologues of Mats), respectively (FIG. 1). In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP atone or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ p rimes both proteins for further phosphorylation events by CK1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the 589 position thereby disrupts its interaction with 14-3-3 and subsequently promotes nuclear translocation.

In some embodiments, phosphorylated YAP/TAZ accumulates in the cytoplasm, and undergoes $SCF^{\beta\text{-}TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein 1A (FBXW1A, βTrCP1, Fbxw1, hsSlimb, p1kappaBalpha-E3 receptor subunit) and S-phase kinase-associated proteins 2 (SKP2). In some embodiments, the SCF complex (e.g. $SCF^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, URA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE21, UBE2J1, UBE2J2, UBE2K, $UBE2L^3$, $UBE2L^6$, UBE2 M, UBE2N, UBE20, UBE2Q1, UBE2Q2, $UBE2R^1$, $UBE2R^2$, UBE2S, UBE2T, UBE2U, UBE2V1, UBE2V2, UBE2Z, ATG2, BIRC5, and UFC1. In some embodiments, the ubiquitinated YAP/TAZ further undergoes the degradation process through the 26S proteasome.

In some embodiments, the Hippo pathway is regulated upstream by several different families of regulators (FIG. 1). In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g. TEAD1, TEAD2, TEAD3, or TEAD4) to activate genes involved in anti-apoptosis and proliferation, such as for example CTFG, Cyr61, and FGF1.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

YAP/TAZ Regulation Mediated by G-Proteins/GPCRs

Figure 2:
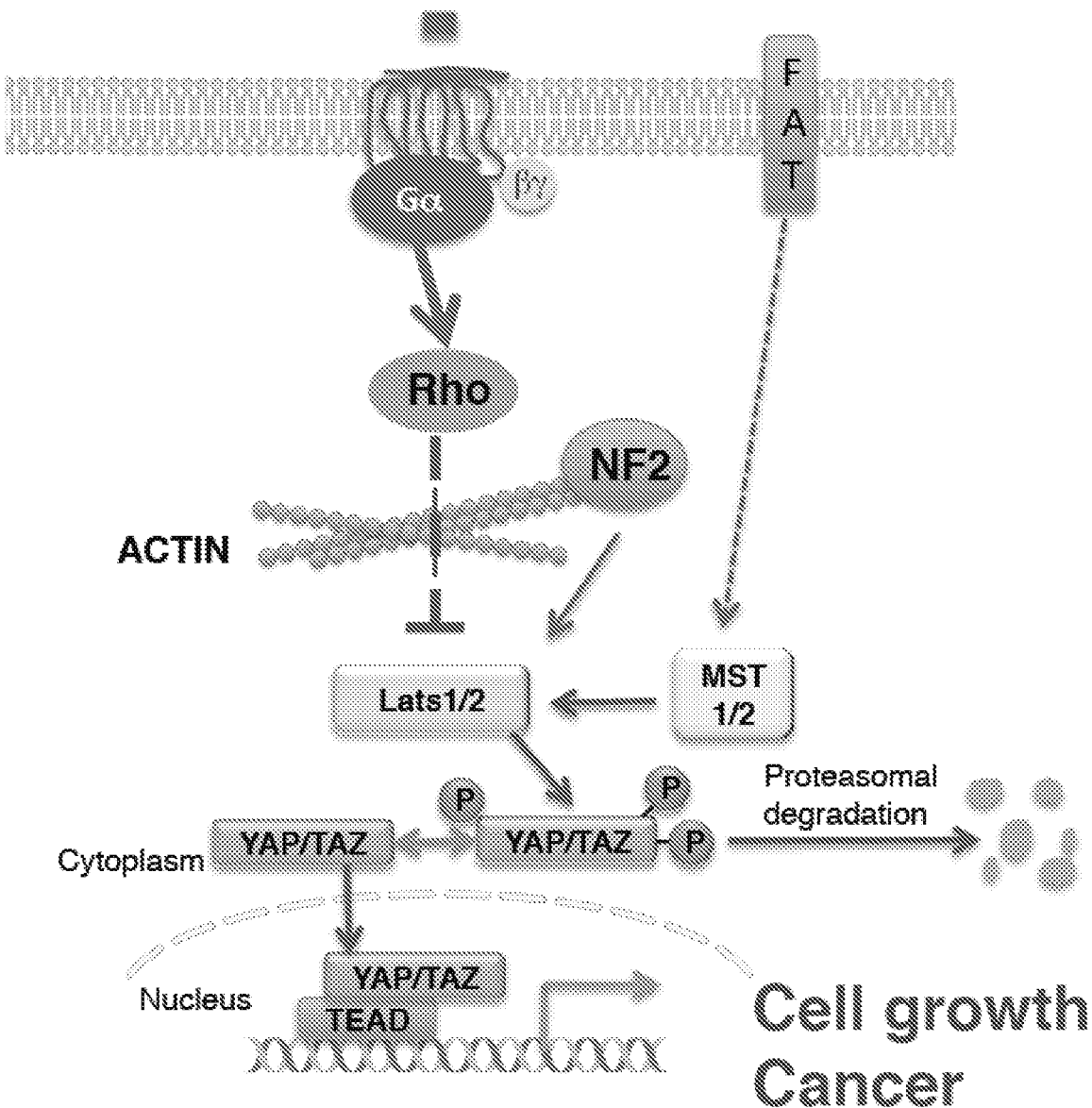
FIG. 2 illustrates a schematic representation of the Hippo signaling pathway regulated by G alpha proteins.

In some embodiments, the Hippo pathway is regulated by the G protein-coupled receptor (GPCR) and G protein (also known as guanine nucleotide-binding proteins) family of proteins (FIG. 2). G proteins are molecular switches that transmit extracellular stimuli into the cell through GPCRs. In some instances, there are two classes of G proteins: monomeric small GTPases and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, $G_i\alpha$ (G inhibitory), $G_o\alpha$ (G other), $G_{q/11}\alpha$, and $G_{12/13}\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate ($IP_3$) signal transduction pathway and calcium ($Ca^{2+}$) release from intracellular storage through the activation of phospholipase C (PLC). The activated PLC hydrolyzes phosphatidylinositol 4,5-bisphosphate ($PIP_2$) to diacyl glycerol (DAG) and $IP_3$. In some instances, $IP_3$ then diffuses through the cytoplasm into the ER or the sarcoplasmic reticulum (SR) in the case of muscle cells, and then binds to inositol trisphosphate receptor (InsP3R), which is a $Ca^{2+}$ channel. In some cases, the binding triggers the opening of the $Ca^{2+}$ channel, and thereby increases the release of $Ca^{2+}$ into the cytoplasm.

In some embodiments, the GPCRs that interact with $G_q\alpha$ include, but are not limited to, 5-hydroxytryptamine receptor (5-HT receptor) types $5-HT_2$ and $5-HT_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors $M_1$, $M_3$, and $M_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12/13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g. Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g. $P2Y_1$, $P2Y_2$, $P2Y_4$, $P2Y_6$); muscarinic acetylcholine receptors M1 and M3; receptors for thrombin [protease-activated receptor (PAR)-1, PAR-2]; thromboxane (TXA2); sphingosine 1-phosphate (e.g. $SIP_2$, $SIP_3$, $SIP_4$ and $SIP_5$); lysophosphatidic acid (e.g. $LPA_1$, $LPA_2$, $LPA_3$); angiotensin II (AT1); serotonin ($5-HT_{2c}$, and $5-HT_4$); somatostatin ($sst_5$); endothelin ($ET_A$ and $ET_B$); cholecystokinin ($CCK_1$); Via vasopressin receptors; $D_5$ dopamine receptors; fMLP formyl peptide receptors; $GAL_2$ galanin receptors; $EP_3$ prostanoid receptors; $A_1$ adenosine receptors; $\alpha_1$ adrenergic receptors; $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other) (also known as $G_i/G_0$ or $G_i$ protein) suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_i\alpha$ include, but are not limited to, 5-hydroxytryptamine receptor (5-HT receptor) types $5-HT_1$ and $5-HT_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP);

somatostatin receptors sst1, sst2, sst3, sst4, and sst5; and trace amine-associated receptor 8.

In some instances, there are several types of $G_i\alpha$: $G_i\alpha1$, $G_i\alpha2$, $G_i\alpha3$, $G_i\alpha4$, $G_o\alpha$, $G_t$, $G_{gust}$ and $G_z$. $G_i\alpha1$ is encoded by GNAI1. $G_i\alpha2$ is encoded by GNA12. $G_i\alpha3$ is encoded by GNAI3. $G_o\alpha$, the $a_o$ subunit, is encoded by GNAQO1. $G_t$ is encoded by GNAT1 and GNAT2. $G_{gust}$ is encoded by GNAT3. $G_z$ is encoded by GNAZ.

$G_s$ Family $G_s\alpha$ (also known as G stimulatory, G, alpha subunit, or G, protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types $5-HT_4$, $5-HT_6$, and $5-HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $β_1$, $β_2$, and $β_3$; calcitonin receptor; calcitonin gene-related peptide receptor; corticotropin-releasing hormone receptor; dopamine receptor D-like family receptors such as $D_1$ and $D_5$; follicle-stimulating hormone receptor (FSH-receptor); gastric inhibitory polypeptide receptor; glucagon receptor; histamine H2 receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein α-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some instances, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZIYAP).

In some embodiments, the compounds disclosed herein are inhibitors of one or more of the proteins encompassed by, or related to, the Hippo pathway. In some instances, the one or more proteins comprise a protein shown in FIGS. 1 and/or 2. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g. 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

Further embodiments provided herein include combinations of one or more of the particular embodiments set forth above.

Diseases

Cancer

In some embodiments, the compounds disclosed herein are useful for treating cancer. In some embodiments, the cancer is mediated by activation of transcriptional coactivator with PDZ binding motif/Yes-associated protein transcription coactivator (TAZ/YAP). In some embodiments, the cancer is mediated by modulation of the interaction of YAP/TAZ with TEAD.

In some embodiments, the cancer is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is $G_q$. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the cancer is a solid tumor. In some instances, the cancer is a hematologic malignancy. In some instances, the solid tumor is a sarcoma or carcinoma. In some instances, the solid tumor is a sarcoma. In some instances, the solid tumor is a carcinoma.

Exemplary sarcoma includes, but is not limited to, alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extra renal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epithelioid cell differentiation, osteosarcoma, periosteal osteosarcoma, neoplasm with perivascular epithelioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

Exemplary carcinoma includes, but is not limited to, adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer. In some instances, the liver cancer is primary liver cancer.

In some instances, the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the cancer is uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the cancer is uveal melanoma, mesothelioma, esophageal cancer, or liver cancer. In some cases, the cancer is uveal melanoma. In some cases, the cancer is mesothelioma. In some cases, the cancer is esophageal cancer. In some cases, the cancer is liver cancer. In some cases, the cancer is primary liver cancer.

In some instances, the cancer is a hematologic malignancy. In some embodiments, the hematologic malignancy is a leukemia, a lymphoma, a myeloma, a non-Hodgkin's lymphoma, a Hodgkin's lymphoma, a T-cell malignancy, or a B-cell malignancy. In some instances, the hematologic malignancy is a T-cell malignancy. Exemplary T-cell malignancy includes, but is not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, and treatment-related T-cell lymphomas.

In some instances, the hematologic malignancy is a B-cell malignancy. Exemplary B-cell malignancy includes, but is not limited to, chronic lymphocytic leukemia (CLL), small lymphocytic lymphoma (SLL), high risk CLL, and a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a relapsed or refractory cancer. In some embodiments, the relapsed or refractory cancer is a relapsed or refractory solid tumor. In some embodiments, the relapsed or refractory solid tumor is a relapsed or refractory sarcoma or a relapsed or refractory carcinoma. In some embodiments, the relapsed or refractory carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the relapsed or refractory cancer is selected from relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the relapsed or refractory cancer is relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the relapsed or refractory cancer is relapsed or refractory uveal melanoma, mesothelioma, esophageal cancer, or liver cancer. In some cases, the relapsed or refractory cancer is relapsed or refractory uveal melanoma. In some cases, the relapsed or refractory cancer is relapsed or refractory mesothelioma. In some cases, the relapsed or refractory cancer is relapsed or refractory esophageal cancer. In some cases, the relapsed or refractory cancer is relapsed or refractory liver cancer. In some cases, the relapsed or refractory cancer is relapsed or refractory primary liver cancer.

In some instances, the relapsed or refractory cancer is a relapsed or refractory hematologic malignancy. In some embodiments, the relapsed or refractory hematologic malignancy is a relapsed or refractory leukemia, a relapsed or refractory lymphoma, a relapsed or refractory myeloma, a relapsed or refractory non-Hodgkin's lymphoma, a relapsed or refractory Hodgkin's lymphoma, a relapsed or refractory T-cell malignancy, or a relapsed or refractory B-cell malignancy. In some instances, the relapsed or refractory hematologic malignancy is a relapsed or refractory T-cell malignancy. In some instances, the relapsed or refractory hematologic malignancy is a relapsed or refractory B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a metastasized cancer. In some instances, the metastasized cancer is a metastasized solid tumor. In some instances, the metastasized solid tumor is a metastasized sarcoma or a metastasized carcinoma. In some embodiments, the metastasized carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the metastasized cancer is metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the metastasized cancer is metastasized uveal melanoma, mesothelioma, esophageal cancer, or liver cancer. In some cases, the metastasized cancer is metastasized uveal melanoma. In some cases, the metastasized cancer is metastasized mesothelioma. In some cases, the metastasized cancer is metastasized esophageal cancer. In some cases, the metastasized cancer is metastasized liver cancer. In some cases, the metastasized cancer is metastasized primary liver cancer.

In some instances, the metastasized cancer is a metastasized hematologic malignancy. In some embodiments, the metastasized hematologic malignancy is a metastasized leukemia, a metastasized lymphoma, a metastasized myeloma, a metastasized non-Hodgkin's lymphoma, a metastasized Hodgkin's lymphoma, a metastasized T-cell malignancy, or a metastasized B-cell malignancy. In some instances, a metastasized hematologic malignancy is a metastasized T-cell malignancy. In some instances, a metastasized hematologic malignancy is a metastasized B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Congenital Diseases

In some embodiments, the compounds disclosed herein are useful for treating a congenital disease. In some embodiments, the congenital disease is mediated by activation of transcriptional coactivator with PDZ binding motif/Yes-associated protein transcription coactivator (TAZ/YAP). In some embodiments, the congenital disease is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the congenital disease is the result of a genetic abnormality, an intrauterine environment, errors related to morphogenesis, infection, epigenetic modifications on a parental germline, or a chromosomal abnormality. Exemplary congenital diseases include, but are not limited to, Sturge-Weber Syndrome, Port-Wine stain, Holt-Oram syndrome, abdominal wall defects, Becker muscular dystrophy (BMD), biotinidase deficiency, Charcot-Marie-Tooth (CMT), cleft lip, cleft palate, congenital adrenal hyperplasia, congenital heart defects, congenital hypothyroidism, congenital muscular dystrophy, cystic fibrosis, Down syndrome, Duchenne muscular dystrophy, Fragile X syndrome, Friedreich's ataxia, galactosemia, hemoglobinopathies, Krabbe disease, limb-girdle muscular dystrophy, medium chain acyl-CoA dehydrogenase deficiency, myasthenia gravis, neural tube defects, phenylketonuria, Pompe disease, severe combined immunodeficiency (SCID), Stickler syndrome (or hereditary progressive arthro-ophthalmopathy), spinal muscular atrophy, and trisomy 18. In some embodiments, the congenital disease is Sturge-Weber Syndrome or Port-Wine stain. In some embodiments, the congenital disease is Sturge-Weber Syndrome. In some embodiments, the congenital disease is Port-Wine stain.

EXAMPLES

These examples are provided for illustrative purposes only and not to limit the scope of the claims provided herein.

LIST OF ABBREVIATIONS

As used above, and throughout the disclosure, the following abbreviations, unless otherwise indicated, shall be understood to have the following meanings:

| ACN or MeCN | acetonitrile |
|---|---|
| Bn | benzyl |
| BOC or Boc | tert-butyl carbamate |
| t-Bu | tert-butyl |
| Cy | cyclohexyl |

-continued

| DBA | dibenzylideneacetone |
|---|---|
| DCE | dichloroethane (ClCH$_2$CH$_2$Cl) |
| DCM | dichloromethane (CH$_2$Cl$_2$) |
| DIPEA or DIEA | diisopropylethylamine |
| DMAP | 4-(N,N-dimethylamino)pyridine |
| DMF | dimethylformamide |
| DMA | N;N-dimethylacetamide |
| DMSO | dimethylsulfoxide |
| Dppf or dppf | 1,1'-bis(diphenylphosphinWerrocene |
| eq | equivalent(s) |
| Et | ethyl |
| Et$_2$O | diethyl ether |
| EtOH | ethanol |
| EtOAc | ethyl acetate |
| HPLC | high performance liquid chromatography |
| LAR | lithium aluminum anhydride |
| LCMS | liquid chromatography mass spectrometry |
| Me | methyl |
| MeOH | methanol |
| MS | mass spectroscopy |
| NMM | N-methyl-morpholine |
| NMP | N-methyl-pyrrolidin-2-one |
| NW_ | nuclear magnetic resonance |
| RP-HPLC | reverse phase-high pressure liquid chromatography |
| TFA | trifluoroacetic acid |
| THF | tetrahydrofuran |
| TLC | thin layer chromatography |

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times were approximate and were not optimized. Column chromatography and thin layer chromatography (TLC) were performed on silica gel unless otherwise noted.

Example 1: Methyl 3-(2-methyltetrazol-S-yl)-4-[4-(trifluoromethyl)anilino]benzoate (Compound 1)

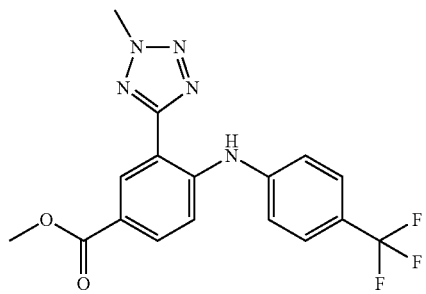 [SMILES: COC(=O)c1ccc(Nc2ccc(C(F)(F)F)cc2)c(-c2nnn(C)n2)c1]

Preparation of Compound 1

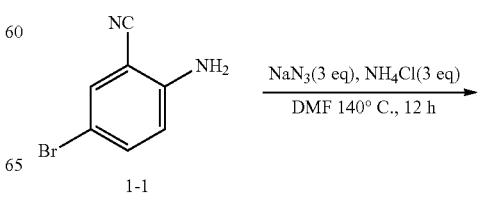

1-1

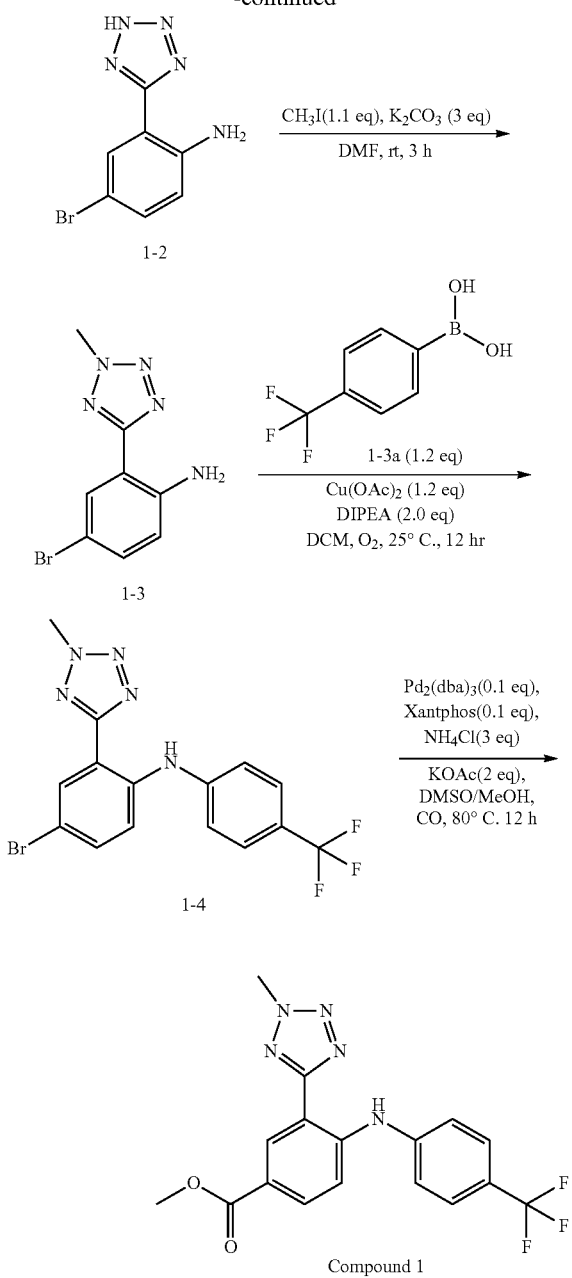

Step 1: 4-bromo-2-(2H-tetrazol-5-yl)aniline

To a solution of compound 1-1 (5 g, 25.38 mmol, 1 eq) in DMF (20 mL) were added NaN₃ (4.89 g, 75.22 mmol, 2.96 eq) and NH₄Cl (4.07 g, 76.13 mmol, 3 eq). The mixture was stirred at 140° C. for 16 hr. The reaction was monitored by LCMS. LCMS showed that the main peak was the desired MS. The reaction solution was added to H₂O (100 mL). The aqueous phase was adjusted to pH=5 and extracted with ethyl acetate (50 mL*3). The combined organic phase was washed with brine (50 mL*5), dried with anhydrous Na₂SO₄, filtered, and concentrated in vacuum. The residue was used the next step without purification. Compound 1-2 (3.3 g, crude).

Step 2: 4-bromo-2-(2-methyltetrazol-5-yl)aniline

To a solution of compound 1-2 (6.6 g, 27.49 mmol, 1 eq) in DMF (30 mL) were added CH₃I (8.63 g, 60.80 mmol, 3.79 mL, 2.21 eq) and K₂CO₃ (11.40 g, 82.48 mmol, 3 eq). The mixture was stirred at 25° C. for 3 hr. TLC showed the reaction was finished. The reaction solution was added to H₂O (200 mL). The aqueous phase was extracted with ethyl acetate (50 mL*3). The combined organic phase was washed with brine (50 mL*5), dried with anhydrous Na₂SO₄, filtered, and concentrated in vacuum. The residue was purified by column chromatography (SiO₂) to provide compound 1-3.

Step 3: 4-bromo-2-(2-methyltetrazol-5-yl)-N-[4-(trifluoromethyl)phenyl]aniline

To the solution of 1-3 (1.2 g, 4.74 mmol, 1 eq) in DCM (10 mL) were added compound 1-3a (1.08 g, 5.69 mmol, 1.2 eq), Cu(OAc)₂ (1.03 g, 5.69 mmol, 1.2 eq) and DIPEA (1.84 g, 14.22 mmol, 2.48 mL, 3 eq). The mixture was stirred at 25° C. for 16 hr under O₂ at 15 psi. The reaction was monitored by LCMS. LCMS showed that the starting material remained and the main peak was the desired MS. The reaction solution was added to H₂O (100 mL). The aqueous phase was extracted with ethyl acetate (50 mL*3). The combined organic phase was washed with brine (50 mL*5), dried with anhydrous Na₂SO₄, filtered, and concentrated in vacuum. The residue was purified by column chromatography (SiO₂) to provide compound 1-4 (1.3 g, 3.04 mmol, 64.04% yield).

Step 4: 4-bromo-2-(2-methyltetrazol-5-yl)-N-[4-(trifluoromethyl)phenyl]aniline

To a mixture of compound 1-4 (0.56 g, 1.41 mmol, 1 eq) in DMSO (10 mL) and MeOH (2 mL) were added Xantphos (81.3 mg, 0.14 mmol, 0.1 eq), Pd₂ (dba)₃ (128.7 mg, 0.14 mmol, 0.1 eq) and KOAc (414.0 mg, 4.22 mmol, 3 eq). The suspension was degassed under vacuum and purged with CO several times. The mixture was stirred for 12 hrs at 45 psi at 80° C. TLC showed the reaction was finished. The mixture was quenched by EA (30 mL), and the mixture was filtered and the filtered cake was washed with EA (20 mL*3). The combined organic phase was washed with brine (20 mL*3), dried with anhydrous Na₂SO₄, filtered, and concentrated in vacuum. The residue was purified by column chromatography (SiO₂) to give the title compound (0.45 g, 1.07 mmol, 7632% yield). 30 mg of the title compound was re-purified by prep-HPLC to give Compound 1 (15.28 mg, 0.040 mmol, 2.88% yield). LCMS (ESI): RT=0.847 min, mass calc. for: $C_{17}H_{14}F_3N_5O_2$ 377.11, m/z found 377.9 [M+H]⁺; ¹H NMR (400 MHz, CD₃OD) δ8.83 (d, J=2.0 Hz, 1H), 7.97 (dd, J=2.0, 8.8 Hz, 1H), 7.66 (d, J=8.5 Hz, 2H), 7.55-7.41 (m, 3H), 4.48 (s, 3H), 3.91 (s, 3H).

Example 2: Preparation of 4-bromo-2-(2-methyltetrazol-5-yl)-N-[3-(trifluoromethyl)phenyl]aniline (Compound 2)

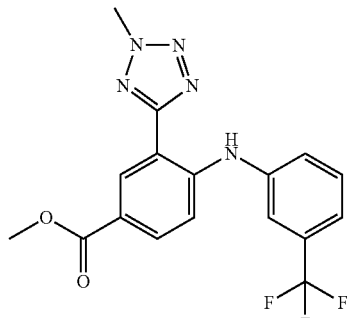

Preparation of Compound 2

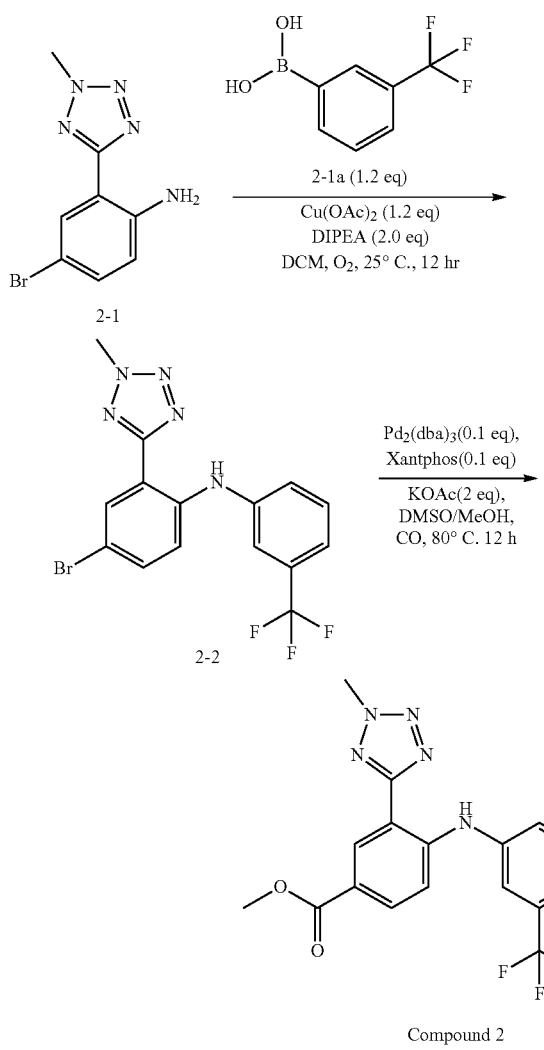

Step 1: 4-bromo-2-(2-methyl-2H-tetrazol-5-yl)-N-(3-(trifluoromethyl)phenyl)aniline To a mixture of compound 2-1 (2 g, 7.87 mmol, 1 eq) and compound 2-1a (1.49 g, 7.87 mmol, 1 eq) in DCM (20 mL) were added Cu(OAc)$_2$ (1.43 g, 7.87 mmol, 1 eq) and DIPEA (1.02 g, 7.87 mmol, 1.37 mL, 1 eq) in one portion at 25° C. under O$_2$. The mixture was stirred for 48 hrs under 15 Psi. TLC (PE/EA=3/1) showed the reaction was finished. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered, and concentrated in vacuum. The residue was triturated by PE (20 mL), and the mixture was filtered and the filtered cake was washed with PE (10 mL*3). The filtered cake was concentrated in vacuum. The crude product was used for next step directly. Compound 2 (2.6 g, crude) was obtained. LCMS (ESI): RT=0.926 min, mass calc. for: C$_{15}$H$_{11}$BrF$_3$N$_5$ 397.01, m/z found 399.7 [M+H]$^+$; $^1$H NMR (400 MHz, CDCl$_3$) δ 8.96 (s, 1H), 8.32 (d, J=2.3 Hz, 1H), 7.50-7.36 (m, 4H), 7.28 (s, 1H), 4.45 (s, 3H).

Step 2: methyl 3-(2-methyltetrazol-5-yl)-4-[3-(trifluoromethyl)anilino]benzoate To a mixture of 2-2 (1 g, 2.51 mmol, 1 eq) in DMSO (10 mL) and MeOH (2 mL) were added Xantphos (145.3 mg, 0.25 mmol, 0.1 eq), Pd$_2$(dba)$_3$ (229.9 mg, 0.25 mmol, 0.1 eq) and KOAc (739.4 mg, 7.53 mmol, 3 eq). The suspension was degassed under vacuum and purged with CO several times. The mixture was stirred for 12 hrs at 45 psi at 80° C. TLC (PE/EA=5/1) showed the reaction was finished. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered, and concentrated in vacuum. The residue was purified by column chromatography (Si$_2$O) to give Compound 2 (0.8 g, 1.91 mmol, 76.05% yield). 30 mg of the product was re-purified by prep-HPLC to give Compound 2 (10.7 mg, 0.028 mmol, 1.13% yield). LCMS (ESI): RT=0.853 min, mass calc. for: C$_{17}$H$_{14}$F$_3$N$_5$O$_2$ 377.11, m/z found 377.9 [M+H]$^+$; $^1$H NMR (400 MHz, CD$_3$OD) S 8.85 (d, J=2.3 Hz, 1H), 7.99-7.93 (m, 1H), 7.62-7.55 (m, 3H), 7.46-7.40 (m, 1H), 7.39-7.33 (m, 1H), 4.52-4.47 (m, 3H), 3.91 (s, 3H).

Example 3: 3-(2-methyl-2H-tetrazol-5-yl)-4-((4-(trifluoromethyl)phenyl)amino)benzoic Acid (Compound 3)

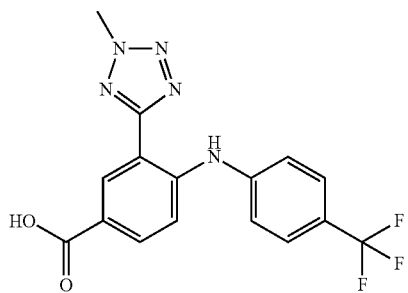 [SMILES: Cn1nnc(-c2cc(C(=O)O)ccc2Nc2ccc(C(F)(F)F)cc2)n1]

169

Preparation of Compound 3

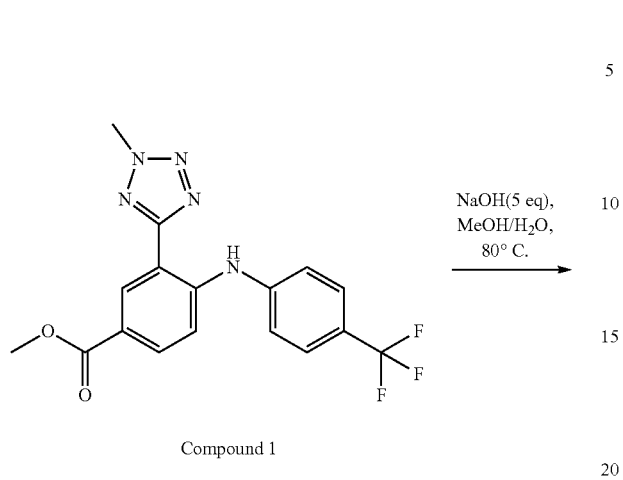

Compound 1

Compound 3

170

Example 4: 3-(2-methyl-2H-tetrazol-5-yl)-4-((3-(trifluoromethyl)phenyl)amino)benzoic Acid (Compound 4)

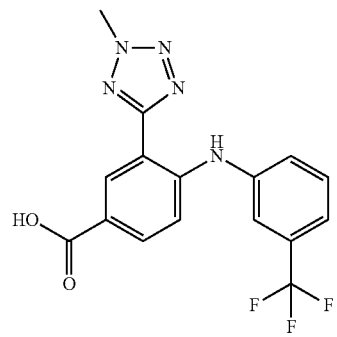 [SMILES: Cn1nnc(-c2cc(C(=O)O)ccc2Nc2cccc(C(F)(F)F)c2)n1]

Preparation of Compound 4

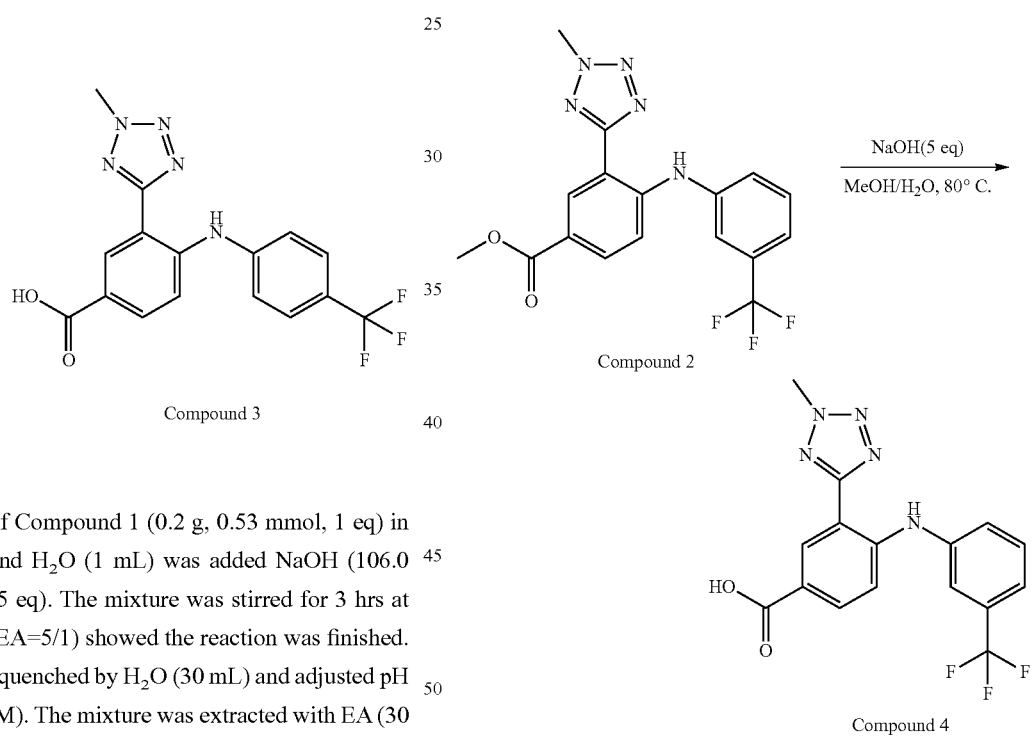

Compound 2

Compound 4

To a mixture of Compound 1 (0.2 g, 0.53 mmol, 1 eq) in MeOH (5 mL) and $H_2O$ (1 mL) was added NaOH (106.0 mg, 2.65 mmol, 5 eq). The mixture was stirred for 3 hrs at 80° C. TLC (PE/EA=5/1) showed the reaction was finished. The mixture was quenched by $H_2O$ (30 mL) and adjusted pH to 4 with HCl (4 M). The mixture was extracted with EA (30 mL*3). The combined organic phase was washed with brine (20 mL*3), dried with anhydrous $Na_2SO_4$, filtered, and concentrated in vacuum. The crude product was used for next step directly. After repurification by prep-HPLC, 30 mg of Compound 3 (0.120 g, 0.28 mmol, 54.22% yield) was obtained. Further purification resulted in Compound 3 (9.09 mg, 0.024 mmol, 4.67% yield). LCMS (ESI): RT=0.779 min, mass calc. for: $C_{16}H_{12}F_3N_5O_2$ 363.09, m/z found 363.9 $[M+H]^+$; $^1H$ NMR (400 MHz, $CD_3OD$) δ8.83 (d, J=2.0 Hz, 1H), 7.98 (dd, J=2.0, 8.8 Hz, 1H), 7.64 (d, J=8.5 Hz, 2H), 7.58-7.42 (m, 3H), 4.48 (s, 3H).

To a mixture of Compound 2 (0.35 g, 0.92 mmol, 1 eq) in MeOH (10 mL) and $H_2O$ (2 mL) was added NaOH (37.1 mg, 0.92 mmol, 1 eq). The mixture was stirred for 3 hrs at 80° C. TLC (PE/EA=5/1) showed the reaction was finished. The mixture was quenched by $H_2O$ (30 mL) and adjusted pH to 4 with HCl (4 M). The mixture was extracted with EA (30 mL*3). The combined organic phase was washed with brine (20 mL*3), dried with anhydrous $Na_2SO_4$, filtered, and concentrated in vacuum to give Compound 4. (0.2 g, 0.53 mmol, 58.16% yield). The crude product was used for next step directly. 30 mg of the product was re-purified by prep-HPLC to give Compound 4 (19.87 mg, 0.054 mmol, 5.90% yield). LCMS (ESI): RT=0,771 min, mass calc. for: $C_{16}H_{12}F_3N_5O_2$ 363.09, m/z found 363.9 $[M+H]^+$; $^1H$ NMR (400 MHz, CD₃OD) δ8.85 (d, J=2.3 Hz, 1H), 7.99-7.93 (m, 1H), 7.62-7.55 (m, 3H), 7.46-7.40 (m, 1H), 7.39-7.33 (m, 1H), 4.52-4.47 (m, 3H), 3.91 (s, 3H).

Example 5: N-methyl-3-(2-methyl-2H-tetrazol-5-yl)-4-((3-(trifluoromethyl)phenyl)amino) benzamide (Compound 5)

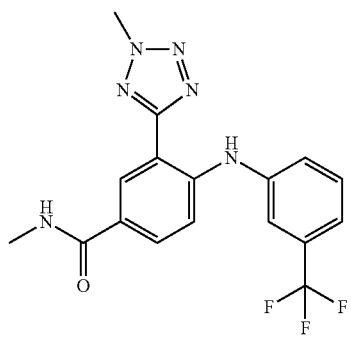 [SMILES: CNC(=O)c1ccc(Nc2cccc(C(F)(F)F)c2)c(-c2nnn(C)n2)c1]

Preparation of Compound 5

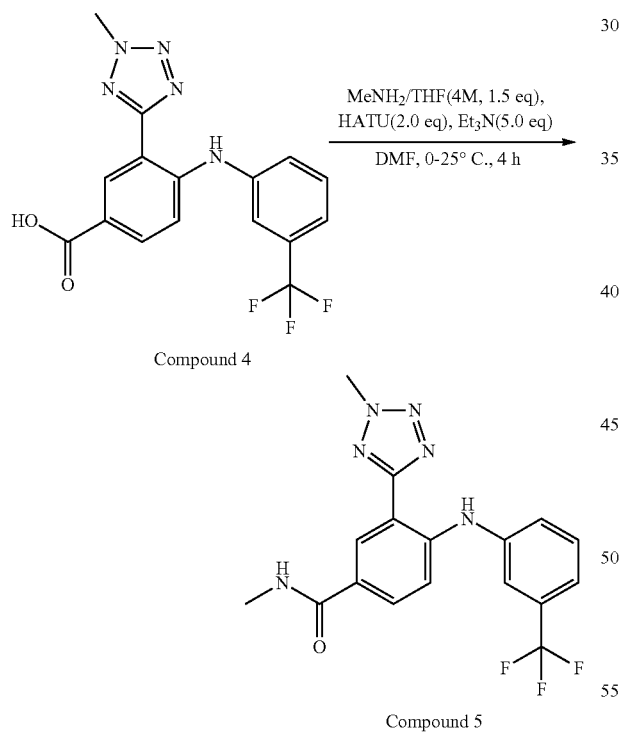

To a mixture of Compound 4 (80 mg, 0.22 mmol, 1 eq) in DMF (10 ml) were added HATU (167.4 mg, 0.44 mmol, 2 eq) and Et₃N (22.2 mg, 0.22 mmol, 30.65 μL, 1 eq). The mixture was stirred for 0.5 hrs at 25° C. Then MeNH₂ (2 M, 0.55 mL, 5 eq) was added to the mixture. The mixture was stirred for 1.5 hrs at 25° C. LCMS showed the reaction was finished. The mixture was quenched by H₂O (30 mL), and the mixture was extracted with EA (20 mL*3). The combined organic phase was washed with brine (20 mL*3), dried with anhydrous Na₂SO₄, filtered, and concentrated in vacuum. The residue was purified by prep-HPLC, and Compound 5 (34.4 mg, 0.091 mmol, 41.61% yield) was obtained. LCMS (ESI): RT=0.742 min, mass calc. for: $C_{17}H_{15}F_3N_6O$, 376.13, m/z found 376.9 [M+H]+; ¹H NMR (400 MHz, CD₃OD) δ 8.69 (d, J=2.3 Hz, 1H), 7.79 (dd, J=2.0, 8.8 Hz, 1H), 7.57-7.51 (m, 3H), 7.41-7.34 (m, 2H), 4.47 (s, 3H), 2.93 (s, 3H).

Example 6: 3-(2-methyl-2H-tetrazol-5-yl)-4-((3Z(trifluoromethyl)phenyl)amino)benzamide (Compound 6)

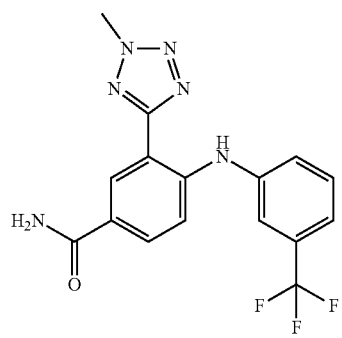 [SMILES: Cn1nnc(-c2cc(C(N)=O)ccc2Nc2cccc(C(F)(F)F)c2)n1]

Preparation of Compound 6

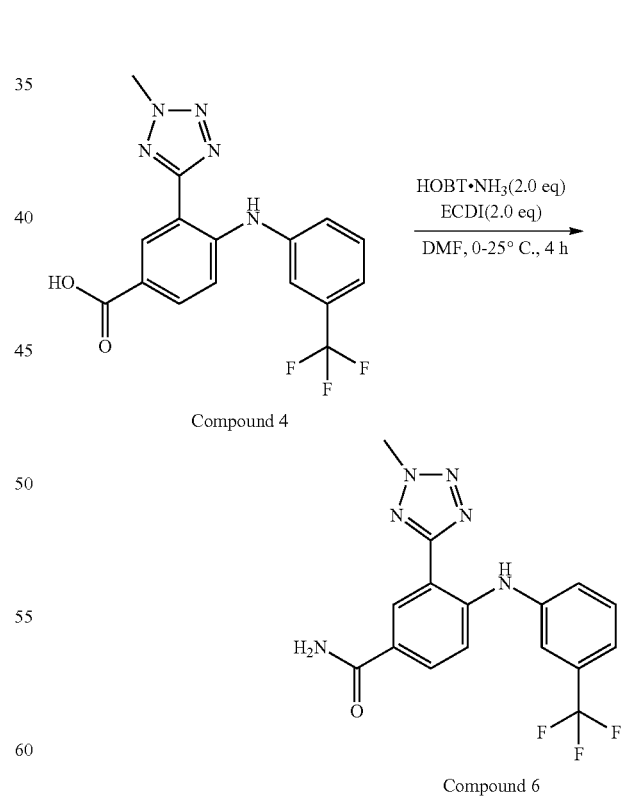

To a mixture of Compound 4 (0.1 g, 0.27 mmol, 1 eq) in DMF (10 mL) was added ammonium; 1-oxidobenzotriazole (83.7 mg, 0.55 mmol, 2 eq). The mixture was stirred for 0.5 hrs at 25° C. Then EDCI (105.5 mg, 0.55 mmol, 2 eq) was added to the mixture. The mixture was stirred for 1.5 hrs at 25° C. LCMS showed the reaction was finished. The mixture was quenched by H₂O (30 mL), and the mixture was extracted with EA (20 mL*3). The combined organic phase was washed with brine (20 mL*3), dried with anhydrous Na₂SO₄, filtered, and concentrated in vacuum. The residue was purified by prep-HPLC to give Compound 6 (22.42 mg, 61.26 umol, 22.26% yield). LCMS (ESI): RT=0.722 min, mass calc. for: $C_{16}H_{13}F_3N_6O$ 362.11, m/z found 362.9 [M+H]$^+$; ¹H NMR (400 MHz, CD₃OD) δ8.74 (d, J=2.3 Hz, 1H), 7.85 (dd, J=2.0, 8.8 Hz, 1H), 7.57-7.51 (m, 3H), 7.40-7.33 (m, 2H), 4.47 (s, 3H)

Example 7: 3-(2-methyl-2H-tetrazol-5-yl)-4-((4-(trifluoromethyl)phenyl)amino)benzamide (Compound 7)

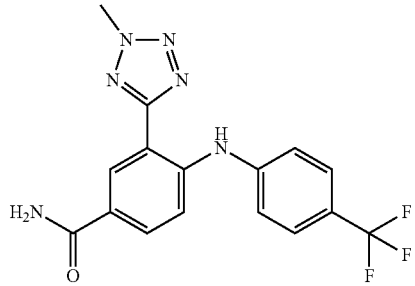 [SMILES: Cn1nnc(-c2cc(C(N)=O)ccc2Nc2ccc(C(F)(F)F)cc2)n1]

Preparation of Compound 7

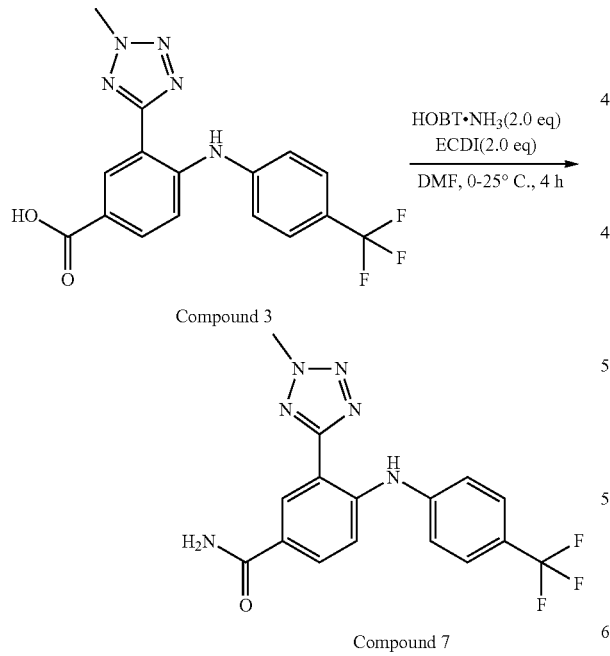

To a mixture of Compound 3 (0.03 g, 0.082 mmol, 1 eq) in DMF (10 mL) was added ammonium; 1-oxidobenzotriazole (25.1 mg, 0.16 mmol, 2 eq). The mixture was stirred for 0.5 hrs at 0° C. Then EDCI (31.6 mg, 0.16 mmol, 2 eq) was added to the mixture. The mixture was stirred for 1.5 hrs at 25° C. LCMS showed the reaction was complete. The mixture was quenched by H₂O (30 mL), and the mixture was extracted with EA (20 mL*3). The combined organic phase was washed with brine (20 mL*3), dried with anhydrous Na₂SO₄, filtered, and concentrated in vacuum. The residue was purified by prep-HPLC to obtain Compound 7 (21.70 mg, 0.059 mmol, 71.80% yield). LCMS (ESI): RT=0.732 min, mass calc. for: $C_{16}H_{13}F_3N_6O$ 362.11, m/z found 362.9 [M+H]$^+$; ¹H NMR (400 MHz, DMSO-d6) δ 9.08 (s, 1H), 8.59 (d, J=2.3 Hz, 1H), 8.02 (br s, 11H), 7.96 (dd, J=2.1, 8.7 Hz, 11H), 7.67-7.62 (m, J=8.5 Hz, 2H), 7.54 (d, J=8.8 Hz, 1H), 7.42-7.36 (m, J=8.5 Hz, 2H), 7.30 (br s, 1H), 4.47 (s, 3H).

Example 8: N-methyl-3-(2-methyl-2H-tetrazol-5-yl)-4-((4-(trifluoromethyl)phenyl)amino) benzamide (Compound 8)

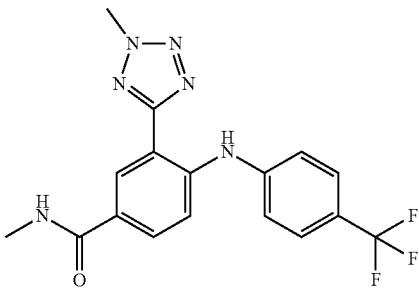 [SMILES: CNC(=O)c1ccc(Nc2ccc(C(F)(F)F)cc2)c(-c2nnn(C)n2)c1]

Preparation of Compound 8

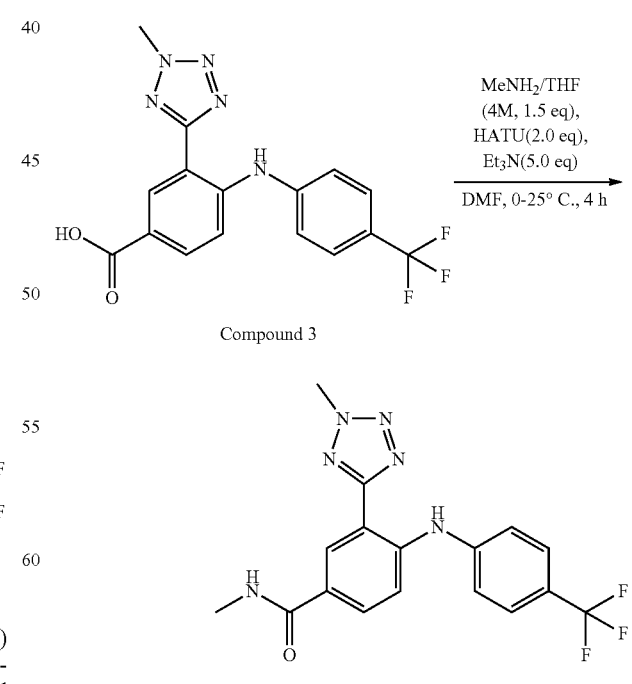

To a mixture of Compound 3 (30 mg, 0.082 mmol, 1 eq) in DMF (10 mL) were added HATU (62.8 mg, 0.16 mmol, 2 eq) and Et$_3$N (8.3 mg, 0.082 mmol, 11.49 µL, 1 eq). The mixture was stirred for 0.5 hr at 25° C. Then MeNH$_2$ (2 M, 0.20 mL, 5 eq) was added to the mixture. The mixture was stirred for 1.5 hr at 25° C. LCMS showed the reaction was finished. The mixture was quenched by H$_2$O (30 mL), and the mixture was extracted with EA (20 mL*3). The combined organic phase was washed with brine (20 mL*3), dried with anhydrous Na$_2$SO$_4$, filtered, and concentrated in vacuum. The residue was purified by prep-HPLC to obtain Compound 8 (5.16 mg, 0.013 mmol, 16.60% yield). LCMS (ESI): RT=0.739 min, mass calc. for: C$_{17}$H$_{15}$F$_3$N$_6$O, 376.13, m/z found 376.9 [M+H]$^+$; $^1$H NMR (400 MHz, CD$_3$OD) δ 8.69 (d, J=2.0 Hz, 1H), 7.83 (dd, J=2.1, 8.7 Hz, 1H), 7.66-7.60 (m, J=8.5 Hz, 2H), 7.54 (d, J=8.5 Hz, 1H), 7.47-7.39 (m, J=8.5 Hz, 2H), 4.48 (s, 3H), 2.94 (s, 3H).

Example 9: methyl 4-((4-(ethylcarbamoyl)phenyl)amino)-3-(2-methyl-2H-tetrazol-5-yl)benzoate (Compound 9)

And N-ethyl-3-(2-methyl-2H-tetrazol-5-yl)-4-((4-(trifluoromethyl)phenyl)amino)benzamide (Compound 10)

Preparation of Compound 9 and Compound 10

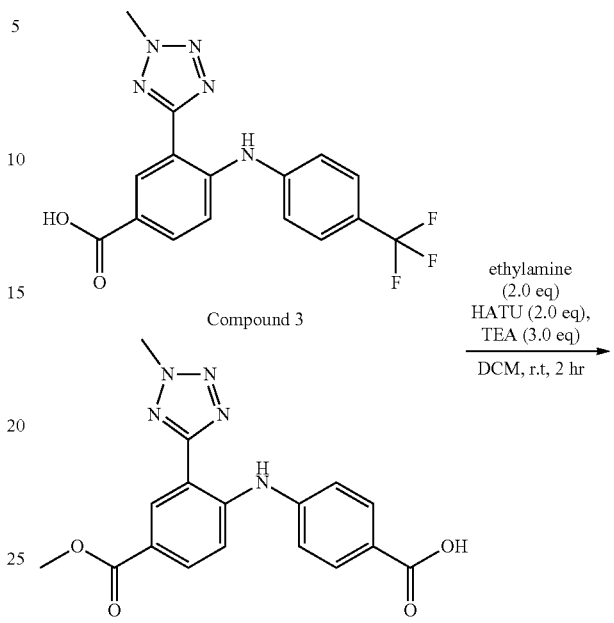

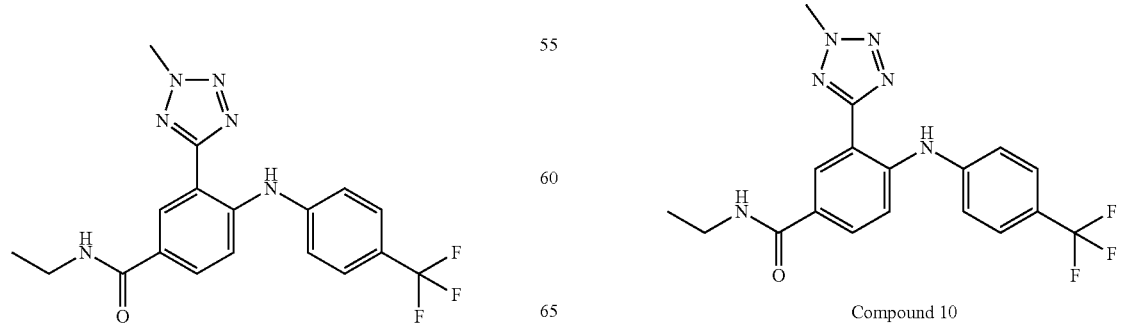

To a solution of Compound 3 (80 mg, 0.22 mmol, 1 eq) and 9-1 (77.8 mg, 0.22 mmol, 1 eq) in DCM (5 mL) were added TEA (66.8 mg, 0.66 mmol, 91.95 µL, 3 eq), HATU (167.4 mg, 0.44 mmol, 2 eq) in one portion. The mixture was stirred at 25° C. for 1 hr. Then the ethylamine (19.8 mg, 0.44 mmol, 28.82 µL, 2 eq) was added to the mixture. The mixture was stirred at 25° C. for 15 hr. LCMS showed the reactant was consumed completely, 50% Compound 10 and 35% Compound 9 was detected. The mixture was washed by NaCl (2 mL*3), dried with anhydrous $Na_2SO_4$, filtered, and concentrated in vacuum. The residue was purified by prep-HPLC, and Compound 10 (3.72 mg, 0.0092 mmol, 4.20% yield) was obtained. It was checked by LCMS and 1HNMR. LCMS (ESI): RT=0.772 min, mass calc. for $C_{18}H_{17}F_3N_6O$, 390.14, m/z found 391.9[M+H]+; $^1$H NMR (400 MHz, DMSO-d6) δ 9.07 (s, 1H), 8.59-8.52 (m, 2H), 7.93 (dd, J=2.3, 8.8 Hz, 11H), 7.65 (d, J=8.5 Hz, 2H), 7.56 (d, J=8.8 Hz, 1H), 7.38 (d, J=8.5 Hz, 2H), 4.50-4.46 (m, 3H), 3.33-3.28 (m, 2H), 1.18-1.10 (m, 3H). Compound 9 (8.85 mg, 0.022 mmol, 10.35% yield) was also obtained. LCMS (ESI): RT=0.704 min, mass calc. for $C_{19}H_{20}N_6O_3$ 380.40, m/z found 381.0 [M+H]+; $^1$H NMR (400 MHz, DMSO-d6) δ 9.12 (s, 1H), 8.58-8.52 (m, 2H), 7.97-7.93 (m, 1H), 7.90 (d, J=8.5 Hz, 2H), 7.59 (d, J=8.8 Hz, 1H), 7.29 (d, J=8.8 Hz, 2H), 4.50-4.45 (m, 3H), 3.85-3.79 (m, 3H), 3.33-3.28 (m, 3H), 1.14 (t, J=7.2 Hz, 3H).

Example 10: N-isopropyl-3-(2-methyl-2H-tetrazol-5-yl)-4-((4 (trifluoromethyl)phenyl)amino) benzamide (Compound 11)

And methyl 4-((4-(isopropylcarbamoyl)phenyl)amino)-3-(2-methyl-2H-tetrazol-5-yl)benzoate (Compound 12)

Preparation of Compound 11 and Compound 12

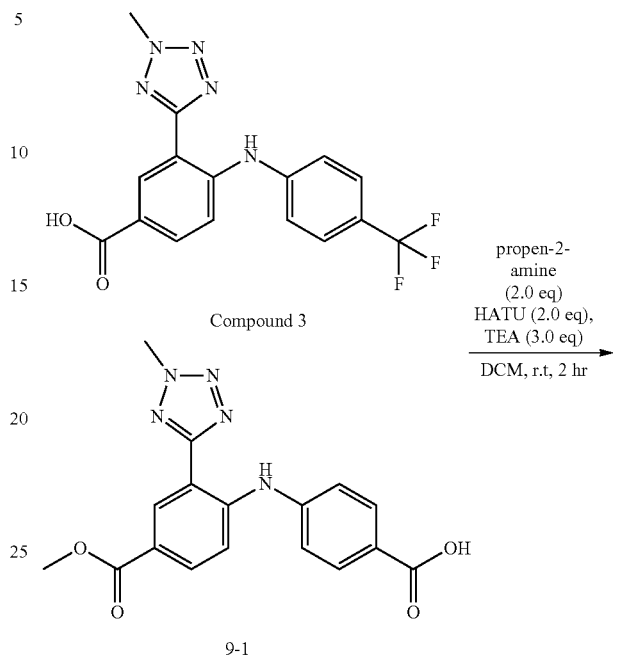

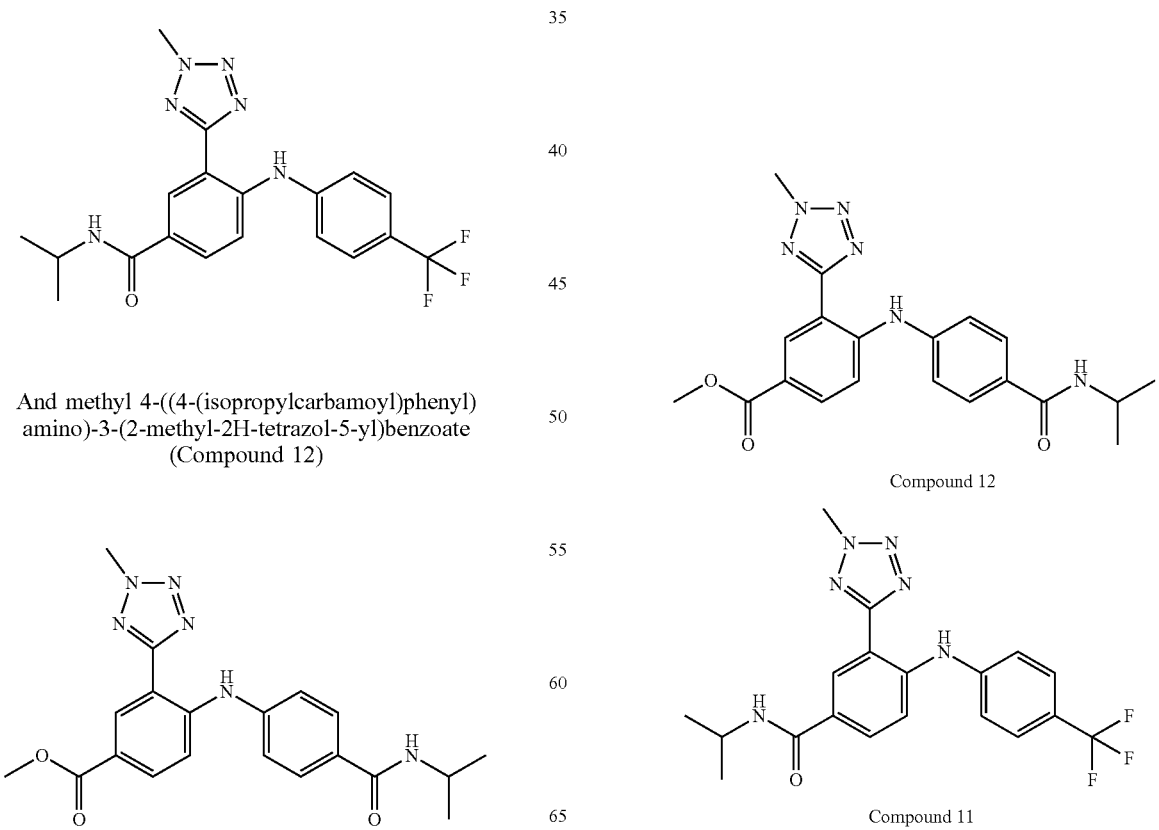

To a solution of Compound 3 (70 mg, 0.19 mmol, 1 eq) and 9-1 (68.0 mg, 0.19 mmol, 1 eq) in DCM (5 mL) were added HATU (146.5 mg, 0.38 mmol, 2 eq), propan-2-amine (22.7 mg, 0.38 mmol, 33.11 μL, 2 eq), TEA (58.4 mg, 0.57 mmol, 80.46 μL, 3 eq) in one portion. The mixture was stirred at 25° C. for 1 hr. Then the propan-2-amine (22.7 mg, 0.38 mmol, 33.11 μL, 2 eq) was added to the mixture. The mixture was stirred at 25° C. for 15 hr. LCMS showed the reactant was consumed completely, and 39% Compound 11 and 51% Compound 12 was detected. The mixture was washed by NaCl (3 ml*3) then dried with anhydrous Na$_2$SO$_4$, filtered, and concentrated in vacuum. The residue was purified by prep-HPLC to obtain Compound 11 (12.77 mg, 0.030 mmol, 15.73% yield). LCMS (ESI): RT=0.790 min, mass calc. for C$_{19}$H$_{19}$F$_3$N$_6$O, 404.39, m/z found 405.0 [M+H]+; 1H NMR (400 MHz, DMSO-d6) δ 9.05 (s, 1H), 8.55 (d, J=2.0 Hz, 1H), 8.31 (d, J=7.8 Hz, 1H), 7.94 (dd, J=2.1, 8.7 Hz, 1H), 7.67-7.62 (m, J=8.5 Hz, 2H), 7.55 (d, J=8.8 Hz, 1H), 7.39-7.34 (m, J=8.5 Hz, 2H), 4.47 (s, 3H), 4.17-4.08 (m, 1H), 1.19 (s, 3H), 1.17 (s, 3H). Compound 12 (25.3 mg, 0.063 mmol, 32.98% yield) was also obtained. LCMS (ESI): RT=0.727 min, mass calc. for C$_{20}$H$_{22}$N$_6$O$_3$ 394.43, m/z found 395.0[M+H]$^+$; 1H NMR (400 MHz, DMSO-d6) δ 9.10 (s, 1H), 8.55 (d, J=2.0 Hz, 1H), 8.32 (d, J=7.5 Hz, 1H), 7.95 (dd, J=2.0, 8.8 Hz, 1H), 7.89 (d, J=8.8 Hz, 2H), 7.58 (d, J=8.8 Hz, 1H), 7.28 (d, J=8.8 Hz, 2H), 4.47 (s, 3H), 4.18-4.08 (m, 1H), 3.82 (s, 3H), 1.19 (s, 3H), 1.17 (s, 3H)

Example 11: N,N-dimethyl-3-(2-methyl-2H-tetrazol-5-yl)-4-((4-(trifluoromethyl)phenyl)amino) benzamide (Compound 13)

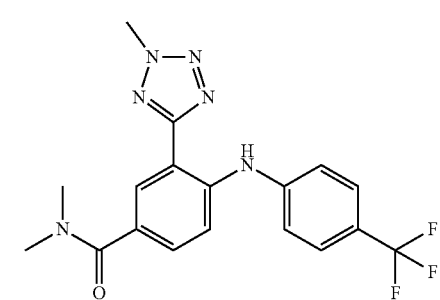 [SMILES: CN(C)C(=O)c1ccc(Nc2ccc(C(F)(F)F)cc2)c(-c2nnn(C)n2)c1]

And methyl 4-((4-(dimethylcarbamoyl)phenyl)amino)-3-(2-methyl-2H-tetrazol-5-yl)benzoate (Compound 14)

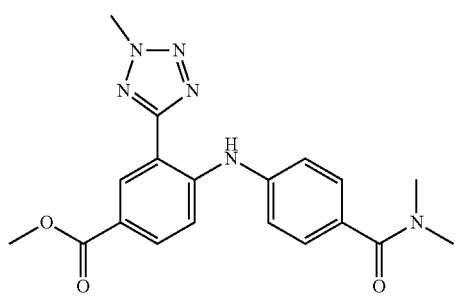

Preparation of Compound 13 and Compound 14

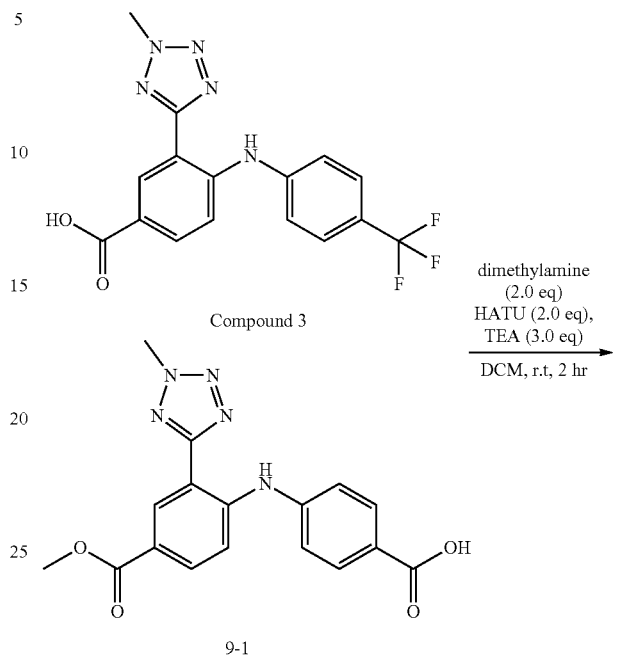

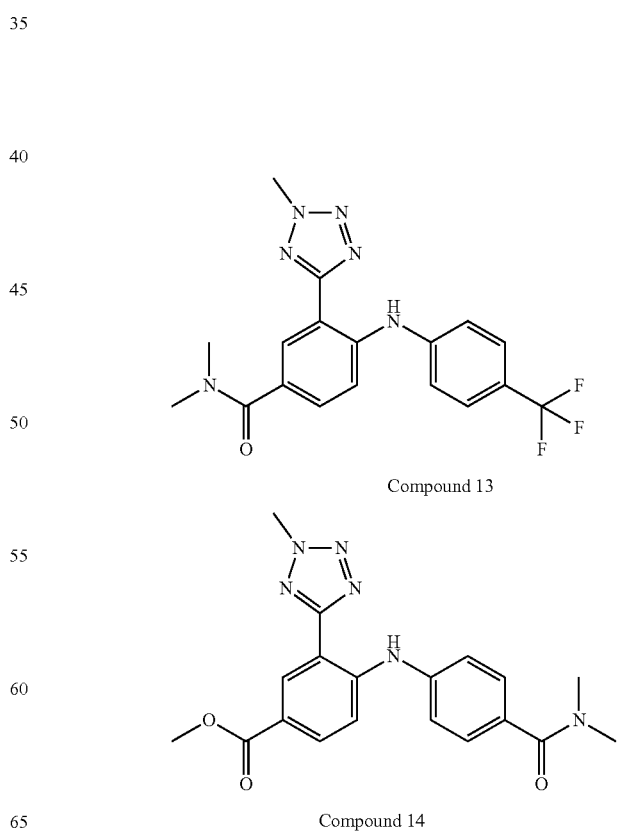

To a solution of Compound 3 (70 mg, 0.19 mmol, 1 eq), 9-1 (68.0 mg, 0.19 mmol, 1 eq) in DCM (3 mL) were added HATU (146.5 mg, 0.38 mmol, 2 eq) and TEA (58.4 mg, 0.57 mmol, 80.46 μL, 3 eq). The mixture was stirred at 25° C. for 1 hr. Then the N-methylmethanamine (2 M, 192.68 μL, 2 eq) was added to the mixture. The mixture was stirred at 25° C. for 15 hr. LCMS showed the reactant was consumed completely, and 17% Compound 13 and 35% Compound 14 was detected. The mixture was washed by NaCl (3 mL*3) then dried with anhydrous Na$_2$SO$_4$, filtered, and concentrated in vacuum. The residue was purified by prep-HPLC to obtain Compound 13 (7.92 mg, 20.29 umol, 10.53% yield) was obtained. LCMS (ESI): RT=0.771 min, mass calc. for C$_{18}$H$_{17}$F$_3$N$_6$O, 390.14, m/z found 391.0 [M+H]$^+$; $^1$H NMR (400 MHz, DMSO-d$_6$) δ 8.97 (s, 1H), 8.07 (s, 1H), 7.63-7.61 (d, J=8.4 Hz, 2H), 7.55-7.50 (m, 2H), 7.36-7.34 (d, J=8.4 Hz, 2H), 4.45 (s, 3H), 3.01 (s, 6H). Compound 14 (32.71 mg, 0.085 mmol, 44.63% yield) was also obtained. LCMS (ESI): RT=0.708 min, mass calc. for C$_{19}$H$_{20}$N$_6$O$_3$ 380.16, m/z found 381.1 [M+H]$^+$; $^1$H NMR (400 MHz, DMSO-d$_6$) δ 9.02 (s, 1H), 8.07-8.06 (d, J=1.6 Hz, 11H), 7.89-7.87 (d, J=8.8 Hz, 2H), 7.59-7.52 (m, 2H), 7.27-7.25 (d, J=8.8 Hz, 2H), 4.45 (s, 3H), 3.81 (s, 3H), 3.01 (s, 3H).

Example 12: 3-(2-methyl-2H-tetrazol-5-yl)-N-(methylsulfonyl)-4-((4-(trifluoromethyl)phenyl) amino)benzamide (Compound 15)

And methyl 3-(2-methyl-2H-tetrazol-5-yl)-4-((4-((methylsulfonyl)carbamoyl)phenyl)amino) benzoate (Compound 16)

Preparation of Compound 15 and Compound 16

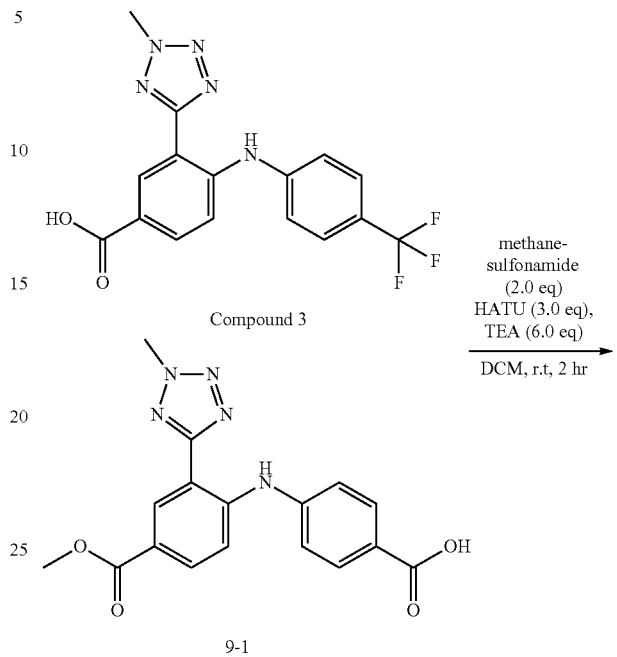

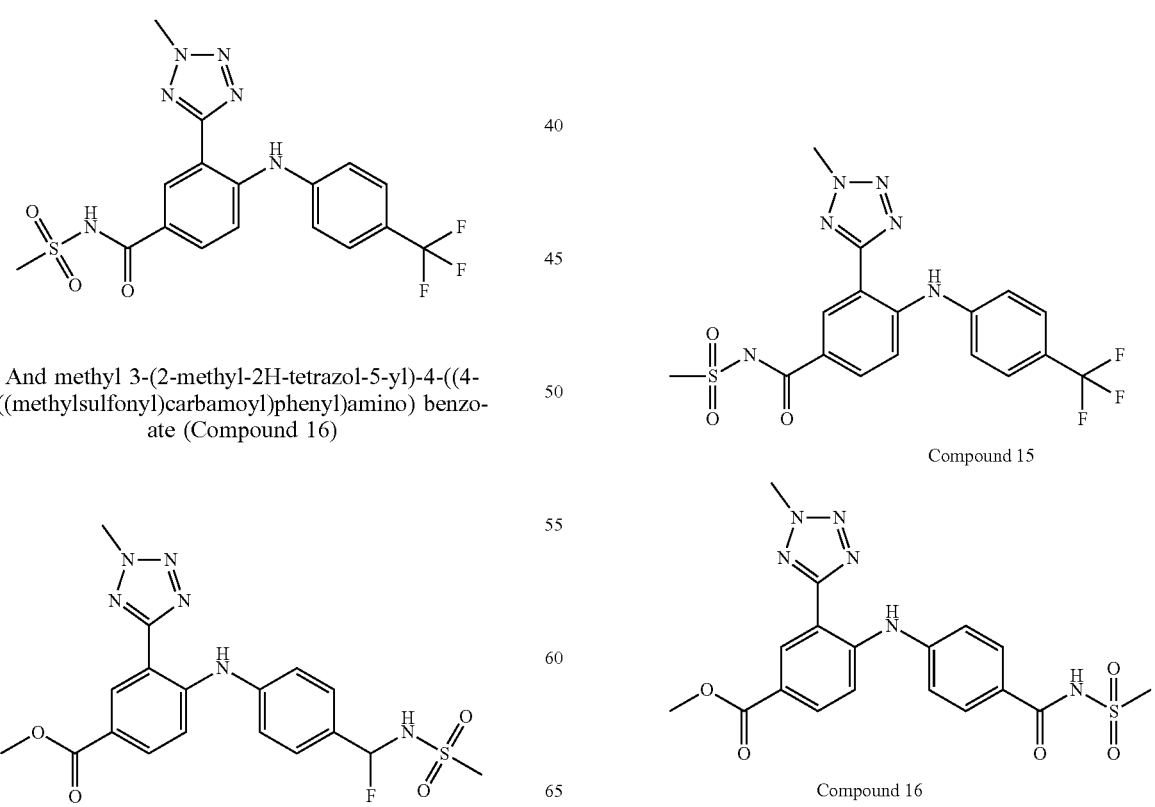

To a solution Compound 3 (70 mg, 0.19 mmol, 1 eq) and 9-1 (68.0 mg, 0.19 mmol, 1 eq) in DCM (3 mL) were added TEA (116.9 mg, 1.16 mmol, 160.91 μL, 6 eq) HATU (219.7 mg, 0.57 mmol, 3 eq) in one portion. The mixture was stirred at 25° C. for 1 hr. Then the methanesulfonamide (36.6 mg, 0.38 mmol, 2 eq) was added to the mixture. The mixture was stirred at 25° C. for 15 hr. LCMS showed the reactant was consumed completely. The mixture was washed by NaCl (3 mL*3) then dried with anhydrous Na$_2$SO$_4$, filtered, and concentrated in vacuum. The residue was purified by prep-HPLC to give Compound 15 (4.73 mg, 0.010 mmol, 5.57% yield). LCMS (ESI): RT=0.761 min, mass calc. for C$_{17}$H$_{15}$F$_3$N$_6$O$_3$S, 440.40, m/z found 463.0 [M+Na]$^+$; $^1$H NMR (400 MHz, CDCl$_3$) δ 9.65 (s, 1H), 8.68 (d, J=2.3 Hz, 2H), 7.86 (dd, J=2.3, 8.8 Hz, 1H), 7.66 (d, J=8.3 Hz, 2H), 7.46 (d, J=9.0 Hz, 1H), 7.40 (d, J=8.3 Hz, 2H), 4.49 (s, 3H), 3.47 (s, 3H) Compound 16 (6.22 mg, 0.014 mmol, 7.50% yield) was also obtained. LCMS (ESI): RT=0.696 min, mass calc. for C18H18N$_6$O5S, 430.44, m/z found 453.0[M+Na]$^+$; $^1$H NMR (400 MHz, CDCl$_3$) δ 9.67 (s, 1H), 8.85 (s, 1H), 8.69 (d, J=2.3 Hz, 1H), 8.07 (d, J=8.5 Hz, 2H), 7.88 (dd, J=2.3, 9.0 Hz, 1H), 7.53 (d, J=8.8 Hz, 1H), 7.34 (d, J=8.5 Hz, 2H), 4.49 (s, 3H), 3.93 (s, 3H), 3.47 (s, 3H).

Example 13: N,N-diethyl-3-(2-methyl-2H-tetrazol-5-yl)-4-((4-(trifluoromethyl)phenyl)amino) benzamide (Compound 17)

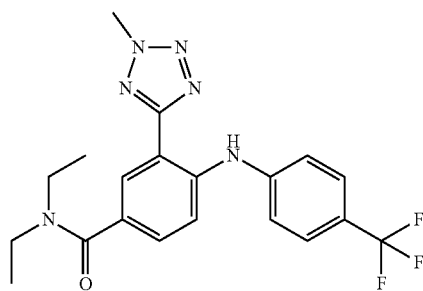 [SMILES: CCN(CC)C(=O)c1ccc(Nc2ccc(C(F)(F)F)cc2)c(-c2nnn(C)n2)c1]

And methyl 4-((4-(diethylcarbamoyl)phenyl)amino)-3-(2-methyl-2H-tetrazol-5-yl)benzoate (Compound 18)

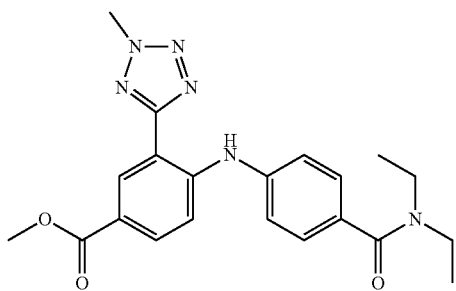 [SMILES: CCN(CC)C(=O)c1ccc(Nc2ccc(C(=O)OC)cc2-c2nnn(C)n2)cc1]

Preparation of Compound 17 and Compound 18

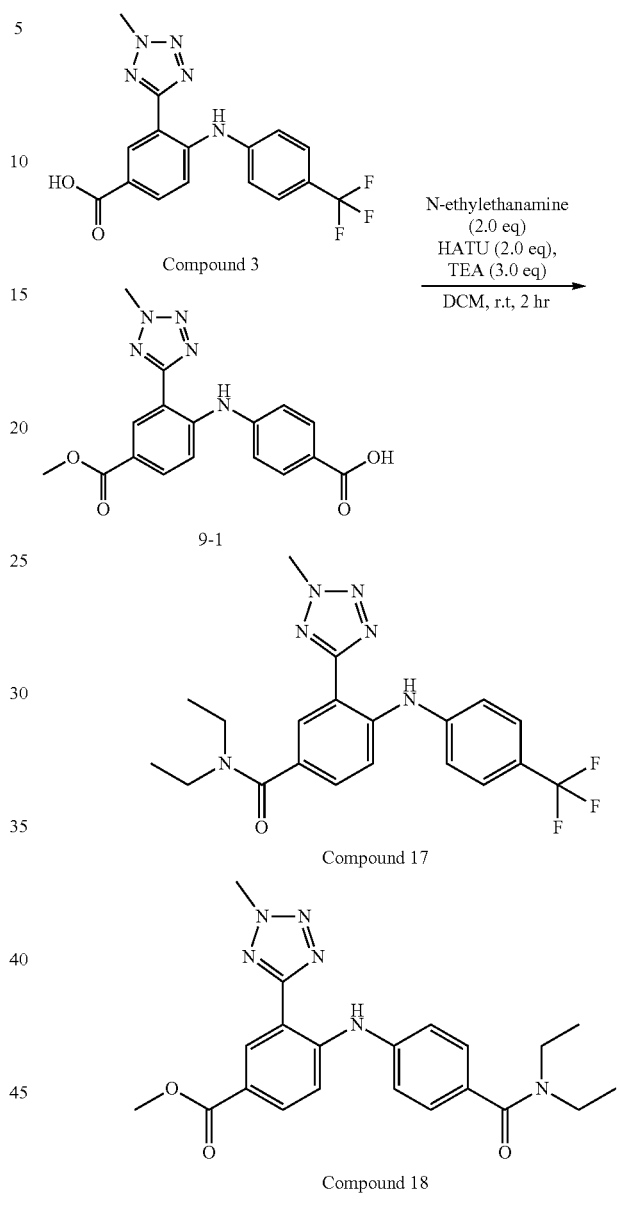

To a solution of Compound 3 (70 mg, 0.19 mmol, 1 eq) and 9-1 (68.0 mg, 0.19 mmol, 1 eq) in DCM (3 mL) were added TEA (58.4 mg, 0.57 mmol, 80.46 μL, 3 eq) and HATU (146.5 mg, 0.38 mmol, 2 eq). The mixture was stirred at 25° C. for 1 hr. Then the N-ethylethanamine (28.1 mg, 0.38 mmol, 39.70 μL, 2 eq) was added to the mixture. The mixture was stirred at 25° C. for 15 hr. LCMS showed the reactant was consumed completely, and 46% Compound 17 and 40% Compound 18 was detected. The mixture was washed by NaCl (3 mL*3) then dried with anhydrous Na$_2$SO$_4$, filtered, and concentrated in vacuum. The residue was purified by prep-HPLC to obtain Compound 17 (9.61 mg, 0.022 mmol, 11.92% yield). LCMS (ESI): RT=0.809 min, mass calc. for C$_{20}$H$_{21}$F$_3$N$_6$O, 418.41, m/z found 419.1 [M+H]$^+$; $^1$H NMR (400 MHz, CD$_3$OD) δ8.26 (d, J=2.0 Hz, 1H), 7.63 (t, J=8.8 Hz, 3H), 7.52-7.45 (m, 1H), 7.45-7.40 (m, 2H), 4.49 (s, 3H), 3.50 (br s, 4H), 1.38-1.18 (m, 9H).

Compound 18 was also obtained (7.22 mg, 0.017 mmol, 9.17% yield). LCMS (ESI): RT=0.748 min, mass calc. for $C_2H_{24}N_6O_3$ 408.45, m/z found 409.0[M+H]$^+$; $^1$H NMR (400 MHz, CD$_3$OD) δ 8.25 (d, J=1.8 Hz, 1H), 8.00 (d, J=8.8 Hz, 2H), 7.66 (d, J=8.5 Hz, 1H), 7.48 (dd, J=2.1, 8.7 Hz, 1H), 7.34 (d, J=8.8 Hz, 2H), 4.49 (s, 3H), 3.90 (s, 3H), 3.50 (br s, 4H), 1.27 (br s, 6H).

Example 14: N,N-dimethyl-3-(2-methyl-2H-tetrazol-5-yl)-4-((3-(trifluoromethyl)phenyl)amino) benzamide (Compound 19)

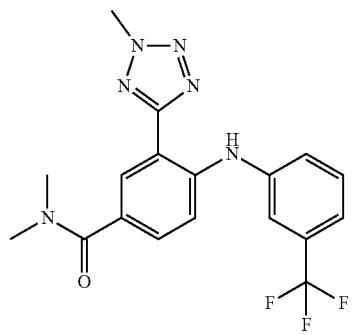 [SMILES: CN(C)C(=O)c1ccc(Nc2cccc(C(F)(F)F)c2)c(-c2nnn(C)n2)c1]

Preparation of Compound 19

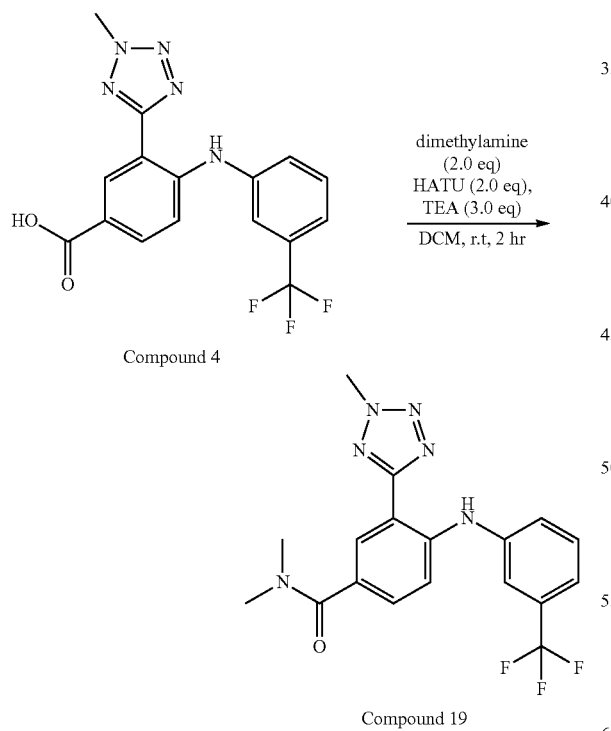

To a mixture of Compound 4 (50 mg, 0.14 mmol, 1 eq) and TEA (41.8 mg, 0.41 mmol, 57.5 μL, 3 eq) in DCM (2 mL) was added HATU (104.7 mg, 0.28 mmol, 2 eq) in one portion at 25° C. under N$_2$. The mixture was stirred at 25° C. for 1 hr. dimethylamine (12.4 mg, 0.28 mmol, 13.9 μL, 2 eq) was added in the mixture under N$_2$, the reaction was stirred at 25° C. for 1 hr. LCMS showed the starting material was consumed completely and the desired mass was detected. The reaction mixture was quenched by addition brine (5 mL) and extracted with DCM (10 mL*2). The combined organic layers was dried over Na$_2$SO$_4$, filtered, and concentrated under reduced pressure to give a residue. The residue was purified by prep-HPLC to give Compound 19 (28.4 mg, 0.065 mmol, 46.90% yield). LCMS (ESI): RT=0.763 min, mass calcd for $C_{18}H_{17}F_3N_6O$, 390.36, m/z found 391 [M+H]$^+$. $^1$H NMR (400 MHz, CDCl$_3$) δ 9.20 (br s, 1H), 8.33 (s, 1H), 7.53 (s, 1H), 7.47 (br d, J=5.0 Hz, 3H), 7.39-7.30 (m, 2H), 4.46 (s, 3H), 3.13 (s, 6H).

Example 14: N,N-diethyl-3-(2-methyl-2H-tetrazol-5-yl)-4-((3-(trifluoromethyl)phenyl)amino) benzamide (Compound 20)

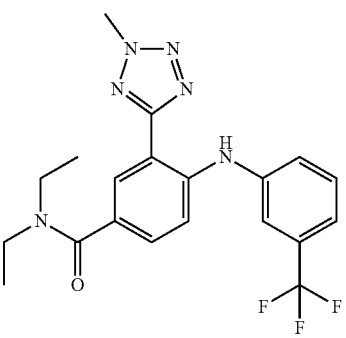 [SMILES: CCN(CC)C(=O)c1ccc(Nc2cccc(C(F)(F)F)c2)c(-c2nnn(C)n2)c1]

Preparation of Compound 20

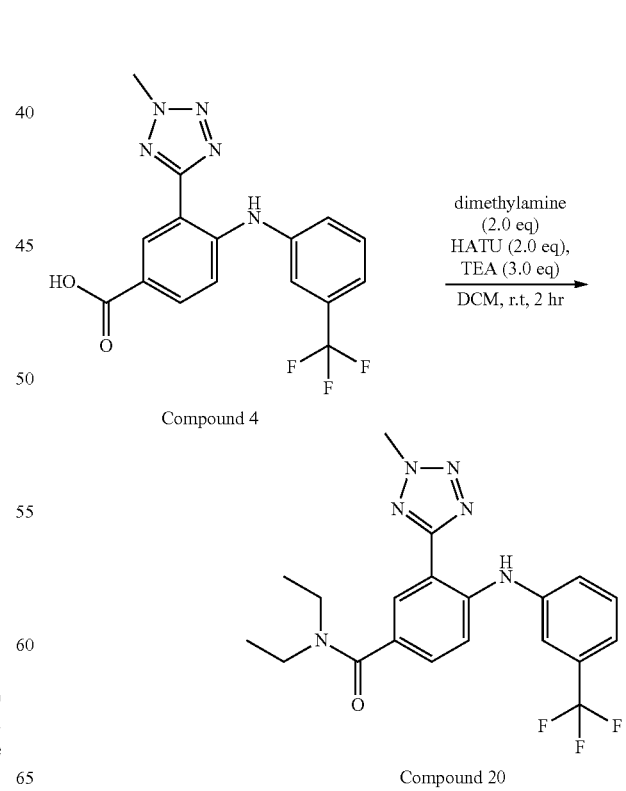

To a mixture of Compound 4 (50 mg, 0.13 mmol, 1 eq) and TEA (41.7 mg, 0.41 mmol, 57.47 µL, 3 eq) in DCM (2 mL) was added HATU (104.6 mg, 0.27 mmol, 2 eq) in one portion at 25° C. and stirred for 1 hr. Diethylamine (20.1 mg, 0.27 mmol, 28.3 µL, 2 eq) was added in the mixture, the mixture was stirred at 25° C. and stirred for 1 hr. LCMS showed the starting material was consumed completely and 96% of desired mass was detected. The reaction mixture was quenched by addition brine (5 mL) and extracted with DCM (10 mL*2). The combined organic layers was dried over $Na_2SO_4$, filtered, and concentrated under reduced pressure to give a residue. The residue was purified by prep-HPLC to give Compound 20 (29.2 mg, 0.06 mmol, 46.64% yield). LCMS and $^1$HNMR indicated it was desired compound. LCMS (ESI): RT=0.812 min, mass calcd for $C_{20}H_{21}F_3N_6O$, 418.42, m/z found 441 [M+Na]$^+$. $^1$H NMR (400 MHz, $CDCl_3$) δ 9.16 (br s, 1H), 8.29 (d, J=1.5 Hz, 1H), 7.52 (s, 1H), 7.47 (d, J=5.0 Hz, 2H), 7.43-7.36 (m, 2H), 7.33 (br d, J=4.0 Hz, 1H), 4.46 (s, 3H), 3.49 (br s, 4H), 1.24 (br t, J=6.5 Hz, 6H).

Example 15: N-isopropyl-3-(2-methyl-2H-tetrazol-5-yl)-4-((3-(trifluoromethyl)phenyl)amino) benzamide (Compound 21)

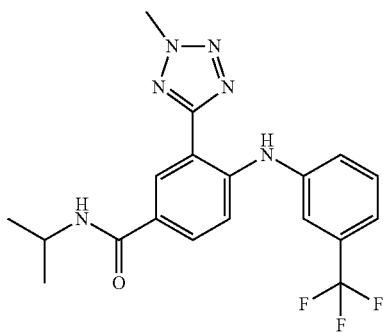 [SMILES: CC(C)NC(=O)c1ccc(Nc2cccc(C(F)(F)F)c2)c(-c2nnn(C)n2)c1]

Preparation of Compound 21

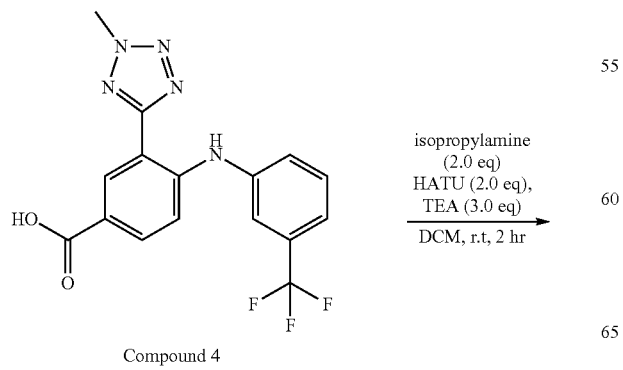

Compound 4

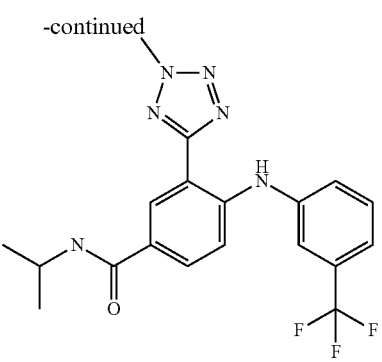

Compound 21

To a mixture of Compound 4 (50 mg, 0.13 mmol, 1 eq) and TEA (41.7 mg, 0.41 mmol, 57.4 µL, 3 eq) in DCM (2 mL) was added HATU (104.6 mg, 0.27 mmol, 2 eq) in one portion, the mixture was stirred at 25° C. for 1 hr. Isopropylamine (16.2 mg, 0.27 mmol, 23.65 µL, 2 eq) was added in the mixture and stirred for 1 hr at the temperature. LCMS showed the starting material was consumed completely and 91.4% of desired mass was detected. The reaction mixture was quenched by addition of brine (5 mL) and extracted with DCM (10 mL*2). The combined organic layers was dried over $Na_2SO_4$, filtered, and concentrated under reduced pressure to give a residue. The residue was purified by prep-HPLC to give Compound 21 (42.3 mg, 0.095 mmol, 69.72% yield). LCMS and $^1$HNMR indicated it was desired compound. LCMS (ESI): RT=0.788 min, mass calcd for $C_{19}H_{19}F_3N_6O$, 404.39, m/z found 405 [M+H]$^+$. $^1$H NMR (400 MHz, $CDCl_3$) δ 9.25 (s, 1H), 8.57 (d, J=2.0 Hz, 1H), 7.82 (dd, J=2.3, 8.8 Hz, 1H), 7.52 (s, 1H), 7.51-7.46 (m, 2H), 7.39-7.34 (m, 2H), 5.96 (br d, J=8.5 Hz, 1H), 4.48 (s, 3H), 4.37-4.28 (m, 1H), 1.29 (d, J=6.5 Hz, 6H).

Example 16: N-ethyl-3-(2-methyl-2H-tetrazol-5-yl)-4-((3-(trifluoromethyl)phenyl) amino)benzamide (Compound 22)

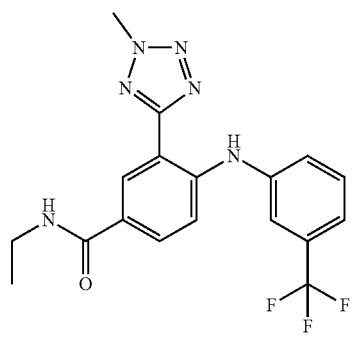 [SMILES: CCNC(=O)c1ccc(Nc2cccc(C(F)(F)F)c2)c(-c2nnn(C)n2)c1]

189
Preparation of Compound 22

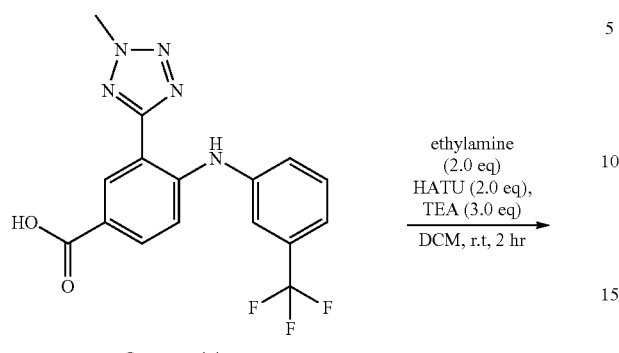

Compound 4 ethylamine (2.0 eq)
HATU (2.0 eq),
TEA (3.0 eq)
DCM, r.t, 2 hr

To a mixture of Compound 4 (50 mg, 0.13 mmol, 1 eq) and TEA (41.7 mg, 0.41 mmol, 57.47 μL, 3 eq) in DCM (2 mL) was added HATU (104.6 mg, 0.27 mmol, 2 eq) in one portion at 25° C. under $N_2$. The mixture was stirred at 25° C. for 1 hr, ethylamine (12.4 mg, 0.27 mmol, 18.01 μL, 2 eq) was added in the reaction. The mixture was stirred at 25° C. for 1 hr. LCMS showed the starting material was consumed completely and the desired mass was detected. The reaction mixture was quenched by addition brine (5 mL) and extracted with DCM (10 mL*2). The combined organic layers was dried over $Na_2SO_4$, filtered, and concentrated under reduced pressure to give a residue. The residue was purified by prep-HPLC to give Compound 22 (38 mg, 0.086 mmol, 62.75% yield). LCMS (ESI): RT=0.772 min, mass calcd for $C_{18}H_{17}F_3N_6O$, 390.36, m/z found 391 $[M+H]^+$. $^1H$ NMR (400 MHz, $CDCl_3$) δ 9.27 (s, 1H), 8.59 (d, J=2.5 Hz, 1H), 7.82 (dd, J=2.3, 8.8 Hz, 1H), 7.53 (s, 1H), 7.50-7.46 (m, 2H), 7.39-7.34 (m, 2H), 6.15 (br s, 1H), 4.47 (s, 3H), 3.61-3.46 (m, 2H), 1.28 (t, J=7.3 Hz, 3H).

190
Example 17: 3-(2-methyl-2H-tetrazol-5-yl)-N-(methylsulfonyl)-4-((3-(trifluoromethyl)phenyl)amino)benzamide (Compound 23)

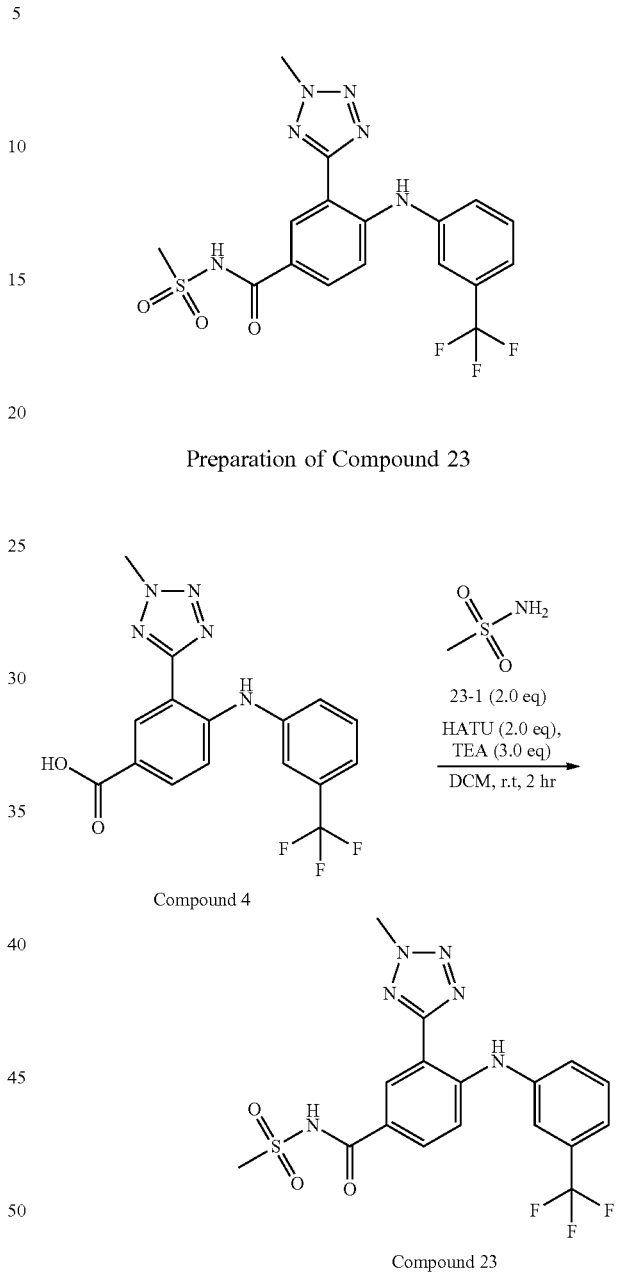

Preparation of Compound 23

To a mixture of Compound 4 (50 mg, 0.13 mmol, 1 eq) and TEA (41.7 mg, 0.41 mmol, 57.47 μL, 3 eq) in DCM (2 mL) was added HATU (104.6 mg, 0.27 mmol, 2 eq) in one portion, the mixture was stirred at 25° C. for 1 hr, methanesulfonamide 23-1 (26.1 mg, 0.27 mmol, 2 eq) was added in the mixture and stirred for 1 hr at 25° C. LCMS showed the starting material was consumed completely and 84.3% of desired mass was detected. The reaction mixture was quenched by addition brine (5 mL) and extracted with DCM (10 mL*2). The combined organic layers was dried over $Na_2SO_4$, filtered, and concentrated under reduced pressure to give a residue. The residue was purified by prep-HPLC to give Compound 23 (10 mg, 0.02 mmol, 15.24% yield).

LCMS and ¹HNMR indicated it was desired compound. LCMS (ESI): RT=0.754 min, mass calcd for $C_{17}H_{15}F_3N_6O_3S$, 440.40, m/z found 441 [M+H]⁺ 0.1H NMR (400 MHz, CDCl₃) δ 9.58 (s, 1H), 8.72-8.67 (m, 2H), 7.85 (dd, J=2.3, 8.8 Hz, 1H), 7.57-7.49 (m, 3H), 7.47-7.43 (m, 1H), 7.33 (d, J=9.0 Hz, 1H), 4.50 (s, 3H), 3.47 (s, 3H).

Example 18: methyl 3-(2-(2-fluorobenzyl)-2H-tetrazol-5-yl)-4-((4-(trifluoromethyl)phenyl) amino)benzoate (Compound 24)

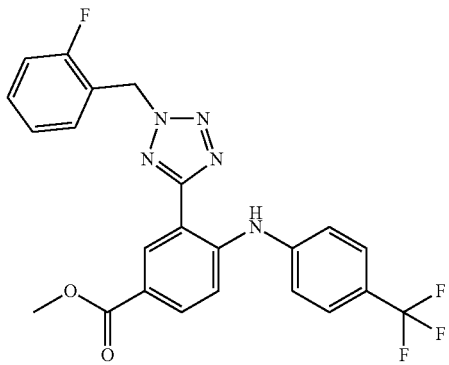 [SMILES: COC(=O)c1ccc(Nc2ccc(C(F)(F)F)cc2)c(-c2nnn(Cc3ccccc3F)n2)c1]

Preparation of Compound 24

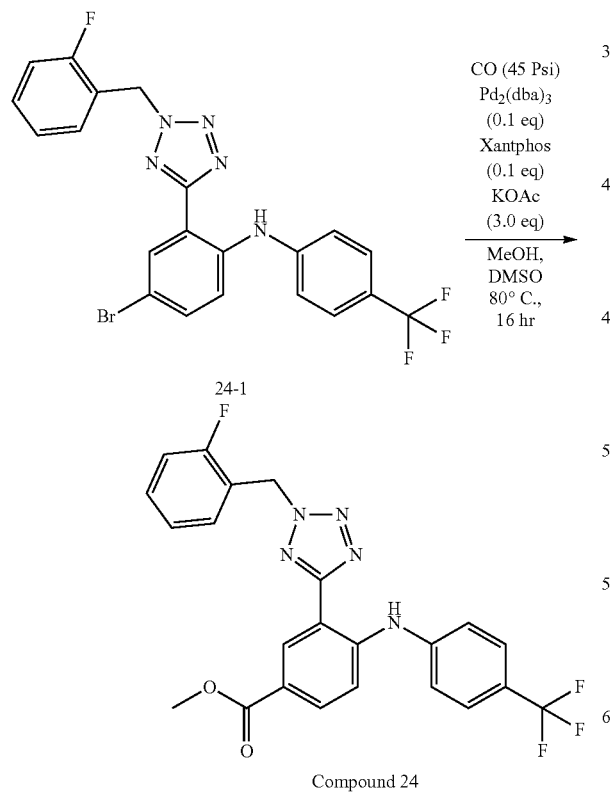

To a mixture of 24-1 (1.2 g, 2.44 mmol, 1 eq) in DMSO (10 mL) and MeOH (2 mL) were added Xantphos (141.0 mg, 0.24 mmol, 0.1 eq), Pd₂(dba)₃ (223.2 mg, 0.24 mmol, 0.1 eq) and KOAc (717.7 mg, 7.31 mmol, 3 eq). The suspension was degassed under vacuum and purged with CO several times. The mixture was stirred for 12 hrs under CO 45 psi at 80° C. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na₂SO₄, filtered, and concentrated in vacuum. The residue was purified by column chromatography (Si₂O) to obtain crude Compound 24 (0.15 g, 0.31 mmol, 13.05% yield) was obtained, and (0.03 g, 0.063 mmol, 1 eq) was separated by prep-HPLC. Tt was monitored by LCMS. It was re-purified by prep-HPLC to obtain Compound 24 (9.51 mg, 0.020 mmol). LCMS (ESI): RT=0.930 min, mass calc. for: $C_{23}H_{17}F_4N_5O_2$ 471.13, m/z found 472.0 [M+H]⁺; ¹H NMR (400 MHz, CD₃OD) δ8.82 (d, J=2.0 Hz, 1H), 7.98 (dd, J=2.1, 8.9 Hz, 1H), 7.68-7.64 (m, J=8.5 Hz, 2H), 7.58-7.39 (m, 5H), 7.29-7.20 (m, 2H), 6.06 (s, 2H), 3.91 (s, 3H).

Example 19: 3-(2-(2-fluorobenzyl)-2H-tetrazol-5-yl)-4-((4-(trifluoromethyl)phenyl)amino) benzoic Acid (Compound 25)

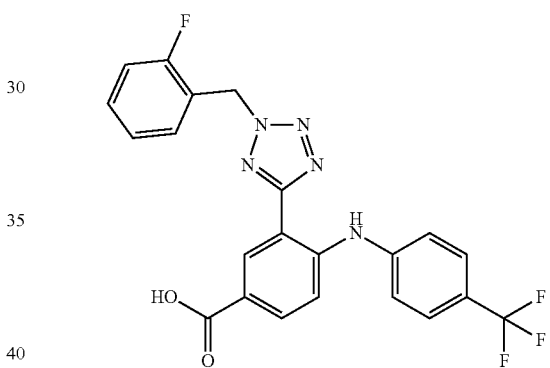

Preparation of Compound 25

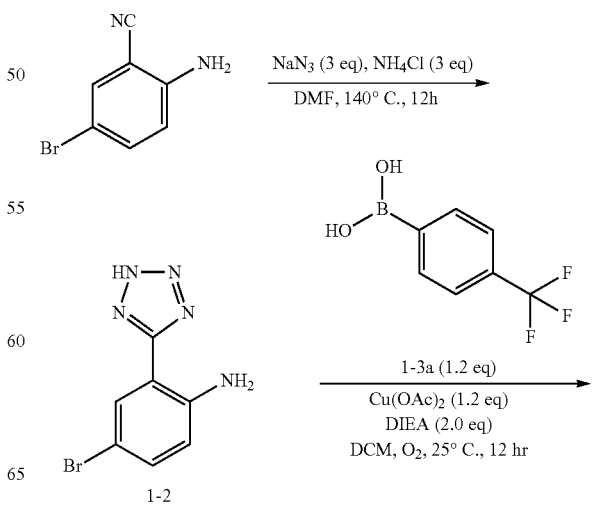

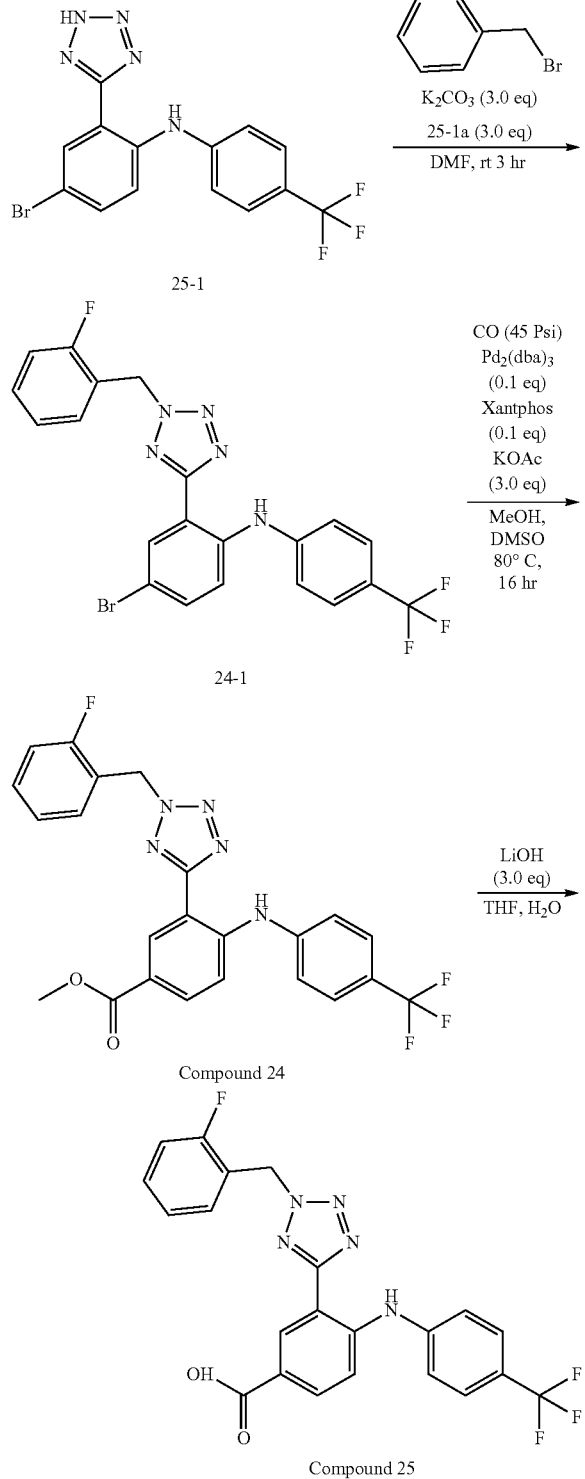

Compound 24

Compound 25

Step 1: 4-bromo-2-(2H-tetrazol-5-yl)aniline

To a solution of 1-1 (10 g, 50.75 mmol, 1 eq) in DMF (50 mL) were added NaN$_3$ (24.42 g, 375.6 mmol, 7.40 eq) and NH$_4$Cl (8.14 g, 152.2 mmol, 5.32 mL, 3 eq). The mixture was stirred at 140° C. for 12 hr. TLC showed that the reaction was complete. The reaction solution was added to H$_2$O (200 mL). The aqueous phase was adjust to pH=5 with NaHCO$_3$ and extracted with ethyl acetate (150 mL*3). The combined organic phase was washed with brine (50 mL*5), dried with anhydrous Na$_2$SO$_4$, filtered, and concentrated in vacuum. The residue was used the next step without purification. Compound 1-2 (30 g, crude) was obtained.

Step 2: 4-bromo-2-(2H-tetrazol-5-yl)-N-(4-(trifluoromethyl)phenyl)aniline

To a mixture of 1-2 (3 g, 12.50 mmol, 1 eq) and [4-(trifluoromethyl)phenyl]boronic acid 1-3a (2.37 g, 12.5 mmol, 1 eq) in DCM (20 mL) were added Cu(OAc)$_2$ (4.54 g, 25.0 mmol, 2 eq) and DIPEA (8.08 g, 62.50 mmol, 10.88 mL, 5 eq) in one portion at 25° C. under O$_2$. The mixture was stirred for 18 hrs under O$_2$ (15 psi). LCMS showed the reaction was finished. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered, and concentrated in vacuum. The residue was triturated by PE (20 mL), and the mixture was filtered and the filtered cake was washed with PE (10 mL*3). The filtered cake was concentrated in vacuum. The crude product Compound 25-1 (4 g, crude) was used for next step directly.

Step 3: 4-bromo-2-(2-(2-fluorobenzyl)-2H-tetrazol-5-yl)-N-(4-(trifluoromethyl)phenyl)aniline To the solution of 25-1 (4 g, 10.41 mmol, 1 eq) in DMF (20 mL) were added 25-1a (3.94 g, 20.8 mmol, 2.51 mL, 2 eq) and Cs$_2$CO$_3$ (6.79 g, 20.8 mmol, 2 eq). The mixture was stirred at 25° C. for 3 hr. TLC showed the reaction was complete. The reaction solution was added to H$_2$O (30 mL). The mixture was extracted with ethyl acetate (20 mL*3). The combined organic phase was washed with brine (10 mL*5), dried with anhydrous Na$_2$SO$_4$, filtered, and concentrated in vacuum. The residue was purified by column chromatography (Si$_2$O). 24-1 (1.5 g, 2.36 mmol, 22.71% yield) was obtained.

Step 4: methyl 3-(2-(2-fluorobenzyl)-2H-tetrazol-5-yl)-4-((4-(trifluoromethyl)phenyl)amino) benzoate To a mixture of 24-1 (1.2 g, 2.44 mmol, 1 eq) in DMSO (10 mL) and MeOH (2 mL) were added Xantphos (141.0 mg, 0.24 mmol, 0.1 eq), Pd$_2$ (dba)$_3$ (223.2 mg, 0.24 mmol, 0.1 eq) and KOAc (717.7 mg, 7.31 mmol, 3 eq). The suspension was degassed under vacuum and purged with CO several times. The mixture was stirred for 12 hrs under CO 45 psi at 80° C. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered, and concentrated in vacuum. The residue was purified by column chromatography (Si$_2$O). Compound 24 (0.15 g, 0.31 mmol, 13.05% yield) was obtained.

Step 5: 3-(2-(2-fluorobenzyl)-2H-tetrazol-5-yl)-4-((4-(trifluoromethyl)phenyl)amino)benzoic Acid To a solution of Compound 24 (0.03 g, 0.063 mmol, 1 eq) in MeOH (1 mL) and H$_2$O (0.1 mL) was added LiOH (7.6 mg, 0.031 mmol, 5 eq). The mixture was stirred at 60° C. for 3 hr. LCMS showed the reaction was complete. The mixture was quenched by H₂O (30 mL) and adjusted pH to 4 with HCl (4 M). The mixture was extracted with EA (30 mL*3). The combined organic phase was washed with brine (20 mL*3), dried with anhydrous Na₂SO₄, filtered, and concentrated in vacuum. The residue was purified by prep-HPLC to give Compound 25 (5.08 mg, 0.011 mmol, 17.45% yield) was obtained. LCMS (ESI): RT=0.848 min, mass calc. for: $C_{22}H_{15}F_4N_5O_2$ 457.12, m/z found 458.0 [M+H]⁺; ¹H NMR (400 MHz, CD₃OD) δ 8.86 (d, J=2.0 Hz, 11H), 8.02 (dd, J=1.8, 8.8 Hz, 1H), 7.66 (d, J=8.5 Hz, 2H), 7.59-7.53 (m, 2H), 7.50-7.40 (m, 3H), 7.29-7.20 (m, 2H), 6.06 (s, 2H).

Example 20: methyl 3-(2-(2-fluorobenzyl)-2H-tetrazol-5-yl)-4-((3-(trifluoromethyl)phenyl)amino)benzoate (Compound 26)

Preparation of Compound 26

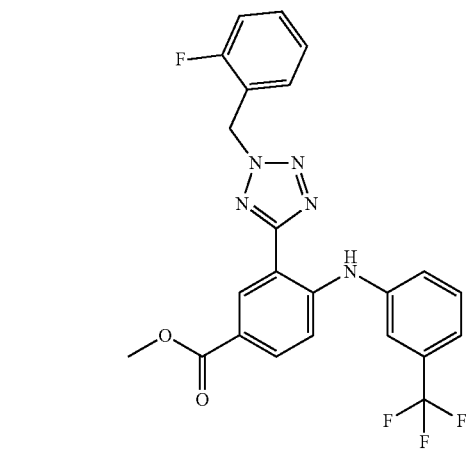 [SMILES: COC(=O)c1ccc(Nc2cccc(C(F)(F)F)c2)c(-c2nnn(Cc3ccccc3F)n2)c1]

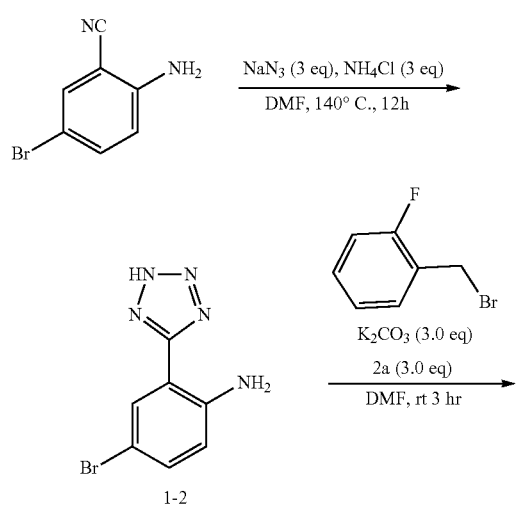

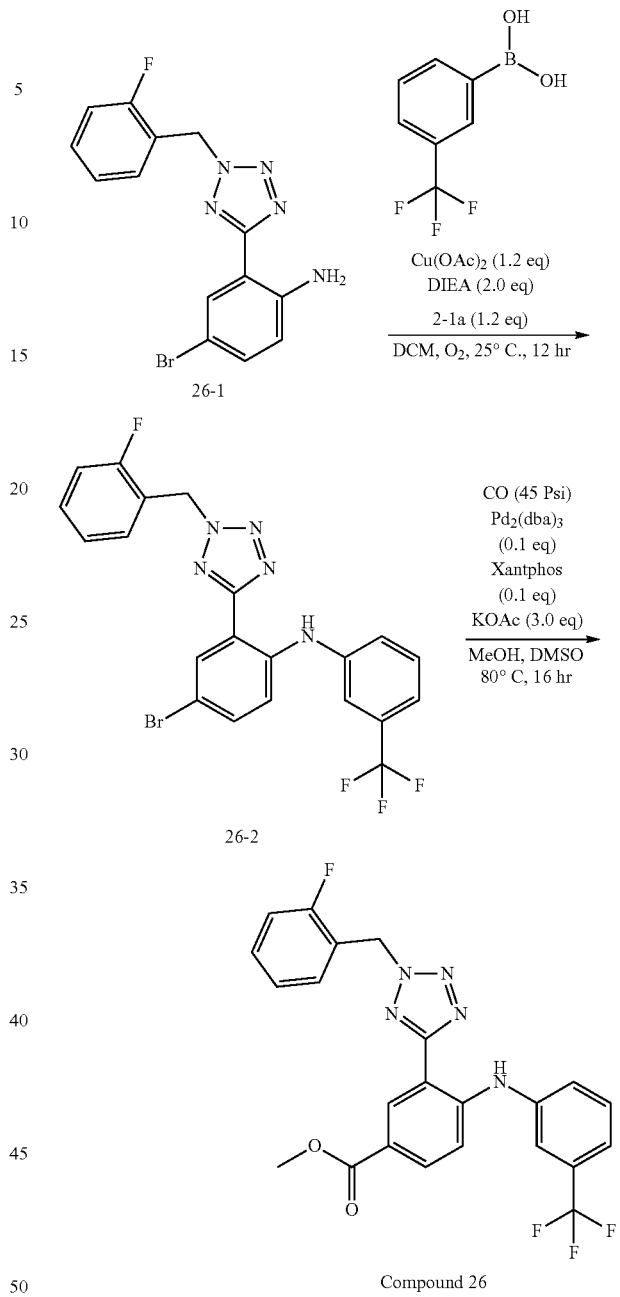

Step 1: 4-bromo-2-(2H-tetrazol-5-yl)aniline

To a solution of 1-1 (10 g, 50.75 mmol, 1 eq) in DMF (50 mL) were added NaN₃ (24.42 g, 375.64 mmol, 7.40 eq) and NH₄Cl (8.14 g, 152.26 mmol, 5.32 mL, 3 eq). The mixture was stirred at 140° C. for 12 hr. TLC showed that the reaction was complete. The reaction solution was added to H₂O (200 mL). The aqueous phase was adjusted to pH=5 and extracted with ethyl acetate (150 mL*3). The combined organic phase was washed with brine (50 mL*5), dried with anhydrous Na₂SO₄, filtered, and concentrated in vacuum. The residue was used the next step without purification. 1-2 (30 g, crude) was obtained.

Step 2: 4-bromo-2-(2-(2-fluorobenzyl)-2H-tetrazol-5-yl)aniline

To a solution of 1-2 (3 g, 12.50 mmol, 1 eq) in DMF (20 mL) were added 1-(bromomethyl)-2-fluoro-benzene (4.72 g, 24.99 mmol, 3.01 mL, 2 eq) and $Cs_2CO_3$ (8.14 g, 24.99 mmol, 2 eq). The mixture was stirred at 25° C. for 3 hr. TLC (PE/EA=5/1) showed the reaction was complete. The reaction solution was added to $H_2O$ (50 mL). The mixture was extracted with ethyl acetate (20 mL*3). The combined organic phase was washed with brine (10 mL*5), dried with anhydrous $Na_2SO_4$, filtered, and concentrated in vacuum. The residue was purified by column chromatography ($SiO_2$), and 26-1 (1.5 g, 4.08 mmol, 32.68% yield) was obtained.

Step 3: 4-bromo-2-[2-[(2-fluorophenyl)methyl]tetrazol-5-yl]-N-[3-(trifluoromethyl)phenyl]aniline To a mixture of 26-1 (1.5 g, 4.31 mmol, 1 eq) and 2-1a (981.9 mg, 5.17 mmol, 1.2 eq) in DCM (20 mL) were added $Cu(OAc)_2$ (1.56 g, 8.62 mmol, 2 eq) and DIPEA (2.78 g, 21.54 mmol, 3.75 mL, 5 eq) in one portion at 25° C. under 02. The mixture was stirred for 18 hrs under 15 psi. TLC showed the reaction was finished. The mixture was quenched by EA (30 mL), and the mixture was extracted with EA (20 mL*3). The combined organic phase was washed with brine (20 mL*3), dried with anhydrous $Na_2SO_4$, filtered, and concentrated in vacuum. The residue was purified by column chromatography ($SiO_2$). 26-2 (1.2 g, 2.14 mmol, 49.68% yield) was obtained.

Step 4: methyl 3-[2-[(2-fluorophenyl)methyl]tetrazol-5-yl]-4-[3-(trifluoromethyl)anilino]benzoate To a mixture of 26-2 (1.2 g, 2.44 mmol, 1 eq) in DMSO (10 mL) and MeOH (2 mL) were added Xantphos (141.0 mg, 0.24 mmol, 0.1 eq), $Pd_2(dba)_3$ (223.2 mg, 0.24 mmol, 0.1 eq) and KOAc (717.7 mg, 7.31 mmol, 3 eq). The suspension was degassed under vacuum and purged with CO several times. The mixture was stirred for 12 hrs at 45 psi at 80° C. TLC showed the reaction was complete. The mixture was quenched by EA (30 mL), and the mixture was filtered and the filtered cake was washed with EA (20 mL*3). The combined organic phase was washed with brine (20 mL*3), dried with anhydrous $Na_2SO_4$, filtered, and concentrated in vacuum. The residue was purified by column chromatography ($SiO_2$). Compound 26 (0.2 g, 0.28 mmol, 11.83% yield) was obtained. Compound 26 (0.03 g, 0.063 mmol, 1 eq) was further separated by prep-HPLC. It was monitored by LCMS and HPLC. Compound 26 (8.67 mg, 0.018 mmol, 28.90% yield) was obtained. LCMS (ESI): RT=0.921 min, mass calc. for: $C_{23}H_{17}F_4N_5O_2$ 471.13, m/z found 472.0 [M+H]+; $^1$H NMR (400 MHz, $CD_3OD$) δ 8.84 (d, J=2.0 Hz, 1H), 7.97 (dd, J=2.0, 8.8 Hz, 1H), 7.61-7.36 (m, 7H), 7.29-7.19 (m, 2H), 6.06 (s, 2H), 3.91 (s, 3H).

Example 21: 3-(2-(2-fluorobenzyl)-2H-tetrazol-5-yl)-4-((3-(trifluoromethyl)phenyl)amino) benzoic Acid (Compound 27)

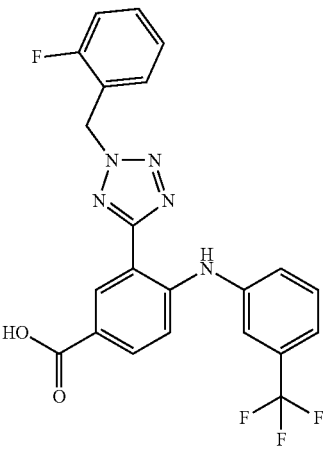 [SMILES: O=C(O)c1ccc(Nc2cccc(C(F)(F)F)c2)c(-c2nnn(Cc3ccccc3F)n2)c1]

Preparation of Compound 27

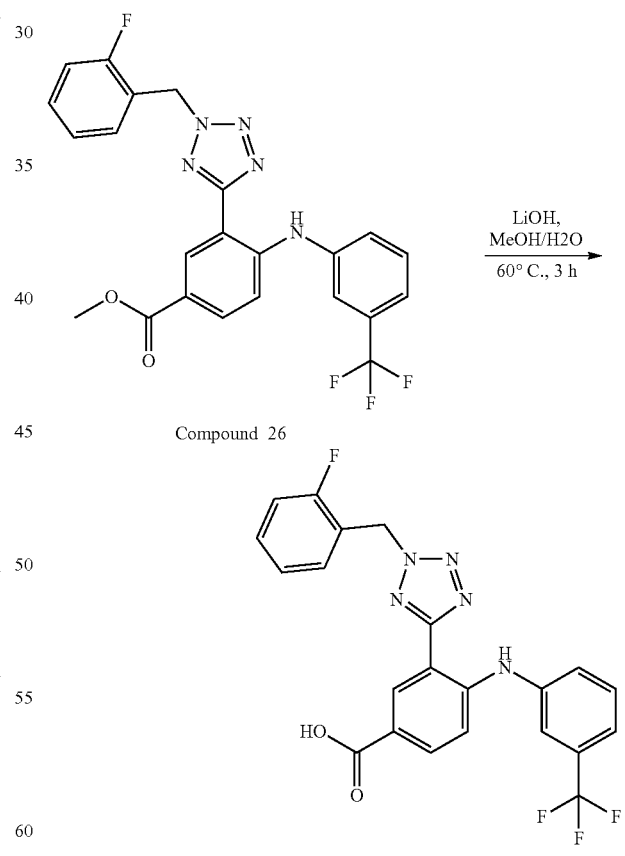

To a solution of Compound 26 (30 mg, 0.063 mmol, 1 eq) in MeOH (1 mL) and $H_2O$ (0.1 mL) was added LiOH (15.24 mg, 0.63 mmol, 10 eq). The mixture was stirred at 60° C. for 3 hr. LCMS showed the reaction was complete. The mixture was quenched by H₂O (30 mL) and adjusted pH to 4 with HCl (4 M). The mixture was extracted with EA (30 mL*3). The combined organic phase was washed with brine (20 mL*3), dried with anhydrous Na₂SO₄, filtered, and concentrated in vacuum. The residue was purified by pre-HPLC. Compound 27 (6.62 mg, 0.014 mmol, 22.74% yield) was obtained. LCMS (ESI): RT=0.844 min, mass calc. for: $C_{22}H_{15}F_4N_5O_2$ 458.12, m/z found 458.0 [M+H]⁺; ¹H NMR (400 MHz, CD₃OD) δ8.87 (d, J=2.0 Hz, 1H), 7.99 (dd, J=1.9, 8.9 Hz, 1H), 7.61-7.38 (m, 7H), 7.29-7.19 (m, 2H), 6.07 (s, 2H).

Example 22: 3-(1-methyl-1H-imidazol-4-yl)-4-((4-(trifluoromethyl)phenyl)amino)benzoic Acid (Compound 28)

Preparation of Compound 28

Step 1: methyl 3-bromo-4-((4-(trifluoromethyl)phenyl)amino)benzoate

To a solution of methyl 4-amino-3-bromo-benzoate (28-1, 400 mg, 1.74 mmol, 1 eq) and [4-(trifluoromethyl)phenyl] boronic acid (1-3a, 396.3 mg, 2.09 mmol, 1.2 eq) in DCM (3 mL) were added Cu(OAc)₂ (379.0 mg, 2.09 mmol, 1.2 eq) and DIPEA (449.4 mg, 3.48 mmol, 0.6 mL, 2 eq) under O₂ (15 psi). The mixture was stirred at 25° C. for 16 hr. TLC indicated that the starting material was consumed and that several new spots were formed. The reaction mixture was combined with another batch to work up. The reaction mixture was filtered. The filtered cake was washed with ethyl acetate (10 ml*3) and the combined organic layers was washed by NaCl (15 mL*3) then concentrated in vacuum to give crude product. The residue was purified by column chromatography (SiO₂). Methyl 3-bromo-4-[4-(trifluoromethyl)anilino]benzoate (28-2, 200 mg, 0.22 mmol, 6.6% yield) was obtained.

201

Step 2: methyl 3-(4,4,5,5-tetramethyl-1,3,2-dioxaborolan-2-yl)-4-((4-(trifluoromethyl)phenyl) amino) benzoate The mixture of methyl 3-bromo-4-[4-(trifluoromethyl) anilino]benzoate (28-2,200 mg, 0.53 mmol, 1 eq) and 4,4,5,5-tetramethyl-2-(4,4,5,5-tetramethyl-1,3,2-dioxaborolan-2-yl)-1,3,2-dioxaborolane (28-2a, 203.6 mg, 0.80 mmol, 1.5 eq) in dioxane (2 mL) were added Pd(dppt)Cl$_2$ (19.5 mg, 27 umol, 0.05 eq) and AcOK (104.9 mg, 1.07 mmol, 2 eq). The mixture was stirred at 90° C. for 2 hr. LCMS showed the starting material was consumed completely and the desired mass was detected. H$_2$O (8 mL) was added to the solution. The mixture was extracted with ethyl acetate (12 mL*3). The combined organic layers were washed with brine (20 mL*2), dried over anhydrous Na$_2$SO$_4$, filtered, and concentrated in vacuum. The residue was purified by column chromatography (SiO$_2$). Methyl 3-(4,4,5,5-tetramethyl-1,3,2-dioxaborolan-2-yl)-4-[4-(trifluoromethyl)anilino]benzoate (28-3, 150 mg, 0.35 mmol, 66.62% yield) was obtained.

Step 3: methyl 3-(1-methyl-1H-imidazol-4-yl)-4-((4-(trifluoromethyl)phenyl)amino)benzoate To a solution of methyl 3-(4,4,5,5-tetramethyl-1,3,2-dioxaborolan-2-yl)-4-[4-(trifluoromethyl)anilino]benzoate (28-3, 150 mg, 0.35 mmol, 1 eq) and 4-bromo-1-methylimidazole (28-3a, 57.3 mg, 0.35 mmol, 1 eq) in dioxane (2 mL) was added Cs$_2$CO$_3$ (232 mg, 0.71 mmol, 2 eq), Pd(dppf)Cl$_2$ (13 mg, 17.8 umol, 0.05 eq), H$_2$O (6.42 mg, 0.35 mmol, 6.4 µL, 1 eq). The mixture was stirred at 90° C. for 2 hr. LCMS showed the starting material was consumed completely and the desired mass was detected. TLC indicated that the starting material was consumed completely and that two new spots were formed. 1-120 (8 mL) was added to the solution. The mixture was extracted with ethyl acetate (12 mL*3). The combined organic layers were washed with brine (15 mL*2), dried over anhydrous Na$_2$SO$_4$, filtered, and concentrated in vacuum. The residue was purified by column chromatography (SiO$_2$). Methyl 3-(1-methylimidazol-4-yl)-4-[4-(trifluoromethyl)anilino]benzoate (28-4, 50 mg, 0.13 mmol, 37.4% yield) was obtained.

Step 4: 3-(1H-imidazol-4-yl)-4-((4-(trifluoromethyl)phenyl)amino)benzoic Acid The mixture of methyl 3-(1-methyl-1H-imidazol-4-yl)-4-((4-(trifluoromethyl)phenyl)amino)benzoate (28-4.25 mg, 66.6 umol, 1 eq) in THF (1 mL) was added into a solution of LiOH (7.9 mg, 0.33 mmol, 5 eq) and H$_2$O (1.20 mg, 66.6 umol, 1.20 µL, 1 eq). The mixture was stirred at 60° C. for 16 hr. LCMS showed the starting material was consumed and the desired mass was detected. The reaction mixture was combined with another batch to work up. H$_2$O (6 mL) was added to the solution. The mixture was extracted with ethyl acetate (10 mL*3). The combined organic layers were washed with brine (15 mL*2), dried over anhydrous Na$_2$SO$_4$, filtered, and concentrated in vacuum. The residue was purified by prep-HPLC. Compound 28 (4.01 mg, 9.8 umol, 7.42% yield, HCl) was obtained. LCMS (ESI): RT=0.673 min, mass calc. for C$_{18}$H$_{14}$F$_3$N$_3$O$_2$ 361.10, m/z found 361.9 [M+H]$^+$; δ $^1$H NMR (400 MHz, CD$_3$OD) δ=8.95 (s, 1H), 8.16 (s, 1H), 8.07 (d, J=8.6 Hz, 1H), 7.81 (s, 1H), 7.56 (d, J=8.3 Hz, 2H), 7.52 (d, J=8.5 Hz, 1H), 7.22 (d, J=8.3 Hz, 2H), 3.98 (s, 3H).

202

Example 23: 3-(2-aminopyridin-4-yl)-N-isopropyl-4-((4-(trifluoromethyl)phenyl)amino) benzamide (Compound 29)

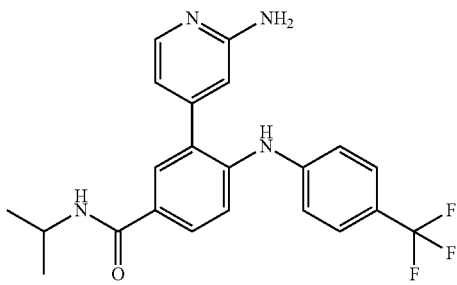 [SMILES: CC(C)NC(=O)c1ccc(Nc2ccc(C(F)(F)F)cc2)c(-c2ccnc(N)c2)c1]

Preparation of Compound 29

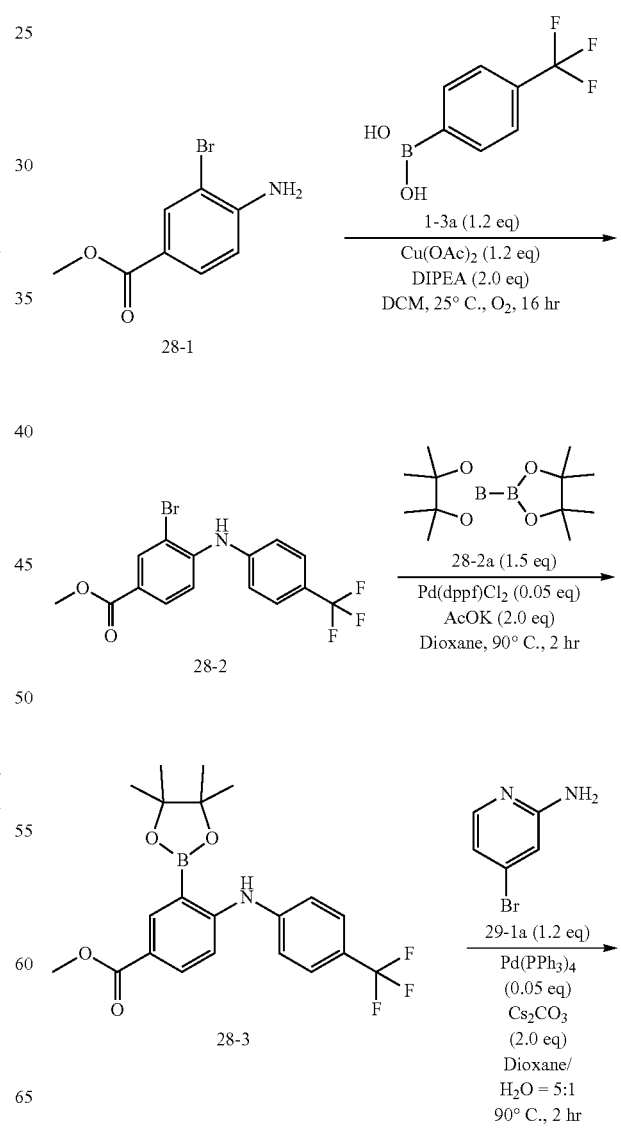

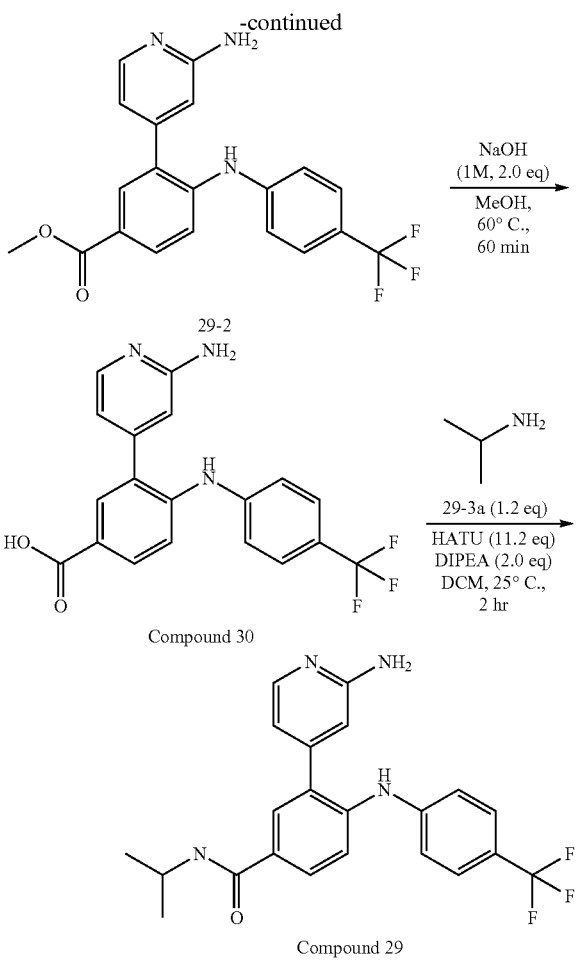

over Na$_2$SO$_4$, filtered, and concentrated to dryness under reduced pressure. The residue was purified by column chromatography (SiO$_2$) to obtain 28-3 (100 mg, 0.24 mmol, 88.8% yield).

Step 3: methyl 3-(2-amino-4-pyridyl)-4-[4-(trifluoromethyl)anilino]benzoate

To a solution of 28-3 (100 mg, 0.24 mmol, 1.0 eq), 29-1a (49 mg, 0.28 mmol, 1.2 eq) and Cs$_2$CO$_3$ (155 mg, 0.47 mmol, 2.0 eq) in dioxane (1.5 mL) and H$_2$O (0.3 mL) was added Pd(dppf)Cl$_2$ (8.7 mg, 12 mmol, 0.05 eq) under N$_2$. The mixture was stirred at 90° C. for 3 hr LCMS showed that 28-3 was consumed completely and one main peak with desired MS was detected. TLC indicated 28-3 was consumed completely and one new spot formed. The reaction mixture was concentrated under reduced pressure. The mixture was diluted with water (10 mL) and the resultant mixture was extracted with EA (30 mL*3). The combined organic layers were dried over Na$_2$SO$_4$, filtered, and concentrated to dryness under reduced pressure. The residue was purified by column chromatography (SiO$_2$) to obtain 29-2 (70 mg, 0.18 mmol, 76.1% yield).

Step 4: 3-(2-amino-4-pyridyl)-4-[4-(trifluoromethyl) anilino]benzoic Acid

To a solution of 29-2 (40 mg, 0.10 mmol, 1.0 eq) in MeOH (0.5 mL) was added NaOH (1 M, 0.2 mL, 2.0 eq). The mixture was stirred at 60° C. for 1 hr. LCMS showed 29-2 was consumed completely and one main peak with desired MS was detected. The reaction mixture was adjusted with HC (1 M) to pH-6. The mixture was diluted with water (10 mL) and the resultant mixture was extracted with EA (40 mL*3). The combined organic layers were dried over Na$_2$SO$_4$, filtered, and concentrated to dryness under reduced pressure to obtain Compound 30 (25 mg, crude).

Step 5: 33-(2-amino-4-pyridyl)-N-isopropyl-4-[4-(trifluoromethyl)anilino]benzamide To a solution of Compound 30 (25 mg, 67 umol, 1.0 eq), 29-3a (4.8 mg, 80 umol, 1.2 eq) and DIPEA (17 mg, 0.13 mmol, 2.0 eq) in DCM (1 mL) was added HATU (285 mg, 0.75 mmol, 11.2 eq) at 0° C. for 5 min. And then the mixture was stirred at 25° C. for 2 hr. LCMS showed Compound 30 was consumed completely, and one main peak with desired MS was detected. The mixture was diluted with water (15 mL) and the resultant mixture was extracted with EA (40 mL*3). The combined organic layers were dried over Na$_2$SO$_4$, filtered, and concentrated to dryness under reduced pressure. The residue was purified by prep-HPLC to obtain Compound 29 (8.17 mg, 29.4% yield). LCMS (ESI): RT=0.832 min, mass calcd. for C$_{22}$H$_{21}$F$_3$N$_4$O, 414.17, m/z found 415.4 [M+H]$^+$, $^1$H NMR (400 MHz, CDCl$_3$) δ 8.15 (d, J=5.02 Hz, 1H), 7.69 (m, 2H), 7.53 (d, J=8.53 Hz, 2H), 7.43 (d, J=8.28 Hz, 1H), 7.12 (d, J=8.53 Hz, 2H), 6.72 (d, J=5.27 Hz, 1H), 6.57 (s, 1H), 5.96 (s, 1H), 5.85 (br d, J=6.27 Hz, 1H), 4.61 (br s, 2H), 4.30 (m, 1H), 1.27 (d, J=6.53 Hz, 6H).

Step 1: methyl 3-bromo-4-[4-(trifluoromethyl)anilino]benzoate

To a solution of 28-1 (1.00 g, 4.35 mmol, 1.0 eq), 1-3a (991.0 mg, 5.22 mmol, 1.2 eq) and Cu(OAc)$_2$ (947.0 mg, 5.22 mmol, 1.2 eq) in DCM (10 mL) was added DIPEA (1.12 g, 8.69 mmol, 2.0 eq) under O$_2$. The mixture was stirred at 25° C. for 16 hr under O$_2$. TLC indicated that 28-1 remained, and that several new spots were formed. LCMS showed that 28-1 remained with several new peaks and 27% of desired compound was detected. The reaction mixture was concentrated under reduced pressure. The residue was purified by column chromatography (SiO$_2$) to obtain 28-2 (300.0 mg, 17.7% yield).

Step 2: methyl 3-(4,4,5,5-tetramethyl-1,3,2-dioxaborolan-2-yl)-4-[4-(trifluoromethyl)anilino]benzoate To a solution of 28-2 (100 mg, 0.27 mmol, 1.0 eq), 28-2a (102 mg, 0.40 mmol, 1.5 eq) and AcOK (52.5 mg, 0.53 mmol, 2.0 eq) in dioxane (1 mL) was added Pd(dppf)Cl$_2$ (9.8 mg, 13 umol, 0.05 eq). The mixture was stirred at 90° C. for 2 br. LCMS showed that 28-2 was completely consumed and detected several new peaks and 68% of the desired compound. TLC indicated 28-2 was consumed completely and several new spots were formed. The mixture was diluted with water (15 mL) and the resultant mixture was extracted with EA (40 mL*3). The combined organic layers were dried

Example 24: 3-(2-aminopyridin-4-yl)-4-((4-(trifluoromethyl)phenyl)amino)benzoic Acid (Compound 30)

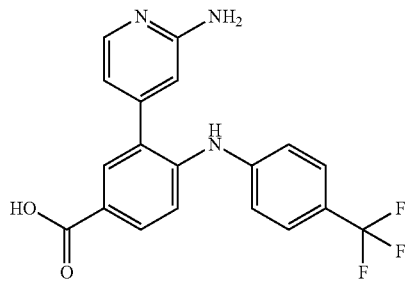

Preparation of Compound 30

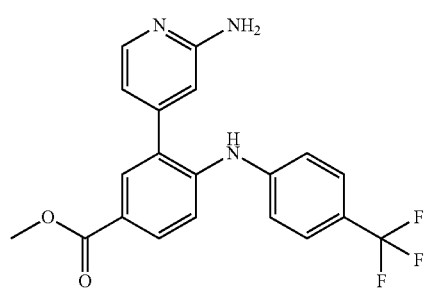

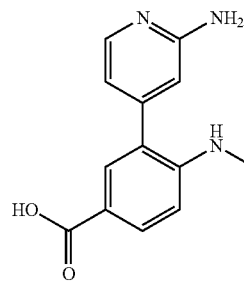

Compound 30

To a solution of 29-2 (30.0 mg, 77 umol, 1.0 eq) in MeOH (0.5 mL) was added NaOH (1 M, 0.2 mL, 2.0 eq). The mixture was stirred at 60° C. for 1 hr. LCMS showed that 29-2 was consumed completely and one main peak with desired MS was detected. The reaction mixture was adjusted with HCl (1 M) to pH-~$^6$. The mixture was diluted with water (10 mL) and the resultant mixture was extracted with EA (40 mL*3). The combined organic layers were dried over $Na_2SO_4$, filtered, and concentrated to dryness under reduced pressure. The residue was purified by prep-HPLC to obtain Compound 30 (2.93 mg, 10.1% yield). LCMS (ESI): RT=0.811 min, mass calcd. for $C_{19}H_{14}F_3N_3O_2$ 373.10, m/z found 374.4 [M+H]$^+$, $^1$H NMR (400 MHz, DMSO-$d_6$) δ ppm 8.33 (s, 1H), 7.90 (m, 2H), 7.82 (s, 1H), 7.52 (d, J=8.38 Hz, 2H), 7.46 (d, J=8.50 Hz, 1H), 7.16 (d, J=8.25 Hz, 2H), 6.54 (s, 2H), 5.98 (s, 2H).

Example 25: 3-(2-aminopyridin-4-yl)-N-isopropyl-4-((3-(trifluoromethyl)phenyl)amino) benzamide (Compound 31)

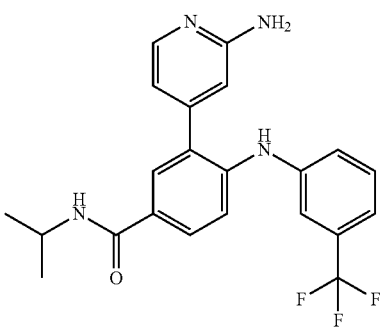 [SMILES: CC(C)NC(=O)c1ccc(Nc2cccc(C(F)(F)F)c2)c(-c2ccnc(N)c2)c1]

Preparation of Compound 31

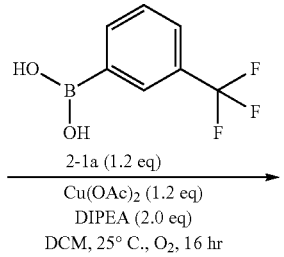

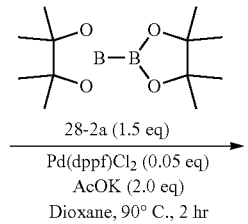

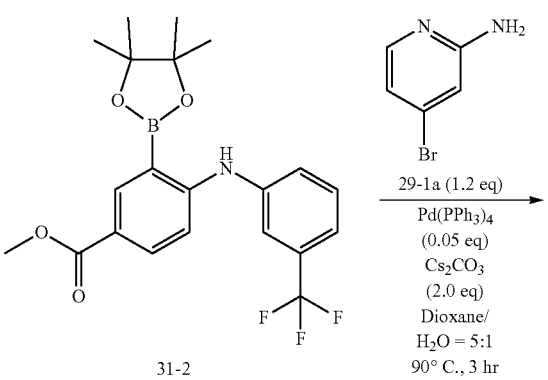

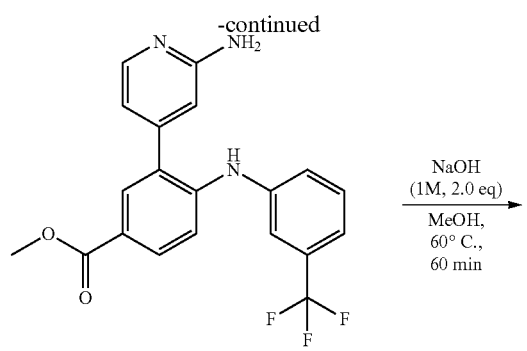

31-3

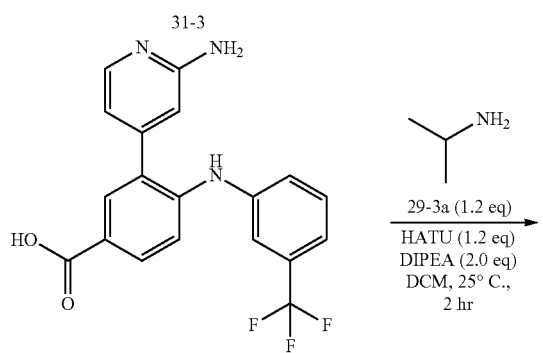

Compound 32

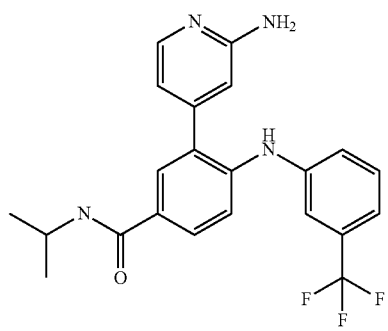

Compound 31

Step 1: methyl 3-bromo-4-[3-(trifluoromethyl)anilino]benzoate

To a solution of 28-1 (3.50 g, 15.2 mmol, 1.0 eq), 2-2a (3.47 g, 18.3 mmol, 1.2 eq) and Cu(OAc)$_2$ (3.32 g, 18.3 mmol, 1.2 eq) in DCM (10 mL) was added DIPEA (3.93 g, 30.4 mmol, 2.0 eq) under O$_2$. The mixture was stirred at 25° C. for 16 hr under O$_2$. TLC indicated that 28-1 remained with several new spots detected. The reaction mixture was concentrated under reduced pressure. The residue was purified by column chromatography (SiO$_2$) to obtain 31-1 (1.8 g, 29.7% yield).

Step 2: methyl 3-(4,4,5,5-tetramethyl-1,3,2-dioxaborolan-2-yl)-4-[3-(trifluoromethyl)anilino]benzoate To a solution of 31-1 (1.8 g, 4.80 mmol, 1.0 eq), 28-2a (1.80 g, 7.2 mmol, 1.5 eq) and AcOK (944 g, 9.6 mmol, 2.0 eq) in dioxane (10 mL) was added Pd(dppf)Cl$_2$ (176 mg, 0.24 mmol, 0.05 eq). The mixture was stirred at 90° C. for 2 hr under N$_2$. LCMS showed that 31-1 was completely, and one main peak with desired MS was detected. TLC indicated that 31-1 was consumed completely, and one new spot was formed. The reaction mixture was concentrated under reduced pressure. The mixture was diluted with water (20 mL), and the resultant mixture was extracted with EA (60 mL*3). The combined organic layers were dried over Na$_2$SO$_4$, filtered, and concentrated to dryness under reduced pressure. The residue was purified by column chromatography (SiO$_2$) to obtain 31-2 (1.9 g, 93.8% yield).

Step 3: Methyl 3-(4,4,5,5-tetramethyl-1,3,2-dioxaborolan-2-yl)-4-[3-(trifluoromethyl)anilino]benzoate To a solution of 31-2 (800.0 mg, 1.90 mmol, 1.0 eq), 29-1a (394.0 mg, 2.28 mmol, 1.2 eq) and Cs$_2$CO$_3$ (1.24 g, 3.80 mmol, 2.0 eq) in dioxane (1.5 mL) and H$_2$O (0.3 mL) was added Pd(dppf)Cl$_2$ (69.0 mg, 95 umol, 0.05 eq) under N$_2$. The mixture was stirred at 90° C. for 3 hr. TLC indicated that 31-2 was consumed completely, and one new spot was formed. The reaction mixture was concentrated under reduced pressure. The mixture was diluted with water (15 mL) and the resultant mixture was extracted with EA (40 mL*3). The combined organic layers were dried over Na$_2$SO$_4$, filtered, and concentrated to dryness under reduced pressure. The residue was purified by column chromatography (SiO$_2$) to obtain compound 31-3 (250 mg, 34.0% yield).

Step 4: 3-(2-Amino-4-pyridyl)-4-[3-(trifluoromethyl)anilino]benzoic Acid

To a solution of 31-3 (200 mg, 0.52 mmol, 1.0 eq) in MeOH (0.5 mL) was added NaOH (1 M, 1.0 mL, 2.0 eq). The mixture was stirred at 60° C. for 1 hr. LCMS showed 31-3 was consumed completely and one main peak with desired MS was detected. The reaction mixture was adjusted with HCl (1 M) to pH-6. The mixture was diluted with water (10 mL) and the resultant mixture was extracted with EA (40 mL*3). The combined organic layers were dried over Na$_2$SO$_4$, filtered and concentrated to dryness under reduced pressure to obtain Compound 32 (150 mg, crude).

Step 5: 3-(2-amino-4-pyridyl)-N-isopropyl-4-[3-(trifluoromethyl)anilino]benzamide To a solution of Compound 32 (50 mg, 0.13 mmol, 1.0 eq), 29-3a (10 mg, 0.16 mmol, 1.2 eq) and DIPEA (35 mg, 0.27 mmol, 2.0 eq) in DCM (1 mL) was added HATU (61 mg, 0.16 mmol, 1.2 eq) at 0° C. for 5 min. And then the mixture was stirred at 25° C. for 2 hr. LCMS showed Compound 32 was consumed completely and one main peak with desired MS was detected. The reaction mixture was concentrated under reduced pressure. Then the mixture was diluted with water (15 mL) and the resultant mixture was extracted with EA (40 mL*3). The combined organic layers were dried over Na$_2$SO$_4$, filtered, and concentrated to dryness under reduced pressure. The residue was purified by prep-HPLC to obtain Compound 31 (14.74 mg, 26.3% yield). LCMS (ESI): RT=0.813 min, mass calcd. for C$_{22}$H$_{21}$F$_3$N$_4$O, 414.17, m/z found 415.4 [M+H]$^+$, $^1$H NMR (400 MHz, CDCl$_3$) δ ppm 8.16 (br s, 1H), 7.68 (m, 2H), 7.41 (m, 1H), 7.33 (m, 2H), 7.25 (m, 2H), 6.75 (d, J=4.63 Hz, 1H), 6.59 (s, 1H), 5.92 (m, 2H), 4.59 (br s, 2H), 4.38-4.22 (m, 1H), 1.27 (d, J=6.50 Hz, 6H).

Example 26: 3-(2-aminopyridin-4-yl)-4-((3-(trifluoromethyl)phenyl)amino)benzoic Acid (Compound 32)

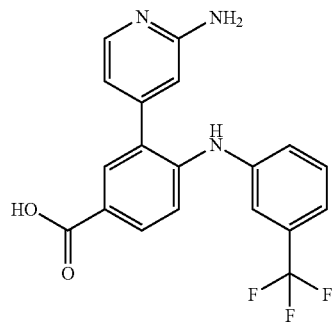 [SMILES: Nc1cc(-c2cc(C(=O)O)ccc2Nc2cccc(C(F)(F)F)c2)ccn1]

Preparation of Compound 32

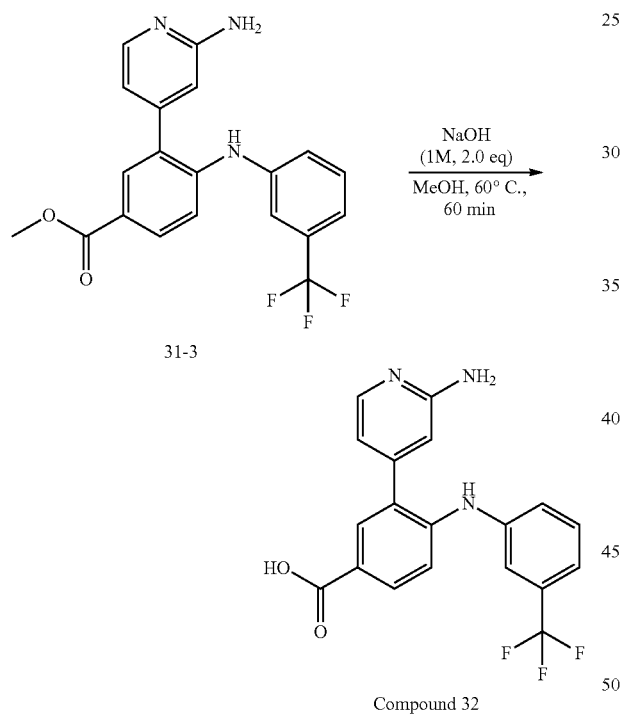

To a solution of 31-3 (50.0 mg, 0.13 mmol, 1.0 eq) in MeOH (0.5 mL) was added NaOH (1 M, 0.3 mL, 2.0 eq). The mixture was stirred at 60° C. for 30 min. LCMS showed that 31-3 was consumed completely and one main peak with desired MS was detected. The reaction mixture was adjusted with HCl (1 M) to pH~6. The mixture was diluted with water (10 mL) and the resultant mixture was extracted with EA (40 mL*3). The combined organic layers were dried over $Na_2SO_4$, filtered, and concentrated to dryness under reduced pressure. MeOH (10 mL) was added, and then the suspension was filtered and washed with MeOH (10 mL*3) to obtain Compound 32 (4.78 mg, 9.7% yield). LCMS (ESI): RT=0.808 min, mass calcd. for $C_{19}H_{14}F_3N_3O_2$ 373.10, m/z found 374.4 [M+H]+, $^1$H NMR (400 MHz, DMSO-$d_6$) δ ppm 8.20 (s, 1H), 7.91 (d, J=5.25 Hz, 1H), 7.86 (dd, J=8.50, 2.00 Hz, 1H), 7.79 (d, J=2.13 Hz, 1H), 7.43 (m, 1H), 7.37 (m, 2H), 7.31 (s, 1H), 7.17 (d, J=7.63 Hz, 1H), 6.55 (m, 2H), 5.97 (s, 2H).

Example 27: methyl 3-(1-methyl-1H-imidazol-4-yl)-4-((4-(trifluoromethyl)phenyl)amino)benzoate (Compound 33)

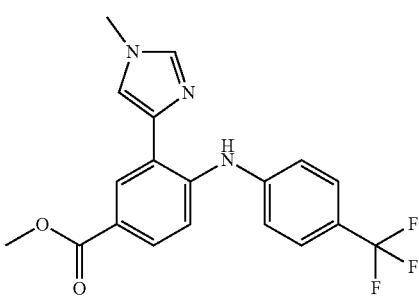 [SMILES: COC(=O)c1ccc(Nc2ccc(C(F)(F)F)cc2)c(-c2cn(C)cn2)c1]

Preparation of Compound 33

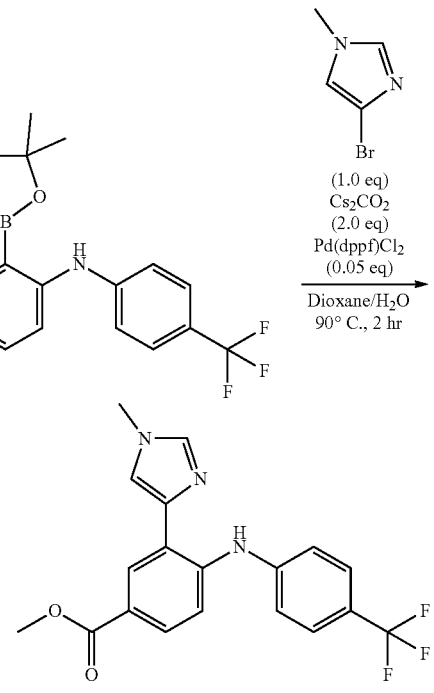

To a solution of methyl 3-(4,4,5,5-tetramethyl-1,3,2-dioxaborolan-2-yl)-4-[4-(trifluoromethyl)anilino]benzoate (100 mg, 0.23 mmol, 1 eq) and 4-bromo-1-methyl-imidazole (38.2 ng, 0.23 mmol, 1 eq) in dioxane (3 mL) was added $Cs_2CO_3$ (154.7 mg, 0.47 mmol, 2 eq) and $H_2O$ (4.2 mg, 0.23 mmol, 4.28 μL, 1 eq), Pd(dppf)Cl$_2$ (8.6 mg, 11.8 umol, 0.05 eq). The mixture was stirred at 90° C. for 2 hr. $H_2O$ (6 mL) was added to the solution. The mixture was extracted with ethyl acetate (10 mL*3). The combined organic layers were washed with brine (15 mL*2), dried over anhydrous Na$_2$SO$_4$, filtered and concentrated in vacuum. The residue was purified by prep-HPLC to obtain the title compound (1.49 mg, 3.6 umol, 1.52% yield, HC). Mass calc. for C$_{19}$H$_{16}$F$_3$N$_3$O$_2$ 375.12, m/z found 375.9 [M+H]$^+$; 1H NMR (400 MHz, CD$_3$OD) 1H NMR (400 MHz, METHANOL-d$_4$) δ=8.93 (br s, 1H), 8.16 (d, J=2.0 Hz, 1H), 8.06 (dd, J=1.8, 8.5 Hz, 1H), 7.82 (br s, 1H), 7.57 (d, J=8.3 Hz, 2H), 7.52 (d, J=8.8 Hz, 1H), 7.22 (d, J=8.3 Hz, 2H), 3.97 (s, 3H), 3.93 (s, 3H).

Example 28: methyl 3-(2-amino-4-pyridyl)-4-[4-(trifluoromethyl)anilino]benzoate (Compound 34)

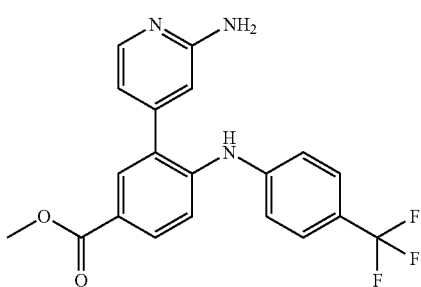 [SMILES: COC(=O)c1ccc(Nc2ccc(C(F)(F)F)cc2)c(-c2ccnc(N)c2)c1]

Preparation of Compound 34

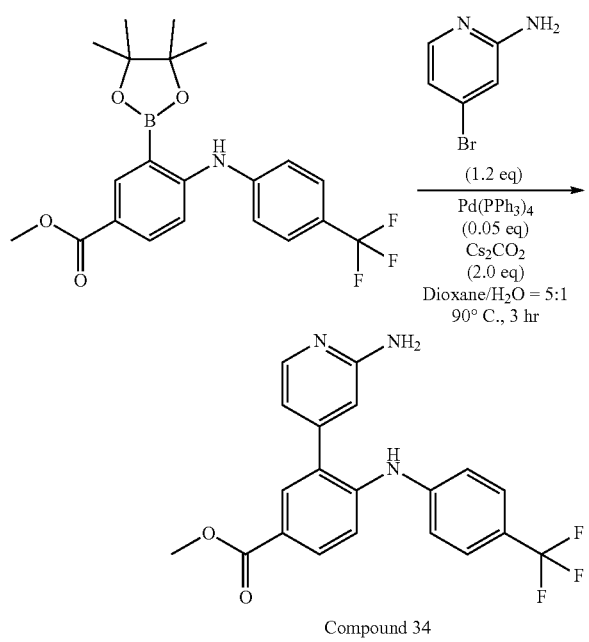

Compound 34

To a solution of methyl 3-(4,4,5,5-tetramethyl-1,3,2-dioxaborolan-2-yl)-4-[4-(trifluoromethyl)anilino]benzoate (30 mg, 71 umol, 1.0 eq), 4-bromopyridin-2-anine (15 mg, 86 umol, 1.2 eq) and Cs$_2$CO$_3$ (46 mg, 0.14 mmol, 2.0 eq) in dioxane (1.0 mL) and H$_2$O (0.2 mL) was added Pd(dppf)Cl$_2$ (2.6 mg, 3.6 umol, 0.05 eq) under N$_2$. The mixture was stirred at 90° C. for 3 hr. The reaction mixture was concentrated under reduced pressure. Then the mixture was diluted with water (15 mL) and the resultant mixture was extracted with EA (40 mL*3). The combined organic layers were dried over Na$_2$SO$_4$, filtered and concentrated to dryness under reduced pressure. The residue was purified by prep-HPLC to obtain the title compound (6.96 mg, 24.7% yield). Mass calcd. for C$_{20}$H$_{16}$F$_3$N$_3$O$_2$ 387.12, m/z found 388.4 [M+H]$^+$, $^1$HNMR (400 MHz, CDCl$_3$) δ 8.09 (d, J=5.13 Hz, 1H), 7.88 (m, 2H), 7.49 (d, J=8.38 Hz, 2H), 7.34 (d, J=8.63 Hz, 1H), 7.10 (d, J=8.25 Hz, 2H), 6.67 (d, J=5.13 Hz, 1H), 6.51 (s, 1H), 6.01 (s, 1H), 4.57 (br s, 2H), 3.83 (m, 3H).

Example 29: methyl 3-(2-amino-4-pyridyl)-4-[3-(trifluoromethyl)anilino]benzoate (Compound 35)

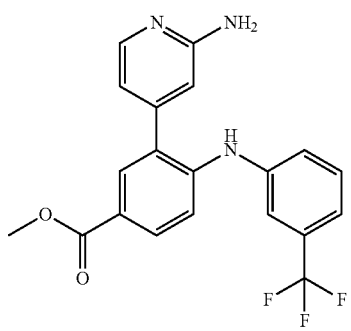 [SMILES: COC(=O)c1ccc(Nc2cccc(C(F)(F)F)c2)c(-c2ccnc(N)c2)c1]

Preparation of Compound 35

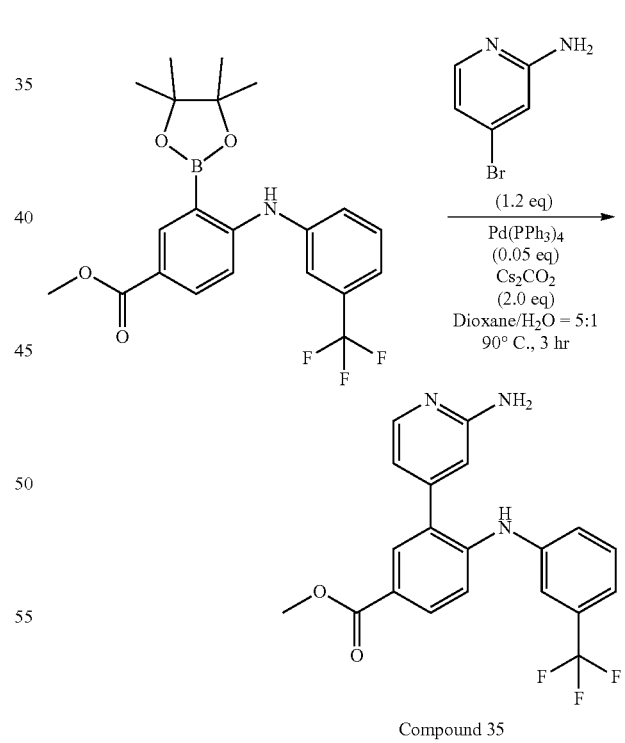

Compound 35

To a solution of methyl 3-(4,4,5,5-tetramethyl-1,3,2-dioxaborolan-2-yl)-4-((3-(trifluoromethyl)phenyl)amino)benzoate (50 mg, 0.12 mmol, 1.0 eq), 4-bromopyridin-2-amine (25 mg, 0.14 mmol, 1.2 eq) and Cs$_2$CO$_3$ (77 mg, 0.24 mmol, 2.0 eq) in dioxane (1.5 mL) and H$_2$O (0.3 mL) was added Pd(dppf)Cl$_2$ (4.3 mg, 6 umol, 0.05 eq) under N$_2$. The mixture was stirred at 90° C. for 3 hr. The reaction mixture was concentrated under reduced pressure. Then the mixture was diluted with water (10 mL) and the resultant mixture was extracted with EA (30 mL*3). The combined organic layers were dried over $Na_2SO_4$, filtered and concentrated to dryness under reduced pressure. The residue was purified by prep-HPLC to obtain the title compound (2.59 mg, 5.52% yield). Mass calcd. for $C_{20}H_{16}F_3N_3O_2$ 387.12, m/z found 388.4 [M+H]$^+$, $^1$H NMR (400 MHz, CDCl$_3$) δ 8.10 (d, J=5.25 Hz, 1H), 7.86 (m, 2H), 7.37 (m, 1H), 7.29 (s, 1H), 7.23 (dd, J=8.07, 5.82 Hz, 3H), 6.68 (d, J=5.25 Hz, 1H), 6.52 (s, 1H), 6.00 (s, 1H), 4.52 (br s, 2H), 3.83 (s, 3H).

Example 30: N-Isopropyl-3-(1-methylimidazol-4-yl)-4-[4-(trifluoromethyl)anilino]benzamide (Compound 36)

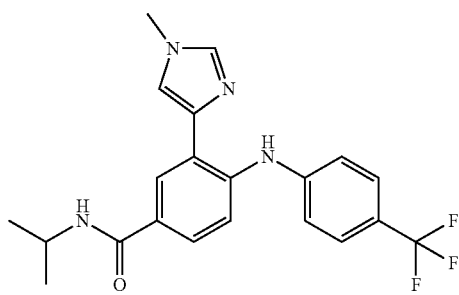 [SMILES: CC(C)NC(=O)c1ccc(Nc2ccc(C(F)(F)F)cc2)c(-c2cn(C)cn2)c1]

Preparation of Compound 36

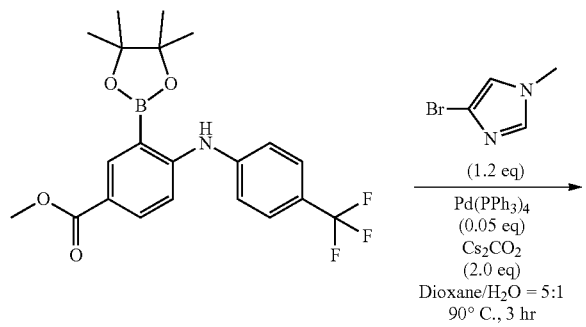

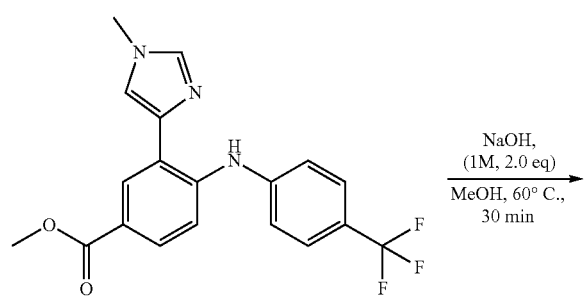

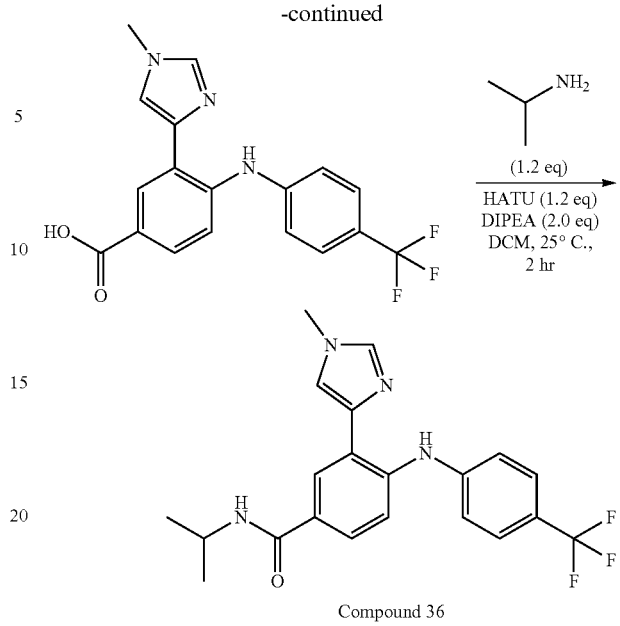

Compound 36

Step 1: methyl 3-(1-methylimidazol-4-yl)-4-[4-(trifluoromethyl)anilino]benzoate

To a solution of methyl 3-(4,4,5,5-tetramethyl-1,3,2-dioxaborolan-2-yl)-4-[4-(trifluoromethyl)anilino]benzoate (1.35 g, 3.20 mmol, 1.0 eq), 4-bromo-1-methyl-imidazole (619 mg, 3.85 mmol, 1.2 eq) and Cs$_2$CO$_3$ (2.09 g, 6.41 mmol, 2.0 eq) in dioxane (15 mL) and H$_2$O (3 mL) was added Pd(dppf)Cl$_2$ (117 mg, 0.16 mmol, 0.05 eq). The mixture was stirred at 90° C. for 3 hr under N$_2$. The reaction mixture was concentrated under reduced pressure. Then the mixture was diluted with water (15 mL) and the resultant mixture was extracted with EA (40 mL*3). The combined organic layers were dried over Na$_2$SO$_4$, filtered and concentrated to dryness under reduced pressure. The residue was purified by column chromatography (SiO$_2$) to obtain methyl 3-(1-methylimidazol-4-yl)-4-[4-(trifluoromethyl)anilino]benzoate (600 mg, 49.9% yield).

Step 2: 3-(1-methylimidazol-4-yl)-4-[4-(trifluoromethyl)anilino]benzoic Acid

To a solution of methyl 3-(1-methylimidazol-4-yl)-4-[4-(trifluoromethyl)anilino]benzoate (300 mg, 0.80 mmol, 1.0 eq) in MeOH (5 mL) was added NaOH (1 M, 1.6 mL, 2.0 eq). The mixture was stirred at 60° C. for 30 min. The reaction mixture was added HCl (1 M) to PH ~6. The mixture was diluted with water (10 mL) and the resultant mixture was extracted with EA (40 mL*3). The combined organic layers were dried over Na$_2$SO$_4$, filtered and concentrated to dryness under reduced pressure to obtain 3-(1-methylimidazol-4-yl)-4-[4-(trifluoromethyl)anilino]benzoic acid (220 mg, crude).

Step 3: N-isopropyl-3-(1-methylimidazol-4-yl)-4-[4-(trifluoromethyl)anilino]benzamide To a solution of 3-(1-methylimidazol-4-yl)-4-[4-(trifluoromethyl)anilino]benzoic acid (30 mg, 83 umol, 1.0 eq), isopropylamine (5.9 mg, 0.10 mmol, 1.2 eq) and DIPEA (22 mg, 0.17 mmol, 2.0 eq) in DCM (1 mL) was added HATU (38 mg, 0.10 mmol, 1.2 eq) at 0° C. And then the mixture was stirred at 25° C. for 2 hr. The reaction mixture was concentrated under reduced pressure. Then the mixture was diluted with water (15 mL) and the resultant mixture was extracted with EA (40 mL*3). The combined organic layers were dried over $Na_2SO_4$, filtered and concentrated to dryness under reduced pressure. The residue was purified by prep-HPLC to obtain the title compound (12.49 mg, 37.0% yield). Mass calcd. for $C_{22}H_{21}F_3N_4O$, 402.17, m/z found 403.5 [M+H]$^+$, $^1$H NMR (400 MHz, CDCl$_3$) δ ppm 10.61 (s, 1H), 8.02 (s, 1H), 7.51 (m, 3H), 7.44 (s, 2H), 7.29 (m, 3H), 5.86 (br d, J=7.75 Hz, 1H), 4.30 (m, 1H), 3.77 (s, 3H), 1.27 (d, J=6.63 Hz, 6H).

Example 31: N-cyclopropyl-3-(1-methylimidazol-4-yl)-4-[4-(trifluoromethyl)anilino]benzamide (Compound 37)

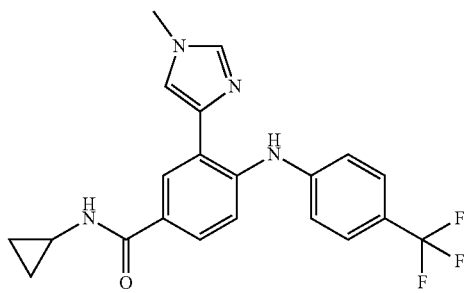 [SMILES: Cn1cnc(-c2cc(C(=O)NC3CC3)ccc2Nc2ccc(C(F)(F)F)cc2)c1]

Preparation of Compound 37

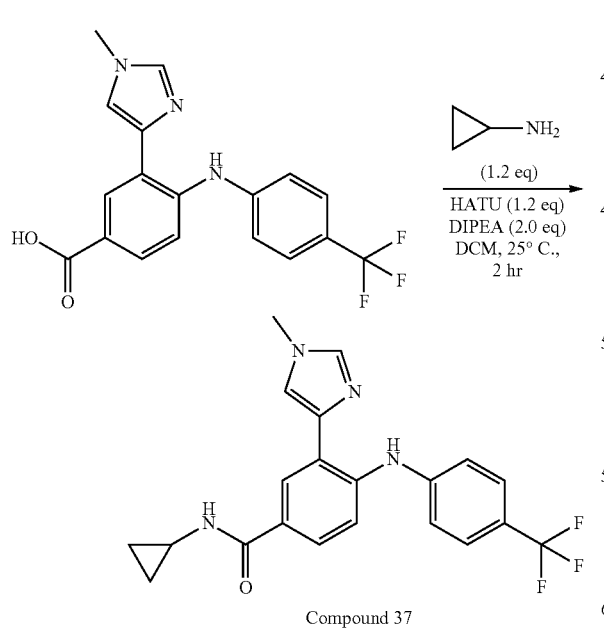

Compound 37

To a solution of 3-(1-methylimidazol-4-yl)-4-[4-(trifluoromethyl)anilino]benzoic acid (30 mg, 83 umol, 1.0 eq) cyclopropylamine (5.7 mg, 0.1 mmol, 1.2 eq) and DIPEA (21.5 mg, 0.17 mmol, 2.0 eq) in DCM (1 mL) was added HATU (38 mg, 0.10 mmol, 1.2 eq) at 0° C. And then the mixture was stirred at 25° C. for 2 hr. The reaction mixture was concentrated under reduced pressure. Then the mixture was diluted with water (5 mL) and the resultant mixture was extracted with EA (20 mL*3). The combined organic layers were dried over $Na_2SO_4$, filtered and concentrated to dryness under reduced pressure. The residue was purified by prep-HPLC to obtain the title compound (15.03 mg, 44.8% yield). Mass calcd. for $C_2H_{19}F_3N_4O$, 400.15, m/z found 401.5 [M+H]$^+$, $^1$H NMR (400 MHz, CDCl$_3$) δ ppm 10.55 (br s, 1H), 7.95 (s, 1H), 7.44 (m, 3H), 7.35 (d, J=1.00 Hz, 2H), 7.22 (m, 3H), 6.13 (br s, 1H), 3.70 (s, 3H), 2.84 (tq, J=7.05, 3.55 Hz, 1H), 0.80 (m, 2H), 0.55 (m, 2H).

Example 32: 3-(1-methylimidazol-4-yl)-N-sulfamoyl-4-[4-(trifluoromethyl)anilino]benzamide (Compound 38)

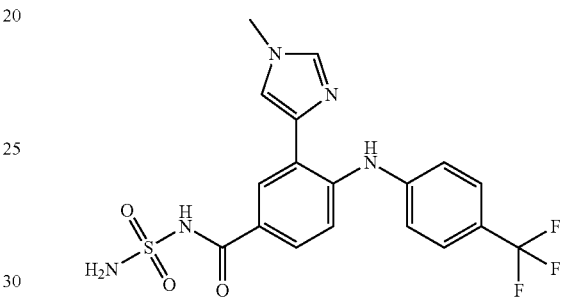

Preparation of Compound 38

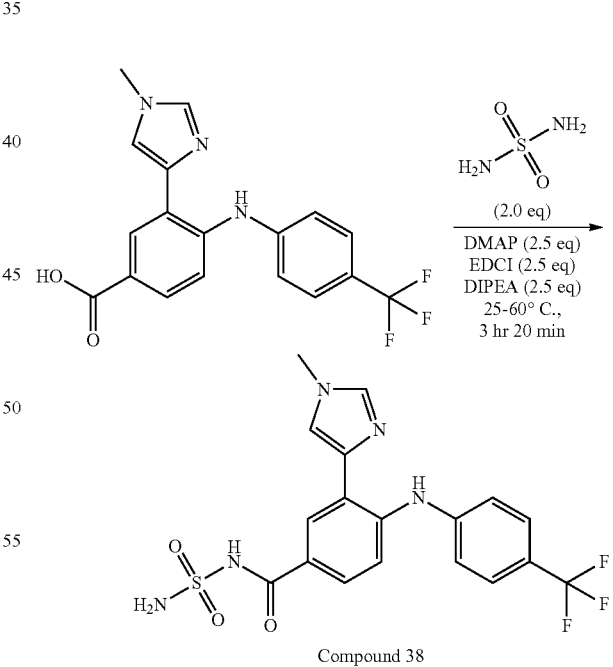

Compound 38

To a solution of 3-(1-methylimidazol-4-yl)-4-[4-(trifluoromethyl)anilino]benzoic acid (48 mg, 0.13 mmol, 1.0 eq) in DCM (2 mL) were added DMAP (41 mg, 0.33 mmol, 2.5 eq), EDCI (64 mg, 0.33 mmol, 2.5 eq) and DIPEA (43 mg, 0.33 mmol, 2.5 eq). And the mixture stirred at 25° C. for 20 minutes. Then sulfuric diamide (26 mg, 0.27 mmol, 2.0 eq)

was added to the solution. The mixture heated at 60° C. for 3 hr under N₂. The mixture was diluted with water (5 mL) and the resultant mixture was extracted with EA (20 mL*3). The combined organic layers were dried over Na₂SO₄, filtered and concentrated to dryness under reduced pressure. The residue was purified by prep-HPLC to obtain the title compound (2.71 mg, 4.6% yield). Mass calcd. for $C_{18}H_{16}F_3N_5O_3S$, 439.09, m/z found 440.4 [M+H]⁺, ¹H NMR (400 MHz, DMSO-d₆) δ 11.67 (br s, 1H), 11.10 (br s, 1H), 8.31 (s, 1H), 7.88 (s, 1H), 7.77 (m, 2H), 7.64 (br d, J=8.25 Hz, 2H), 7.47 (br d, J=8.63 Hz, 1H), 7.35 (br d, J=8.25 Hz, 2H), 7.24 (br s, 2H), 3.77 (s, 3H).

Example 33: 3-(pyridin-2-yl)-4-((4-(trifluoromethyl)phenyl)amino)benzoic Acid (Compound 39)

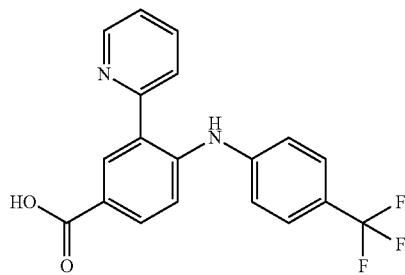 [SMILES: O=C(O)c1ccc(Nc2ccc(C(F)(F)F)cc2)c(-c2ncccn2)c1]

Preparation of Compound 39

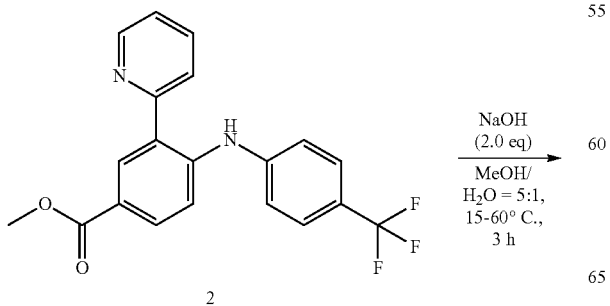

-continued

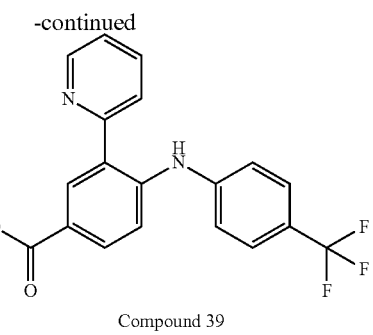

Compound 39

Step 1: methyl 3 (pyridin-2-yl)-4-((4-(trifluoromethyl)phenyl)amino)benzoate

To a solution of methyl 3-(4,4,5,5-tetramethyl-1,3,2-dioxaborolan-2-yl)-4-((4-(trifluoromethyl)phenyl)amino)benzoate (50 mg, 0.12 mmol, 1 eq) in dioxane (0.8 mL) and H₂ (0.2 mL) were added Cs₂CO₃ (77.3 mg, 0.24 mmol, 2 eq), Pd(PPh₃)₄ (7 mg, 5.9 umol, 0.05 eq) and 2-bromopyridine (22.5 mg, 0.14 mmol, 13 μL, 1.2 q). The mixture was stirred at 100° C. for r 1 hr. The reaction mixture was filtered and concentrated in vacuum. The crude product was purified by column chromatography (SiO₂) to obtain methyl 3-(pyridin-2-yl)-4-((4-(trifluoromethyl)phenyl)amino)benzoate (20 mg, 49 umol, 41.6% yield).

Step 2: 3-pyridin-2-yl)-4-((4-trifluoromethyl)phenyl)benzoic Acid

To a solution of methyl 3-(pyridin-2-yl)-4-((4-(trifluoromethyl)phenyl)amino)benzoate (15 mg, 40 mmol, 1 eq) in MeOH (0.5 mL) was added NaOH (8 mg, 0.2 mmol, 5 eq) in H₂O (0.1 mL). The mixture was stirred at 60° C. for 0.5 hr. The reaction mixture was concentrated in vacuum. The residue was dissolve in H₂O (5 mL) and adjust PH=4 with 1 M aq. HCl. The crude product was purified by prep-HPLC to obtain the title compound (6 mg, 16.7 umol, 41% yield). Mass calcd. For $C_{19}H_{113}F_3N_2O_2$, 358.09 m/z found 358.9 [M+H]⁺. ¹H NMR (400 MHz, DMSO-d₆) δ 10.55 (br s, 1H), 8.75 (br d, J=4.3 Hz, 1H), 8.27 (d, J=1.8 Hz, 1H), 8.08-7.99 (m, 1H), 7.97-7.90 (m, 2H), 7.62-7.48 (m, 4H), 7.31 (d, J=8.5 Hz, 2H).

Example 34: 3-(pyrimidin-2-yl)-4-((4-(trifluoromethyl)phenyl)amino)benzoic Acid (Compound 40)

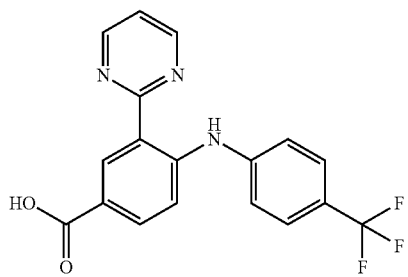

219
Preparation of Compound 40

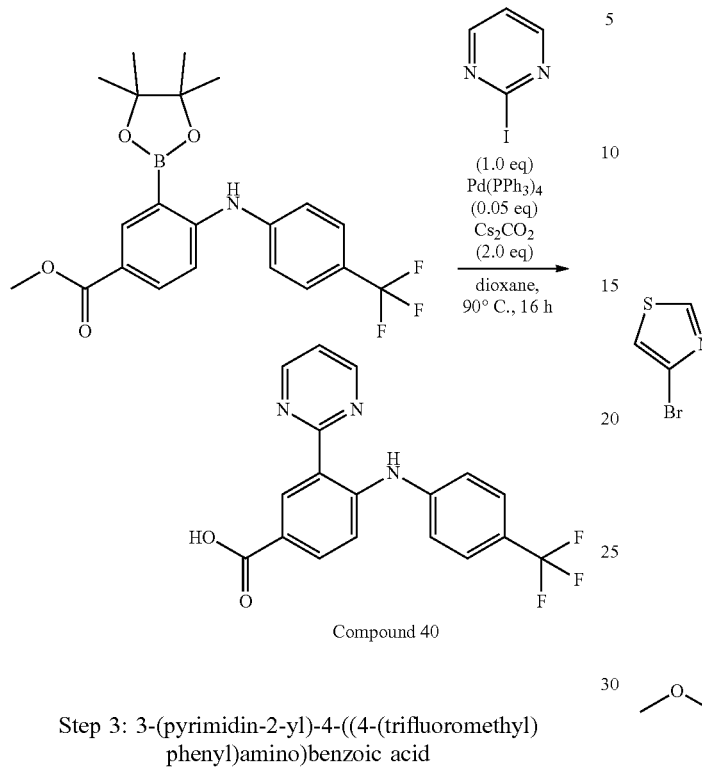

Compound 40

Step 3: 3-(pyrimidin-2-yl)-4-((4-(trifluoromethyl)phenyl)amino)benzoic acid

To a solution of 2-iodopyrimidine (100 mg, 0.48 mmol, 1 eq) in dioxane (2 mL) and H$_2$O (0.4 mL) were added Cs$_2$CO$_3$ (316 mg, 0.97 mmol, 2 eq), Pd(PPh$_3$)$_4$ (28 mg, 24.2 umol, 0.05 eq) and methyl 3-(4,4,5,5-tetramethyl-1,3,2-dioxaborolan-2-yl)-4-((4-(trifluoromethyl)phenyl)amino)benzoate (245.4 mg, 0.58 mmol, 1.2 eq). The mixture was stirred at 90° C. for 16 hr. The reaction mixture was concentrated in vacuum and the residue was diluted with EA (20 mL), washed with brine (5 mL), dried over Na$_2$SO$_4$, filtered and concentrated in vacuum. The crude product was purified by prep-HPLC to give the title compound (33 mg, 90.9 umol, 18.7% yield). Mass calcd. For C$_{18}$H$_{12}$F$_3$N$_3$O$_2$, 359.09 m/z found 359.8 [M+H]$^+$. $^1$H NMR (400 MHz, DMSO-d$_6$) δ 12.68 (br s, 1H), 11.64 (s, 1H), 9.15 (d, J=2.0 Hz, 1H), 9.01 (d, J=5.0 Hz, 2H), 7.93 (dd, J=2.0, 8.8 Hz, 1H), 7.70 (d, J=8.5 Hz, 2H), 7.55-7.49 ((m, 4H).

Example 35: 3-(thiazol-4-yl)-4-((4-(trifluoromethyl)phenyl)amino)benzoic Acid (Compound 41)

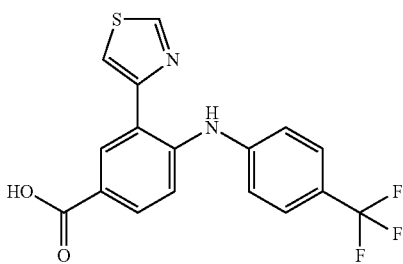

220
Preparation of Compound 41

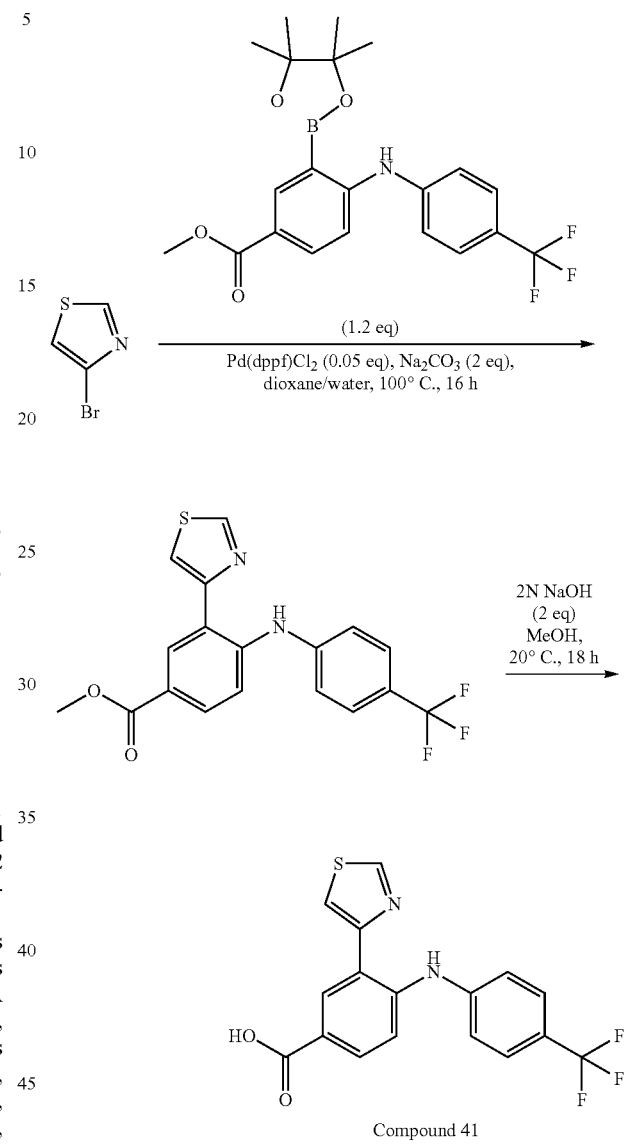

Compound 41

Step 1: methyl 3-(thiazol-4-yl)-4-((4-(trifluoromethyl)phenyl)amino)benzoate The mixture of 4-bromothiazole (100 mg, 0.61 mmol, 1 eq), methyl 3-(4,4,5,5-tetramethyl-1,3,2-dioxaborolan-2-yl)-4-((4-(trifluoromethyl)phenyl)amino)benzoate (308.2 mg, 0.73 mmol, 1.2 eq), Na$_2$CO$_3$ (129.2 mg, 1.22 mmol, 2 eq) and Pd(dppf)Cl$_2$ (22.3 mg, 30.5 umol, 0.05 eq) in Water (0.3 mL) and dioxane (3 mL) at 20° C. was purged and degassed with N$_2$ for 3 times, and then stirred at 100° C. under N$_2$ for 16 h. The mixture was concentrated to give a residue. The residue was purified by flash silica gel chromatography to give methyl 3-(thiazol-4-yl)-4-((4-(trifluoromethyl)phenyl)amino)benzoate (140 mg, 0.35 mmol, 57.1% yield). Mass calc. for C$_{18}$H$_{13}$F$_3$N$_2$O$_2$S, 378.06, m/z found 378.9[M+1]$^+$.

Step 2: 3-(thiazol-4-yl)-4-((4-(trifluoromethyl)phenyl)amino)benzoic Acid

To a solution of methyl 3-(thiazol-4-yl)-4-((4-(trifluoromethyl)phenyl)amino)benzoate (140 mg, 0.37 mmol, 1 eq) in MeOH (5 mL) at 20° C. was added NaOH (2 M, 1.9 mL, 10 eq) drop-wise, and the mixture was stirred at 20° C. for 16 h. The mixture was concentrated to give a residue. The residue was purified by prep-HPLC to give the title compound (36.36 mg, 91.5 umol, 24.7% yield). Mass calc. for $C_{17}H_{11}F_3N_2O_2S$, 364.05, m/z found 365.0[M+1]$^+$. $^1$H NMR (400 MHz, DMSO-$d_6$) δ 12.79 (brs, 1H), 9.76 (s, 1H), 9.33 (d, J=1.8 Hz, 1H), 8.38 (s, 1H), 8.20 (d, J=1.8 Hz, 1H), 7.88 (dd, J=2.0, 8.5 Hz, 1H), 7.60 (d, J=8.3 Hz, 2H), 7.52 (d, J=8.5 Hz, 1H), 7.28 (d, J=8.5 Hz, 2H).

Example 36: 3-(thiazol-2-yl)-4-((4-(trifluoromethyl)phenyl)amino)benzoic Acid (Compound 42)

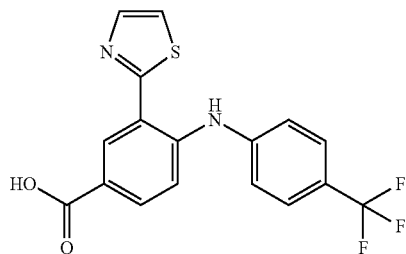 [SMILES: O=C(O)c1ccc(Nc2ccc(C(F)(F)F)cc2)c(-c2nccs2)c1]

Preparation of Compound 42

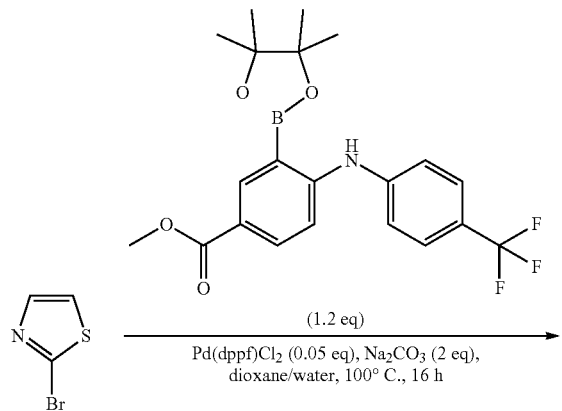

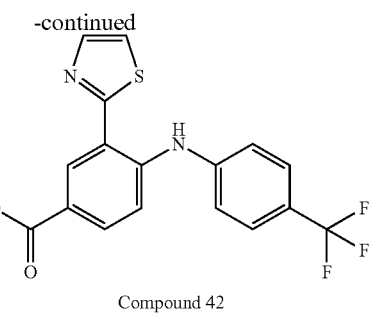

Compound 42

Step 1: Methyl 3-(thiazol-2-yl)-4-((4-(trifluoromethyl)phenyl)amino)benzoate The mixture of 2-bromothiazole (100 mg, 0.61 mmol, 55.0 μL, 1 eq), methyl 3-(4,4,5,5-tetramethyl-1,3,2-dioxaborolan-2-yl)-4-((4-(trifluoromethyl)phenyl)amino)benzoate (308.16 mg, 0.73 mmol, 1.2 eq), Na$_2$CO$_3$ (129.2 mg, 1.22 mmol, 2 eq) and Pd(dppf)Cl$_2$ (22.3 mg, 30.5 umol, 0.05 eq) in Water (0.3 mL) and dioxane (3 mL) at 20° C. was purged and degassed with N$_2$ for 3 times, and then stirred at 100° C. under N$_2$ for 16 h. The mixture was concentrated to give a residue. The residue was purified by flash silica gel chromatography to give methyl 3-(thiazol-2-yl)-4-((4-(trifluoromethyl)phenyl)amino)benzoate (100 mg, 0.26 mmol, 43.4% yield). Mass calc. for $C_{18}H_{13}F_3N_2O_2S$, 378.06, m/z found 378.9[M+1]$^+$.

Step 2: 3-(thiazol-2-yl)-4-((4-(trifluoromethyl)phenyl)amino)benzoic Acid

To a solution of methyl 3-(thiazol-2-yl)-4-((4-(trifluoromethyl)phenyl)amino)benzoate (100 mg, 0.26 mmol, 1 eq) in MeOH (5 mL) at 20° C. was added NaOH (2 M, 1.3 mL, 10 eq), and then the mixture was stirred at 20° C. under N$_2$ for 16 h. The mixture was concentrated to give a residue. The residue was purified by prep-HPLC to give the title compound (18.53 mg, 47.7 umol, 18.1% yield). Mass calc. for $C_{17}H_{11}F_3N_2O_2S$ 364.05, m/z found 364.7[M+1]$^+$. $^1$H NMR (400 MHz, DMSO-$d_6$) δ 10.74 (brs, 1H), 8.46 (s, 1H), 8.04 (d, J=3.0 Hz, 1H), 7.93 (d, J=8.5 Hz, 1H), 7.87 (d, J=3.3 Hz, 1H), 7.68 (d, J=8.5 Hz, 2H), 7.59-7.51 (m, 1H), 7.41 (d, J=8.0 Hz, 2H).

Example 37: 3-(pyrazin-2-yl)-4-((4-(trifluoromethyl)phenyl)amino)benzoic Acid (Compound 43)

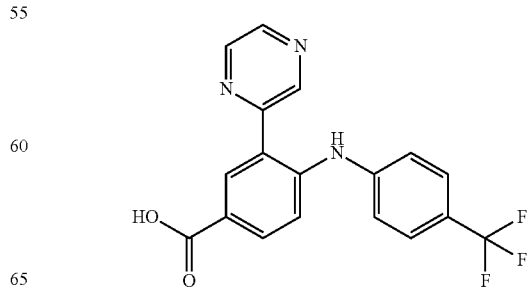

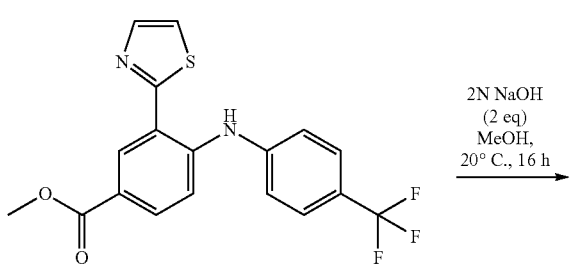

Preparation of Compound 43

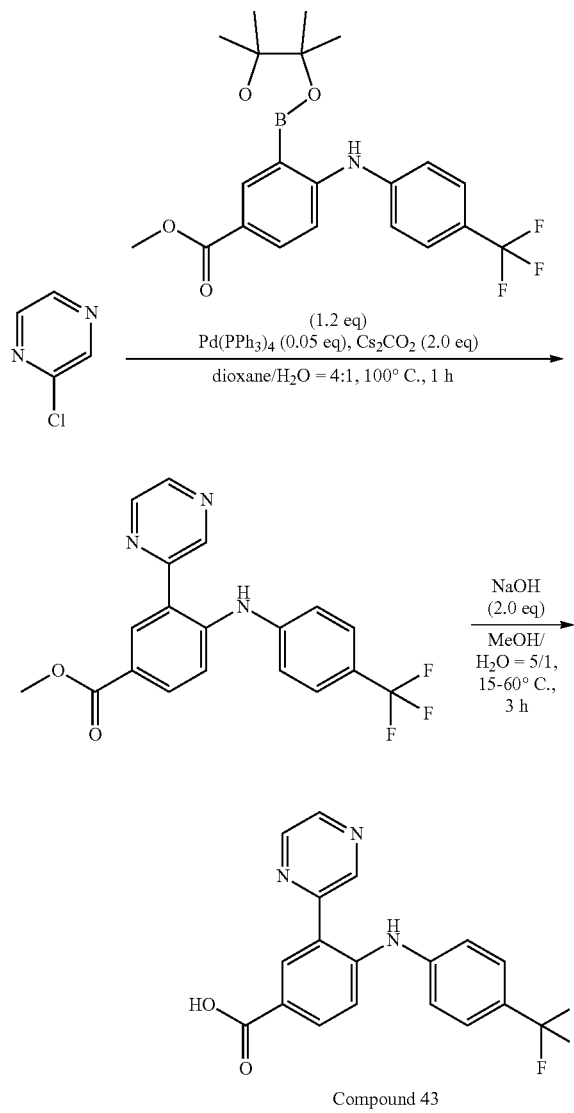

Compound 43

Step 1: methyl 3-(pyrazin-2-yl)-4-((4-(trifluoromethyl)phenyl)amino)benzoate To a solution of 2-chloropyrazine (50 mg, 0.44 mmol, 39 μL, 1 eq) in dioxane (1 mL) and H$_2$O (0.2 mL) were added Cs$_2$CO$_3$ (284 mg, 0.87 mmol, 2 eq), Pd(PPh$_3$)$_4$ (25 mg, 21.8 umol, 0.05 eq) and methyl 3-(4,4,5,5-tetramethyl-1,3,2-dioxaborolan-2-yl)-4-((4-(trifluoromethyl)phenyl)amino)benzoate (340 mg, 0.53 mmol, 1.2 eq). The reaction mixture was degassed for 3 times and stirred at 90° C. for 16 hr. The reaction mixture was concentrated in vacuum. The residue was diluted with EA (20 mL), washed with brine (5 mL). Then the organic phase was dried over Na$_2$SO$_4$, filtered and concentrated in vacuum. The crude product was purified by column chromatography (SiO$_2$) to give methyl 3-(pyrazin-2-yl)-4-((4-(trifluoromethyl)phenyl)amino)benzoate (200 mg, 0.35 mmol, 80% yield).

Step 2: 3-(pyrazin-2-yl)-4 (4-(trifluoromethyl)phenyl)anilino)benzoic Acid

To a solution of methyl 3-(pyrazin-2-yl)-4-((4-(trifluoromethyl)phenyl)amino)benzoate (154 mg, 0.27 mmol, 1 eq) in MeOH (1 mL) were added NaOH (2 M, 0.4 mL, 3 eq). The mixture was stirred at 60° C. for 3 hr. The reaction mixture was concentrated in vacuum. The crude product was purified by prep-HPLC to obtain the title compound (18 mg, 47 umol, 17.5% yield). Mass calcd. For C$_{18}$H$_{12}$F$_3$N$_3$O$_2$, 359.09 m/z found 359.8 [M+H]$^+$. $^1$H NMR (400 MHz, DMSO-d$_6$) δ 12.83 (br s, 1H), 9.59 (s, 1H), 9.02 (d, J=1.5 Hz, 1H), 8.75 (dd, J=1.5, 2.5 Hz, 1H), 8.62 (d, J=2.5 Hz, 1H), 8.26 (d, J=2.0 Hz, 1H), 7.97 (dd, J=2.1, 8.6 Hz, 1H), 7.56 (dd, J=8.6, 11.5 Hz, 3H), 7.23 (d, J:=8.5 Hz, 2H).

Example 38: N-(2-(2-(2-aminoethoxy)ethoxy)ethyl)-3-(2-methyl-2H-tetrazol-5-yl)-4-((4-(trifluoromethyl)phenyl)amino)benzamide (Compound 44)

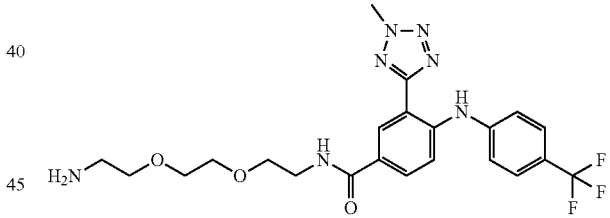

N-(2-(2-(2-acetamidoethoxy)ethoxy)ethyl)-3-(2-methyl-2H-tetrazol-5-yl)-4-((4-(trifluoromethyl)phenyl)amino)benzamide (Compound 45)

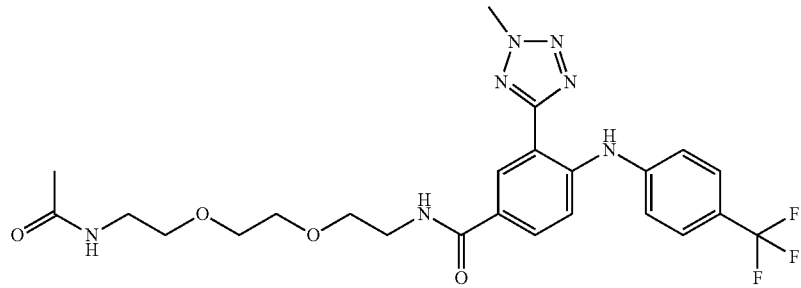 [SMILES: CC(=O)NCCOCCOCCNC(=O)c1ccc(Nc2ccc(C(F)(F)F)cc2)c(-c2nnn(C)n2)c1]

And tert-butyl (2-(2-(2-(3-(2-methyl-2H-tetrazol-5-yl)-4-((4-(trifluoromethyl)phenyl)amino)benzamido)ethoxy)ethoxy)ethyl)carbamate (Compound 47)
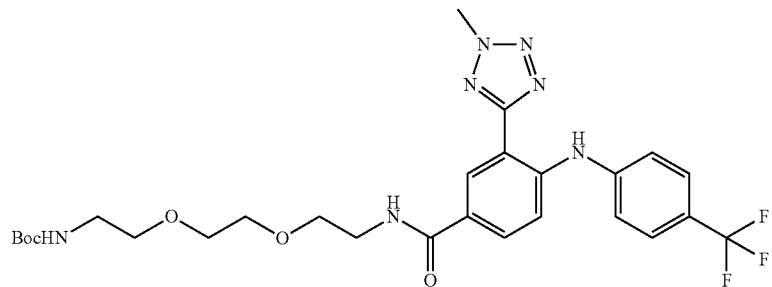 [SMILES: Cn1nnc(-c2cc(C(=O)NCCOCCOCCNC(=O)OC(C)(C)C)ccc2Nc2ccc(C(F)(F)F)cc2)n1]
Preparation of Compound 44, Compound 45, and Compound 47
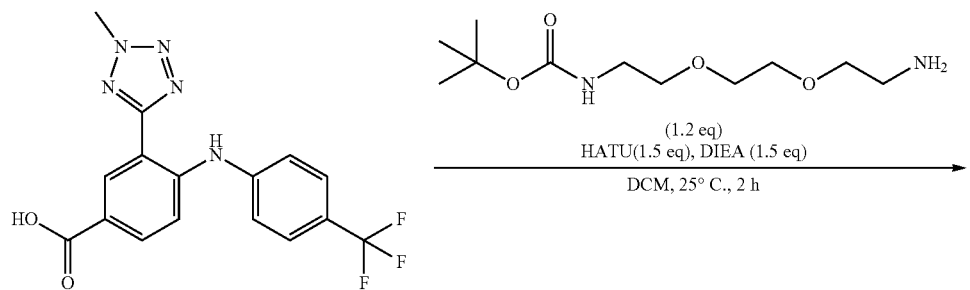
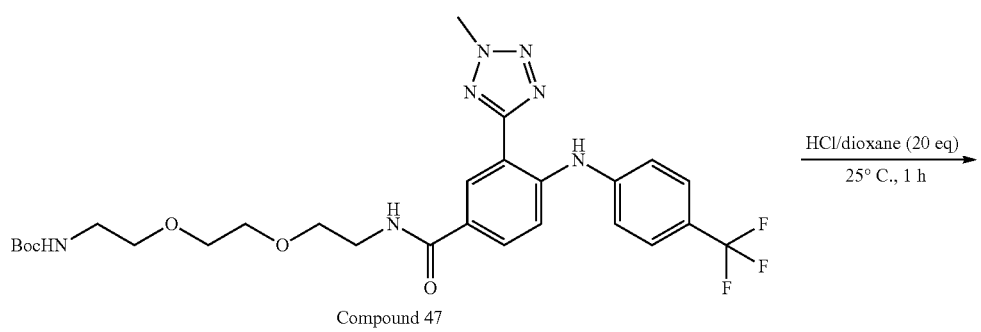
Compound 47
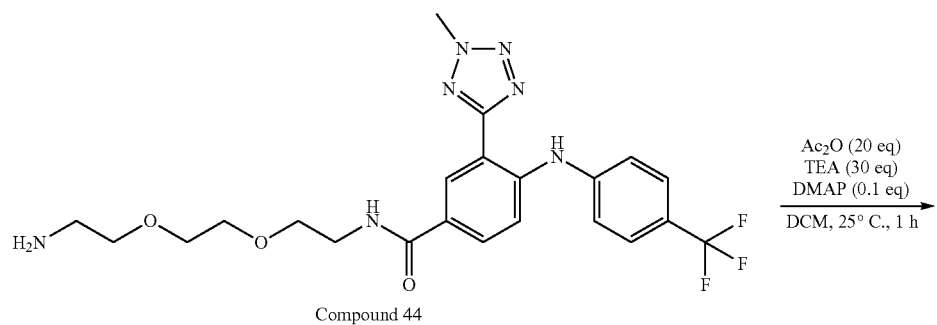
Compound 44

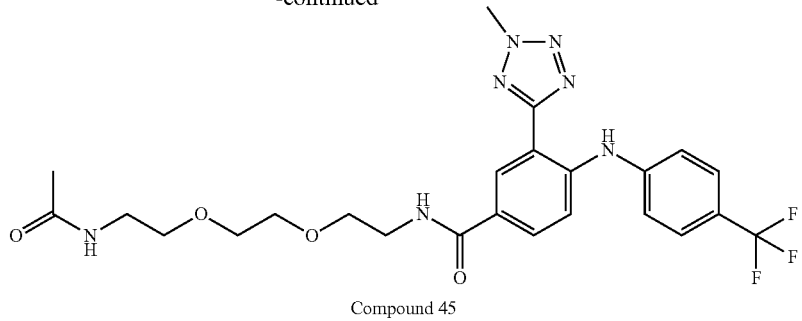

Compound 45

Step 1: tert-butyl (2-(2-(2-(3-(2-methyl-2H-tetrazol-5-yl)-4-((4-(trifluoromethyl)phenyl)amino)benzamido)ethoxy)ethoxy)ethyl)carbamate To a solution of 3-(2-methyltetrazol-5-yl)-4-[4-(trifluoromethyl)anilino]benzoic acid (300 mg, 0.83 mmol, 1 eq) and tert-butyl N-[2-[2-(2-aminoethoxy)ethoxy]ethyl]carbamate (246.1 mg, 0.99 mmol, 1.2 eq) in DCM (2 mL) was added HATU (470.9 mg, 1.24 mmol, 1.5 eq) and DIEA (160.1 mg, 1.24 mmol, 0.22 mL, 1.5 eq). The mixture was stirred at 25° C. for 2 hr. H$_2$O (30 mL) was added to the solution. The mixture was extracted with ethyl acetate (35 mL*3). The combined organic layers were washed with brine (40 mL*2), dried over anhydrous Na$_2$SO$_4$, filtered and concentrated in vacuum. The tert-butyl N-[2-[2-[2-[[3-(2-methyltetrazol-5-yl)-4-[4-(trifluoromethyl)anilino]benzoyl]amino]ethoxy]ethoxy]ethyl]carbamate (300 mg, 0.50 mmol, 60.5% yield) was used to the next step without purification. Part of the residue (100 mg) was purified by prep-HPLC to afford the pure product (21.0 mg). Mass calc. for C$_{27}$H$_{34}$F$_3$N$_7$O$_5$ 593.60, m/z found 616.1 [M+Na]$^+$; $^1$H NMR (400 MHz, DMSO-d$_6$) δ: 9.08 (s, 1H), 8.64-8.53 (m, 2H), 7.94 (dd, J=2.0, 8.8 Hz, 1H), 7.65 (d, J=8.5 Hz, 2H), 7.56 (d, J=8.8 Hz, 1H), 7.39 (d, J=8.5 Hz, 2H), 6.77 (br t, J=5.5 Hz, 1H), 4.48 (s, 3H), 3.57-3.49 (m, 6H), 3.47-3.36 (m, 411), 3.05 (hr d, J=6.0 Hz, 2H), 1.36 (s, 911).

Step 2: N-(2-(2-(2-aminoethoxy)ethoxy)ethyl)-3-(2-methyl-2H-tetrazol-5-yl)-4-((4-(trifluoromethyl)phenyl)amino)benzamide To a solution of tert-butyl N-[2-[2-[2-[[3-(2-methyltetrazol-5-yl)-4-[4-(trifluoromethyl)anilino]benzoyl]amino]ethoxy]ethoxy]ethyl]carbamate (200 mg, 0.34 mmol, 1 eq) in HCV/dioxane (2 mL). The mixture was stirred at 25° C. for 1 hr. The reaction mixture was concentrated in vacuum to give crude product. The N-[2-[2-(2-aminoethoxy)ethoxy]ethyl]-3-(2-methyltetrazol-5-yl)-4-[4-(trifluoromethyl)anilino]benzamide (150 mg, 0.29 mmol, 87.5% yield) was used to the next step without purification. Part of product (70 mg) was purified by prep-HPLC to afford the pure product (27.34 mg). Mass calc. for C$_{22}$H$_{26}$F$_3$N$_7$O$_3$ 493.48, m/z found 494.0 [M+H]$^+$; $^1$H NMR (400 MHz, DMSO-d$_6$) δ 9.08 (s, 1H), 8.65-8.61 (m, 1H), 8.57 (d, J=2.0 Hz, 11H), 7.95 (dd, J=2.1, 8.7 Hz, 1H), 7.88 (hr s, 2H), 7.66 (d, J=8.5 Hz, 2H), 7.57 (d, J=8.8 Hz, 1H), 7.39 (d, J=8.5 Hz, 2H), 4.48 (s, 3H), 3.63-3.53 (m, 8H), 3.48-3.45 (m, 2H), 3.01-2.92 (m, 2H).

Step 3: N-(2-(2-(2-acetamidoethoxy)ethoxy)ethyl)-3-(2-methyl-2H-tetrazol-5-yl)-4-((4-(trifluoromethyl)phenyl)amino)benzamide To a solution of N-[2-[2-(2-aminoethoxy]ethyl]-3-(2-methyltetrazol-5-yl)-4-[4-(trifluoromethyl)anilino]benzamide (50 mg, 0.10 mmol, 1 eq) in DCM (2 mL) was added Ac2O (15.5 mg, 0.15 mmol, 14.2 μL, 1.5 eq), DMAP (1.2 mg, 10.1 umol, 0.1 eq) and TEA (30.8 mg, 0.30 mmol, 42.3 μL, 3 eq). The mixture was stirred at 25° C. for 1 hr. H$_2$O (10 mL) was added to the solution. The mixture was extracted with ethyl acetate (20 mL*3). The combined organic layers were washed with brine (30 mL*2), dried over anhydrous Na$_2$SO$_4$, filtered and concentrated in vacuum. The residue was purified by prep-HPLC to give compound N-[2-[2-(2-acetamidoethoxy)ethoxy]ethyl]-3-(2-methyltetrazol-5-yl)-4-[4-(trifluoromethyl)anilino]benzamide (39.4 mg, 72.9 umol, 71.9% yield). Mass calc. for C$_{24}$H$_{28}$F$_3$N$_7$O$_4$ 535.52, m/z found 536.1 [M+H]$^+$; $^1$H NMR (400 MHz, DMSO-d$_6$) δ 9.08 (s, 1H), 8.65-8.55 (m, 2H), 7.99-7.85 (m, 2H), 7.65 (d, J=8.5 Hz, 2H), 7.56 (d, J=8.6 Hz, 1H), 7.39 (d, J=8.5 Hz, 2H), 4.48 (s, 3H), 3.58-3.51 (m, 7H), 3.46-3.38 (m, 4H), 3.20-3.14 (m, 2H), 1.79 (s, 3H)

Example 39: 3-pyridazin-3-yl-4-[4-(trifluoromethyl)anilino]benzoic Acid (Compound 46)

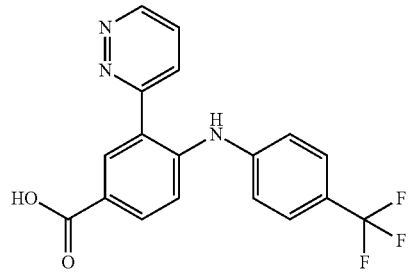

Preparation of Compound 46

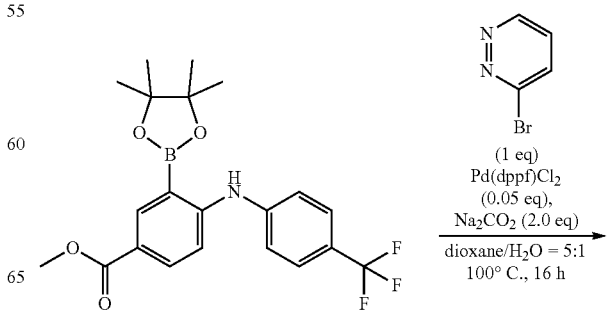

229

-continued

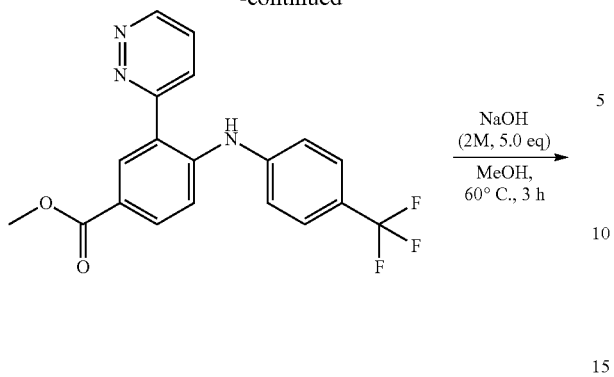

Step 1: methyl 3-pyridazin-3-yl-4-[4-(trifluoromethyl)anilino]benzoate

To a solution of 3-bromopyridazine (50 mg, 0.31 mmol, 1 eq) and methyl 3-(4,4,5,5-tetramethyl-1,3,2-dioxaborolan-2-yl)-4-((4-(trifluoromethyl)phenyl)amino)benzoate (159 mg, 0.38 mmol, 1.2 eq) in dioxane (1 mL) and H$_2$O (0.2 mL) were added Pd(dppf)Cl$_2$ (11.5 mg, 15.72 umol, 0.05 eq) and Na$_2$CO$_3$ (66 mg, 0.63 mmol, 2 eq). The mixture was degassed and purged with N$_2$ for 3 times and stirred at 100° C. for 16 hr. The reaction mixture was filtered and concentrated in vacuum. The residue was diluted with EA (20 mL) and washed with brine (5 mL*2). The organic phase was dried over Na$_2$SO$_4$, filtered and concentrated in vacuum. The crude product was purified by column chromatography (SiO$_2$) to give methyl 3-pyridazin-3-yl-4-[4-(trifluoromethyl)anilino]benzoate (30 mg, 73 umol, 23.2% yield).

Step 2: 3-pyridazin-3-yl-4-[4-(trifluoromethyl)anilino]benzoic Acid

To a solution of methyl 3-pyridazin-3-yl-4-[4-(trifluoromethyl)anilino]benzoate (30 mg, 80.4 umol, 1 eq) in MeOH (1 mL) was added NaOH (2 M, 0.2 mL, 5 eq). The mixture was stirred at 60° C. for 3 hr. The reaction mixture was concentrated in vacuum. The crude product was purified by prep-HPLC to give the title compound (11 mg, 30.6 umol, 38.1% yield). Mass calcd. For C$_{18}$H$_{12}$F$_3$N$_3$O$_2$, 359.09 m/z found 359.9[M+H]$^+$. $^1$H NMR (400 MHz, DMSO-d$_6$) δ 12.87 (br s, 1H), 9.93 (s, 1H), 9.22 (dd, J=1.3, 4.8 Hz, 11H), 8.27 (d, J=1.8 Hz, 1H), 8.10 (d, J=8.8 Hz, 1H), 7.99 (dd, J=1.9, 8.7 Hz, 1H), 7.78 (dd, J=4.9, 8.7 Hz, 1H), 7.58 (dd, J=4.3, 8.5 Hz, 3H), 7.25 (d, J=8.5 Hz, 2H).

Example 40: 3-(1,2,4-oxadiazol-3-yl)-4-[4-(trifluoromethyl)anilino]benzoic Acid (Compound 48)

Preparation of Compound 48

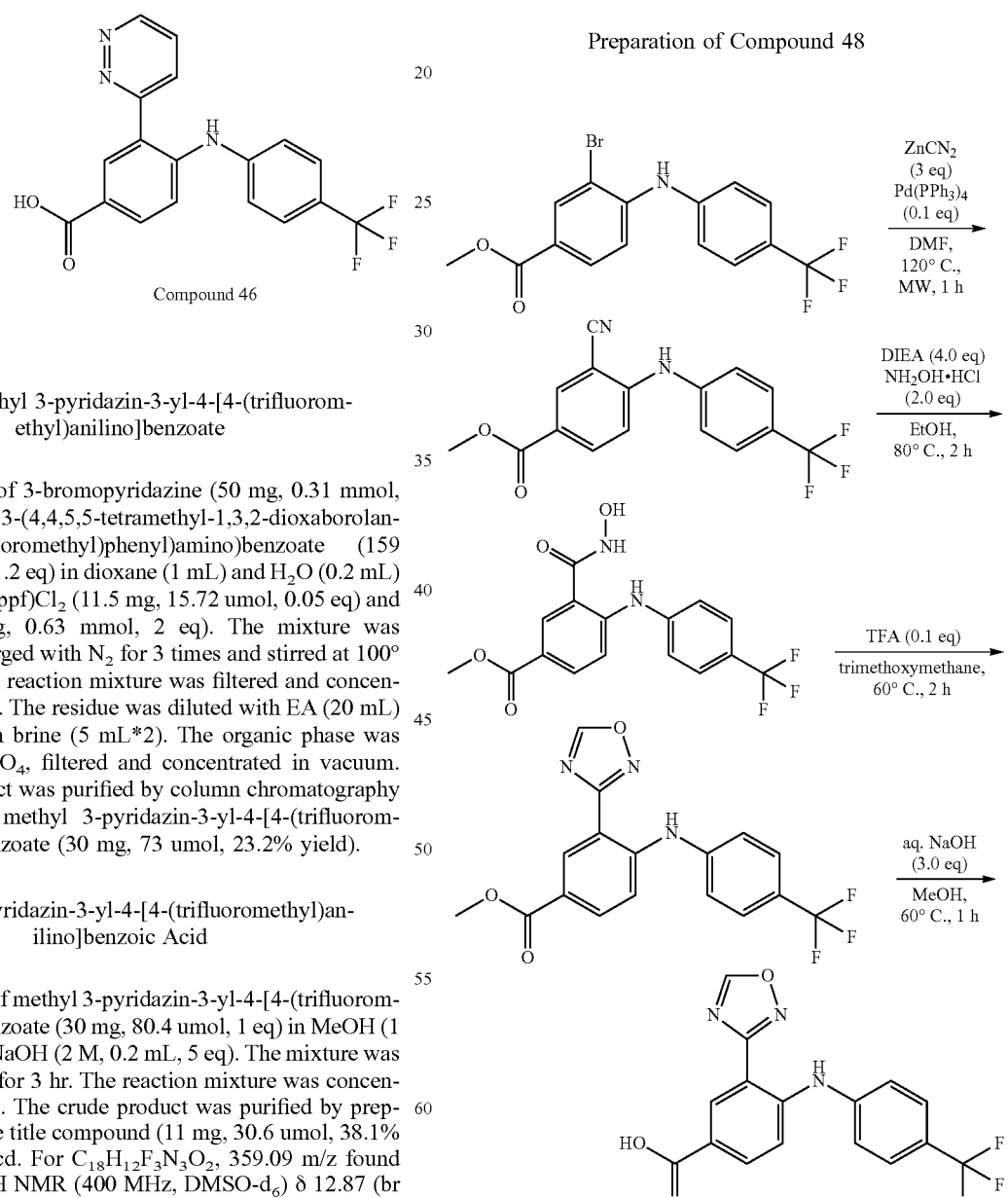

Step 1: methyl 3-cyano-4-((4-(trifluoromethyl)phenyl)amino)benzoate

To a solution of methyl 3-bromo-4-((4-(trifluoromethyl) phenyl)amino)benzoate (300 mg, 0.8 mmol, 1 eq) and Zn(CN)$_2$ (282.4 mg, 2.41 mmol, 3 eq) in N,N-dimethylacetamide (10 mL) was added Pd(PPh$_3$)$_4$ (92.65 mg, 80.2 umol, 0.1 eq). The reaction was bubbled with N$_2$ atmosphere and heated at 120° C. under microwave for 1 hr. The reaction was diluted with EA (30 mL) and washed with brine (2*15 mL). The organic layer was dried over Na$_2$SO$_4$ and concentrated. The residue was purified by column chromatography on silica gel to give methyl 3-cyano-4-((4-(trifluoromethyl) phenyl)amino)benzoate (200 mg, 0.6 mmol, 77.8% yield).

Step 2: methyl 3-(N-hydroxycarbamimidoyl)-4-((4-(trifluoromethyl)phenyl)amino)benzoate To a solution of methyl 3-cyano-4-((4-(trifluoromethyl) phenyl)amino)benzoate (200 mg, 0.62 mmol, 1 eq) and NH$_2$OH.HCl (86.7 mg, 1.25 mmol, 2 eq) in EtOH (10 mL) was added DIEA (322.8 mg, 2.50 mmol, 0.4 mL, 4 eq). The reaction was heated at 80° C. for 2 hr. The reaction was concentrated. The crude product was diluted with EA (20 mL) and washed with water (2*10 mL). The organic layer was dried over Na$_2$SO$_4$ and concentrated to give methyl 3-(N-hydroxycarbamimidoyl)-4-((4-(trifluoromethyl)phenyl)amino)benzoate (140 mg, 0.32 mmol, 52.6% yield).

Step 3: methyl 3-(1,2,4-oxadiazol-3-yl)-4-[4-(trifluoromethyl)anilino]benzoate A solution of methyl 3-(N-hydroxycarbamimidoyl)-4-((4-(trifluoromethyl)phenyl)amino)benzoate (70 mg, 0.19 mmol, 1 eq) and TFA (2.26 mg, 19.8 umol, 1 μL, 0.1 eq) in trimethoxymethane (2 mL) was heated at 60° C. for 2 hr. The reaction was concentrated. The residue was purified by prep-TLC to give methyl 3-(1,2,4-oxadiazol-3-yl)-4-[4-(trifluoromethyl)anilino]benzoate (17 mg, 35.9 umol, 18.1% yield).

Step 4: 3-(1,2,4-oxadiazol-3-yl)-4-[4-(trifluoromethyl)anilino]benzoic Acid

To a solution of methyl 3-(1,2,4-oxadiazol-3-yl)-4-[4-(trifluoromethyl)anilino]benzoate (17 mg, 35.8 umol, 1 eq) in MeOH (1 mL) was added NaOH (2 M, 53 μL, 3 eq). The reaction was heated at 60° C. for 1 hr. The reaction was concentrated. The residue was adjusted pH to 5 with 1N aq. HCl and extracted with EA (3*5 mL). The organic layers was dried over Na$_2$SO$_4$ and concentrated. The crude product was purified by prep-HPLC to give the title compound (3.49 mg, 10 umol, 27.8% yield). Mass calcd. For C$_{16}$H$_{16}$F$_3$N$_3$O, 3, 349.07 m/z found 350.1 [M+H]$^+$. $^1$H NMR. (400 MHz, DMSO-d$_6$) δ 8.06 (d, J=1.51 Hz, 1H), 8.01 (dd, J=8.41, 1.88 Hz, 1H), 7.58 (d, J=8.78 Hz, 2H), 7.32 (d, J=8.28 Hz, 1H), 7.18 (d, J=8.53 Hz, 2H), 6.12 (br s, 1H).

Example 41: 3-(4-fluoro-2-pyridyl)-4-[4-(trifluoromethyl)anilino]benzoic Acid (Compound 49)

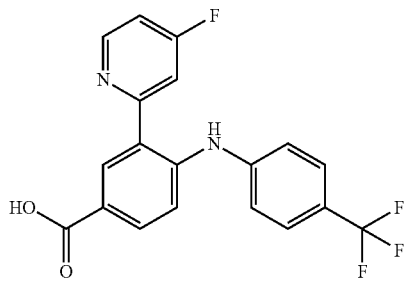

Preparation of Compound 49

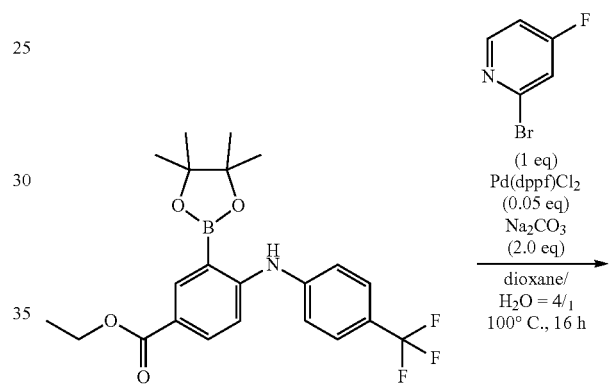

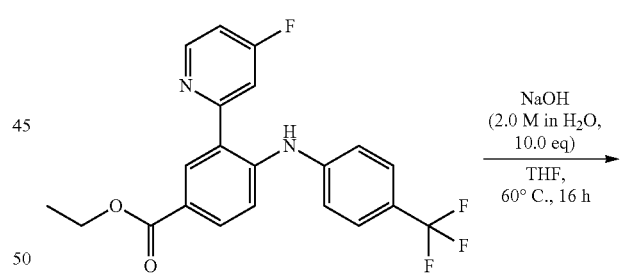

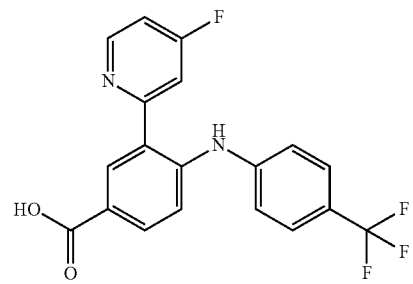 [SMILES: O=C(O)c1ccc(Nc2ccc(C(F)(F)F)cc2)c(-c2cc(F)ccn2)c1]

Compound 49

Step 1: ethyl 3-(4-fluoro-2-pyridyl)-4-[4-(trifluoromethyl)anilino]benzoate

To a solution of 2-bromo-4-fluoropyridine (80 mg, 0.45 mmol, 1 eq) in dioxane (2 mL) and H₂O (0.5 mL) were added Na₂CO₃ (96 mg, 0.90 mmol, 2 eq), Pd(dppf)Cl₂ (16 mg, 22 umol, 0.05 eq) and ethyl 3-(4,4,5,5-tetramethyl-1,3,2-dioxaborolan-2-yl)-4-((4-(trifluoromethyl)phenyl)amino)benzoate (198 mg, 0.45 mmol, 1 eq). The mixture was stirred at 100° C. for 16 hr. The reaction mixture was filtered and concentrated in vacuum. The crude product was purified by column chromatography (SiO₂) to give ethyl 3-(4-fluoro-2-pyridyl)-4-[4-(trifluoromethyl)anilino]benzoate (120 mg, 0.30 mmol, 65% yield). $^1$H NMR (400 MHz, CDCl₃) δ 11.21 (br s, 1H), 8.63 (dd, J=5.6, 8.7 Hz, 1H), 8.37 (d, J=2.0 Hz, 1H), 7.97 (dd, J=2.0, 8.8 Hz, 1H), 7.64-7.54 (m, 3H), 7.49 (d, J=8.8 Hz, 1H₁), 7.32 (d, J=8.5 Hz, 2H), 7.05 (ddd, J=2.3, 5.7, 8.1 Hz, 1H), 4.40 (q, J=7.1 Hz, 2H), 1.42 (t, J=7.2 Hz, 3H).

Step 2: 3-(4-fluoro-2-pyridyl)-4-[4-(trifluoromethyl)anilino]benzoic acid

To a solution of ethyl 3-(4-fluoro-2-pyridyl)-4-[4-(trifluoromethyl)anilino]benzoate (120 mg, 0.30 mmol, 1 eq) in THF (2 mL) was added NaOH (2 M, 1.5 mL, 10 eq). The mixture was stirred at 60° C. for 16 hr. The reaction mixture was concentrated in vacuum. The residue was quenched with H₂O (5 mL), adjusted pH=2-3 with 1 M.aq.HCl and extracted with EA (15 mL*3). The combined organic phase was washed with H₂O (5 mL) and brine (5 mL), dried over Na₂SO₄, filtered and concentrated in vacuum. The crude product was purified by prep-HPLC to give the title compound (61 mg, 0.15 mmol, 51% yield). Mass calcd. For C₁₉H₁₂F₄N₂O₂, 376.08 m/z found 376.9 [M+H]⁺. $^1$H NMR (400 MHz, DMSO-d₆) δ 12.78 (br s, 1H), 10.51 (s, 1H), 8.75 (dd, J=5.8, 9.0 Hz, 1H), 8.28 (d, J=2.0 Hz, 1H), 7.92 (dd, J=2.0, 8.8 Hz, 1H), 7.81 (dd, J=2.3, 11.0 Hz, 1H), 7.60 (d, J=8.5 Hz, 2H), 7.53 (d, J=8.8 Hz, 1H), 7.37 (ddd, J=2.4, 5.9, 8.5 Hz, 1H), 7.32 (d, J=8.5 Hz, 2H).

Example 42: 3-(pyrazin-2-yl)-4-((4-(trifluoromethyl)phenyl)amino)benzoic Acid (Compound 50)

Preparation of Compound 50

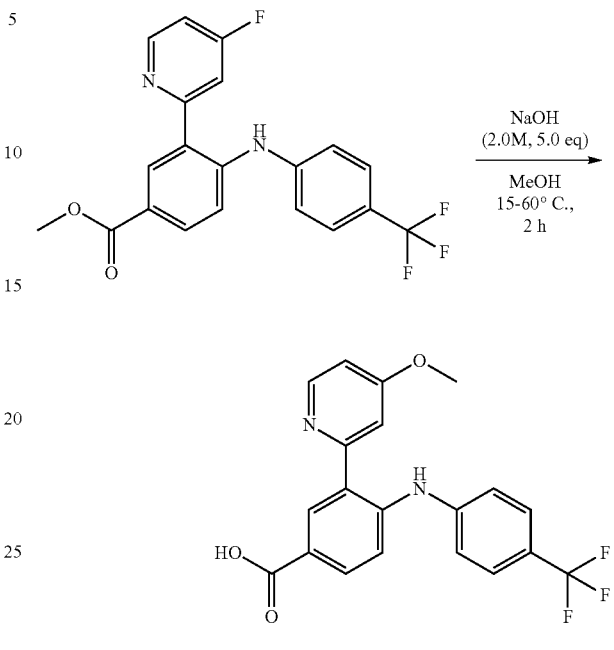

Compound 50

To a solution of methyl 3-(4-fluoropyridin-2-yl)-4-((4-(trifluoromethyl)phenyl)amino)benzoate (30 mg, 77 umol, 1 eq) in MeOH (1 mL) and THF (1 mL) was added NaOH (2 M, 0.2 mL, 5 eq). The mixture was stirred at 60° C. for 2 hr. The reaction mixture was concentrated in vacuum. The aqueous phase was adjust to pH=4 with 1 M. aq. HCl and extracted with EA (10 mL*3). The combined organic phase was washed with brine (5 mL) and dried over Na₂SO₄, filtered and concentrated in vacuum. The crude product was purified by prep-HPLC to give the title compound (4.52 mg, 11.6 umol, 15.1% yield). Mass calcd. For C₂₀H₁₅F₃N₂O3, 388.10 m/z found 388.9 [M+H]⁺ 0.1H NMR (400 MHz, DMSO-d₆) δ 8.70 (br d, J=6.5 Hz, 1H), 8.14 (s, 1H), 8.01 (br d, J=8.5 Hz, 1H), 7.65-7.51 (m, 4H), 7.40 (br s, 1H), 7.24 (br d, J=8.5 Hz, 2H), 4.04 (s, 3H).

Example 43: 3-(5-fluoro-2-pyridyl)-4-[4-(trifluoromethyl)anilino]benzoic Acid (Compound 51)

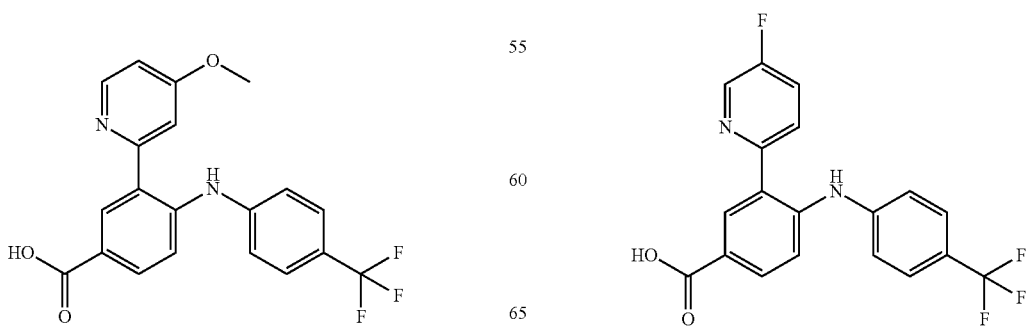

Preparation of Compound 51

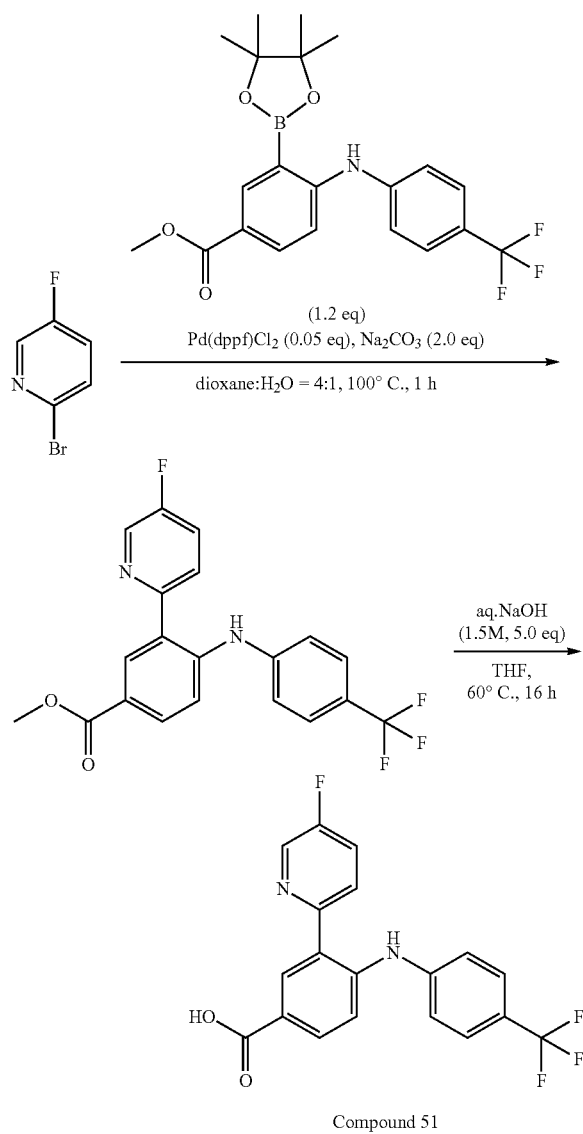

Compound 51

Step 1: methyl 3-(5-fluoro-2-pyridyl)-4-[4-(trifluoromethyl)anilino]benzoate To a solution of 2-bromo-5-fluoropyridine (50 mg, 0.28 mmol, 1 eq) in dioxane (2 mL) and H₂O (0.5 mL) were added Na₂CO₃ (60 mg, 0.56 mmol, 2 eq), Pd(dppf)Cl₂ (10 mg, 14 umol, 0.05 eq) and methyl 3-(4,4,5,5-tetramethyl-1,3,2-dioxaborolan-2-yl)-4-((4-(trifluoromethyl)phenyl)amino)benzoate (143 mg, 0.34 mmol, 1.2 eq). The mixture was stirred at 100° C. for 3 hr. The reaction mixture was filtered and concentrated in vacuum. The residue was purified by column chromatography (SiO₂) to give compound 2 (60 mg, 0.15 mmol, 53% yield).

Step 2: 3-(5-fluoro-2-pyridyl)-4-[4-(trifluoromethyl)anilino]benzoic Acid

To a solution of compound 2 (60 mg, 0.15 mmol, 1 eq) in THF (1 mL) was added NaOH (2 M, 0.4 mL, 5 eq). The mixture was stirred at 60° C. for 16 hr. The reaction mixture was concentrated in vacuum. The aqueous phase was adjusted pH=4 with 1 M aq. HCl and extracted with EA (10 mL*3). The organic phase was washed with brine (5 mL) and dried over Na₂SO₄, filtered and concentrated in vacuum. The crude product was purified by prep-HPLC to give the title compound (25.8 mg, 68 umol, 45% yield). Mass calcd. for $C_{19}H_{12}F_4N_2O_2$, 376.08 m/z found 376.9 [M+H]⁺; ¹H NMR (400 MHz, DMSO-d₆) δ 12.77 (br s, 1H), 9.97 (d, J=2.1 Hz, 1H), 8.71 (d, J=2.8 Hz, 1H), 8.21 (d, J=2.1 Hz, 1H), 7.91 (dd, J=2.4, 8.4 Hz, 2H), 7.88-7.80 (m, 1H), 7.57 (d, J=8.6 Hz, 2H), 7.52 (d, J=8.6 Hz, 1H), 7.26 (d, J=8.6 Hz, 2H).

Example 44: 3-(5-chloro-2-pyridyl)-4-[4-(trifluoromethyl)anilino]benzoic Acid (Compound 52)

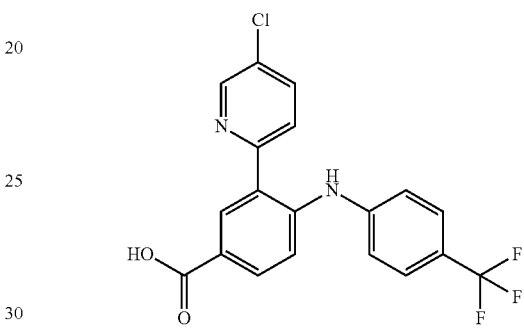

Preparation of Compound 52

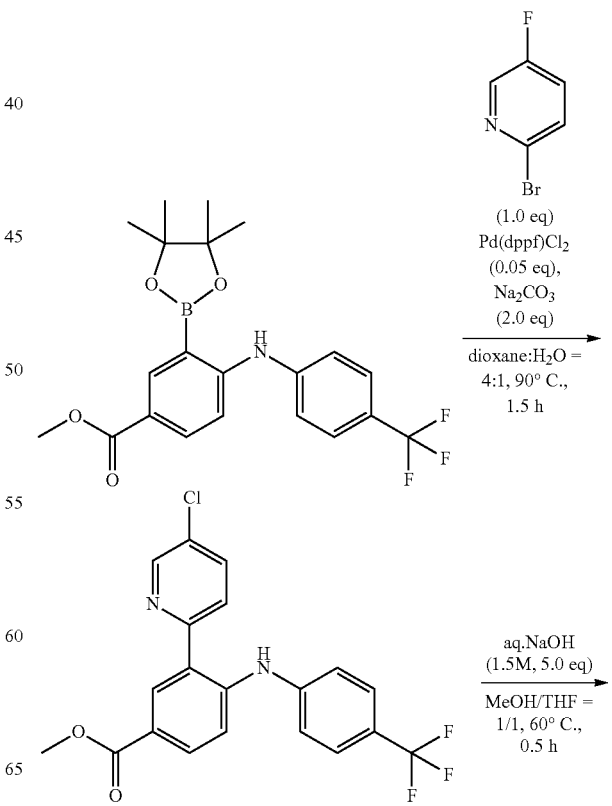

-continued

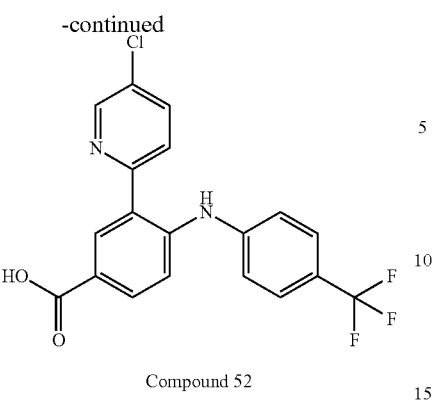

Compound 52

Step 1: methyl 3-(5-chloro-2-pyridyl)-4-[4-(trifluoromethyl)anilino]benzoate To a solution of methyl 3-(4,4,5,5-tetramethyl-1,3,2-dioxaborolan-2-yl)-4-((4-(trifluoromethyl)phenyl)amino)benzoate (109 mg, 0.26 mmol, 1 eq) and 2-bromo-5-chloropyridine (55 mg, 0.29 mmol, 1.1 eq) in dioxane (2 mL) and H$_2$O (0.5 mL) were added Pd(dppf)Cl$_2$ (9.5 mg, 13 umol, 0.05 eq) and Na$_2$CO$_3$ (55 mg, 0.52 mmol, 2 eq). The mixture was stirred at 90° C. for 1.5 hr. The reaction mixture was concentrated in vacuum. The residue was diluted with EA (20 mL), washed with brine (5 mL). The organic phase was dried over Na$_2$SO$_4$, filtered and concentrated in vacuum. The crude product was purified by column chromatography (SiO$_2$) to give methyl 3-(5-chloro-2-pyridyl)-4-[4-(trifluoromethyl)anilino]benzoate (62 mg, 0.15 mmol, 57% yield).

Step 2: 3-(5-chloro-2-pyridyl)-4-[4-(trifluoromethyl)anilino]benzoic Acid

To a solution of methyl 3-(5-chloro-2-pyridyl)-4-[4-(trifluoromethyl)anilino]benzoate (62 mg, 0.15 mmol, 1 eq) in THF (1 mL) and MeOH (1 mL) was added NaOH (1.5 M, 0.5 mL, 5 eq). The mixture was stirred at 60° C. for 0.5 hr. The reaction mixture was concentrated in vacuum and adjust pH=4 with 1 M aq. HCL. Then the mixture was extracted with EA (10 mL*2). The organic phase was washed with brine (5 mL) and dried over Na$_2$SO$_4$, filtered and concentrated in vacuum. The crude product was purified by prep-HPLC to give the title compound (5.35 mg, 13 umol, 8.9% yield). Mass calcd. For C$_{19}$H$_{12}$ClF$_3$N$_2$O$_2$, 392.05 m/z found 392.9 [M+H]$^+$. $^1$H NMR (400 MHz, DMSO-d$_6$)$_\delta$ 9.96 (br s, 1H), 8.76 (d, J=2.4 Hz, 1H), 8.23 (d, J=2.0 Hz, 1H), 8.02 (dd, J=2.6, 8.6 Hz, 1H), 7.91 (dd, J=2.0, 8.6 Hz, 1H), 7.86 (d, J=8.6 Hz, 1H), 7.58 (d, J=8.5 Hz, 2H), 7.52 (d, J=8.5 Hz, 1H), 7.27 (d, J=8.5 Hz, 2H).

Example 45: methyl 3-(5-cyclopropyl-1,3,4-oxadiazol-2-yl)-4-((4-(trifluoromethyl)phenyl)amino)benzoate (Compound 53)

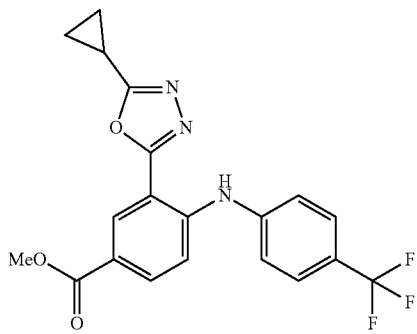 [SMILES: COC(=O)c1ccc(Nc2ccc(C(F)(F)F)cc2)c(-c2nnc(C3CC3)o2)c1]

And 3-(5-cyclopropyl-1,3,4-oxadiazol-2-yl)-4-((4-(trifluoromethyl)phenyl)amino)benzoic Acid (Compound 54)

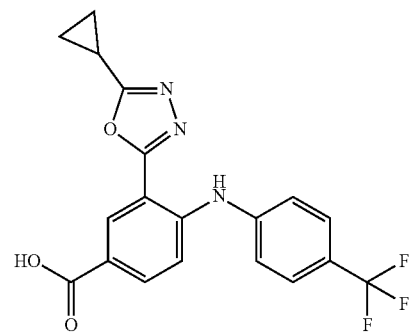 [SMILES: O=C(O)c1ccc(Nc2ccc(C(F)(F)F)cc2)c(-c2nnc(C3CC3)o2)c1]

Preparation of Compound 53 and Compound 54

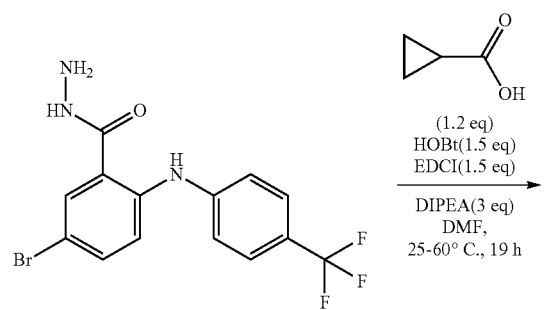

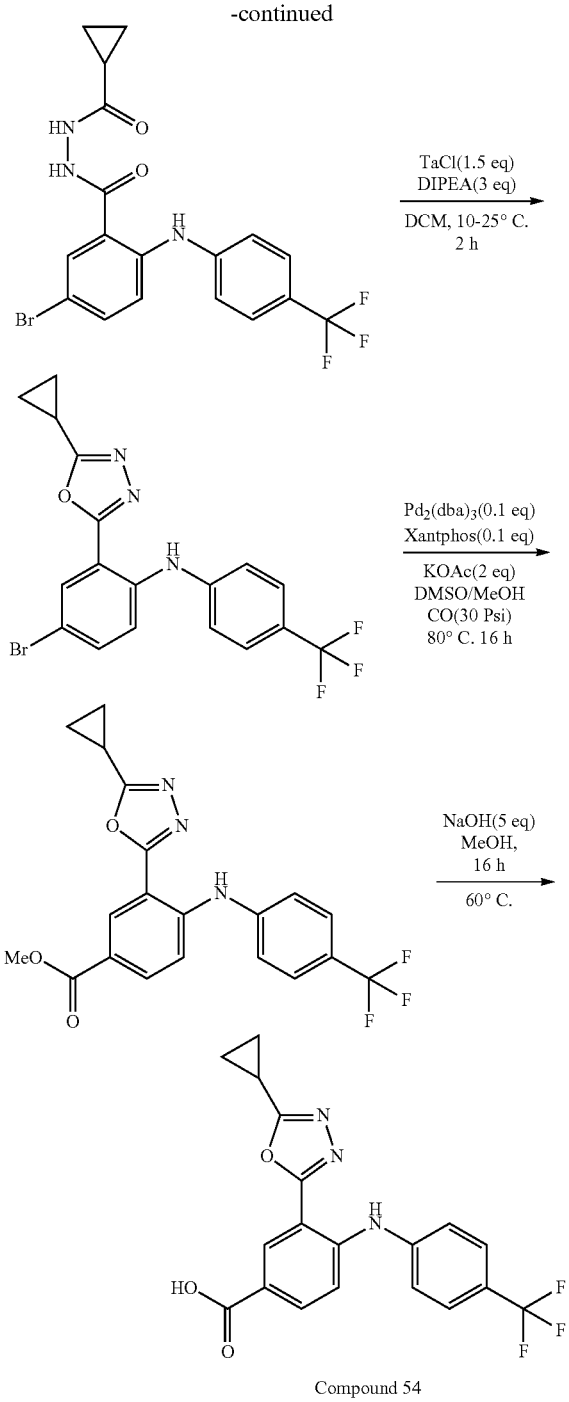

residue. The residue was purified by column chromatography (SiO$_2$) to give 5-bromo-N'-(cyclopropanecarbonyl)-2-((4-(trifluoromethyl)phenyl)amino)benzohydrazide (0.9 g, 2.04 mmol, 50.7% yield). $^1$H NMR (400 MHz, DMSO-d$_6$) δ 10.50 (s, 1H), 10.33-10.19 (m, 11-), 9.34 (br s, 1H), 7.81 (d, J=2.3 Hz, 1H), 7.64-7.54 (m, 3H), 7.41 (d, J=8.8 Hz, 1H), 7.28 (d, J=8.4 Hz, 2H), 1.73-1.64 (m, 1H), 0.84-0.73 (m, 4H).

Step 2: 4-bromo-2-(5-cyclopropyl-1,3,4-oxadiazol-2-yl)-N-(4-(trifluoromethyl)phenyl)aniline To a mixture of 5-bromo-N'-(cyclopropanecarbonyl)-2-((4-(trifluoromethyl)phenyl)amino)benzohydrazide (860 mg, 1.94 mmol, 1 eq) and DIPEA (754.0 mg, 5.83 mmol, 1.0 mL, 3 eq) in DCM (15 mL) was added TosCl (556.1 mg, 2.92 mmol, 1.5 eq) at 10° C. Then the mixture was stirred at 25° C. for 2 h. The mixture was diluted with DCM (200 mL), washed with 1 M HCl (20 mL) and brine (15 mL*2) in turns, dried with Na$_2$SO$_4$, filtered and concentrated to give a residue. The residue was purified by column chromatography (SiO$_2$) to give 4-bromo-2-(5-cyclopropyl-1,3,4-oxadiazol-2-yl)-N-(4-(trifluoromethyl)phenyl)aniline (800 mg, 1.89 mmol, 97.2% yield). 50 mg of the product was additionally purified by TLC (10.64 mg 24.9 umol, 1.3% yield). MS: mass calc. for C$_{18}$H$_3$BrF$_3$N$_3$O, 423.02, m/z found 426.04 [M+1]$^+$. $^1$H NMR (400 MHz, DMSO-d$_6$) δ 9.21 (s, 1H), 8.01 (d, J=2.3 Hz, 1H), 7.69-7.59 (m, 3H), 7.48 (d, J=8.8 Hz, 1H), 7.35 (d, J=8.3 Hz, 2H), 2.38-2.27 (m, 1H), 1.21-1.09 (m, 4H).

Step 3: methyl 3-(5-cyclopropyl-1,3,4-oxadiazol-2-yl)-4-((4-(trifluoromethyl)phenyl)amino)benzoate A mixture of 4-bromo-2-(5-cyclopropyl-1,3,4-oxadiazol-2-yl)-N-(4-(trifluoromethyl)phenyl)aniline (400 mg, 0.94 mmol, 1 eq), Xantphos (54.6 mg, 94 umol, 0.1 eq), KOAc (185.1 mg, 1.89 mmol, 2 eq) and Pd$_2$ (dba)$_3$ (86.4 mg, 94 umol, 0.1 eq) in DMSO (3 mL) and MeOH (5 mL) was degassed and refilled with CO for three times at 10° C. Then the mixture was stirred at 80° C. for 16 h under 30 Psi of CO. The reaction mixture was diluted with DCM (100 mL), washed with 1 M HCl (15 mL*2) and brine (15 mL), dried by anhydrous Na$_2$SO$_4$, filtered and concentrated under reduced pressure to give a residue. The residue was purified by column chromatography (SiO$_2$) to give methyl 3-(5-cyclopropyl-1,3,4-oxadiazol-2-yl)-4-((4-(trifluoromethyl)phenyl)amino)benzoate (270 mg, 0.67 mmol, 71% yield). 50 mg of the product was additionally purified by prep-HPLC (7.92 mg, 19.6 umol, 2.1% yield). Mass calc. for C$_{20}$H$_{16}$F$_3$N$_3$O$_3$ 403.11, m/z found 403.8 [M+1]$^+$. $^1$H NMR (400 MHz, DMSO-d$_6$) δ 9.74 (s, 1H), 8.36 (d, J=2.0 Hz, 1H), 7.97 (dd, J=2.0, 8.8 Hz, 1H), 7.73 (d, J=8.5 Hz, 2H), 7.52 (dd, J=8.7, 11.7 Hz, 3H), 3.86 (s, 3H), 2.42-2.31 (m, 1H), 1.25-1.09 (m, 4H).

Step 4: 3-(5-cyclopropyl-1,3,4-oxadiazol-2-yl)-4-((4-(trifluoromethyl)phenyl)amino)benzoic Acid To a mixture of methyl 3-(5-cyclopropyl-1,3,4-oxadiazol-2-yl)-4-((4-(trifluoromethyl)phenyl)amino)benzoate (220 mg, 0.55 mmol, 1 eq) in MeOH (10 mL) was added NaOH (2 M, 1.4 mL, 5 eq). Then the mixture was stirred at 60° C. for 16 h. The reaction mixture was diluted with water (10 mL) and extracted with EA (10 mL*2). The separated aqueous layer was acidified to pH-2 with 1 M HCl and extracted with EA (15 mL*5). The combined organic layers Compound 54

Step 1: 5-bromo-N'-(cyclopropanecarbonyl)-2-((4-(trifluoromethyl)phenyl)amino)benzohydrazide A mixture of 5-bromo-2-((4-(trifluoromethyl)phenyl) amino)benzohydrazide (1.5 g, 4.01 mmol, 1 eq), cyclopropanecarboxylic acid (517.7 mg, 6.01 mmol, 0.5 mL, 1.5 eq), HOBt (812.6 mg, 6.01 mmol, 1.5 eq), EDCI (1.15 g, 6.01 mmol, 1.5 eq) and DIPEA (1.55 g, 12.03 mmol, 2.1 mL, 3 eq) in DMF (10 mL) was stirred at 25° C. for 16 h. Then the mixture was stirred at 60° C. for 3 h. The mixture was diluted with EA (200 mL), washed with brine (15 mL*4), dried with Na$_2$SO$_4$, filtered and concentrated to give a were dried by anhydrous Na$_2$SO$_4$ to give a residue. The residue was purified by prep-HPLC to give 3-(5-cyclopropyl-1,3,4-oxadiazol-2-yl)-4-((4-(trifluoromethyl)phenyl)amino)benzoic acid (48.93 mg, 0.13 mmol, 23.1% yield). Mass calc. for: C$_{19}$H$_{14}$F$_3$N$_3$O$_3$ 389.10, m/z found 390.0 [M+1]$^+$. $^1$H NMR (400 MHz, DMSO-d$_6$) δ 9.64 (s, 1H), 8.38 (d, J=1.9 Hz, 1H), 7.97 (dd, J=1.8, 8.8 Hz, 1H), 7.70 (d, J=8.5 Hz, 2H), 7.50 (dd, J=8.6, 17.1 Hz, 3H), 2.40-2.29 (m, 1H), 1.24-1.09 (m, 4H).

Example 46: 3-(4-chloro-2-pyridyl)-4-[4-(trifluoromethyl)anilino]benzoic Acid (Compound 55)

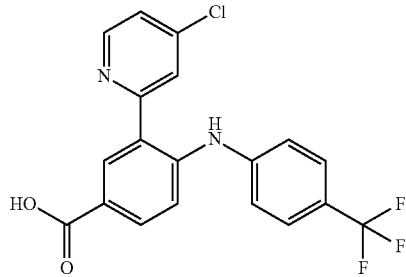

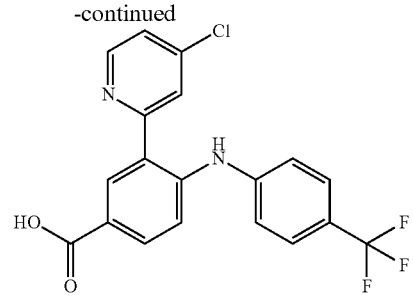

Compound 55

Preparation of Compound 55

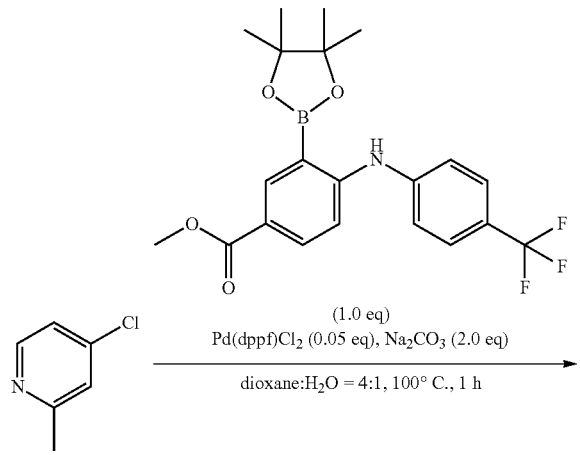

Step 1: methyl 3-(4-chloro-2-pyridyl)-4-[4-(trifluoromethyl)anilino]benzoate To a solution of methyl 3-(4,4,5,5-tetramethyl-1,3,2-dioxaborolan-2-yl)-4-((4-(trifluoromethyl)phenyl)amino)benzoate (110 mg, 0.26 mmol, 1 eq) and 4-chloro-2-iodopyridine (68 mg, 0.29 mmol, 1.1 eq) in dioxane (2 mL) and H$_2$O (0.5 mL) were added Pd(dppf)Cl$_2$ (9 mg, 13 umol, 0.05 eq) and Na$_2$CO$_3$ (55 mg, 0.52 mmol, 2 eq). The mixture was stirred at 90° C. for 1 hr. The reaction mixture was concentrated in vacuum. The residue was diluted with EA (20 mL), washed with brine (5 mL). The organic phase was dried over Na$_2$SO$_4$, filtered and concentrated in vacuum. The crude product was purified by column chromatography (SiO$_2$) to give methyl 3-(4-chloro-2-pyridyl)-4-[4-(trifluoromethyl)anilino]benzoate (63 mg, 0.15 mmol, 59.6% yield).

Step 2: 3-(4-chloro-2-pyridyl)-4-[4-(trifluoromethyl)anilino]benzoic Acid

To a solution of methyl 3-(4-chloro-2-pyridyl)-4-[4-(trifluoromethyl)anilino]benzoate (62 mg, 0.15 mmol, 1 eq) in THF (1 mL) and MeOH (1 mL) was added NaOH (1.5 M, 0.5 mL, 5 eq). The mixture was stirred at 60° C. for 0.5 hr. The reaction mixture was concentrated in vacuum and adjust pH=4 with 1 M aq. HCL. Then the mixture was extracted with EA (10 mL*2). The organic phase was washed with brine (5 mL) and dried over Na$_2$SO$_4$, filtered and concentrated in vacuum. The crude product was purified by prep-HPLC to give the title compound (13 mg, 31 umol, 20.4% yield). Mass calcd. For C$_{19}$H$_{12}$ClF$_3$N$_2$O$_2$, 392.05 m/z found 392.9 [M+H]$^+$. $^1$H NMR (400 MHz, DMSO-d$_6$) δ 10.25 (s, 1H), 8.69 (d, J=5.3 Hz, 1H), 8.26 (d, J=1.8 Hz, 1H), 7.97 (s, 1H), 7.93 (dd, J=2.0, 8.5 Hz, 1H), 7.59 (d, J=8.5 Hz, 2H), 7.56 (dd, J=2.0, 5.5 Hz, 1H), 7.53 (d, J=8.8 Hz, 1H), 7.30 (d, J=8.5 Hz, 2H).

Example 47: methyl 3-(6-aminopyrimidin-4-yl)-4-[4-(trifluoromethyl)anilino]benzoate (Compound 56)

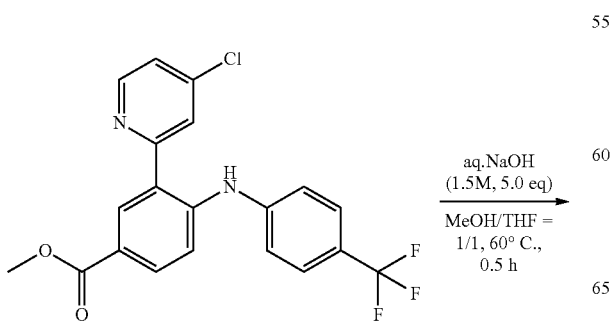

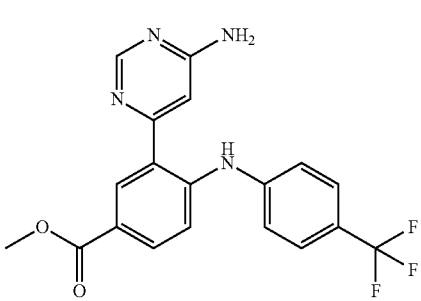 [SMILES: COC(=O)c1ccc(Nc2ccc(C(F)(F)F)cc2)c(-c2cc(N)ncn2)c1]

243
Preparation of Compound 56

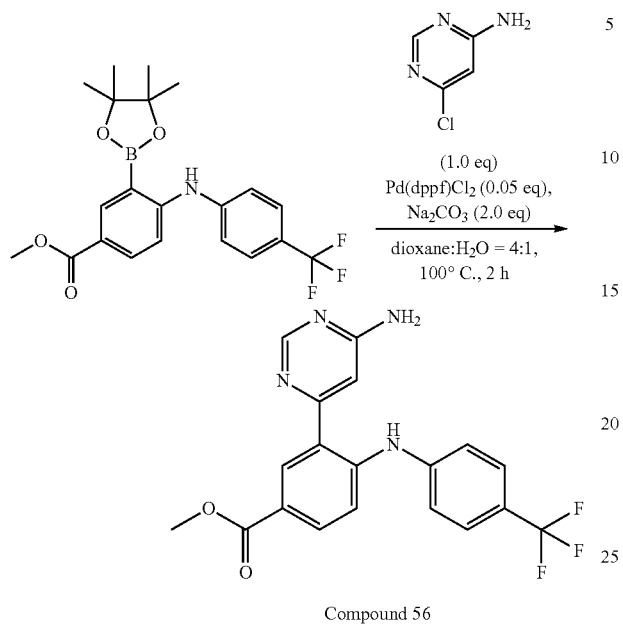

Compound 56

To a solution of 6-chloropyrimidin-4-amine (70 mg, 0.54 mmol, 1 eq) in dioxane (2 mL) and H$_2$O (0.5 mL) were added Na$_2$CO$_3$ (114 mg, 1 mmol, 2 eq), Pd(dppf)Cl$_2$ (20 mg, 27 umol, 0.05 eq) and methyl 3-(4,4,5,5-tetramethyl-1,3,2-dioxaborolan-2-yl)-4-((4-(trifluoromethyl)phenyl)amino) benzoate (273 mg, 0.65 mmol, 1.2 eq). The mixture was stirred at 100° C. for 2 hr. The reaction mixture was concentrated in vacuum to give the residue. Then the residue was diluted with EA (20 mL) and filtered and the filtrate was washed with water (5 mL) and brine (5 mL). The organic phase was dried over Na$_2$SO$_4$, filtered and concentrated in vacuum. The crude product was purified by column chromatography (SiO$_2$) to give the title compound (155 mg, 0.39 mmol, 71.6% yield). Mass calcd. For C$_{19}$H$_{15}$F$_3$N$_4$O$_2$, 388.11 m/z found 388.9 [M+H]$^+$; $^1$H NMR (400 MHz, CDCl$_3$) δ 11.31 (s, 1H), 8.65 (s, 1H), 8.36 (d, J=2.0 Hz, 1H), 7.94 (dd, J=1.9, 8.8 Hz, 1H), 7.58 (d, J=8.4 Hz, 2H), 7.45 (d, J=8.8 Hz, 1H), 7.32 (d, J=8.4 Hz, 2H), 6.92 (d, J=1.0 Hz, 1H), 5.06 (br s, 2H), 4.01-3.90 (m, 3H).

Example 48: 3-(oxazol-4-yl)-4-((4-(trifluoromethyl)phenyl)amino)benzoic Acid (Compound 57)

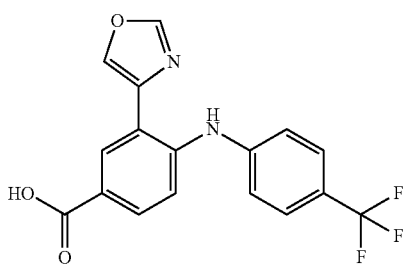 [SMILES: O=C(O)c1ccc(Nc2ccc(C(F)(F)F)cc2)c(-c2cocn2)c1]

244
Preparation of Compound 57

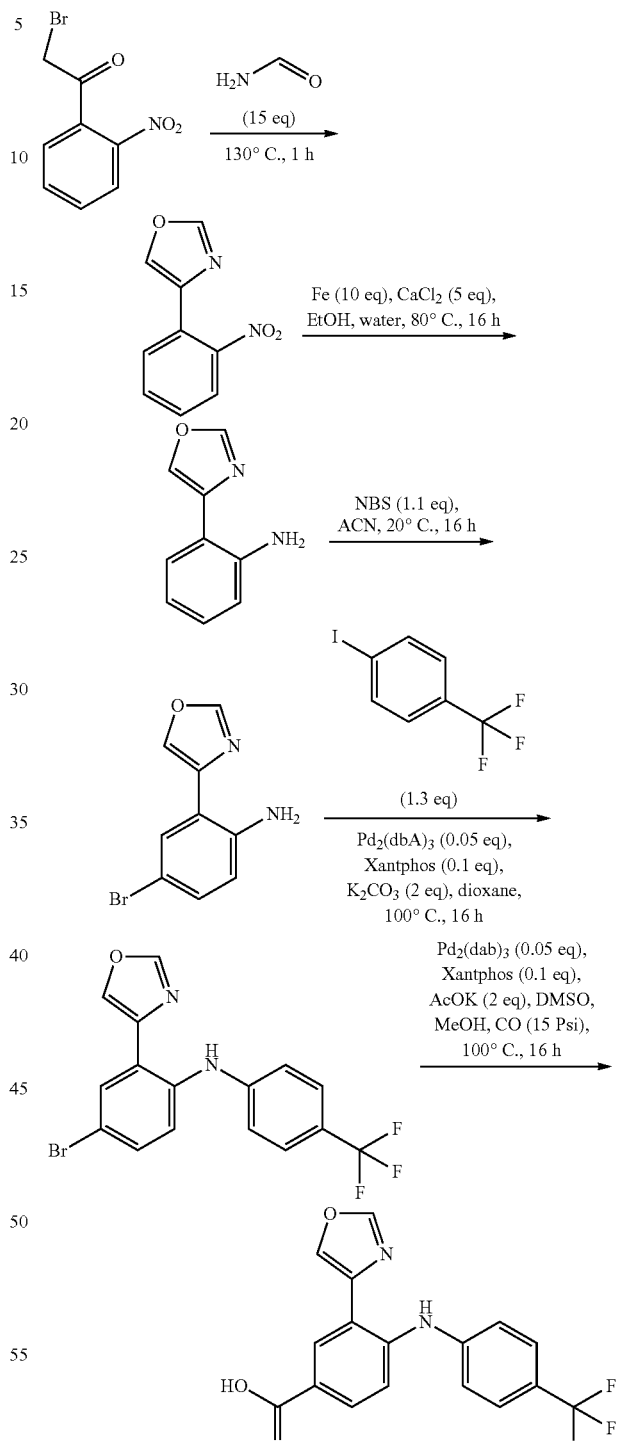

Compound 57

Step 1: 4-(2-nitrophenyl)oxazole

The solution of 2-bromo-1-(2-nitrophenyl)ethan-1-one (8.0 g, 32.78 mmol, 1 eq) and formamide (22.15 g, 491.72 mmol, 19.6 mL, 15 eq) (neat reaction) was stirred at 130° C. for 1 h. The mixture was cooled to 20° C., and then diluted with water (100 mL). The filtrate was extracted with EA (100 mL*3). The combined organic layers were washed with brine (100 mL), dried over anhydrous Na$_2$SO$_4$, filtered and concentrated under reduced pressure to give a residue. The residue was purified by flash silica gel chromatography to give 4-(2-nitrophenyl)oxazole (1.0 g, 5.10 mmol, 15.5% yield). $^1$H NMR (400 MHz, CDCl$_3$) δ 7.98 (d, J=4.6 Hz, 1H), 7.87 (dd, J=1.3, 7.8 Hz, 1H), 7.79 (dd, J=1.1, 8.1 Hz, 1H), 7.65 (dt, J=1.3, 7.6 Hz, 1H), 7.50 (dt, J=1.4, 7.8 Hz, 1H).

Step 2: 2-(oxazol-4-yl)aniline

The mixture of 4-(2-nitrophenyl)oxazole (900 mg, 4.73 mmol, 1 eq), CaCl$_2$ (2.63 g, 23.66 mmol, 5 eq) and Fe (2.64 g, 47.33 mmol, 10 eq) in EtOH (10 mL) and water (2 mL) was stirred at 80° C. for 16 h. The mixture was cooled to 20° C., and then filtered to remove the solid. The filtrate was concentrated under reduced pressure to give a residue. The residue was purified by flash silica gel chromatography to give 2-(oxazol-4-yl)aniline (600 mg, 3.60 mmol, 76.0% yield). Mass calc. for C$_9$H$_8$N$_2$O, 160.06, m/z found 160.8 [M+1]$^+$.

Step 3: 4-bromo-2-(oxazol-4-yl)aniline

To a solution of 2-(oxazol-4-yl)aniline (100 mg, 0.62 mmol, 1 eq) in ACN (2 mL) at 20° C. was added NBS (122.2 mg, 0.69 mmol, 1.1 eq), and the mixture was stirred at 20° C. for 16 h. The reaction mixture was diluted with water (10 mL) and extracted with EA (10 mL*3). The combined organic layers were washed with brine (10 mL), dried over anhydrous Na$_2$SO$_4$, filtered and concentrated under reduced pressure to give a residue. The residue was purified by flash silica gel chromatography to give 4-bromo-2-(oxazol-4-yl)aniline (40 mg, 0.14 mmol, 21.7% yield). Mass calc. for C$_9$H$_7$BrN$_2$O, 237.97, m/z found 240.7 [M+3]$^+$; $^1$H NMR (400 MHz, CDCl$_3$) δ 7.99 (s, 1H), 7.93 (d, J=0.8 Hz, 1H), 7.50 (d, J=2.3 Hz, 1H), 7.21 (dd, J=2.4, 8.7 Hz, 1H), 6.63 (d, J=8.5 Hz, 1H), 5.10 (brs, 2H).

Step 4: 4-bromo-2-(oxazol-4-yl)-N-(4-(trifluoromethyl)phenyl)aniline

The mixture of 4-bromo-2-(oxazol-4-yl)aniline (40 mg, 0.17 mmol, 1 eq), 1-iodo-4-(trifluoromethyl)benzene (59.2 mg, 0.22 mmol, 32 μL, 1.3 eq), Pd$_2$(dba)$_3$ (7.7 mg, 8.4 umol, 0.05 eq), Xantphos (9.7 mg, 16.7 umol, 0.10 eq) and K$_2$CO$_3$ (46.3 mg, 0.33 mmol, 2 eq) in dioxane (2 mL) at 20° C. was purged and degassed with N$_2$ for 3 times, and the mixture was stirred at 100° C. under N$_2$ for 16 h. The reaction mixture was diluted with water (10 ml) and extracted with EA (10 mL*3). The combined organic layers were washed with brine (10 mL), dried over anhydrous Na$_2$SO$_4$, filtered and concentrated under reduced pressure to give a residue. The residue was purified by flash silica gel chromatography to give 4-bromo-2-(oxazol-4-yl)-N-(4-(trifluoromethyl)phenyl)aniline (30 mg, 61.9 umol, 37.0% yield). Mass calc. for C$_{16}$H$_{10}$BrF$_3$N$_2$O, 381.99, m/z found 382.8 [M+1]$^+$; $^1$H NMR (400 MHz, CDCl$_3$) δ 8.73 (s, 1H), 8.02 (s, 1H), 7.97 (s, 1H), 7.68 (d, J=1.8 Hz, 1H), 7.66-7.61 (m, 1H), 7.50 (d, J=8.5 Hz, 2H), 7.43 (d, J=4.1 Hz, 1H), 7.15 (d, J=8.5 Hz, 2H).

Step 5: 3-(oxazol-4-yl)-4-((4-(trifluoromethyl)phenyl)amino)benzoic Acid

The mixture of 4-bromo-2-(oxazol-4-yl)-N-(4-(trifluoromethyl)phenyl)aniline (100 mg, 0.26 mmol, 1 eq), Pd$_2$(dba)$_3$ (12.0 mg, 13.1 umol, 0.05 eq), Xantphos (15.1 mg, 26.1 umol, 0.10 eq) and AcOK (51.2 mg, 0.52 mmol, 2 eq) in DMSO (3 mL) and MeOH (1 mL) at 20° C. was purged and degassed with CO for 3 times and then stirred at 100° C. under CO (15 Psi) for 16 h. The reaction mixture was concentrated under reduced pressure to give a residue. The residue was purified by prep-HPLC to give the title compound (24.53 mg, 70.4 umol, 27.0% yield). Mass calc. for C$_{17}$H$_{11}$F$_3$N$_2$O$_3$ 348.07, m/z found 348.9 [M+1]$^+$; $^1$H NMR (500 MHz, DMSO-d$_6$) δ 12.81 (brs, 1H), 9.00 (s, 1H), 8.61 (s, 1H), 8.54 (s, 1H), 8.44 (d, J=1.5 Hz, 1H), 7.87 (dd, J=1.8, 8.5 Hz, 1H), 7.59 (d, J=8.5 Hz, 2H), 7.49 (d, J=8.5 Hz, 1H), 7.20 (d, J=8.2 Hz, 2H).

Example 49: 4-[4-(trifluoromethyl)anilino]-3-[5-(trifluoromethyl)-1,3,4-thiadiazol-2-yl]benzoic Acid (Compound 58)

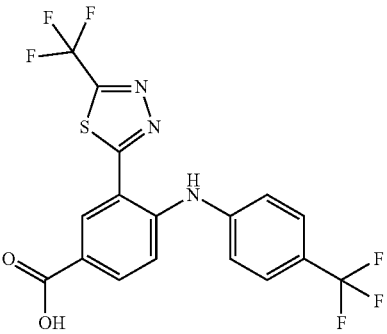 [SMILES: O=C(O)c1ccc(Nc2ccc(C(F)(F)F)cc2)c(-c2nnc(C(F)(F)F)s2)c1]

Preparation of Compound 58

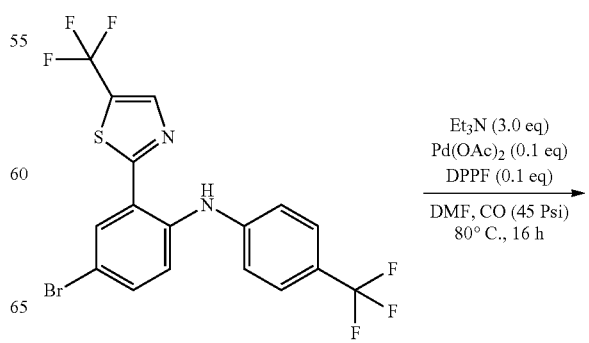

Preparation of Compound 59

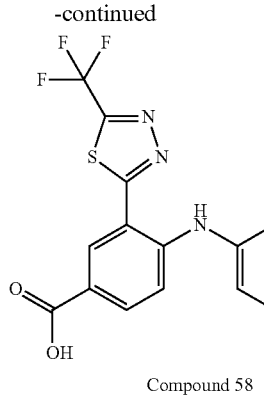

Compound 58

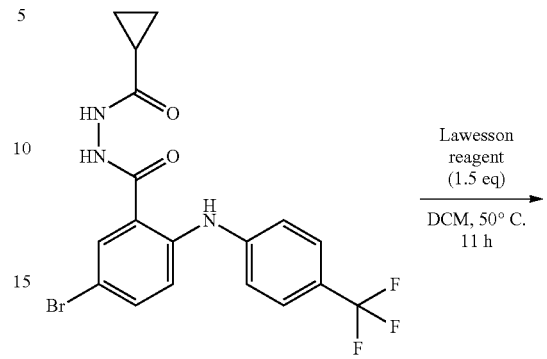

To a mixture of 4-bromo-2-(5-(trifluoromethyl)-1,3,4-thiadiazol-2-yl)-N-(4-(trifluoromethyl)phenyl)aniline (50 mg, 0.1 mmol, 1 eq), DPPF (5.9 mg, 10 umol, 0.1 eq) and Pd(OAc)$_2$ (2.4 mg, 10 umol, 0.1 eq) in DMF (40 ml) was added Et$_3$N (32.4 mg, 0.32 mmol, 44.59 μL, 3 eq), de-gassed and purged with CO for three times. The reaction mixture was heated at 80° C. for 16 hours under CO (45 Psi). The reaction was filtered and concentrated. The residue was purified by prep-HPLC to give the title compound (1.42 mg, 3.28 umol, 3% yield). Mass calc. for C$_{17}$H$_9$F$_6$N$_3$O$_2$S, 433.03, m/z found 434.0 [M+H]$^+$; $^1$H NMR (400 MHz, CDCl$_3$) δ 10.6 (s, 1H), 8.34 (d, J=2.0 Hz, 1H), 7.98 (d, J=7.2 Hz, 2H), 7.61 (d, J=8.4 Hz, 2H), 7.51-7.40 (m, 3H).

Example 50: 3-(5-cyclopropyl-1,3,4-thiadiazol-2-yl)-4-((4-(trifluoromethyl)phenyl)amino)benzoic Acid (Compound 59)

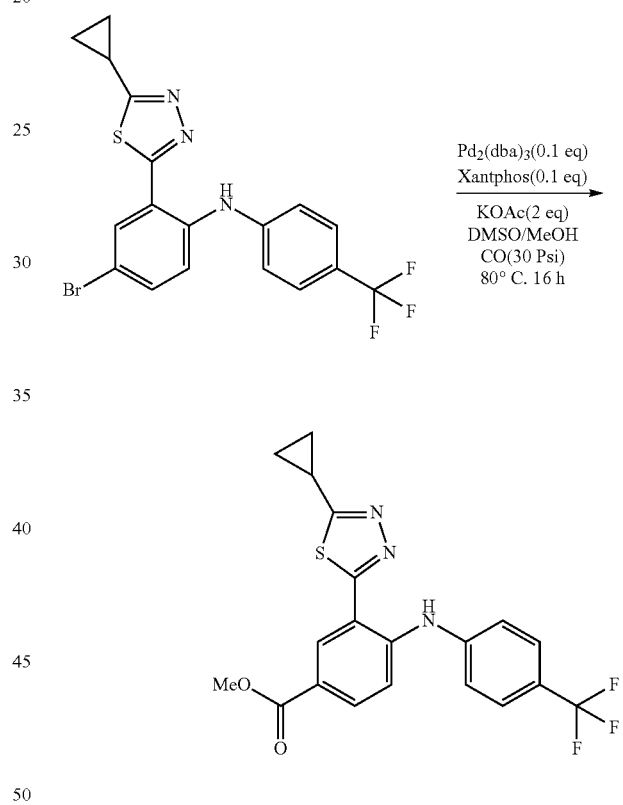

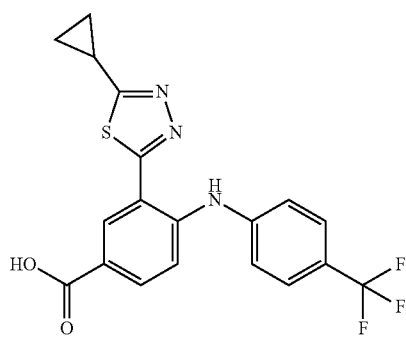

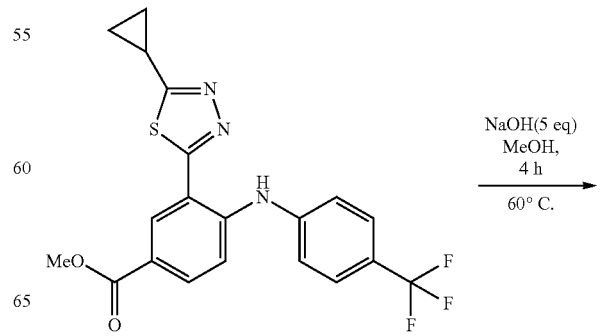

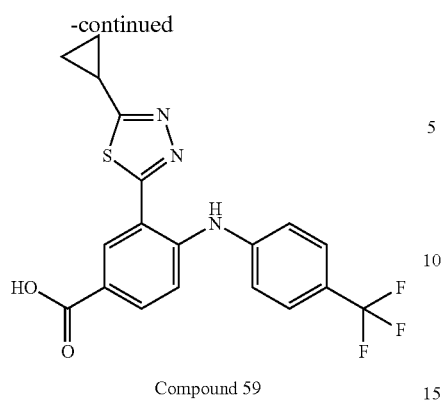

Compound 59

Step 1: 4-bromo-2-(5-cyclopropyl-1,3,4-thiadiazol-2-yl)-N-(4-(trifluoromethyl)phenyl)aniline A mixture of compound 5-bromo-N'-(cyclopropanecarbonyl)-2-((4-(trifluoromethyl)phenyl)amino)benzohydrazide (240 mg, 0.54 mmol, 1 eq) and 2,4-bis(4-methoxyphenyl)-2,4-dithioxo-1,3,2,4dithiadiphosphetane (329.3 mg, 0.81 mmol, 1.5 eq) in DCM (10 mL) was stirred at 50° C. for 5 hr under $N_2$. Then the mixture was stirred at 50° C. for 6 hr. The mixture was directly purified by prep-TLC to give 4-bromo-2-(5-cyclopropyl-1,3,4-thiadiazol-2-yl)-N-(4-(trifluoromethyl)phenyl)aniline (110 mg, 0.23 mmol, 43.1% yield). Mass calc. for $C_{18}H_{13}BrF_3N_3S$, 439.00, m/z found 441.7 [M+3]+.

Step 2: methyl 3-(5-cyclopropyl-1,3,4-thiadiazol-2-yl)-4-((4-(trifluoromethyl)phenyl)amino)benzoate A mixture of 4-bromo-2-(5-cyclopropyl-1,3,4-thiadiazol-2-yl)-N-(4-(trifluoromethyl)phenyl)aniline (50 mg, 0.11 mmol, 1 eq), Xantphos (6.57 mg, 11.4 umol, 0.1 eq), KOAc (22.3 mg, 0.23 mmol, 2 eq) and $Pd_2(dba)_3$ (10.4 mg, 11.4 umol, 0.1 eq) in DMSO (3 mL) and MeOH (3 mL) was degassed and refilled with CO for three times at 10° C., Then the mixture was stirred at 80° C. for 16 h under 30 Psi of CO. The reaction mixture was filtered via a pad of Celite and the filtrate was concentrated to remove most of methanol. The resulting residue was diluted with EA (100 mL), washed with brine (15 mL*3), dried by anhydrous $Na_2SO_4$, filtered and concentrated to give a residue. The residue was purified by prep-TLC to give methyl 3-(5-cyclopropyl-1,3,4-thiadiazol-2-yl)-4-((4-(trifluoromethyl)phenyl)amino)benzoate (70 mg, crude). Mass calc. for $C_{20}H_{16}F_3N_3O_2S$, 419.42, m/z found 420.0 [M+1]+.

Step 3: 3-(5-cyclopropyl-1,3,4-thiadiazol-2-yl)-4-((4-(trifluoromethyl)phenyl)amino)benzoic Acid To a mixture of methyl 3-(5-cyclopropyl-1,3,4-thiadiazol-2-yl)-4-((4-(trifluoromethyl)phenyl)amino)benzoate (70 g, 166.9 mmol, 1 eq) in MeOH (2.5 mL) was added NaOH (2 M, 417.2 mL, 5 eq). Then the mixture was stirred at 60° C. for 4 h. The reaction mixture was acidified to pH~2 with 1 M HCl and extracted with EA (15 mL*5). The combined organic layers were dried over anhydrous $Na_2SO_4$ to give a residue. Then the residue was purified by prep-HPLC to give the title compound (2.63 mg, 6.1 umol, 3.63e-3% yield). Mass calc. for: $C_{19}H_{14}F_3N_3O_2S$, 405.08, m/z found 406.0 [M+1]+; $^1H$ NMR (400 MHz, DMSO-$d_6$) δ 9.92 (s, 1H), 8.33 (d, J=2.0 Hz, 1H), 7.96 (dd, J=2.0, 8.6 Hz, 1H), 7.67 (d, J=8.6 Hz, 2H), 7.54 (d, J=8.8 Hz, 1H), 7.34 (d, J=8.4 Hz, 2H), 2.63-2.55 (m, 1H), 1.29-1.24 (m, 2H), 1.15-1.04 (m, 2H).

Example 51: 3-pyrimidin-4-yl-4-[4-(trifluoromethyl)anilino]benzoic Acid (Compound 60)

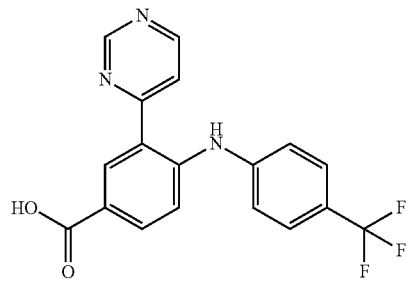

Preparation of Compound 60

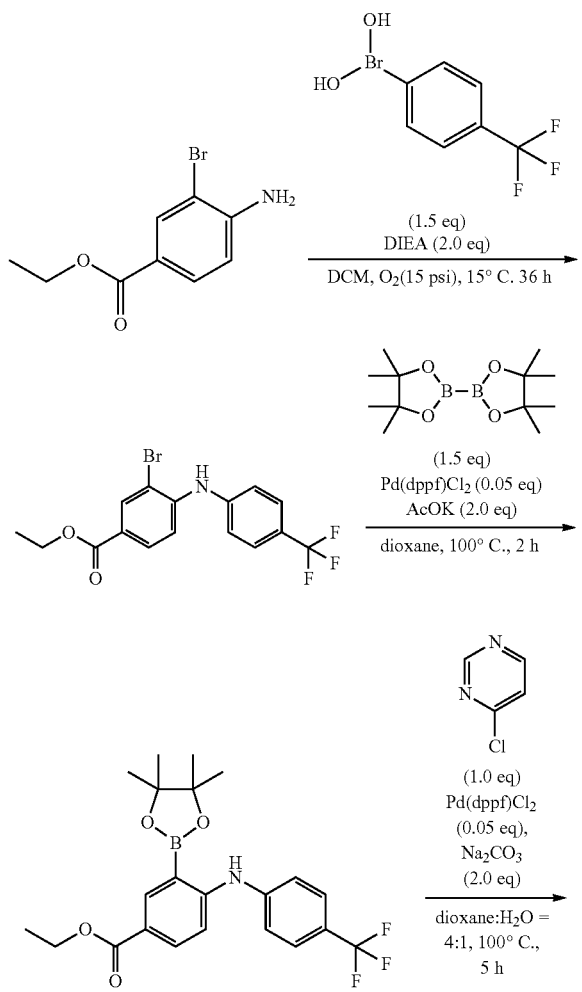

251

-continued

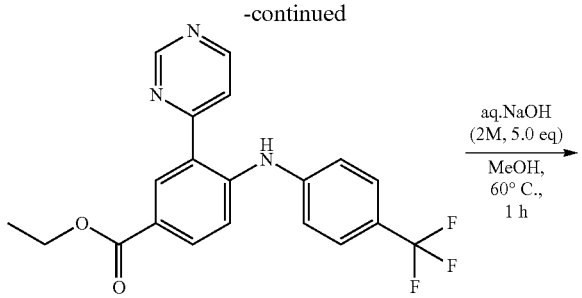

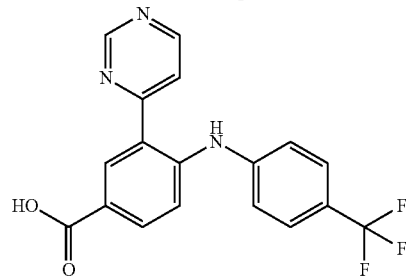 [SMILES: O=C(O)c1ccc(Nc2ccc(C(F)(F)F)cc2)c(-c2ccncn2)c1]

Compound 60

Step 1: ethyl 3-bromo-4-[4-(trifluoromethyl)anilino]benzoate

To a solution of ethyl 4-amino-3-bromobenzoate (4 g, 16.4 mmol, 1 eq) in DCM (70 mL) were added DIEA (4.24 g, 32.8 mmol, 5.7 mL, 2 eq), Cu(OAc)$_2$ (4.46 g, 24.58 mmol, 1.5 eq) and (4-(trifluoromethyl)phenyl)boronic acid (4.67 g, 24.58 mmol, 1.5 eq). The mixture was degassed and purged with 02 for 3 times and stirred at 15° C. for 36 hr under O$_2$ atmosphere (15 psi). The reaction mixture was concentrated in vacuum to give the residue and the residue was diluted with EA (50 mL), washed with H$_2$O (10 mL), brine (10 mL) and dried over Na$_2$SO$_4$, filtered and concentrated in vacuum. The crude product was purified by column chromatography (SiO$_2$) to give ethyl 3-bromo-4-[4-(trifluoromethyl)anilino]benzoate (600 mg, 1.39 mmol, 8.5% yield). $^1$H NMR (400 MHz, CDCl$_3$) δ 8.26 (d, J=2.0 Hz, 1H), 7.89 (dd, J=1.8, 8.5 Hz, 1H), 7.62 (d, J=8.5 Hz, 2H), 7.32-7.29 (m, 2H), 6.57 (s, 1H), 4.37 (q, J=7.2 Hz, 2H), 1.40 (t, J=7.2 Hz, 3H).

Step 2: ethyl 3-(4,4,5,5-tetramethyl-1,3,2-dioxaborolan-2-yl)-4-[4-(trifluoromethyl)anilino]benzoate To a solution of ethyl 3-bromo-4-[4-(trifluoromethyl)anilino]benzoate (600 mg, 1.55 mmol, 1 eq) in dioxane (6 mL) were added AcOK (303 mg, 3.09 mmol, 2 eq), Pd(dppf)Cl$_2$ (56 mg, 77 umol, 0.05 eq) and 4,4,4',4',5,5,5',5'-octamethyl-2,2'-bi(1,3,2-dioxaborolane) (589 mg, 2.32 mmol, 1.5 eq). The mixture was stirred at 100° C. for 2 hr. The reaction mixture was filtered and concentrated in vacuum to give the residue. The crude product was purified by column chromatography (SiO$_2$) to give ethyl 3-(4,4,5,5-tetramethyl-1,3,2-dioxaborolan-2-yl)-4-[4-(trifluoromethyl)anilino] benzoate (340 mg, 0.69 mmol, 45% yield).

Step 3: ethyl 3-pyrimidin-4-yl-4-[4-(trifluoromethyl)anilino]benzoate

To a solution of 4-chloropyrimidine (40 mg, 0.35 mmol, 1 eq) and Na$_2$CO$_3$ (74 mg, 0.70 mmol, 2 eq) in dioxane (2 mL) and H$_2$O (0.5 mL) were added Pd(dppf)Cl$_2$ (12 mg, 17 umol, 0.05 eq) and ethyl ethyl 3-(4,4,5,5-tetramethyl-1,3,2-dioxaborolan-2-yl)-4-[4-(trifluoromethyl)anilino] benzoate (167 mg, 0.38 mmol, 1.1 eq). The mixture was stirred at 100° C. for 5 hr. The reaction mixture was filtered and concentrated in vacuum. The crude product was used for the next step directly (105 mg, 0.20 mmol, 56% yield).

Step 4: 3-pyrimidin-4-yl-4-[4-(trifluoromethyl)anilino]benzoic Acid

To a solution of ethyl 3-pyrimidin-4-yl-4-[4-(trifluoromethyl)anilino]benzoate (100 mg, 0.18 mmol, 1 eq) in MeOH (1 mL) was added NaOH (2 M, 0.5 mL, 5 eq). The mixture was stirred at 60° C. for 1 hr. The reaction mixture was concentrated in vacuum. Then the aqueous phase was adjusted to pH=4 with 1 M.aq.HCl and extracted with EA (15 mL*3). The combined organic phase was washed with H$_2$O (10 mL) and brine (10 mL), dried over Na$_2$SO$_4$, filtered and concentrated in vacuum. The crude product was purified by prep-HPLC to give the title compound (39.6 mg, 0.11 mmol, 59.3% yield). Mass calcd. For C$_{18}$H$_{12}$F$_3$N$_3$O$_2$, 359.09 m/z found 359.8 [M+H]$^+$. $^1$H NMR (400 MHz, DMSO-d$_6$) δ 10.39 (br s, 1H), 9.30 (s, 1H), 8.86 (br d, J=5.0 Hz, 1H), 8.36 (d, J=1.8 Hz, 1H), 8.01-7.93 (m, 2H), 7.62 (br d, J=8.3 Hz, 2H), 7.53 (d, J=8.8 Hz, 1H), 7.33 (br d, J=8.3 Hz, 2H).

Example 52: 3-(oxazol-2-yl)-4-((4-(trifluoromethyl)phenyl)amino)benzoic Acid (Compound 61)

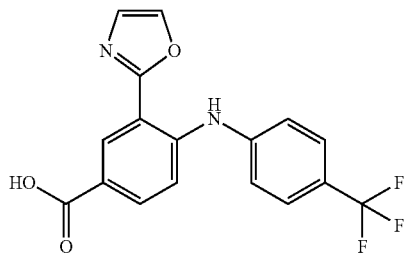 [SMILES: O=C(O)c1ccc(Nc2ccc(C(F)(F)F)cc2)c(-c2ncco2)c1]

Preparation of Compound 61

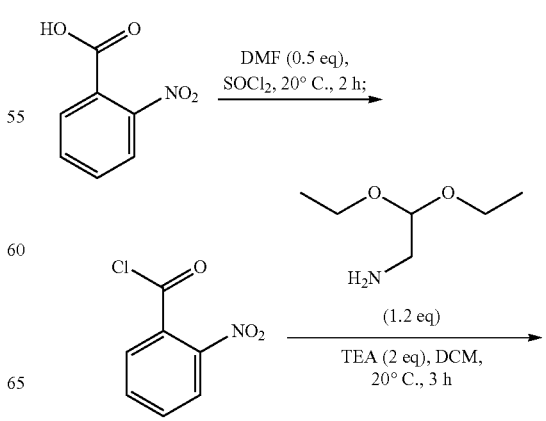

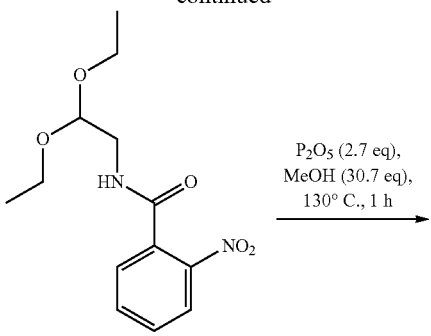

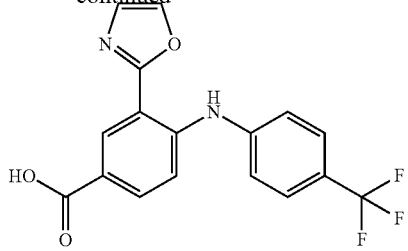

Compound 61

Step 1: 2-nitrobenzoyl Chloride

To a solution of 2-nitrobenzoic acid (1.0 g, 5.98 mmol, 1 eq) in $SOCl_2$ (5 mL) at 20° C. was added DMF (218.7 mg, 2.99 mmol, 0.2 mL, 0.5 eq) drop-wise, and the mixture was stirred at 20° C. for 2 h. The mixture was concentrated to remove $SOCl_2$ and give 2-nitrobenzoyl chloride (1.11 g, 5.98 mmol, 100.00% yield, which was used directly for next step.

Step 2: N-(2,2-diethoxyethyl)-2-nitrobenzamide

To a solution of 2,2-diethoxyethan-1-amine (956.0 mg, 7.18 mmol, 1.0 mL, 1.2 eq) and TEA (1.21 g, 11.96 mmol, 1.7 mL, 2 eq) in DCM (20 mL) at 20° C. was added 2-nitrobenzoyl chloride (1.11 g, 5.98 mmol, 0.8 mL, 1 eq) in DCM (5 mL) drop-wise, and the mixture was stirred at 20° C. for 3 h. The mixture was concentrated to give a residue. The residue was diluted with water (50 mL) and extracted with EA (50 mL*3). The combined organic layers were washed with water (30 mL), saturated $NH_4Cl$ solution (50 mL) and brine (50 mL), dried over anhydrous $Na_2SO_4$, filtered and concentrated under reduced pressure to give N-(2,2-diethoxyethyl)-2-nitrobenzamide (1.60 g, 5.67 mmol, 94.8% yield), which was used directly for next step. $^1H$ NMR (400 MHz, $CDCl_3$) δ 8.08 (dd, J=1.0, 8.0 Hz, 1H), 7.72-7.66 (m, 1H), 7.63-7.57 (m, 1H), 7.54 (dd, J=1.3, 7.5 Hz, 1H), 6.04 (brs, 1H), 4.69 (t, J=5.3 Hz, 1H), 3.77 (qd, J=7.1, 9.4 Hz, 2H), 3.68-3.58 (m, 4H), 1.24 (t, J=7.0 Hz, 6H).

Step 3: 2-(2-nitrophenyl)oxazole

The solution of N-(2,2-diethoxyethyl)-2-nitrobenzamide (1.0 g, 3.54 mmol, 1 eq), $P_2O_5$ (1.35 g, 9.51 mmol, 0.6 mL, 2.7 eq) and MsOH (13.50 g, 140.47 mmol, 10.0 mL, 39.7 eq) (neat reaction) was stirred at 130° C. for 1 h. The reaction mixture was cooled to 20° C., then diluted with water (100 mL) and extracted with EA (100 mL*3). The combined organic layers were washed with brine (100 mL), dried over anhydrous $Na_2SO_4$, filtered and concentrated under reduced pressure to give a residue. The residue was purified by flash silica gel chromatography to give 2-(2-nitrophenyl)oxazole (640 mg, 1.63 mmol, 46.1% yield). $^1H$ NMR (400 MHz, $CDCl_3$) δ 8.01 (dd, J=1.4, 7.7 Hz, 1H), 7.81 (dd, J=1.1, 7.9 Hz, 1H), 7.77 (d, J=0.8 Hz, 1H), 7.69 (dt, J=1.4, 7.6 Hz, 1H), 7.65-7.59 (m, 1H), 7.31 (s, 1H).

Step 4: 2-(oxazol-2-yl)aniline

The mixture of 2-(2-nitrophenyl)oxazole (320 mg, 0.82 mmol, 1 eq), $CaCl_2$ (452.9 mg, 4.08 mmol, 5 eq) and Fe (455.8 mg, 8.16 mmol, 10 eq) in water (2 mL) and EtOH (10 mL) was stirred at 80° C. for 5 h. The mixture was cooled to 20° C., and then filtered to remove the solid. The filtrate was concentrated under reduced pressure to give a residue.

The residue was diluted with water (10 mL) and saturated Na$_2$CO$_3$ solution (10 mL), and then extracted with EA (20 mL*3). The combined organic layers were washed with brine (20 mL), dried over anhydrous Na$_2$SO$_4$, filtered and concentrated under reduced pressure to give 2-(oxazol-2-yl) aniline (110 mg, 0.65 mmol, 79.9% yield), which was used directly for next step. $^1$H NMR (400 MHz, CDCl$_3$) δ 7.91 (dd, J=1.3, 7.9 Hz, 1H), 7.73-7.67 (m, 1H), 7.30 (s, 1H), 7.27-7.21 (m, 1H), 6.84-6.75 (m, 2H), 5.95 (brs, 2H).

Step 5: 4-bromo-2-(oxazol-2-yl)aniline

To a solution of 2-(oxazol-2-yl)aniline (110 mg, 0.69 mmol, 1 eq) in DMF (2 mL) at 20° C. was added NBS (134.5 mg, 0.76 mmol, 1.1 eq) in DMF (1 mL) drop-wise, and the mixture was stirred at 20° C. for 16 h. After addition of 1 eq NBS and the reaction continued to work for another 1 h. The mixture was diluted with water (20 mL) and then extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography to give 4-bromo-2-(oxazol-2-yl)aniline (100 mg, 0.40 mmol, 57.9% yield). Mass calc. for C$_9$H$_7$BrN$_2$O$_2$ 37.97, m/z found 240.7 [M+3]+; $^1$H NMR (400 MHz, CDCl$_3$) δ 7.98 (d, J=2.3 Hz, 1H), 7.67 (s, 1H), 7.29 (d, J=2.3 Hz, 1H), 7.24 (s, 1H), 6.66 (d, J=8.8 Hz, 1H), 5.97 (brs, 2H).

Step 6: 4-bromo-2-(oxazol-2-yl)-N-(4-(trifluoromethyl)phenyl)aniline

The mixture of 4-bromo-2-(oxazol-2-yl)aniline (100 mg, 0.42 mmol, 1 eq), 1-iodo-4-(trifluoromethyl)benzene (170.7 mg, 0.63 mmol, 92 μL, 1.5 eq), Pd$_2$(dba)$_3$ (19.2 mg, 20.9 umol, 0.05 eq), Xantphos (24.2 mg, 41.8 umol, 0.10 eq) and K$_2$CO$_3$ (173.4 mg, 1.25 mmol, 3 eq) in dioxane (3 mL) at 20° C. was purged and degassed with N$_2$ for 3 times, and the mixture was stirred at 100° C. for 16 h. The mixture was concentrated to give a residue. The residue was purified by flash silica gel chromatography to give 4-bromo-2-(oxazol-2-yl)-N-(4-(trifluoromethyl)phenyl)aniline (120 mg, 0.28 mmol, 67.4% yield). Mass calc. for C$_{16}$H$_{10}$BrF$_3$N$_2$O, 381.99, m/z found 382.7 [M+1]+; $^1$H NMR (400 MHz, CDCl$_3$) δ 10.15 (s, 1H), 8.12 (d, J=2.1 Hz, 1H), 7.73 (s, 1H), 7.58 (d, J=8.5 Hz, 2H), 7.39 (d, J:=2.1 Hz, 1H), 7.38 (s, 1H), 7.34 (d, J=8.5 Hz, 2H), 7.29 (s, 1H).

Step 7: methyl 3-(oxazol-2-yl)-4-((4-(trifluoromethyl)phenyl)amino)benzoate

The mixture of 4-bromo-2-(oxazol-2-yl)-N-(4-(trifluoromethyl)phenyl)aniline (120 mg, 0.31 mmol, 1 eq), Pd$_2$(dba)$_3$ (143 mg, 15.7 umol, 0.05 eq), Xantphos (18.1 mg, 31.3 umol, 0.10 eq) and KOAc (61.5 mg, 0.63 mmol, 2 eq) in DMSO (3 mL) and MeOH (1 mL) at 20° C. was purged and degassed with CO for 3 times, and the mixture was stirred at 100° C. under CO (15 Psi) for 16 h. The residue was purified by prep-HPLC to give methyl 3-(oxazol-2-yl)-4-((4-(trifluoromethyl)phenyl)amino)benzoate (30.0 mg, 82.8 umol, 26.4% yield). Mass calc. for C$_{18}$H$_{13}$F$_3$N$_2$O$_3$ 362.09, m/z found 362.9 [M+1]+.

Step 8: 3-(oxazol-2-yl)-4-((4-(trifluoromethyl)phenyl)amino)benzoic Acid

To a solution of methyl 3-(oxazol-2-yl)-4-((4-(trifluoromethyl)phenyl)amino)benzoate (30.0 mg, 82.8 umol, 1 eq) in MeOH (1 mL) and water (1 mL) at 20° C. was added LiOH.H$_2$O (7.0 mg, 0.17 mmol, 2 eq), and the mixture was stirred at 40° C. for 16 h. The mixture was concentrated to give a residue. The residue was purified by prep-HPLC to give the title compound (18.35 mg, 52.2 umol, 63.0% yield). Mass calc. for C$_{17}$H$_{11}$F$_3$N$_2$O$_3$ 348.07, m/z found 348.9 [M+1]+; $^1$H NMR (400 MHz, DMSO-d$_6$) δ 12.81 (brs, 1H), 10.52 (s, 1H), 8.55 (d, J=2.0 Hz, 1H), 8.34 (d, J=0.8 Hz, 1H), 7.94 (dd, J=2.0, 8.8 Hz, 1H), 7.74 (d, J=8.5 Hz, 2H), 7.57 (d, J=0.8 Hz, 1H), 7.54 (dd, J=4.8, 8.5 Hz, 3H).

Example 53: tert-butyl (1-(3-(2-methyl-2H-tetrazol-5-yl)-4-((4-(trifluoromethyl)phenyl)amino)phenyl)-1-oxo-5,8,11-trioxa-2-azatridecan-13-yl)carbamate (Compound 62)

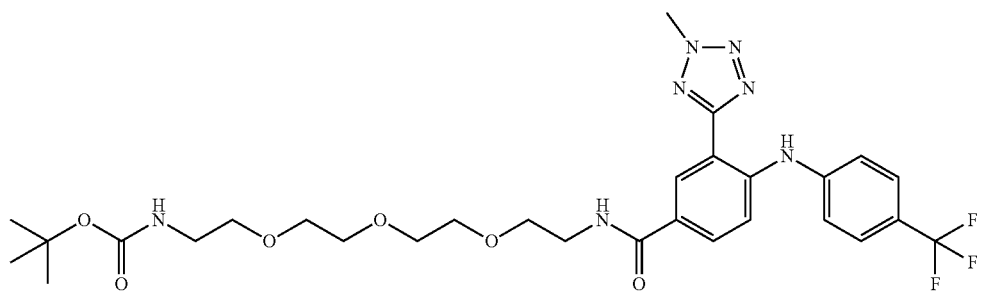 [SMILES: Cn1nnc(-c2cc(C(=O)NCCOCCOCCOCCNC(=O)OC(C)(C)C)ccc2Nc2ccc(C(F)(F)F)cc2)n1]

Preparation of Compound 62

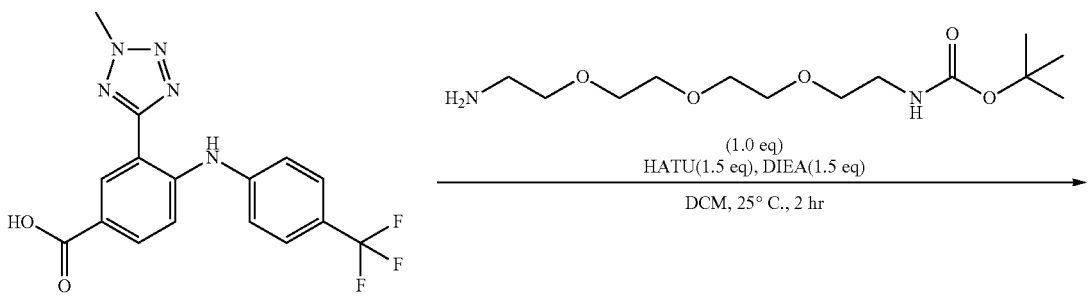

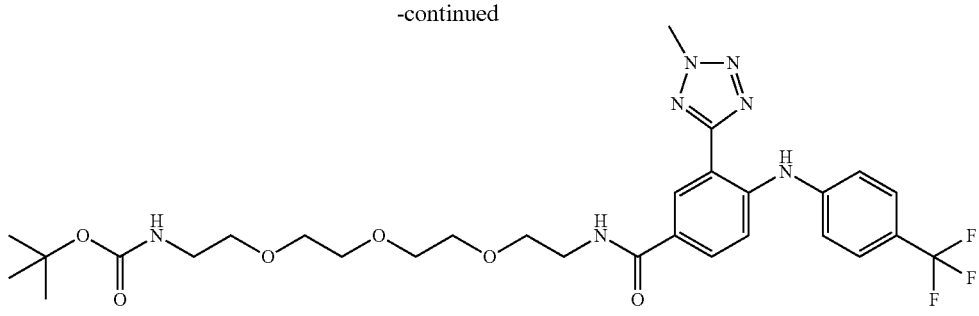

Compound 62

The mixture of 3-(2-methyltetrazol-5-yl)-4-[4-(trifluoromethyl)anilino]benzoic acid (50 mg, 0.13 mmol, 1 eq), DIEA (26.6 mg, 0.20 mmol, 35.9 µL, 1.5 eq) and HATU (78.5 mg, 0.20 mmol, 1.5 eq) in DCM (2 mL) was stirred at 25° C. for 1 hr. Then tert-butyl N-[2-[2-[2-(2-aminoethoxy)ethoxy]ethoxy]ethyl]carbamate (40.2 mg, 0.13 mmol, 1 eq) was added at the mixture and the mixture was stirred at 25° C. for another 1 hr. The reaction mixture was diluted with H$_2$O (5 mL) and the mixture was extracted with EA (15 mL*3). The combined organic phase was washed with brine (10 mL*3), dried with anhydrous Na$_2$SO$_4$, filtered and concentrated in vacuum. The residue was purified by prep-HPLC to give tert-butyl N-[2-[2-[2-[2-[[3-(2-methyltetrazol-5-yl)-4-[4-(trifluoromethyl)anilino]benzoyl]amino]ethoxy]ethoxy]ethoxy]ethyl]carbamate (30 mg, 47.0 umol, 34.1% yield). Mass calcd for C$_{29}$H$_{38}$F$_3$N$_7$O$_6$ 637.65, m/z found 660.2 [M+Na]$^+$; $^1$H NMR (400 MHz, METHANOL-d$_4$) δ=8.74 (d, J=2.3 Hz, 1H), 7.89 (dd, J=2.3, 8.8 Hz, 1H), 7.66 (d, J=8.6 Hz, 2H), 7.57 (d, J=8.9 Hz, 1H), 7.45 (d, J=8.5 Hz, 2W), 4.54-4.48 (m, 3H), 3.74-3.57 (m, 12H), 3.48 (t, J=5.6 Hz, 2H), 3.19 (t, J=5.5 Hz, 2H), 1.42 (s, 9H).

Example 54: tert-butyl (1-(3-(2-methyl-2H-tetrazol-5-yl)-4-((4-(trifluoromethyl)phenyl)amino)phenyl)-1-oxo-5,8,11,14-tetraoxa-2-azahexadecan-16-yl)carbamate (Compound 63)

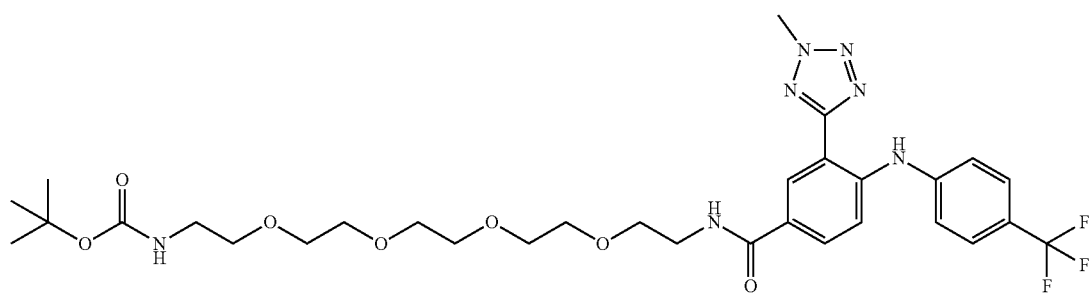 [SMILES: Cn1nnc(-c2cc(C(=O)NCCOCCOCCOCCOCCNC(=O)OC(C)(C)C)ccc2Nc2ccc(C(F)(F)F)cc2)n1]

Preparation of Compound 63

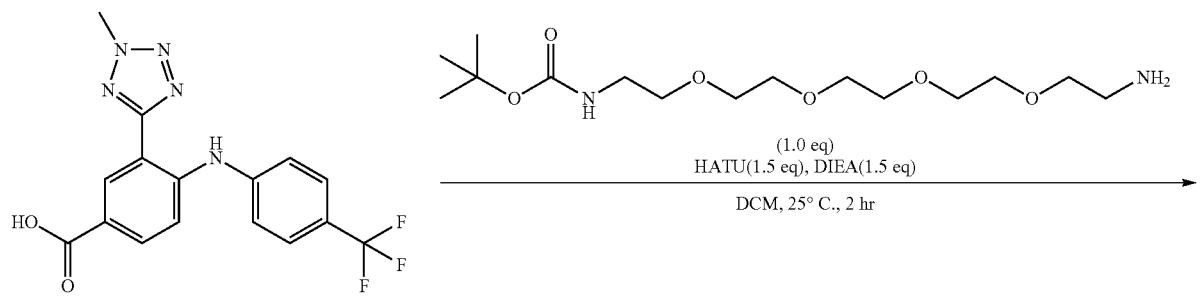

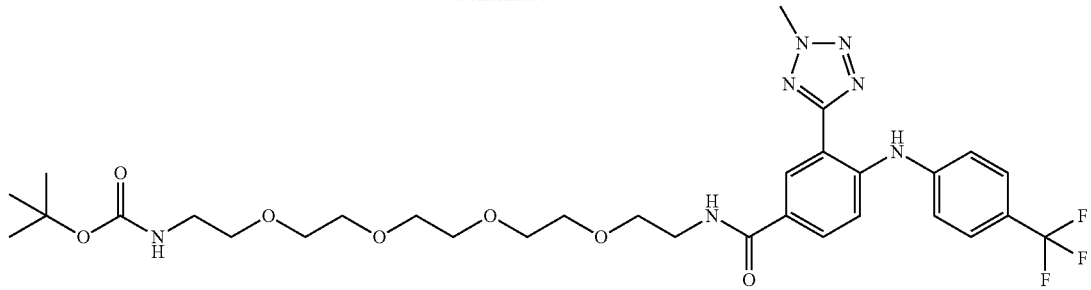

Compound 63

The mixture of 3-(2-methyltetrazol-5-yl)-4-[4-(trifluoromethyl)anilino]benzoic acid (50 mg, 0.13 mmol, 1 eq), HATU (78.5 mg, 0.20 mmol, 1.5 eq) and DIEA (26.6 mg, 0.20 mmol, 35.9 μL, 1.5 eq) in DCM (1 mL) was stirred at 25° C. for 1 hr. Then tert-butyl N-[2-[2-[2-[2-(2-aminoethoxy)ethoxy]ethoxy]ethoxy]ethyl]carbamate (46.3 mg, 0.13 mmol, 1 eq) was added at the mixture and the mixture was stirred at 25° C. for another 1 hr. The reaction mixture was diluted with H$_2$O (5 mL) and the mixture was extracted with EA (10 mL*3). The combined organic phase was washed with brine (10 mL*3), dried with anhydrous Na$_2$SO$_4$, filtered and concentrated in vacuum. The residue was purified by prep-HPLC to give compound tert-butyl N-[2-[2-[2-[2-[2-[[3-(2-methyltetrazol-5-yl)-4-[4-(trifluoromethyl)anilino]benzoyl]amino]ethoxy]ethoxy]ethoxy]ethoxy]ethyl]carbamate (30 mg, 44.0 umol, 31.9% yield). Mass calcd for C$_{31}$H$_{42}$F$_3$N$_7$O$_7$ 681.70, m/z found 704.2 [M+Na]$^+$. $^1$H NMR (400 MHz, METHANOL-d$_4$) δ=8.74 (d, J=2.0 Hz, 1H), 7.89 (dd, J=2.3, 8.8 Hz, 1H), 7.66 (d, J=8.5 Hz, 2H), 7.58 (d, J=8.8 Hz, 1H), 7.46 (d, J=8.5 Hz, 2H), 3.65-3.58 (m, 1H), 3.74-3.53 (m, 17H), 3.47 (t, J=5.5 Hz, 2H), 3.19 (t, J=5.6 Hz, 2H), 1.43 (s, 9H).

Example 55: 3-(2-methyl-2H-tetrazol-5-yl)-N-(4-oxo-2,8,11-trioxa-5-azatridecan-13-yl)-4-((4-(trifluoromethyl)phenyl)amino)benzamide (Compound 64)

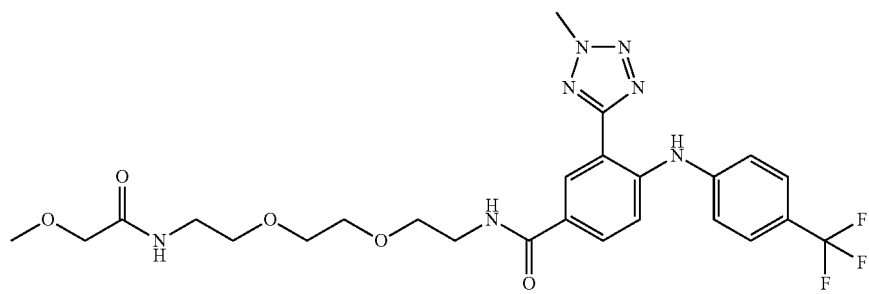 [SMILES: COCC(=O)NCCOCCOCCNC(=O)c1ccc(Nc2ccc(C(F)(F)F)cc2)c(-c2nnn(C)n2)c1]

Preparation of Compound 64

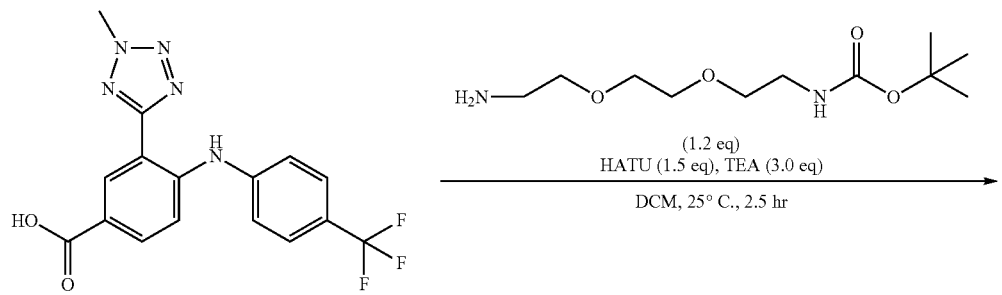

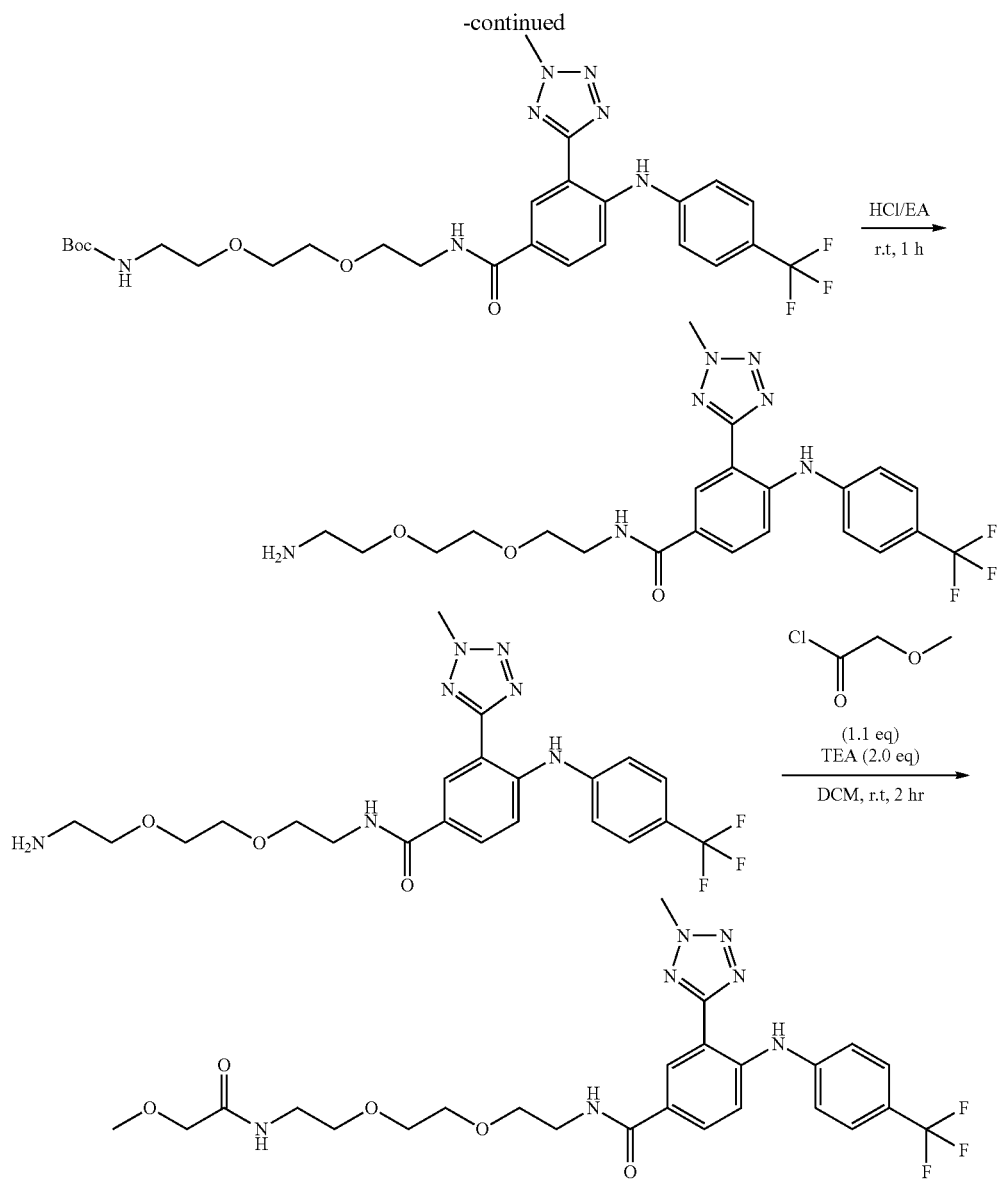

Compound 64

Step 1: tert-butyl (2-(2-(2-(3-(2-methyl-2H-tetrazol-5-yl)-4-((4-(trifluoromethyl)phenyl)amino)benzamido)ethoxy)ethoxy)ethyl)carbamate To a solution of 3-(2-methyltetrazol-5-yl)-4-[4-(trifluoromethyl)anilino]benzoic acid (200 mg, 0.55 mmol, 1 eq) in DCM (5 mL) was added HATU (0.31 g, 0.82 mmol, 1.5 eq) and TEA (0.16 g, 1.65 mmol, 0.22 mL, 3 eq). The mixture was stirred at 25° C. for 0.5 hr. Then tert-butyl N-[2-[2-(2-aminoethoxy)ethoxy]ethyl]carbamate (0.16 g, 0.66 mmol, 1.2 eq) was added to the solution. The reaction was stirred at 25° C. for 2 hr. H₂O (6 mL) was added to the solution. The mixture was extracted with ethyl acetate (5 mL*3). The combined organic layers were washed with brine (10 mL*2), dried over anhydrous Na₂SO₄, filtered and concentrated in vacuum. Compound tert-butyl N-[2-[2-[2-[[3-(2-methyltetrazol-5-yl)-4-[4-(trifluoromethyl)anilino]benzoyl]amino]ethoxy]ethoxy]ethyl]carbamate (210 mg, crude).

Step 2: N-(2-(2-(2-aminoethoxy)ethoxy)ethyl)-3-(2-methyl-2H-tetrazol-5-yl)-4-((4-(trifluoromethyl)phenyl)amino)benzamide To a 0° C. solution of tert-butyl N-[2-[2-[2-[[3-(2-methyltetrazol-5-yl)-4-[4-(trifluoromethyl)anilino]benzoyl]amino]ethoxy]ethoxy]ethyl]carbamate (160 mg, 0.26 mmol, 1 eq) in EtOAc (5 mL) was added HCl/EtOAc (4 M, 1.35 mL, 20 eq). The mixture was stirred at 15° C. for 1 hr, and then the reaction mixture was concentrated under reduced pressure to give crude N-[2-[2-(2-aminoethoxy)ethoxy]ethyl]-3-(2-methyltetrazol-5-yl)-4-[4-(trifluoromethyl)anilino]benzamide hydrochloride (150 mg) as a yellow oil.

Step 3: 3-(2-methyl-2H-tetrazol-5-yl)-N-(4-oxo-2,8,11-trioxa-5-azatridecan-13-yl)-4-((4-(trifluoromethyl)phenyl)amino)benzamide To a solution of N-[2-[2-(2-aminoethoxy)ethoxy]ethyl]-3-(2-methyltetrazol-5-yl)-4-[4-(trifluoromethyl)anilino]

benzamide (35 mg, 70.9 umol, 1 eq) in DCM (1 mL) was added TEA (14.3 mg, 0.14 mmol, 19.7 μL, 2 eq) and 2-methoxyacetyl chloride (8.4 mg, 78.0 umol, 7.1 uL, 1.1 eq). The mixture was stirred at 1° C. for 2 hr. H$_2$O (6 mL) was added to the solution. The mixture was extracted with ethyl acetate (10 mL*3). The combined organic layers were washed with brine (15 mL*2), dried over anhydrous Na$_2$SO$_4$, filtered and concentrated in vacuum. The residue was purified by prep-HPLC to give compound N-[2-[2-[2-[(2-methoxyacetyl)amino]ethoxy]ethoxy]ethyl]-3-(2-methyltetrazol-5-yl)-4-[4-(trifluoromethyl)anilino]benzamide (3.3 mg, 5.6 umol, 7.8% yield, HCl). Mass calc. for C$_{25}$H$_{30}$F$_3$N$_7$O$_5$ 565.54, m/z found 566.1 [M+H]$^+$; $^1$H NMR (400 MHz, METHANOL-d$_4$) δ=8.73 (d, J=2.3 Hz, 1H), 7.89 (dd, J=2.3, 8.8 Hz, 1H), 7.66 (d, J=8.5 Hz, 2H), 7.57 (d, J=8.8 Hz, 1H), 7.45 (d, J=8.4 Hz, 2H), 4.50 (s, 3H), 3.86 (s, 2H), 3.73-3.67 (m, 6H), 3.64-3.58 (m, 4H), 3.43 (s, 2H), 3.38 (s, 3H).

Example 56: 3-(2-methyl-2H-tetrazol-5-yl)-N-(5-oxo-2,9,12-trioxa-6-azatetradecan-14-yl)-4-((4-(trifluoromethyl)phenyl)amino)benzamide (Compound 65)

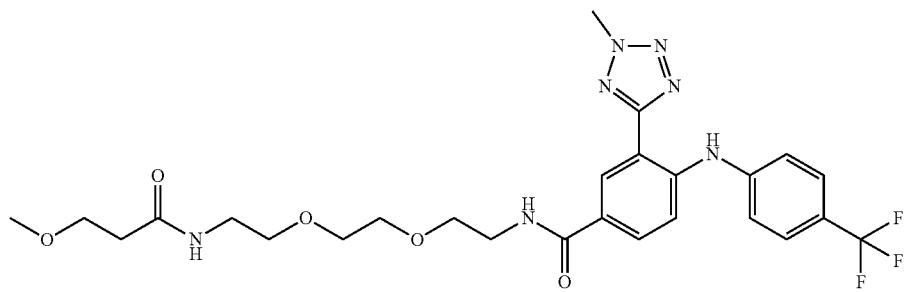 [SMILES: COCCC(=O)NCCOCCOCCNC(=O)c1ccc(Nc2ccc(C(F)(F)F)cc2)c(-c2nnn(C)n2)c1]

Preparation of Compound 65

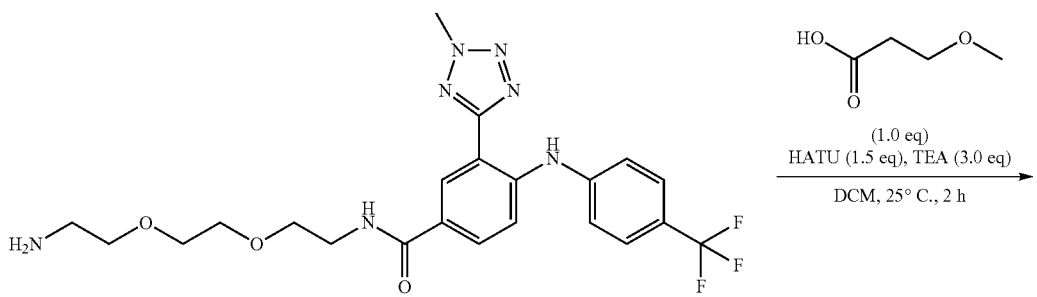

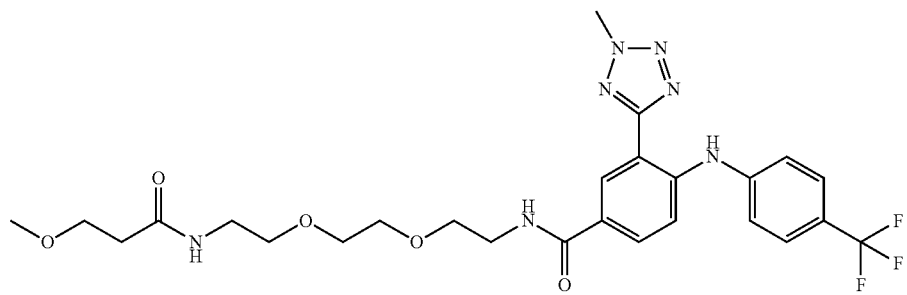

Compound 65

To a solution of N-[2-[2-(2-aminoethoxy)ethoxy]ethyl]-3-(2-methyltetrazol-5-yl)-4-[4-trifluoromethyl)anilino]benzamide (50 mg, 0.10 mmol, 1 eq) and 3-methoxypropionic acid (10.5 mg, 0.10 mmol, 9.5 µL, 1 eq) in DCM (2 mL) was added HATU (57.7 mg, 0.15 mmol, 1.5 eq) and TEA (30.7 mg, 0.30 mmol, 42.3 uL, 3 eq). The mixture was stirred at 15 (C for 2 hr. $H_2O$ (6 mL) was added to the solution. The mixture was extracted with ethyl acetate (10 mL*3). The combined organic layers were washed with brine (15 mL*2), dried over anhydrous $Na_2SO4$, filtered and concentrated in vacuum. The residue was purified by prep-HPLC. Compound N-[2-[2-[2-(3-methoxypropanoylamino)ethoxy]ethoxy]ethyl]-3-(2-methyltetrazol-5-yl)-4-[4-(trifluoromethyl)anilino]benzamide (16.2 mg, 26.3 umol, 25.9% yield, HCl). Mass calc. for $C_{26}H_{32}F_3N_7O_5$ 579.57, m/z found 580.1 $[M+H]^+$; $^1H$ NMR (400 MHz, METHANOL-$d_4$) δ=8.71 (d, J=2.3 Hz, 1H), 7.87 (dd, J=2.3, 8.8 Hz, 1H), 7.65 (d, J=8.5 Hz, 2H), 7.55 (d, J=8.8 Hz, 1H), 7.44 (d, J=8.5 Hz, 2H), 4.49 (s, 3H), 3.73-3.56 (m, 12H), 3.40-3.36 (m, 2H), 3.30 (s, 3H), 2.45 (t, J=6.1 Hz, 2H).

II. Biological Evaluation

Example A1: YAP Reporter Assay

HEK293T cells stably transfected with 8×TBD luciferase reporter and pRLTK in 384-well plates were treated with the test compounds, starting from 3 µM (final concentration in assay plate), 1:3 dilution, and 10 points in quadruplicates. Post 24-hr incubation with compounds at 37° C. and 5% CO2, cells were lysed and 8×TBD-driven firefly luciferase and control TK-driven renilla luciferase activities were measured using Promega Dual-Luciferase Reporter Assay System.

Reagents: The reagents used for this study are: DMEM: Invitrogen #11960077, Dual-Glo Luciferase Assay System: Promega-E2980, Puromycin Dihydrochloride: Invitrogen-A1113803, 384-well plate: PerkinElmer-6007480, L-GLUTAMINE: Invitrogen-25030164, Hygromycin B: Invitrogen-10687010, and Penicillin-Streptomycin: Merk-TMS-AB2-C Media: The media used for this assay were: Culture Medium: DMEM+1 ug/mL puromycin+200 ug/mL hygromycin (with 10% FBS+1 mM L-glutamine); and Assay Medium: DMEM (with 10% FBS+1 mM L-glutamine+1× P/S).

Cell Plating: The appropriate media was warmed at 37° C. by water bath: Culture Medium, Assay Medium, 1*D-PBS, 0.05% trypsin-EDTA. The cells were trypsinized after removing all media, then washed with 1* sterile D-PBS and then with 2 ml 0.05% trypsin-EDTA. The cells were then incubated at RT for one minute. Then 10 ml/75 cm2 flask Assay Medium was added to each flask. Using a 10 ml pipette, the cells were then gently resuspended in the media, until the clumps completely disappeared. The cells were then transferred into 50 ml centrifuge tubes and were centrifuged at 800 rpm for 5 mins. The medium was removed and the cells were resuspended with Assay Medium. An aliquot of cells was used to count the cell density (cells/ml). The cell suspension was then diluted with Assay Medium to a concentration of 6×104 cells/ml. 50 ul cells suspension was then plated to 384-well plate (PerkinElmer-6007480), 3×103 cells/well and the cells were incubated in an incubator at 37° C., 5% CO2.

Compound Treatment: In the afternoon (incubation of the plate with 3-4 hrs), the test compounds were added by Echo, starting from 3 uM (final concentration in the assay plate), 1:3 dilution, 10 points, quadruplicates. The plate was placed at 37° C., 5% $CO_2$ incubator for 24 hrs.

Detection: The Dual-Glo Luciferase Reagent was prepared by transferring the contents of one bottle of Dual-Glo Luciferase Buffer to one bottle of Dual-Glo Luciferase Substrate to create the Dual-Glo Luciferase Reagent. Mixing was performed by inversion until the substrate was thoroughly dissolved. After mixing, the reagent was aliquoted into 15 ml tubes. In the afternoon (24 hrs post compound treatment), the DMEM+ medium in the 384 well plates were aspirated by Microplate Washer.

Measuring firefly luciferase activity: 20 ul Dual-Glo Luciferase Reagent was added to the 384-well plates. The plates were protected from light to prevent interference with the assay. The plates were shaken for 1 min followed centrifuging plates at 1000 rpm for 30 seconds. After waiting at least 10 minutes, the firefly luminescence was measured by Envision.

Measuring renilla luciferase activity: 20 ul Stop-Glo Reagent was added to the 384-well plates. The plates were shaken for 1 min and then centrifuged at 1000 rpm for 30 seconds. After waiting at least 10 minutes, the renilla luminescence was measured by Envision.

Compound $IC_{50}$ and maximum inhibition on the firefly luciferase and renilla luciferase activities were reported separately. $IC_{50}$ for firefly luciferase activity are shown in the table below.

TABLE 2

| Compound No. | Name | Firefly Luciferase $IC_{50}$ (µM) |
|---|---|---|
| 1 | methyl 3-(2-methyl-2H-tetrazol-5-yl)-4-((4-(trifluoromethyl)phenyl)amino)benzoate | A |
| 2 | methyl 3-(2-methyl-2H-tetrazol-5-yl)-((3-(trifluoromethyl)phenyl)amino)benzoate | A |
| 3 | 3-(2-methyl-2H-tetrazol-5-yl)-4-((4-(trifluoromethyl)phenyl)amino)benzoic acid | A |
| 4 | 3-(2-methyl-2H-tetrazol-5-yl)-4-((3-(trifluoromethyl)phenyl)amino)benzoic acid | A |
| 5 | N-methyl-3-(2-methyl-2H-tetrazol-5-yl)-((3-(trifluoromethyl)phenyl)amino)benzamide | A |
| 6 | 3-(2-methyl-2H-tetrazol-5-yl)-4-((3-(trifluoromethyl)phenyl)amino)benzamide | A |
| 7 | 3-(2-methyl-2H-tetrazol-5-yl)-4-((4-(trifluoromethyl)phenyl)amino)benzamide | A |
| 8 | N-methyl-3-(2-methyl-2H--tetrazol-5-yl)-4-((4-(trifluoromethyl)phenyl)amino)benzamide | A |
| 10 | N-ethyl-3-(2-methyl-2H-tetrazol-5-yl)-4-((4-(trifluoromethyl)phenyl)amino)benzamide | A |
| 11 | N-isopropyl-3-(2-methyl-2H-tetrazol-5-yl)-4-((4-(trifluoromethyl)phenyl)amino)benzarnide | A |
| 12 | methyl 4-((4-(isopropylcarbamoyl)phenyl)amino)-3-(2-methyl-2H-tetrazol-5-yl)benzoate | C |
| 13 | N,N-dimethyl-3-(2-methyl-2H-tetrazol-5-yl)-4-((4-(trifluoromethyl)phenyl)arnino)benzamide | B |
| 15 | 3-(2-methyl-2H-tetrazol-5-yl)-N-(methylsulfonyl)-4-((4-(trifluoromethyl)phenyl)amino)benzamide | A |
| 17 | N,N-diethyl-3-(2-methyl-2H-tetrazol-5-yl)-4-((4-(trifluoromethyl)phenyl)amino)benzamide | B |
| 19 | N,N-dimethyl-3-(2-methyl-2H-tetrazol-5-yl)-4-((3-(trifluoromethyl)phenyl)amino)benzamide | B |
| 20 | N,N-diethyl-3-(2-methyl-2H-tetrazol-5-yl)-4((3-(trifluoromethyl)phenyl)amino)benzamide | B |
| 21 | N-isopropyl-3 -(2-methyl-2H-tetrazol-5-yl)-4-((3-(trifluoromethyl)phenyl)amino)benzamide | A |
| 22 | N-ethyl-3-(2-methyl-2H-tetrazol-5-yl)-4-((3-(trifluoromethyl)phenyl)amino)benzamide | A |
| 23 | 3-(2-methyl-2H-tetrazol-5-yl)-N-(methylsulfonyl)-4-((3-(trifluoromethyl)phenyl)amino)benzamide | A |

TABLE 2-continued

| Compound No. | Name | Firefly Luciferase IC$_{50}$ (μM) |
|---|---|---|
| 24 | methyl 3-(2-(2-fluorohenzyl)-2H-tetrazol-5-yl)-4-((4-(trifluoromethyl)phenyl)amino)benzoate | B |
| 25 | 3-(2-(2-fluorobenzyl)-2H-tetrazol-5-yl)-4-((4-(trifluoromethyl)phenyl)amino)benzoic acid | A |
| 26 | methyl 3-(2(2-fluorobenzyl)-2H-tetrazol-5-yl)-4-((3-(trifluoromethyl)phenyl)amino)benzoate | B |
| 27 | 3-(2-(2-fluorobenzyl)-2H-tetrazol-5-yl)-4-((3-(trifluoromethypphenyl)amino)benzoic acid | A |
| 28 | 3-(1-methyl)-1H-imidazol-4-yl)-4-((4-(trifluoromethyl)phenyl)amino)benzoic acid | A |
| 29 | 3-(2-aminopyridin-4-yl)-N-isopropyl-4-((4-(trifluoromethyl)phenyl)amino)benzamide | B |
| 30 | 3-(2-aminopyridin-4-yl)-4-((4-(trifluoromethyl)phenyl)amino)benzoic acid | A |
| 33 | methyl 3-(1-methyl-1H-imidazol-4-yl)-4-((4 -(trifluoromethyl)phenyl)amino)benzoate | A |
| 34 | methyl 3-(2-amino-4-pyridyl)-4-[4-(trifluoromethyl)anilino]benzoate | A |
| 36 | N-isopropyl-3-(1-methylimidazol-4-yl)-4-[4-(trifluoromethyl)anilino]benzarnide | A |
| 37 | N-cyclopropyl-3-(1-methylimidazol-4-yl)-4-[4-(trifluoromethyl)anilino+benzamide | A |
| 38 | 3 -(1-methylimidazol-4-yl)-N-sulfamoyl-4-[4-(trifluoromethyl)anilino]benzamide | A |
| 39 | 3-(pyridin-2-yl)-4-((4-(trifluoromethyl)phenyl)amino)benzoic acid | A |
| 40 | 3-(pyrimidin-2-yl)-4-((4-(trifluoromethyl)phenyl)amino)benzoic acid | A |
| 41 | 3-(thiazol-4-yl)-4-((4-(trifluoromethyl)phenyl)amino)benzoic acid | A |
| 42 | 3-(thiazol-2-yl)-4-((4-(trifluoromethyl)phenyl)amino)benzoic acid | A |
| 43 | 3-(pyrazin-2-yl)-4-((4-(trifluoromethyl)phenyl)amino)benzoic acid | A |
| 44 | N-(2-(2-(2-aminoethoxy)ethoxy)ethyl)-3-(2-methyl-2H-tetrazol-5-yl)-4-((4-(trifluoromethyl)phenyl)amino)benzamide | B |
| 45 | N-(2-(2-(2-acetamidoethoxy)ethoxy)ethyl)-3-(2-methyl-2H-tetrazol-5-yl)-4-((4-(trifluoromethyl)phenyl)amino)benzamide | A |
| 46 | 3-pyrida2in-3-yl-4-[4-(trifluoromethyl)anilino]benzoic acid | A |
| 47 | tert-butyl (2-(2-(2-(3-(2-methyl-2H-tetrazol-5-yl)-4-((4-(trifluoromethyl)phenyt)amino)benzamido)ethoxy)ethoxy)ethyl)carbamate | B |
| 49 | 3-(4-fluoro-2-pyridyl)-4-[4-(trifluoromethyl)anilino]benzoic acid | A |
| 50 | 3-(pyrazin-2-yl)-4-((4-(trifluoromethyl)phenyl)amino)benzoic acid | A |
| 51 | 3-(5-fluoro-2-pyridyl)-4-[4-(trifluoromethyl)anilino]benzoic acid | A |
| 52 | 3-(5-chloro-2-pyridyl)-4-[4-(trifluoromethyl)anilino]benzoic acid | A |
| 53 | methyl 3-(5-cyclopropyl-1,3,4-oxadiazol-2-yl)-4-((4-(trifluoromethyl)phenyl)amino)benzoate | A |
| 54 | 3-(5-cyclopropyl-1,3,4-oxadiazol-2-yl)-4-((4-(trifluoromethyl)phenyl)amino)benzoic acid | A |
| 55 | 3-(4-chloro-2-pyridyl)-4-[4-(trifluoromethyl)anilino]benzoic acid | A |
| 56 | methyl 3-(6-aminopyrimidin-4-yl)-4-[4-(trifluoromethyl)anilino]benzoate | A |
| 57 | 3-(oxazol-4-yl)-4-((4-(trifluoromethyl)phenypamino)benzoic acid | A |
| 58 | 4-[4-(trifluoromethyl)anilino]-3-[5-(trifluoromethyl)-1,3,4-thiadiazol-2-yl]benzoic acid | A |
| 59 | 3-(5-cyclopropyl-1,3,4-thiadiazol-2-yl)-4-((4-(triflooromethyl)phenyl)amino)benzoic acid | A |
| 60 | 3-pyrimidin-4-yl-4-[4-(trifluoromethyl)anilino]benzoic acid | B |
| 61 | 3-(oxazol-2-yl)-4-((4-(trifluoromethyl)phenyl)amino)benzoic acid | A |
| 63 | tert-butyl (1-(3-(2-methyl-2H-tetrazol-5-yl)-4-(4-(trifluoromethyl)phenyl)amino)phenyl)-1-oxo-5,8,11,14-tetraoxa-2-azahexadecan-16-yl)carbamate | B |
| 64 | 3-(2-methyl-2H-tetrazol-5-yl)-N-(4-oxo-2,8,11-trioxa-5-azatridecan-13-yl)-4-((4-(trifluoromethyl)phenyl)amino)benzamide | B |
| 65 | 3-(2-methyl-2H-tetrazol-5-yl)-N-(5-oxo-2,9,12-trioxa-6-azatetradecan-14-yl)-4-((4-(trifluoromethyl)phenyl)amino)benzamide | B |

Note: Biochemical assay IC$_{50}$ data are designated within the following ranges:

A: ≤0.100 μM

B: >0.100 μM to ≤1.000 μM

C: >1.000 μM to ≤3.000 μM

D: >3.000 μM

Example A2: Tumor Suppression Assay

The procedures described herein for the tumor suppression assay is as described in PCT/US2013/043,752 (WO2013/188,138). Mouse procedures are performed according to the guidelines of approved animal protocol and based on the methods. After the cells are grown to 90%> confluence, these cells are harvested by trypsinization, washed in phosphate-buffered saline (PBS), and resuspended in PBS supplemented with 50% Matrigel (BD Biosciences). An appropriate amount of cells is prepared for administration, such as 200 μL per injection site. Immunocompromised mice are injected on the dorsolateral sites subcutaneously. Any one of the compounds described herein is formulated accordingly and is then administered at a suitable dose. Control mice received vehicle alone. The average tumor diameter (two perpendicular axes of the tumor are measured) are recorded. The data are expressed in tumor volume estimated by ([width]2×length/2). Paired, two-tailed Student's t-test is performed to access the statistical significance.

Example A3: Cell Proliferation Assay

Cancer cell lines are plated in 384-well plates 24h before drug treatment. Post incubation for various time periods with the test compounds, starting from 3 μM (final concentration in assay plate), 1:3 dilution, and 10 points in duplicates, the number of viable cells and proliferative cells are determined using CellTiter-Glo® Luminescent Cell Viability Assay Kit (Promega) and Click-iT EdU HCS Assay Kit (Invitrogen) according to the manufacturers' protocols. The IC$_{50}$ values and maximum % inhibition of the test compounds are calculated using the dose response curves.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt thereof:

Formula (I)

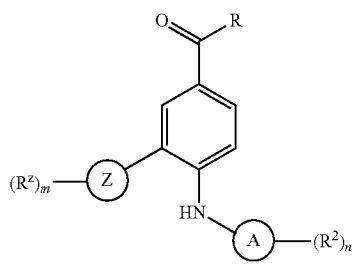

wherein,

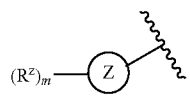

is pyrrolyl, imidazolyl, pyrazolyl, oxazolyl, isoxazolyl, thiazolyl, isothiazol, triazolyl, tetrazolyl, oxadiazolyl, thiadiazolyl, or dithiazolyl, each of which is substituted with —(R$^z$)$_m$; or

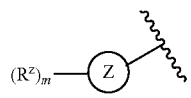

is a pyridinyl, pyrazinyl, pyrimidinyl, or pyridazinyl, each of which is substituted with —(R$^z$)$_m$;

each R$^z$ is independently H, halogen, —CN, C$_1$-C$_6$ alkyl, C$_1$-C$_6$ haloalkyl, substituted or unsubstituted C$_3$-C$_{10}$ cycloalkyl, substituted or unsubstituted aralkyl, substituted or unsubstituted aryl, L$^1$-Y$^1$, or —N(R$^3$)(Y$^2$);

m is 0, 1, 2, 3, 4, or 5;

L$^1$ is C$_1$-C$_6$ alkylene,

Y$^1$ is substituted or unsubstituted C$_3$-C$_{10}$ cycloalkyl or substituted or unsubstituted aryl;

each R$^3$ is independently H or C$_1$-C$_6$ alkyl;

each Y$^2$ is independently H or C$_1$-C$_6$ alkyl;

R is —OR$^1$ or —N(R$^1$)$_2$;

each R$^1$ is independently H, —(SO$_2$)R$^4$, C$_1$-C$_6$ haloalkyl, substituted or unsubstituted C$_1$-C$_6$ heteroalkyl, substituted or unsubstituted C$_3$-C$_{10}$ cycloalkyl, substituted or unsubstituted aralkyl, substituted or unsubstituted aryl;

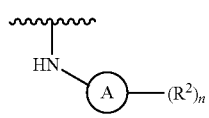

is

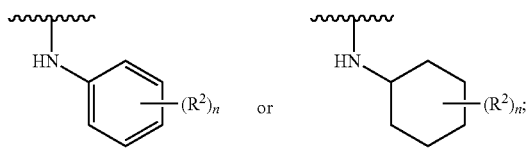

each R$^2$ is independently H, —F, —I, —Cl, —N$_3$, —CN, —OR$^4$, —SR$^4$, —(SO$_2$)R$^4$, —N(R$^4$)$_2$, —CO$_2$R$^4$, C$_1$-C$_6$ alkyl, or C$_1$-C$_6$ haloalkyl;

n is 0, 1, 2, 3, 4, or 5; and each R$^4$ is independently H, C$_1$-C$_6$alkyl, C$_1$-C$_6$ haloalkyl, C$_1$-C$_6$ heteroalkyl, substituted or unsubstituted C$_3$-C$_{10}$ cycloalkyl, substituted or unsubstituted aralkyl, or substituted or unsubstituted aryl wherein "heteroalkyl" refers to an alkyl group in which one or more skeletal atoms of the alkyl are selected from oxygen —NH—, and —N(alkyl)-, and the heteroalkyl is attached to the rest of the molecule at a carbon atom of the heteroalkyl;

wherein each substituted alkyl, and substituted heteroalkyl is substituted with one or two substituents independently selected from the group consisting of halo, cyano, nitro, oxo, thioxo, imino, oximo —OR$^a$, —OC(O)—R$^a$, —N(R$^a$)$_2$, C(O)R$^a$, —C(O)OR$^a$, —C(O)N(R$^a$)$_2$, —N(R$^a$)C(O)OR$^f$, —OC(O)— NR$^a$R$^f$, —N(R$^a$)C(O)R$^f$, where each R$^a$ is independently hydrogen, C$_1$-C$_6$ alkyl, C$_1$-C$_6$ fluoroalkyl, C$_3$-C$_6$ cycloalkyl, aryl, or aralkyl, and each R$^f$ is independently C$_1$-C$_6$ alkyl, C$_1$-C$_6$ fluoroalkyl, C$_3$-C$_6$ cycloalkyl, aryl, or aralkyl;

wherein each substituted cycloalkyl, substituted aryl, and substituted aralkyl is substituted with one or two substituents independently selected from the group consisting of C$_1$-C$_6$ alkyl, halo, C$_1$-C$_6$ fluoroalkyl, cyano, nitro, —R$^b$—CN, R$^b$—OR$^a$, and —R$^b$—N(R$^a$)$_2$, where each R$^a$ is independently hydrogen, C$_1$-C$_6$ alkyl, or C$_1$-C$_6$ fluoroalkyl, and each R$^b$ is independently a direct bond or a straight or branched C$_1$-C$_6$ alkylene.

2. The compound, or pharmaceutically acceptable salt thereof, of claim 1, wherein:

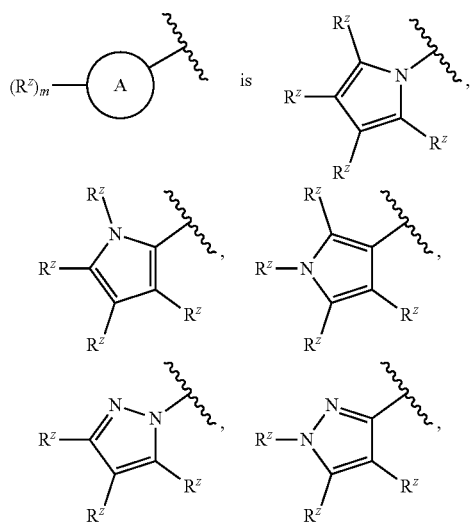

-continued
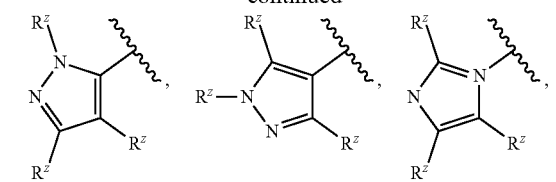
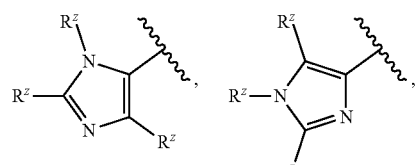
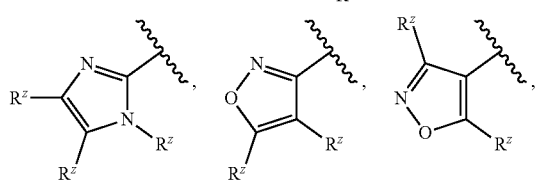
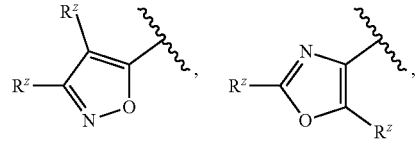
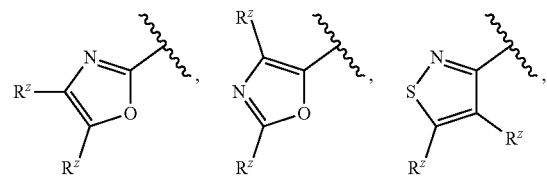
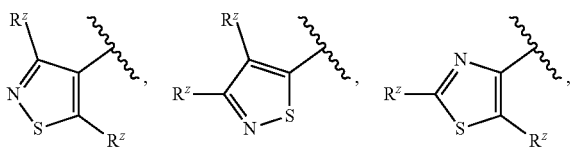
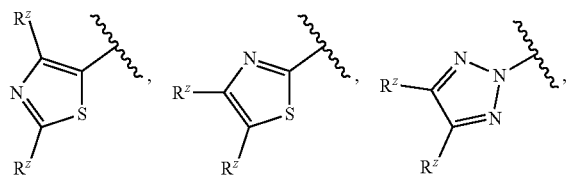
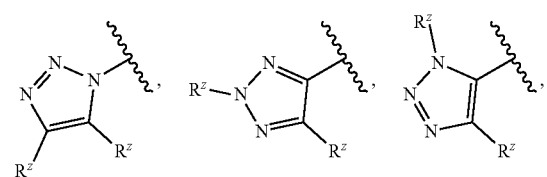
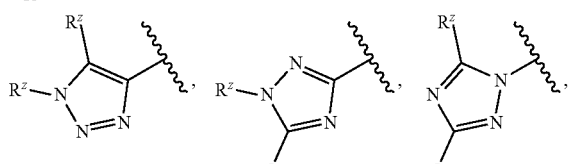
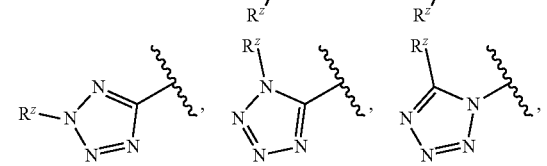
-continued
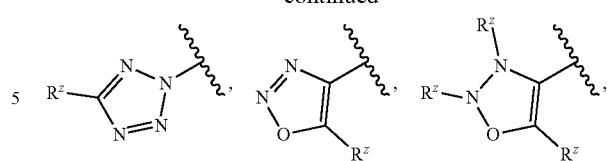
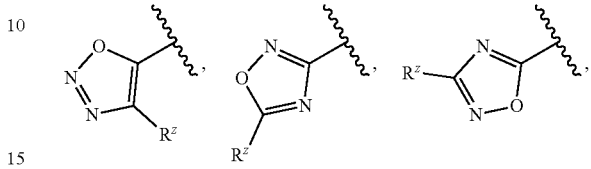
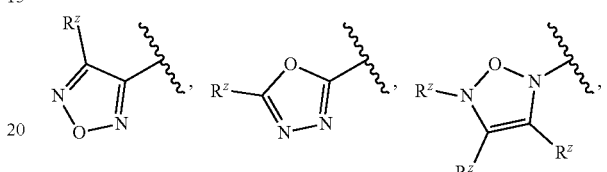
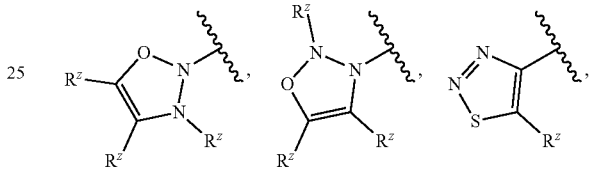
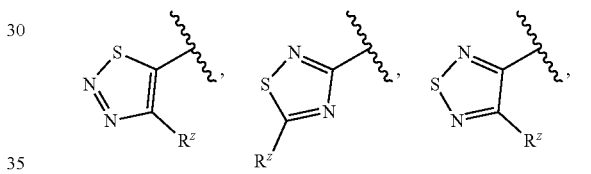
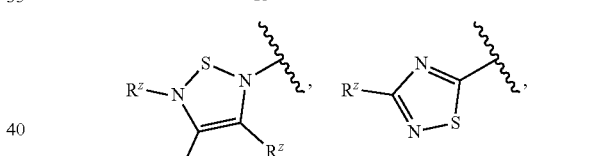
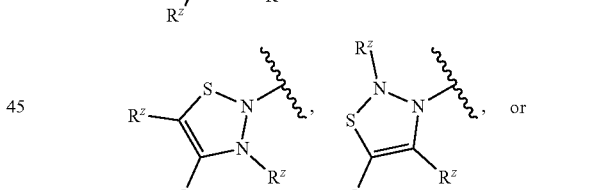
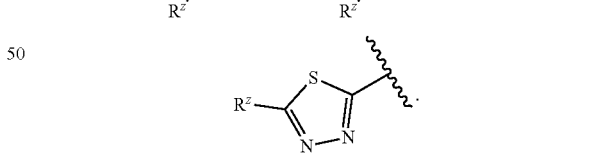
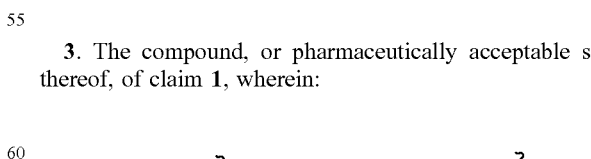
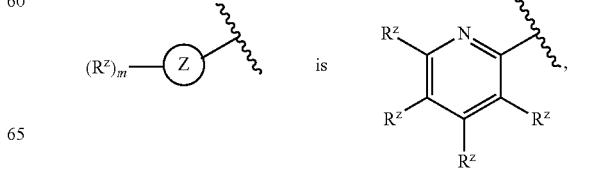
3. The compound, or pharmaceutically acceptable salt thereof, of claim 1, wherein:
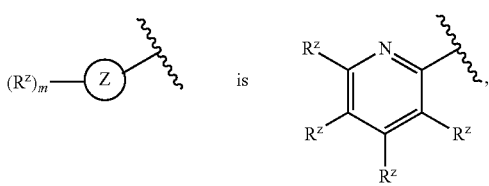

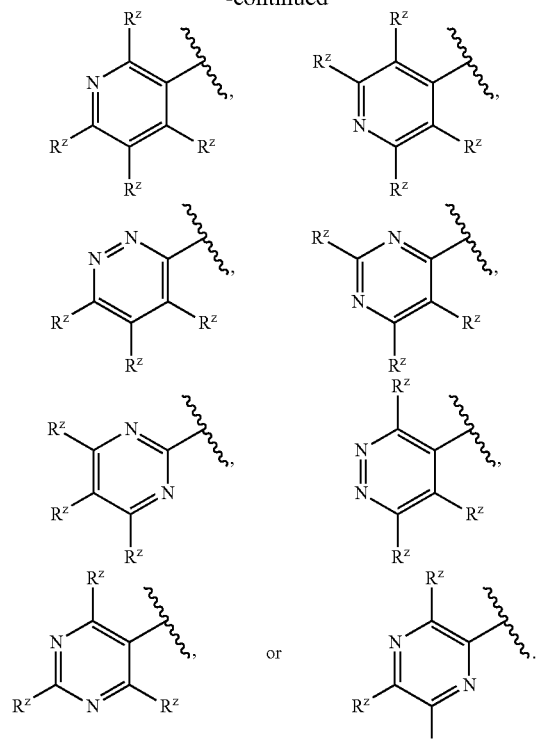

4. The compound, or pharmaceutically acceptable salt thereof, of claim 1, wherein:
each $R^z$ is independently H, halogen, $C_1$-$C_6$ alkyl, $C_1$-$C_6$ haloalkyl, $C_3$-$C_{10}$ cycloalkyl, or substituted or unsubstituted aryl.

5. The compound, or pharmaceutically acceptable salt thereof, of claim 4, wherein
each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

6. The compound, or pharmaceutically acceptable salt thereof, of claim 1, wherein:
R is —$OR^1$; and
$R^1$ is H, $C_1$-$C_6$ alkyl, $C_1$-$C_6$ haloalkyl, substituted or unsubstituted $C_1$-$C_6$ heteroalkyl, $C_3$-$C_{10}$ cycloalkyl, substituted or unsubstituted aralkyl, or substituted or unsubstituted aryl.

7. The compound, or pharmaceutically acceptable salt thereof, of claim 6, wherein:
$R^1$ is methyl, ethyl, n-propyl, iso-propyl, n-butyl, iso-butyl, tert-butyl, cyclopropyl, cyclobutyl, cyclopentyl, cyclohexyl, or phenyl.

8. The compound, or pharmaceutically acceptable salt thereof, of claim 1, wherein:
R is —$N(R^1)_2$; and
each $R^1$ is independently H, —$(SO_2)R^4$, $C_1$-$C_6$ alkyl, $C_1$-$C_6$ haloalkyl, $C_1$-$C_6$ heteroalkyl, substituted or unsubstituted $C_3$-$C_{10}$ cycloalkyl, substituted or unsubstituted aralkyl, or substituted or unsubstituted aryl.

9. The compound, or pharmaceutically acceptable salt thereof, of claim 1, wherein the compound has the structure of Formula (Ib), or a pharmaceutically acceptable salt thereof:

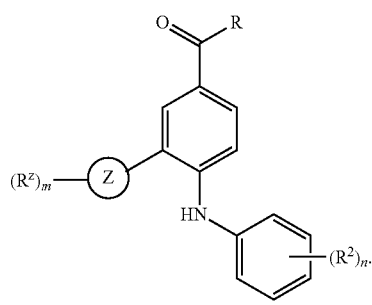

Formula (Ib)

10. The compound, or pharmaceutically acceptable salt thereof, of claim 9, wherein:

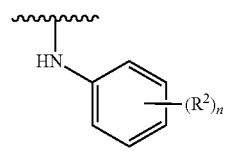

is

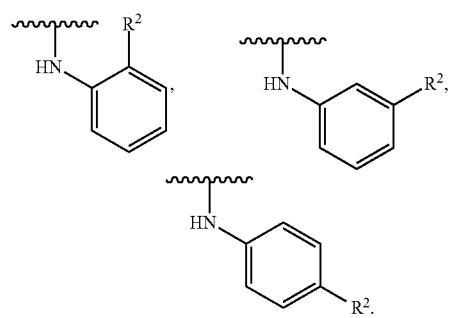

11. The compound, or pharmaceutically acceptable salt thereof, of claim 1, wherein:
each $R^2$ is independently —F, —I, —Cl, —CN, —$OR^4$, —$SR^4$, or $C_1$-$C_6$ haloalkyl.

12. The compound, or pharmaceutically acceptable salt thereof, of claim 1, wherein the compound has the structure of Formula (Id), or a pharmaceutically acceptable salt thereof:

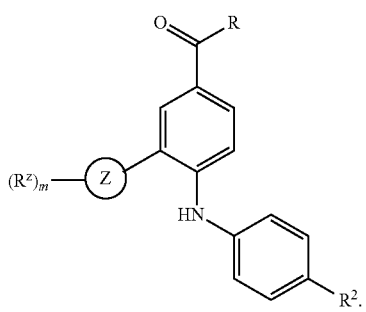

Formula (Id)

13. The compound of claim 1, wherein the compound is selected from the group consisting of:
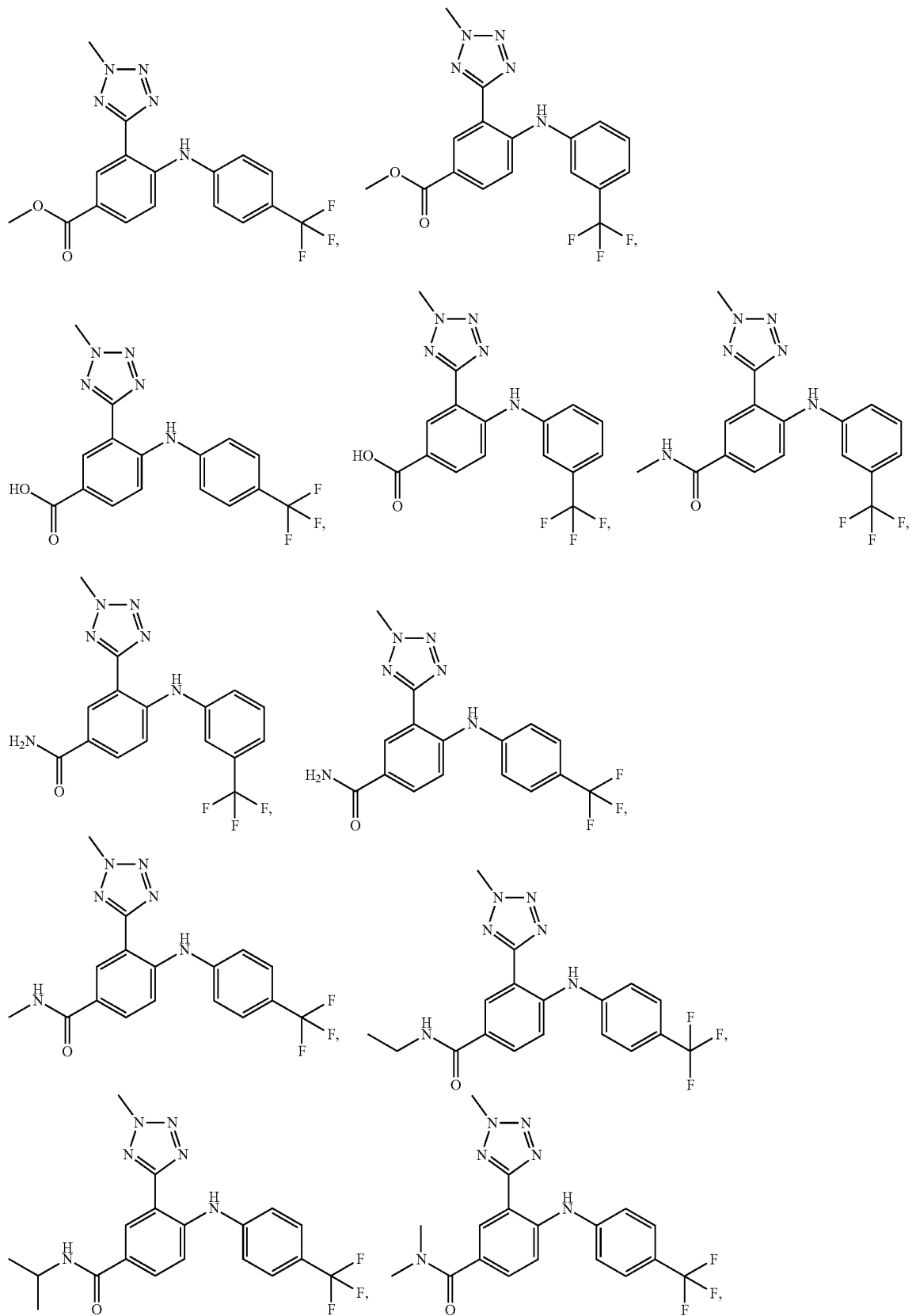

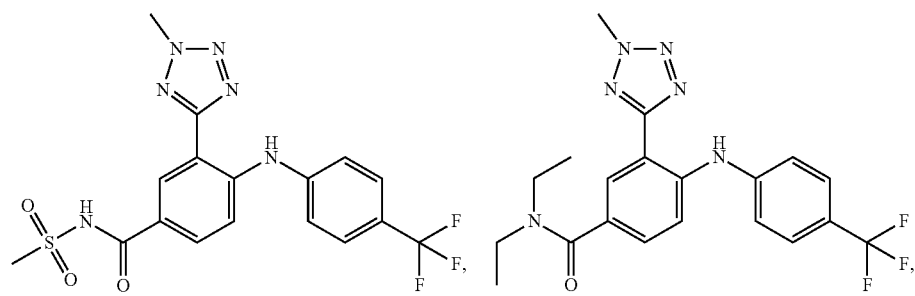
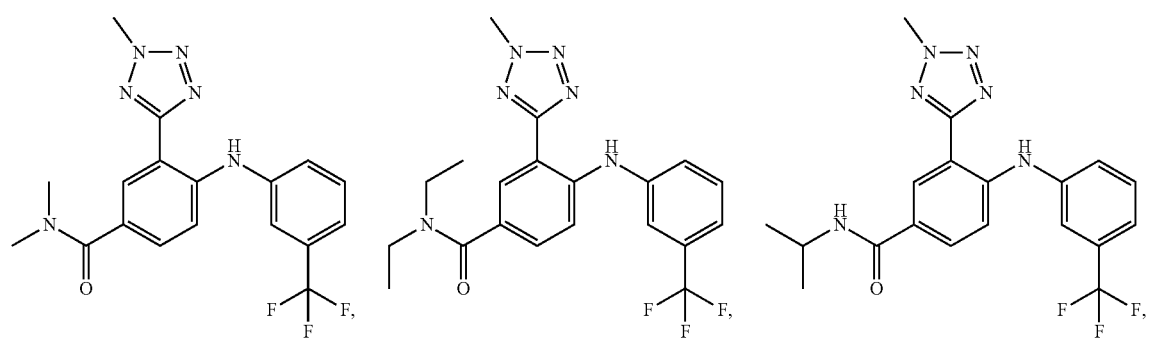
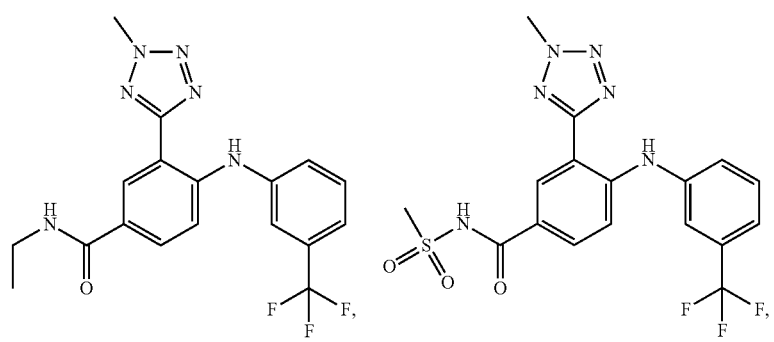
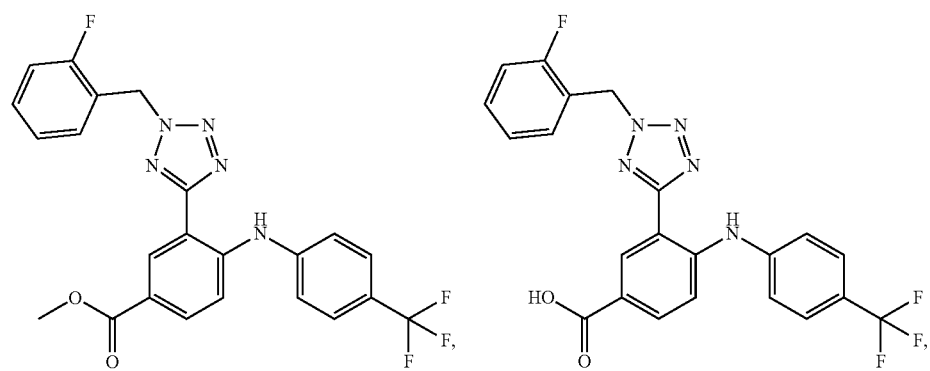

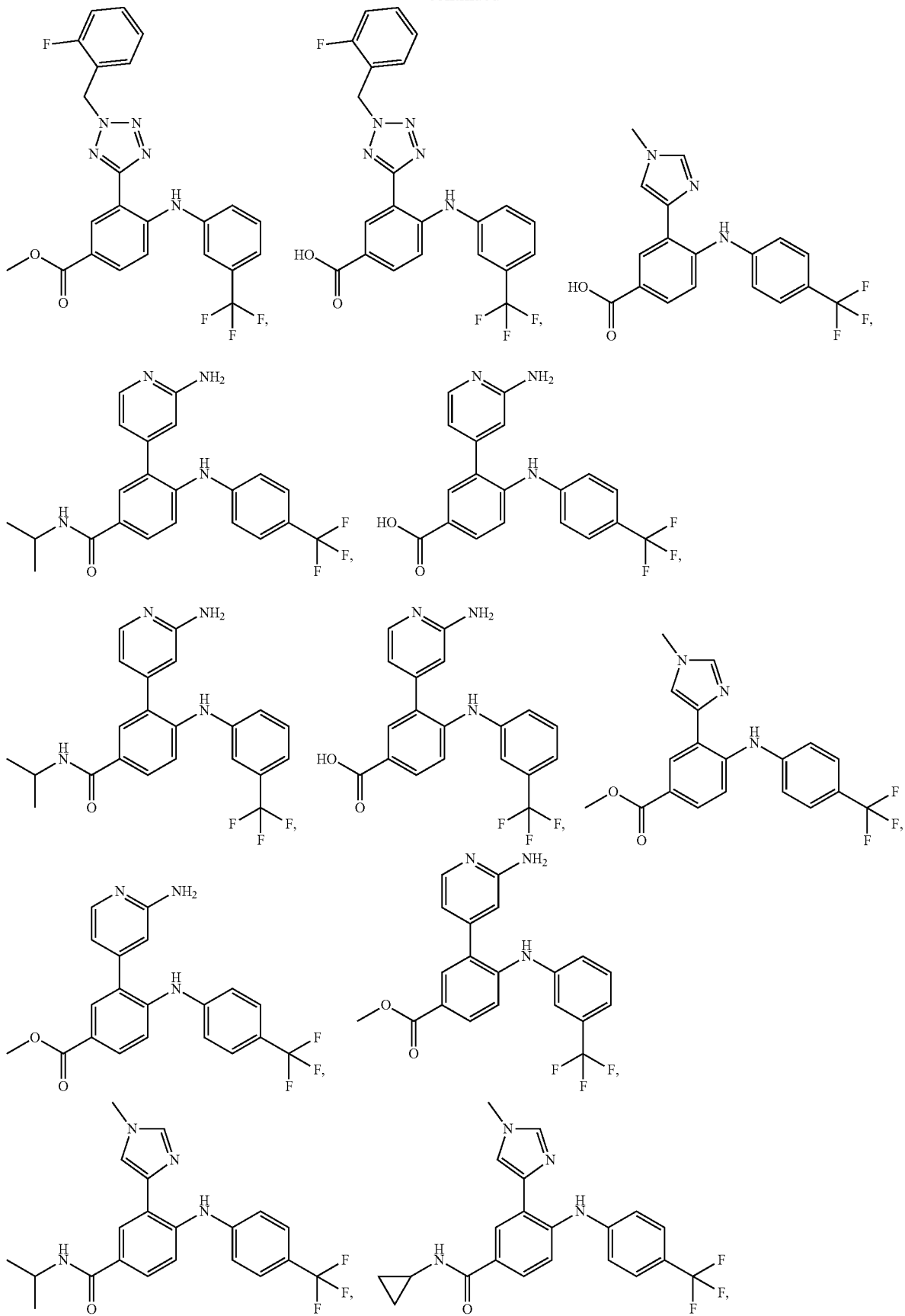

281
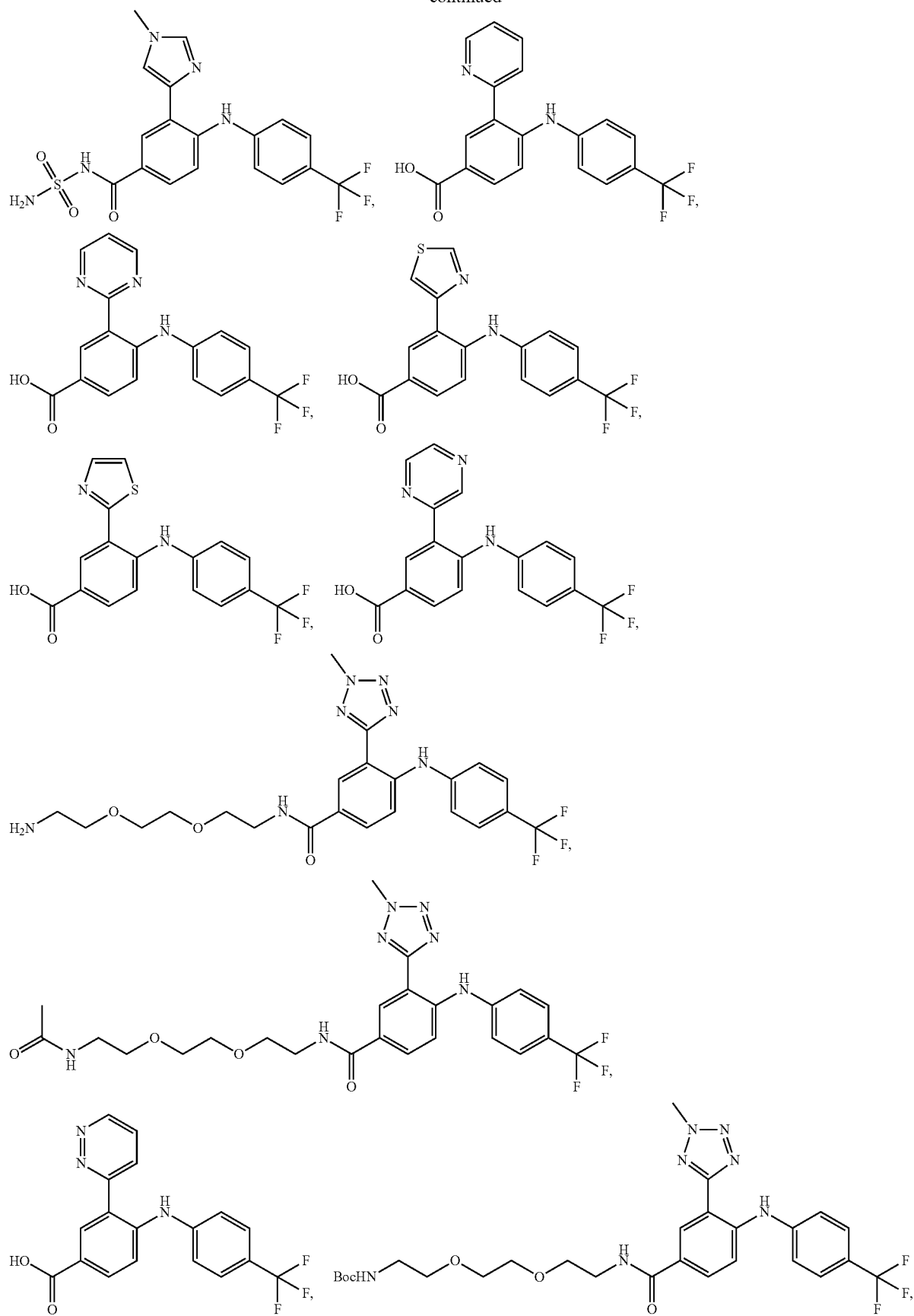
-continued
282

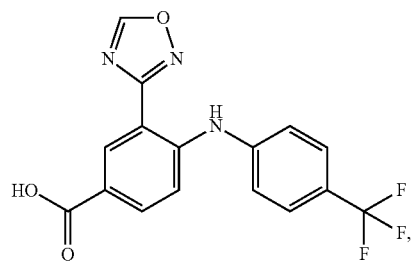
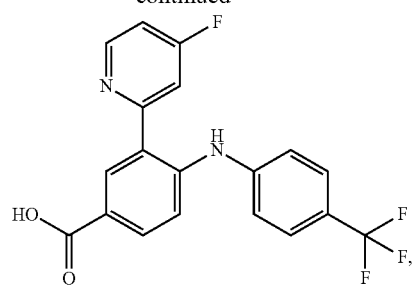
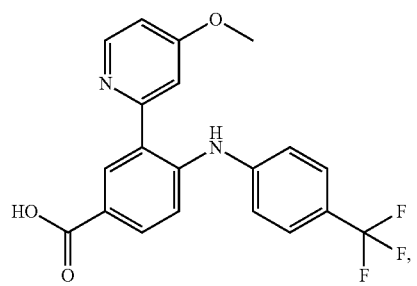
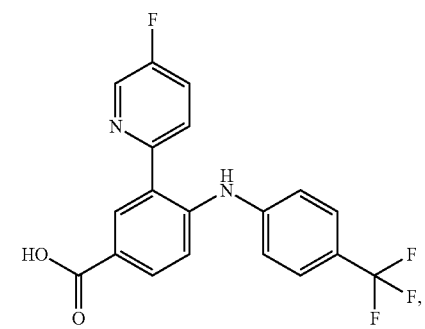
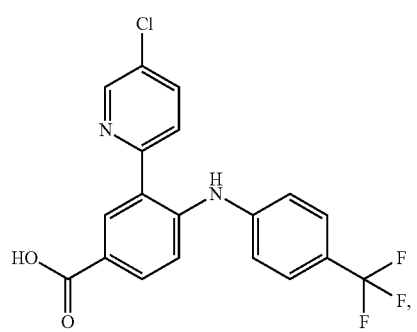
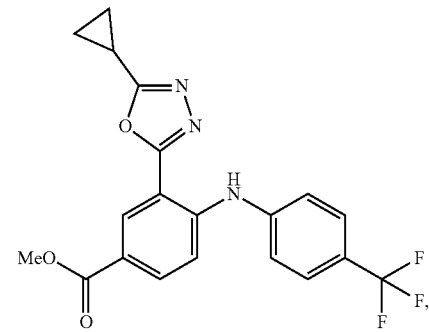
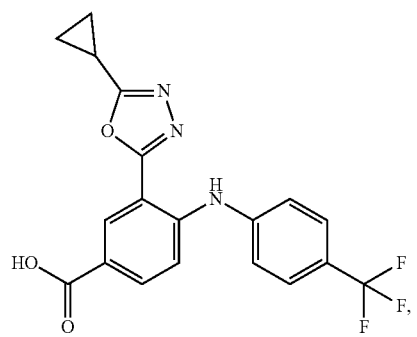
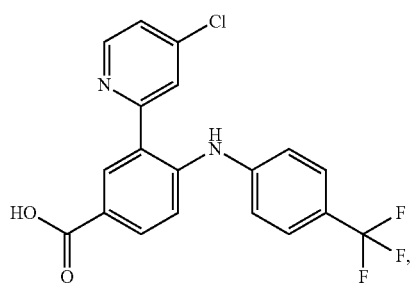
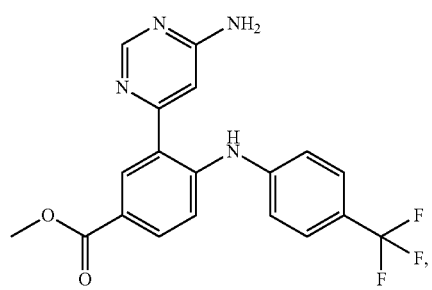
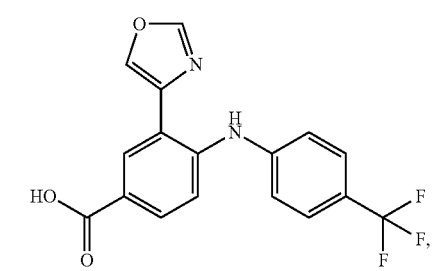

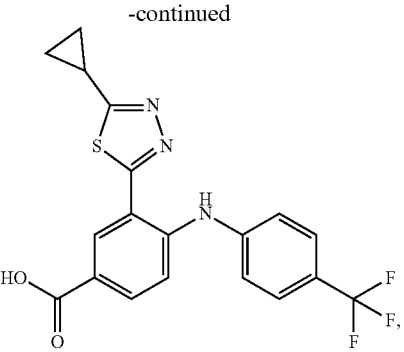
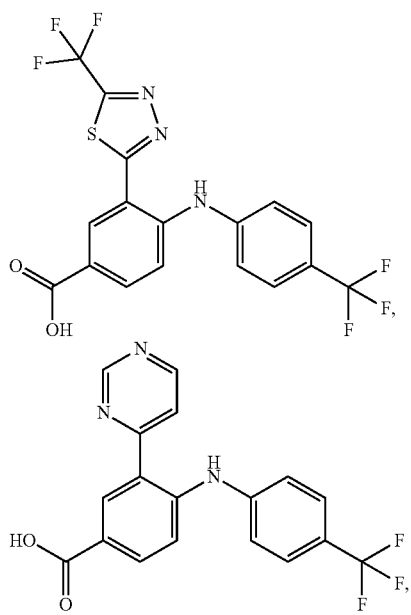
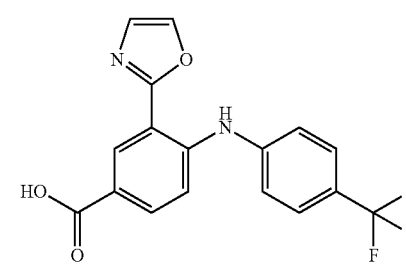
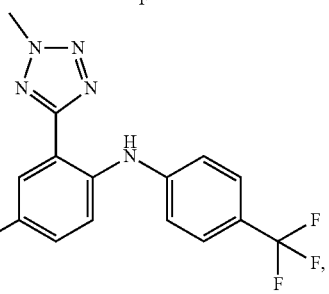
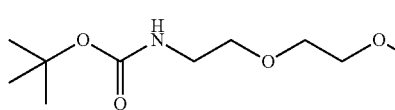

or a pharmaceutically acceptable salt thereof.

14. A pharmaceutical composition comprising a pharmaceutically acceptable excipient and a compound of claim 1, or a pharmaceutically acceptable salt thereof.

15. A method for treating a cancer in a subject in need thereof comprising administering a therapeutically effective amount of a compound of claim 1, or a pharmaceutically acceptable salt thereof; wherein the cancer is selected from mesothelioma, hepatocellular carcinoma, meningioma, malignant peripheral nerve sheath tumor, lung cancer, prostate cancer, pancreatic cancer, adenosquamous carcinoma, thyroid cancer, gastric cancer, esophageal cancer, ovarian cancer, melanoma, and breast cancer.

16. The compound, or pharmaceutically acceptable salt thereof, of claim 1, wherein: $R^2$ is —$CF_3$.

17. The compound, or pharmaceutically acceptable salt thereof, of claim 1, wherein:

each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl;

$R^2$ is —$CF_{13}$;

R is —$OR^1$; and $R^1$ is H, or substituted or unsubstituted $C_1$-$C_6$ alkyl.

18. The compound, or pharmaceutically acceptable salt thereof, of claim 17, wherein each $R^z$ is independently H or methyl.

19. The compound, or pharmaceutically acceptable salt thereof, of claim 17, wherein $R^1$ is H.

20. The compound, or pharmaceutically acceptable salt thereof, of claim 17, wherein $R^1$ is H.

* * * * *